United States Patent
Lee et al.

(10) Patent No.: US 10,526,337 B2
(45) Date of Patent: Jan. 7, 2020

(54) HETEROARYL DERIVATIVE OR PHARMACEUTICALLY ACCEPTABLE SALT THEREOF, PREPARATION METHOD THEREFOR, AND PHARMACEUTICAL COMPOSITION FOR PREVENTING OR TREATING DISEASES ASSOCIATED WITH PI3 KINASES, CONTAINING SAME AS ACTIVE INGREDIENT

(71) Applicant: KOREA RESEARCH INSTITUTE OF CHEMICAL TECHNOLOGY, Daejeon (KR)

(72) Inventors: Ge Hyeong Lee, Daejeon (KR); Hee-Jong Lim, Daejeon (KR); Heeyeong Cho, Daejeon (KR); Woo Kyu Park, Chungcheongbuk-do (KR); Seong Hwan Kim, Daejeon (KR); Jung Hwan Choi, Gyeongsangnam-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/567,692

(22) PCT Filed: Jun. 1, 2016

(86) PCT No.: PCT/KR2016/005798
§ 371 (c)(1),
(2) Date: Oct. 19, 2017

(87) PCT Pub. No.: WO2016/204429
PCT Pub. Date: Dec. 22, 2016

(65) Prior Publication Data
US 2018/0105527 A1  Apr. 19, 2018

(30) Foreign Application Priority Data
Jun. 18, 2015 (KR) .................. 10-2015-0086372
May 31, 2016 (KR) .................. 10-2016-0067210

(51) Int. Cl.
*C07D 487/04* (2006.01)
*A61K 31/506* (2006.01)
*C07D 471/04* (2006.01)

(52) U.S. Cl.
CPC .......... *C07D 487/04* (2013.01); *C07D 471/04* (2013.01)

(58) Field of Classification Search
CPC ................................................. C07D 487/04
See application file for complete search history.

(56) References Cited

U.S. PATENT DOCUMENTS

2015/0291593 A1  10/2015 Su et al.
2015/0307520 A1  10/2015 Su et al.

FOREIGN PATENT DOCUMENTS

| CN | 104151311 A | 11/2014 |
| EP | 1277738 A1 | 1/2003 |
| WO | 2004048365 A1 | 6/2004 |
| WO | 2009099801 A1 | 8/2009 |
| WO | 2010151740 A2 | 12/2010 |
| WO | 2011053861 A1 | 5/2011 |
| WO | 2014/015523 A1 | 1/2014 |
| WO | 2014015675 A1 | 1/2014 |
| WO | 2014167347 A1 | 10/2014 |

OTHER PUBLICATIONS

International Search Report for PCT Application No. PCT/KR2016/005798, dated Sep. 12, 2016.
Supplementary European Search Report issued in European Patent Application No. 16811842.0 dated Nov. 14, 2018.

*Primary Examiner* — Emily A Bernhardt
(74) *Attorney, Agent, or Firm* — Greenberg Traurig, LLP

(57) ABSTRACT

The present invention relates to a heteroaryl derivative represented by Formula 1

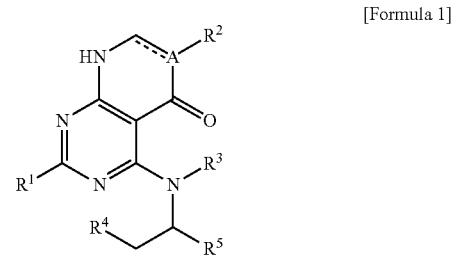

[Formula 1]

wherein
----, A, $R^1$, $R^2$, $R^3$, $R^4$, and $R^5$ are as defined herein, or a pharmaceutically acceptable salt thereof, a preparation method therefor, and a pharmaceutical composition for preventing or treating diseases associated with PI3 kinases, containing the same as an active ingredient. The heteroaryl derivative according to the present invention has an excellent effect of selectively inhibiting PI3 kinases, thereby being useful in preventing or treating PI3 kinase diseases such as cancers, autoimmune diseases, and respiratory diseases.

12 Claims, No Drawings

HETEROARYL DERIVATIVE OR PHARMACEUTICALLY ACCEPTABLE SALT THEREOF, PREPARATION METHOD THEREFOR, AND PHARMACEUTICAL COMPOSITION FOR PREVENTING OR TREATING DISEASES ASSOCIATED WITH PI3 KINASES, CONTAINING SAME AS ACTIVE INGREDIENT

CROSS-REFERENCE

This is a U.S. 371 National Phase application that claims priority to International Application No. PCT/KR2016/005798, filed Jun. 1, 2016, which claims priority to KR. Patent Application No. 1020160067210, filed on May 31, 2016 and KR Patent Application No. 1020150086372, filed on Jun. 18, 2015, the entire contents of which are incorporated by reference in their entirety.

BACKGROUND OF THE INVENTION

1. Field of the Invention

The present invention relates to a heteroaryl derivatives or a pharmaceutically acceptable salt thereof, a preparation method thereof, and a pharmaceutical composition comprising the same as an active ingredient for the prevention or treatment of PI3 kinase related diseases.

2. Description of the Related Art

As indicated in the fluid mosaic model, the eukaryotic cell membrane is not even and floated or anchored to form a specialized compartment, which is called a lipid raft. This lipid raft is rich in cholesterol so as to prevent lysis of the membrane by a detergent. Some proteins prefer lipid attachment than being hydrophobic transmembrane anchored. Phosphatidyl inositol is an intracellular protein found in the lipid raft on cell membrane, which is attached on cell membrane by fatty acid or prenyl link. The lipid raft is very dynamic and can coagulate proteins to make them very active.

The protein phosphorylation mediated by kinase is an important way for a cell to regulate physiological activities. The activity of many enzymes is regulated by the phosphorylation mediated by kinase. Another important role of the kinase-mediated phosphorylation is to provide a protein binding site. That is, other proteins are gathered together in the binding site of the phosphorylated area and bound together there without changing the inherent characteristics of the phosphorylated protein. Many kinases involved in signal transduction are found in the lipid raft on the intracellular surface of cell membrane. When a membrane-associated protein is phosphorylated by the activation of a cell surface receptor, this phosphorylated area becomes the protein binding site for those proteins floating alone. These target proteins are not active when they are floating alone without being attached in cytoplasm but become phosphorylated and active when they are gathered together in the binding site to increase their concentration there.

Phosphatidylinositol 3-kinase (PI3 kinase; PI3K) is the lipid kinase that is responsible for the phosphorylation of a lipid molecule instead of a protein, which plays an important role in cell survival, signal transduction, and control of membrane trafficking. Once there is a problem in any of these regulations, a disease such as cancer, inflammatory disease, and autoimmune disease is developed.

Signal transduction in the cell through 3'-phosphorylated phosphoinositide is associated with various cellular processes such as malignant transformation, growth factor signaling, inflammation, and immunity. PI3 kinase playing a role in producing the phosphorylated signal transduction product was first identified in the course of investigation of the interaction between the viral oncoprotein that induced the phosphorylation of phosphatidylinositol (PI) and its phosphorylated derivative at 3-OH of inositol ring and the growth factor receptor tyrosin kinase.

Phosphatidylinositol-3,4,5-triphosphate (PIP3), the primary product of the PI3 kinase activation, is up-regulated by treating cells with various stimuli which are exemplified by growth factor and inflammatory stimuli, hormone, neurotransmitter, and antigen receptor mediated signal transduction, etc. So, the activation of PI3 kinase, even though it is not dominant, presents one of the cell surface receptor activation associated signal transductions in mammals. Therefore, the PI3 kinase activation is believed to be involved in a variety of cell responses including cell growth, migration, differentiation, and apoptosis.

PI3 kinase is the enzyme to phosphorylate the $3^{rd}$ position (3-OH) of the inositol ring moiety of phosphatidylinositol by using ATP (adenosine triphosphate). Precisely, PI3 kinase phosphorylates 3'-OH of inositol ring of phosphatidylinositide to change PIP2 into PIP3. This PIP3 is then functioning as a binding site for the protein kinases containing pleckstrin homology. These protein kinases regulate important cell functions one another. Among the PIP3 binding protein kinases, the most important one is the serine/threonine kinase that is AKT or PKB (protein kinase B), which regulates cell growth, cell survival, and cell division via its downstream mTOR, GSK3β, Foxo 3a, p70S6K, and NF-κB.

It was confirmed by the primary purification and molecular cloning of PI3 kinase that PI3 kinase is a heterodimer composed of p85 and p110 subunits. Considering sequence homology and substrate specificity, it belongs to class I and class I is also classified into class IA and class IB.

Class IA includes PI3Kα, PI3Kβ, and PI3Kδ, and class IA is the downstream of RTK (receptor tyrosine kinase). Class IB represents PI3Kγ, and is the downstream of G protein coupled receptor. Each class is composed of the 110 kDa catalytic subunit and the control subunit.

More particularly, three catalytic subunits, p110α, p110β, and p110δ, contain ATP binding domain and interact with the control subunit p85 equally and also are activated by receptor tyrosine kinase. In the meantime, PI3Kγ interacts with another control subunit p101 and is activated by the heterotrimer G-protein. Control domain includes the domain for anchoring on the cell surface receptor.

When ATP binding is inhibited, PIP2 phosphorylation is suppressed and therefore PIP3 is not generated. As a result, an important regulatory protein such as AKT cannot be functioning for anchoring on the cell membrane. So, it is an important target of drug development to inhibit such a catalytic subunit and its ATP binding site.

As explained hereinafter, the expression pattern of each PI3K differs from each other in human cells and tissues. PI3Kα and PI3Kβ display a wide tissue distribution, while PI3Kγ is mainly found in white blood cells and also found in skeleton muscle, liver, pancreas, and heart. PI3Kδ is only expressed in spleen, thymus, and peripheral blood lymphocytes. The expression pattern above indicates that PI3Kα and PI3Kβ are deeply involved in cancer, while PI3Kγ and PI3Kδ are rather associated with adaptive immune system such as rheumatoid arthritis (RA), systemic lupus erythematosus (SLE), and hematological malignance.

Particularly, p110α mutation has been found in some solid tumors. For example, α amplification has been confirmed to be associated with 50% of ovarian cancer, cervical cancer, lung cancer, and breast cancer, and hyperactivation has been confirmed to be associated with at least 50% of colon cancer and at least 25% of breast cancer. P110β is confirmed to be involved in thrombopoiesis and the p110γ associated compounds have been developed as an immunosuppressant for autoimmune disease. The autoimmune disease herein includes rheumatoid arthritis and systemic lupus erythematosus.

P110δ plays a key role in B and T cell activation. Further, δ is also partly involved in neutrophil migration and sudden increase of respiration. It is also confirmed that δ can partially interrupt the antigen-IgE mediated mast cell degranulation. P110δ draws our attention as an important mediator for not only autoimmune disease and allergic reaction but also multiple major inflammatory reactions including abnormal inflammatory diseases. Target evaluation data for p110δ have been filed up from the studies using the genetic tools and pharmacological agonists, which support the confirmation above. The inhibition of δ results in the significant improvement of inflammation and the related disease, confirmed in the ovalbumin induced airway inflammation murine asthma model. Rituximab and Belimumab, the PI3Kδ monoclonal antibodies, are effective in RA and SLE.

It is also disclosed recently that PI3K is involved in the inflammation in the lung and the ear. The mechanism involved in there is not completely explained yet the over-expressed p110δ-AKT-mTOR pathway increases aerobic glycolysis but decreases the function and survival of lymphocytes, leading to the decrease of immune response.

Chronic inflammation is not unique in autoimmune disease, but PI3Kδ and phosphorylated-AKT are characteristically up-regulated in chronic obstructive pulmonary disease (COPD). The over-expression of PI3Kδ and phosphorylated-AKT is not only associated with immune disease but also associated with inflammation.

Therefore, it is suggested that the inhibition of PI3Kδ can be effective not only in treating autoimmune disease such as rheumatoid arthritis (RA) and systemic lupus erythematosus (SLE) but also in treating chronic non-autoimmune disease such as chronic obstructive pulmonary disease (COPD).

It has been recently reported that a novel compound with a novel structure to inhibit selectively PI3 kinase has been developed. Precisely, patent reference 1 presents a compound useful for cancer treatment which displays the PI3K enzyme inhibiting activity. Patent reference 2 describes that 4-morpholino-substituted bicyclic heteroaryl compound has the PI3K activity inhibiting effect.

Thus, the present inventors tried to develop a novel compound with a novel structure that is effective in inhibiting PI3 kinase selectively. In the course of the study, the inventors confirmed that the heteroaryl derivative with a specific structure had the activity of inhibiting PI3K α, β, δ, and γ selectively and particularly was more excellent in inhibiting PI3K δ and γ. Therefore, the inventors confirmed that the heteroaryl derivative can be effectively used as a pharmaceutical composition for the prevention and treatment of PI3 kinase related diseases, leading to the completion of this invention.

PRIOR ART REFERENCE

Patent Reference (Patent Reference 1) International Patent Publication No. 2004/048365
(Patent Reference 2) European Patent No. 1,277,738

SUMMARY OF THE INVENTION

It is an object of the present invention to provide a heteroaryl derivative, an optical isomer thereof, or a pharmaceutically acceptable salt of the same.

It is another object of the present invention to provide a method for preparing the said heteroaryl derivative, the optical isomer thereof, or the pharmaceutically acceptable salt of the same.

It is also an object of the present invention to provide a pharmaceutical composition for the prevention or treatment of PI3 kinase related diseases which comprises the said heteroaryl derivative, the optical isomer thereof, or the pharmaceutically acceptable salt of the same as an active ingredient.

It is further an object of the present invention to provide a health food composition for the prevention or improvement of PI3 kinase related diseases which comprises the said heteroaryl derivative, the optical isomer thereof, or the pharmaceutically acceptable salt of the same as an active ingredient.

To achieve the above objects, the present invention provides the compound represented by formula 1, the optical isomer thereof, or the pharmaceutically acceptable salt of the same:

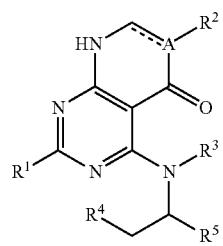

[Formula 1]

In the formula 1,

---- is single bond or double bond;

A is carbon (C) or nitrogen (N);

$R^1$ is hydrogen (H), —$NH_2$, or $C_{1-5}$ straight or branched alkylthio;

$R^2$ is H, —CN, $C_{1-5}$ straight or branched alkyl, unsubstituted $C_{3-7}$ cycloalkyl or halogen;

$R^3$ and $R^4$ are independently H or $C_{1-5}$ straight or branched alkyl; or $R^3$ and $R^4$ can form 5~7 membered unsubstituted heterocycloalkyl containing one or more hetero atoms of N along with the atoms which are conjugated to the same; and $R^5$ is

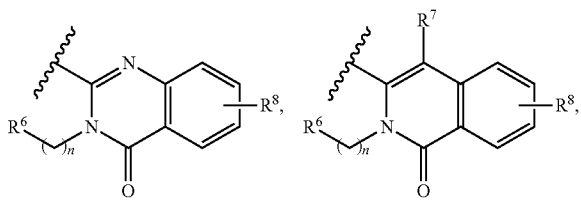

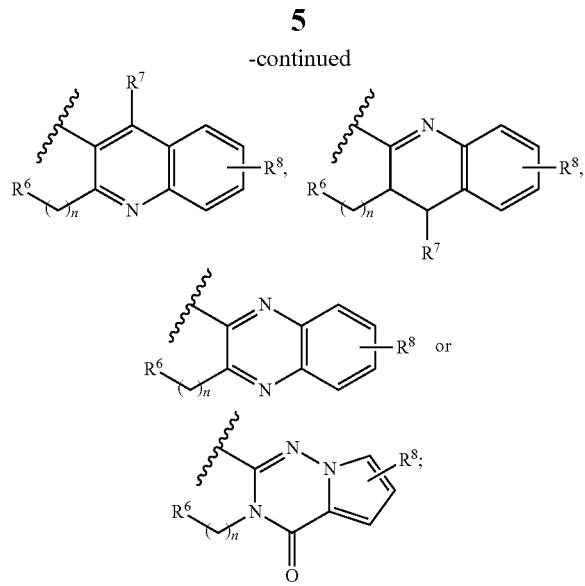

wherein, n is an integer of 0~3, $R^6$ is unsubstituted or substituted $C_{6-10}$ aryl or unsubstituted or substituted 5~10 membered heteroaryl containing one or more hetero atoms selected from the group consisting of N, O, and S. In the said substituted aryl and the substituted heteroaryl, one or more substituents selected from the group consisting of halogen, $C_{1-5}$ straight or branched alkyl, and $C_{1-5}$ straight or branched alkylsulfonyl can be substituted, $R^7$ and $R^8$ are independently H, halogen, —CN, —OH, unsubstituted or substituted $C_{6-10}$ aryl, unsubstituted or substituted 5~10 membered heteroaryl containing one or more hetero atoms selected from the group consisting of N, O, and S, $C_{1-5}$ straight or branched alkyl, $C_{1-5}$ straight or branched alkoxy, $C_{1-5}$ straight or branched alkyloxyalkyl, $C_{1-5}$ straight or branched alkylsulfonyl, $C_{1-5}$ straight or branched alkylthio, or —$NR^9R^{10}$, wherein $R^9$ and $R^{10}$ are independently H, $C_{1-5}$ straight or branched alkyl, $C_{1-5}$ straight or branched alkylamino, unsubstituted or substituted $C_{6-10}$ aryl, unsubstituted or substituted 5~10 membered heteroaryl containing one or more hetero atoms selected from the group consisting of N, O, and S, or unsubstituted or substituted 3~8 membered heterocycloalkyl containing one or more hetero atoms selected from the group consisting of N, O, and S. In the said substituted $C_{6-10}$ aryl, the substituted 5~10 membered heteroaryl, and the substituted 3~8 membered heterocycloalkyl, one or more substituents selected from the group consisting of halogen and $C_{1-5}$ straight or branched alkyl can be substituted.

The present invention also provides a method for preparing the compound represented by formula 1 comprising the following steps as shown in the below reaction formula 1:

preparing the compound represented by formula 2A by reacting the compound represented by formula 2 and the compound represented by formula 3 (step 1);

preparing the compound represented by formula 5 by reacting the compound represented by formula 2A prepared in step 1 and the compound represented by formula 4 (step 2);

preparing the compound represented by formula 7 by reacting the compound represented by formula 5 prepared in step 2 and the compound represented by formula 6 (step 3);

preparing the compound represented by formula 8 by reacting the compound represented by formula 7 prepared in step 3 and the compound represented by formula 2B under basic condition (step 4);

preparing the compound represented by formula 10 by reacting the compound represented by formula 8 prepared in step 4 and the compound represented by formula 9 (step 5);

preparing the compound represented by formula 11 by reacting the compound represented by formula 10 prepared in step 5 under acidic condition (step 6);

preparing the compound represented by formula 12 by reacting the compound represented by formula 11 prepared in step 6 and the compound represented by formula 2C (step 7); and preparing the compound represented by formula 1a by eliminating the amine protecting group from the compound represented by formula 12 prepared in step 7 under acidic condition (step 8):

[Reaction Formula 1]

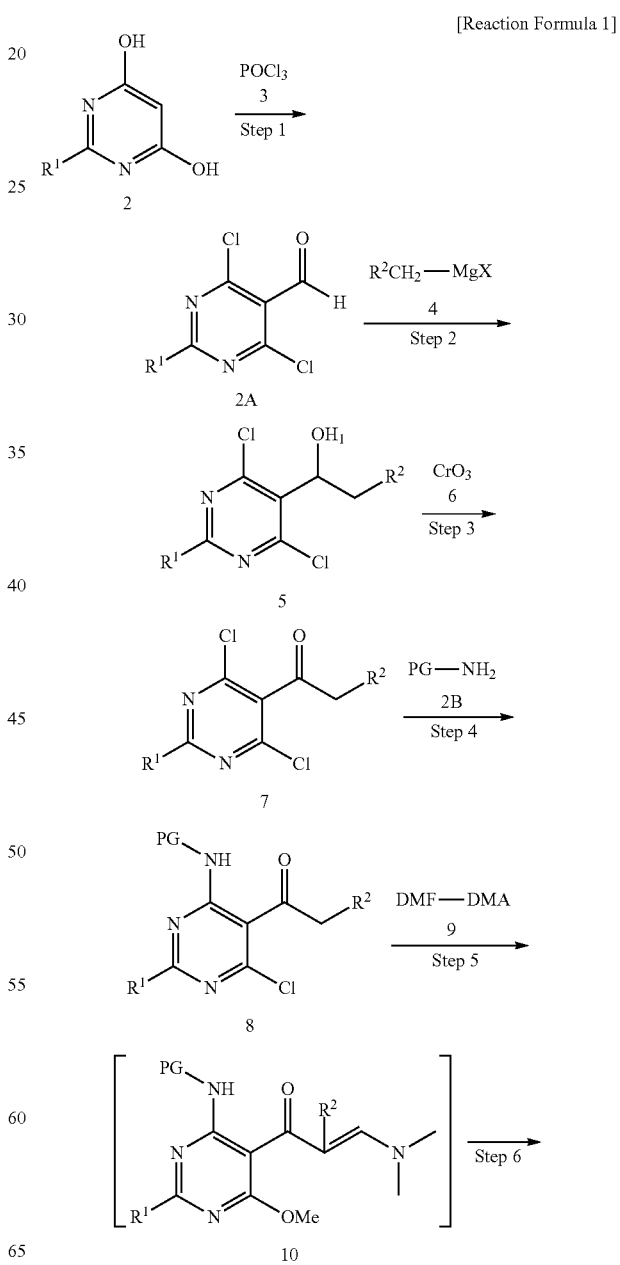

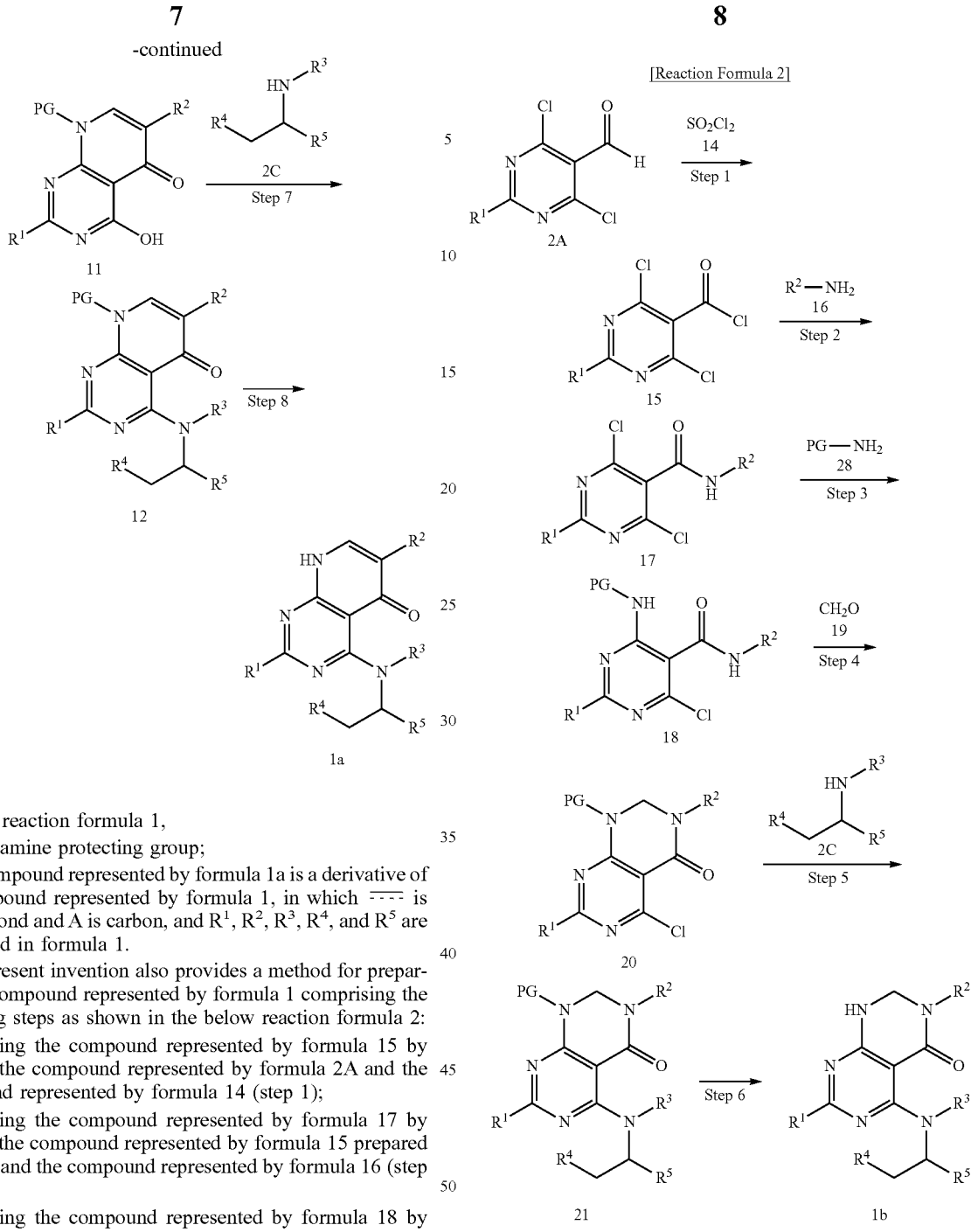

In the reaction formula 1,

PG is amine protecting group;

the compound represented by formula 1a is a derivative of the compound represented by formula 1, in which ---- is double bond and A is carbon, and $R^1$, $R^2$, $R^3$, $R^4$, and $R^5$ are as defined in formula 1.

The present invention also provides a method for preparing the compound represented by formula 1 comprising the following steps as shown in the below reaction formula 2:

preparing the compound represented by formula 15 by reacting the compound represented by formula 2A and the compound represented by formula 14 (step 1);

preparing the compound represented by formula 17 by reacting the compound represented by formula 15 prepared in step 1 and the compound represented by formula 16 (step 2);

preparing the compound represented by formula 18 by reacting the compound represented by formula 17 prepared in step 2 and the compound represented by formula 2B (step 3);

preparing the compound represented by formula 20 by reacting the compound represented by formula 18 prepared in step 3 and the compound represented by formula 19 (step 4);

preparing the compound represented by formula 21 by reacting the compound represented by formula 20 prepared in step 4 and the compound represented by formula 2C under basic condition (step 5); and preparing the compound represented by formula 1b by eliminating the amine protecting group from the compound represented by formula 21 prepared in step 5 under acidic condition (step 6):

In the reaction formula 2,

PG is amine protecting group;

the compound represented by formula 1b is a derivative of the compound represented by formula 1, in which ---- is single bond and A is nitrogen, and $R^1$, $R^2$, $R^3$, $R^4$, and $R^5$ are as defined in formula 1.

The present invention also provides a method for preparing the compound represented by formula 1 comprising the following steps as shown in the below reaction formula 3:

preparing the compound represented by formula 15 by reacting the compound represented by formula 2A and the compound represented by formula 14 (step 1);

preparing the compound represented by formula 23 by reacting the compound represented by formula 15 prepared in step 1 and the compound represented by formula 22 (step 2); and preparing the compound represented by formula 1c by reacting the compound represented by formula 23 prepared in step 2 and the compound represented by formula 2C under basic condition (step 3):

[Reaction Formula 3]

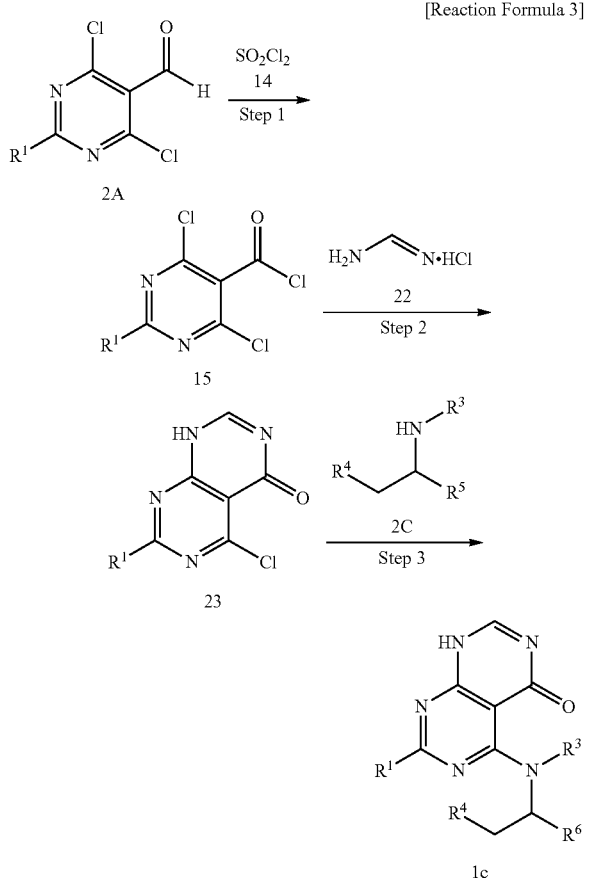

In the reaction formula 3,
PG is amine protecting group;
the compound represented by formula 1c is a derivative of the compound represented by formula 1, in which ---- is double bond and A is nitrogen, and $R^1$, $R^2$, $R^3$, $R^4$, and $R^5$ are as defined in formula 1.

The present invention also provides a pharmaceutical composition for the prevention or treatment of PI3 kinase related diseases which comprises the said heteroaryl derivative, the optical isomer thereof, or the pharmaceutically acceptable salt of the same as an active ingredient.

In addition, the present invention provides a health food composition for the prevention or improvement of PI3 kinase related diseases which comprises the said heteroaryl derivative, the optical isomer thereof, or the pharmaceutically acceptable salt of the same as an active ingredient.

Advantageous Effect

The heteroaryl derivative of the present invention is excellent in inhibiting PI3 kinase selectively, so that it can be effectively used for the prevention or treatment of PI3 kinase related diseases including cancer such as hematological malignance, ovarian cancer, cervical cancer, breast cancer, colorectal cancer, liver cancer, stomach cancer, pancreatic cancer, colon cancer, peritoneal metastasis, skin cancer, bladder cancer, prostate cancer, thyroid cancer, lung cancer, osteosarcoma, fibrous tumor, and brain tumor; autoimmune disease such as rheumatoid arthritis, systemic lupus erythematosus, multiple sclerosis, type 1 diabetes, hyperthyroidism, myasthenia, Crohn's disease, ankylosing spondylitis, psoriasis, autoimmune pernicious anemia, and Sjogren's syndrome; and respiratory disease such as chronic obstructive pulmonary disease (COPD), rhinitis, asthma, chronic bronchitis, chronic inflammatory lung disease, silicosis, pulmonary sarcoidosis, pleurisy, alveolitis, vasculitis, emphysema, pneumonia, and bronchiectasis.

DESCRIPTION OF THE PREFERRED EMBODIMENTS

Hereinafter, the present invention is described in detail.

The present invention provides the compound represented by formula 1, the optical isomer thereof, or the pharmaceutically acceptable salt of the same:

[Formula 1]

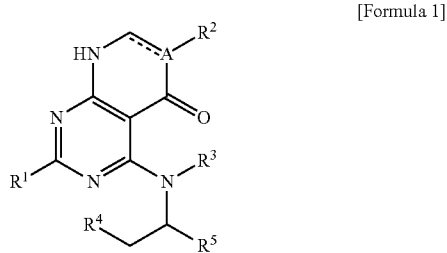

In the formula 1,
---- is single bond or double bond;
A is carbon (C) or nitrogen (N);
$R^1$ is hydrogen (H), —$NH_2$, or $C_{1-5}$ straight or branched alkylthio;
$R^2$ is H, —CN, $C_{1-5}$ straight or branched alkyl, unsubstituted $C_{3-7}$ cycloalkyl or halogen;
when ---- is double bond and A is N, $R^2$ is not existed,
$R^3$ and $R^4$ are independently H or $C_{1-5}$ straight or branched alkyl; or
$R^3$ and $R^4$ can form 5~7 membered unsubstituted heterocycloalkyl containing one or more hetero atoms of N along with the atoms which are conjugated to the same; and
$R^5$ is

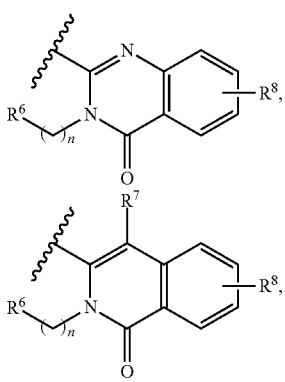

-continued

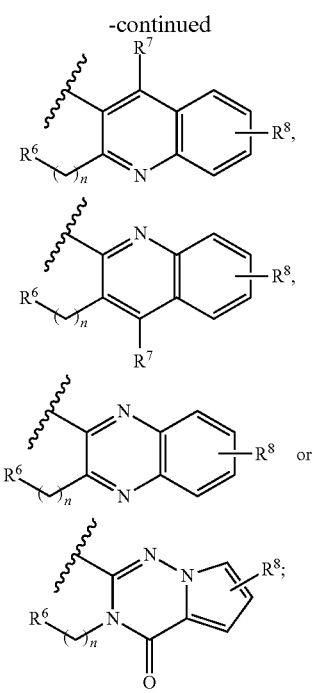

$R^5$ is

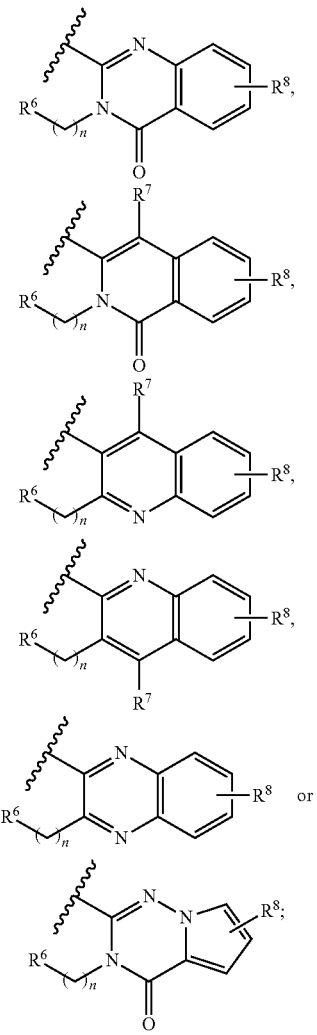

wherein, n is an integer of 0~3, $R^6$ is unsubstituted or substituted $C_{6-10}$ aryl or unsubstituted or substituted 5~10 membered heteroaryl containing one or more hetero atoms selected from the group consisting of N, O, and S. In the said substituted aryl and the substituted heteroaryl, one or more substituents selected from the group consisting of halogen, $C_{1-5}$ straight or branched alkyl, and $C_{1-5}$ straight or branched alkylsulfonyl can be substituted, $R^7$ and $R^8$ are independently H, halogen, —CN, —OH, unsubstituted or substituted $C_{6-10}$ aryl, unsubstituted or substituted 5~10 membered heteroaryl containing one or more hetero atoms selected from the group consisting of N, O, and S, $C_{1-5}$ straight or branched alkyl, $C_{1-5}$ straight or branched alkoxy, $C_{1-5}$ straight or branched alkyloxyalkyl, $C_{1-5}$ straight or branched alkylsulfonyl, $C_{1-5}$ straight or branched alkylthio, or —$NR^9R^{10}$, wherein $R^9$ and $R^{10}$ are independently H, $C_{1-5}$ straight or branched alkyl, $C_{1-5}$ straight or branched alkylamino, unsubstituted or substituted $C_{6-10}$ aryl, unsubstituted or substituted 5~10 membered heteroaryl containing one or more hetero atoms selected from the group consisting of N, O, and S, or unsubstituted or substituted 3~8 membered heterocycloalkyl containing one or more hetero atoms selected from the group consisting of N, O, and S. In the said substituted $C_{6-10}$ aryl, the substituted 5~10 membered heteroaryl, and the substituted 3~8 membered heterocycloalkyl, one or more substituents selected from the group consisting of halogen and $C_{1-5}$ straight or branched alkyl can be substituted.

Preferably,

In the formula 1,

---- is single bond or double bond;

A is carbon (C) or nitrogen (N);

$R^1$ is H, —$NH_2$, or methylthio;

$R^2$ is H, —CN, $C_{1-3}$ straight or branched alkyl, unsubstituted $C_{3-5}$ cycloalkyl or halogen;

$R^3$ and $R^4$ are independently H or $C_{1-5}$ straight or branched alkyl; or $R^3$ and $R^4$ can form 5~7 membered unsubstituted heterocycloalkyl containing one or more hetero atoms of N along with the atoms which are conjugated to the same; and wherein, n is an integer of 0 or 1, $R^6$ is unsubstituted or substituted $C_{6-10}$ aryl or unsubstituted or substituted 5~10 membered heteroaryl containing one or more hetero atoms selected from the group consisting of N, O, and S. In the said substituted aryl and the substituted heteroaryl, one or more substituents selected from the group consisting of halogen and $C_{1-5}$ straight or branched alkyl can be substituted, $R^7$ is H, halogen, unsubstituted or substituted $C_{6-10}$ aryl, or unsubstituted or substituted 5~7 membered heteroaryl containing one or more hetero atoms selected from the group consisting of N, O, and S. In the said substituted aryl and the substituted heteroaryl, one or more substituents selected from the group consisting of halogen and $C_{1-5}$ straight or branched alkyl can be substituted, and $R^8$ is H, halogen, $C_{1-3}$ straight or branched alkyl, or $C_{1-3}$ straight or branched alkoxy.

More preferably,

In the formula 1,

---- is single bond or double bond;

A is carbon (C) or nitrogen (N);

$R^1$ is H, —$NH_2$, or methylthio;

$R^2$ is H, —CN, $C_{1-3}$ straight or branched alkyl, unsubstituted $C_{3-5}$ cycloalkyl or halogen;

R³ is H;
R⁴ is H or C$_{1-3}$ straight or branched alkyl; or
R³ and R⁴ can form 5~7 membered unsubstituted heterocycloalkyl containing one atom of N along with the atoms which are conjugated to the same; and
R⁵ is

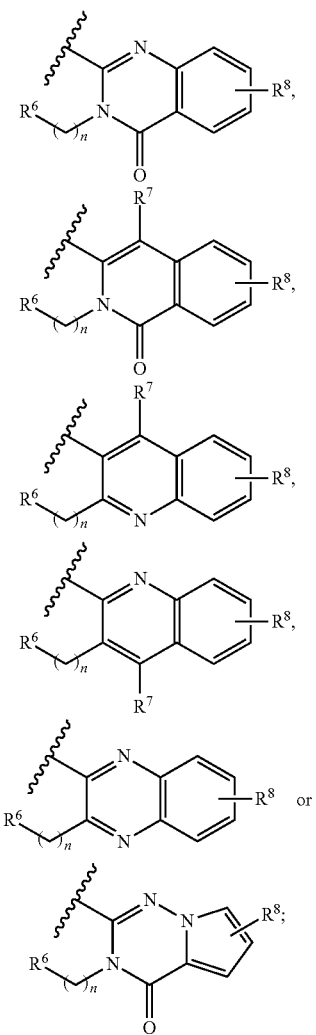

wherein, n is an integer of 0 or 1,
R⁶ is unsubstituted or substituted phenyl or pyridinyl,
in the said substituted phenyl and pyridinyl, one or more substituents selected from the group consisting of halogen and C$_{1-3}$ straight or branched alkyl can be substituted;
R⁷ is H, halogen, or unsubstituted or substituted 5~7 membered heteroaryl containing one or more hetero atoms of N. In the said substituted aryl and the substituted heteroaryl, one or more substituents selected from the group consisting of halogen and C$_{1-3}$ straight or branched alkyl can be substituted, and
R⁸ is H, halogen, or C$_{1-3}$ straight or branched alkyl.

More preferably,
In the formula 1,
---- is single bond or double bond;
A is carbon (C) or nitrogen (N);
R¹ is H or —NH₂;
R² is H, —F, —Cl, —CN, methyl, ethyl, propyl, isopropyl, cyclopropyl, or cyclopentyl;
R³ is H;
R⁴ is H or methyl; or
R³ and R⁴ can form pyrrolidine along with the atoms which are conjugated to the same; and
R⁵ is

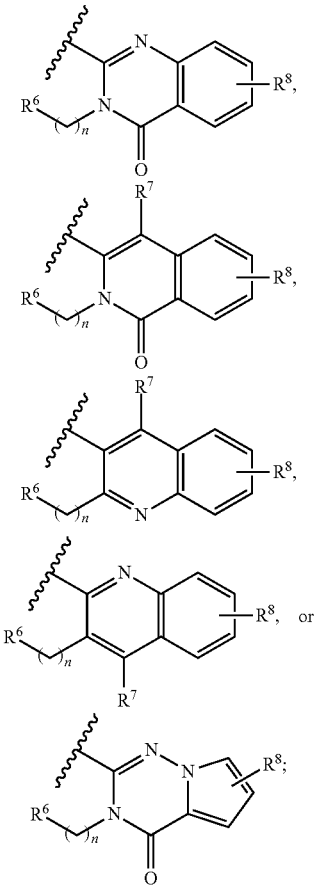

wherein, n is an integer of 0 or 1,
R⁶ is unsubstituted or substituted phenyl or pyridinyl,
in the said substituted phenyl and pyridinyl, one or more substituents selected from the group consisting of —F, —Cl, and methyl can be substituted;
R⁷ is H, —F, —Cl, or pyridinyl; and
R⁸ is H, —F, or —Cl.

The compound represented by formula 1 herein can be the compound represented by formula 1A, the optical isomer thereof, or the pharmaceutically acceptable salt of the same.

[Formula 1A]

In the formula 1A,
⁓, A, $R^1$, $R^2$, $R^3$, $R^4$, and $R^5$ are as defined in formula 1.
In the compound represented by formula 1 of the present invention, the ring containing A and $R^2$ is preferably exemplified by
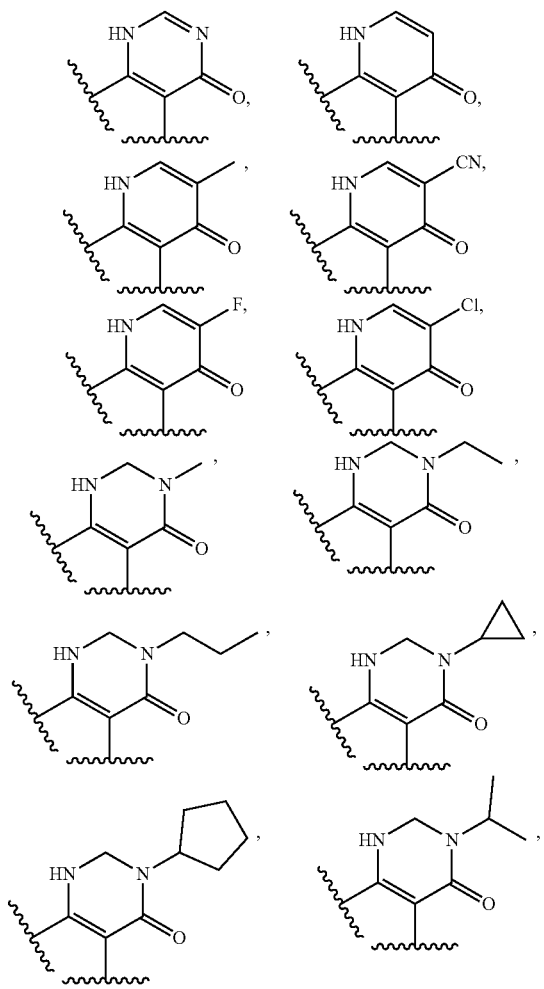
or
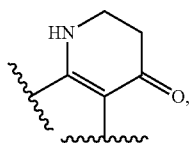 [SMILES: *C1=C(*)C(=O)CCN1]
and $R^5$ is preferably exemplified by
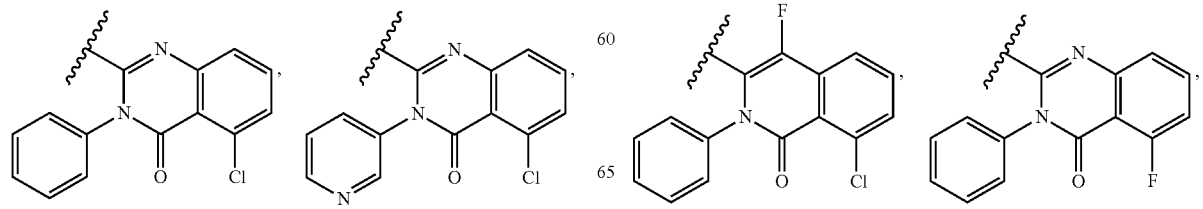

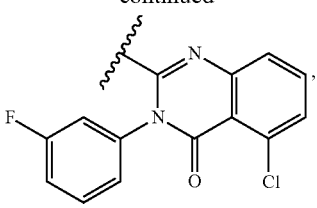

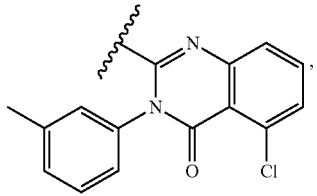

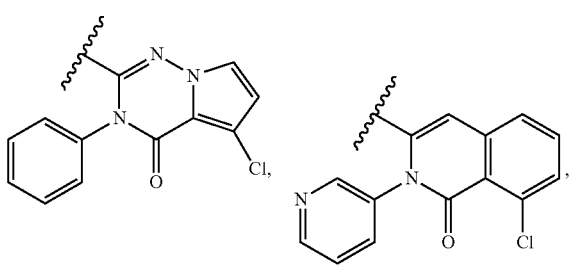

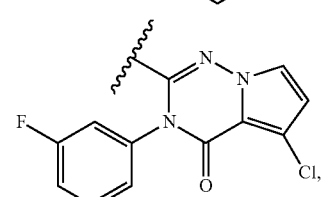

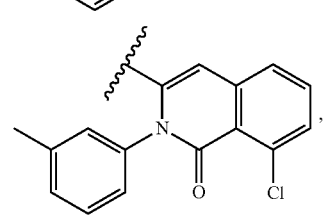

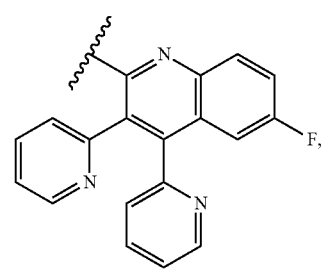

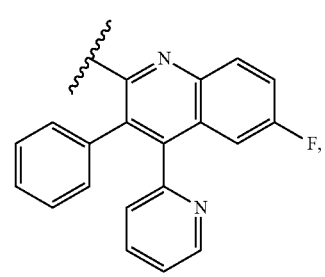

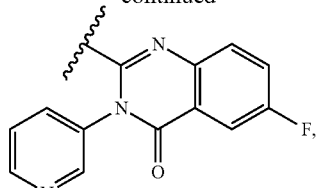

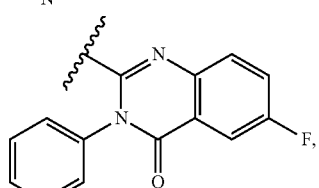

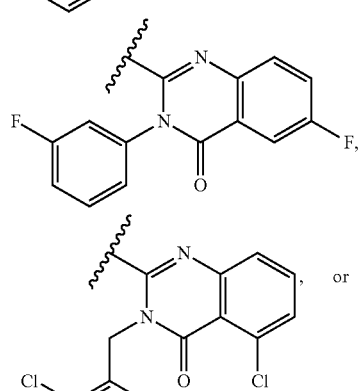

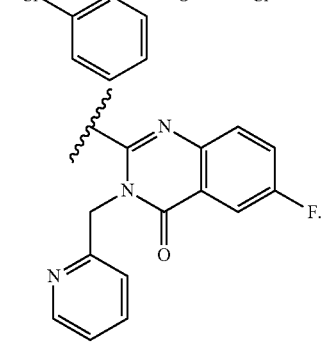

The compound represented by formula 1 of the present invention can be exemplified by the following compounds:

<1> 4-((1-(5-chloro-4-oxo-3-phenyl-3,4-dihydroquinazoline-2-yl)ethyl)amino)pyrido[2,3-d]pyrimidine-5(8H)-one;

<2> 4-((1-(5-chloro-4-oxo-3-(pyridine-3-yl)-3,4-dihydroquinazoline-2-yl)ethyl)amino)pyrido[2,3-d]pyrimidine-5(8H)-one;

<3> 4-((1-(5-chloro-4-oxo-3-(pyridine-2-yl)-3,4-dihydroquinazoline-2-yl)ethyl)amino)pyrido[2,3-d]pyrimidine-5(8H)-one;

<4> 4-((1-(5-chloro-3-(3,5-difluorophenyl)-4-oxo-3,4-dihydroquinazoline-2-yl)ethyl)amino)pyrido[2,3-d]pyrimidine-5(8H)-one;

<5> 4-((1-(8-chloro-1-oxo-2-phenyl-1,2-dihydroisoquinoline-3-yl)ethyl)amino)pyrido[2,3-d]pyrimidine-5(8H)-one;

<6> 4-((1-(2-phenylquinoline-3-yl)ethyl)amino)pyrido[2,3-d]pyrimidine-5(8H)-one;

<7> 4-((1-(6-fluoro-3-(pyridine-2-yl)quinoline-2-yl)ethyl)amino)pyrido[2,3-d]pyrimidine-5(8H)-one;

<8> 4-((1-(7-fluoro-2-(3-fluorophenyl)quinoline-3-yl)ethyl)amino)pyrido[2,3-d]pyrimidine-5(8H)-one;

<9> 4-(1-(7-fluoro-2-(pyridine-2-yl)quinoline-3-yl)ethylamino)pyrido[2,3-d]pyrimidine-5(8H)-one;
<10> 4-((1-(4,8-dichloro-1-oxo-2-phenyl-1,2-dihydroisoquinoline-3-yl)ethyl)amino)pyrido[2,3-d]pyrimidine-5(8H)-one;
<11> 4-((1-(8-chloro-4-fluoro-1-oxo-2-phenyl-1,2-dihydroisoquinoline-3-yl)ethyl)amino)pyrido[2,3-d]pyrimidine-5(8H)-one;
<12> 4-((1-(5-fluoro-4-oxo-3-phenyl-3,4-dihydroquinazoline-2-yl)propyl)amino)pyrido[2,3-d]pyrimidine-5(8H)-one;
<13> 4-(2-(5-chloro-4-oxo-3-phenyl-3,4-dihydroquinazoline-2-yl)pyrrolidine-1-yl)pyrido[2,3-d]pyrimidine-5(8H)-one;
<14> 4-(2-(8-chloro-1-oxo-2-phenyl-1,2-dihydroisoquinoline-3-yl)pyrrolidine-1-yl)pyrido[2,3-d]pyrimidine-5(8H)-one;
<15> 2-amino-4-((1-(8-chloro-1-oxo-2-phenyl-1,2-dihydroisoquinoline-3-yl)ethyl)amino)pyrido[2,3-d]pyrimidine-5(8H)-one;
<16> 2-amino-4-(2-(8-chloro-1-oxo-2-phenyl-1,2-dihydroisoquinoline-3-yl)pyrrolidine-1-yl)pyrido[2,3-d]pyrimidine-5(8H)-one;
<17> 4-((1-(8-chloro-1-oxo-2-phenyl-1,2-dihydroisoquinoline-3-yl)ethyl)amino)-6-methylpyrido[2,3-d]pyrimidine-5(8H)-one;
<18> 2-amino-4-((1-(8-chloro-1-oxo-2-phenyl-1,2-dihydroisoquinoline-3-yl)ethyl)amino)-6-methylpyrido[2,3-d]pyrimidine-5(8H)-one;
<19> 4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile;
<20> 4-((1-(8-chloro-1-oxo-2-phenyl-1,2-dihydroisoquinoline-3-yl)ethyl)amino)-6-fluoropyrido[2,3-d]pyrimidine-5(8H)-one;
<21> 4-((1-(5-chloro-4-oxo-3-phenyl-3,4-dihydroquinazoline-2-yl)ethyl)amino)-6-fluoropyrido[2,3-d]pyrimidine-5(8H)-one;
<22> 6-chloro-4-((1-(5-chloro-4-oxo-3-phenyl-3,4-dihydroquinazoline-2-yl)ethyl)amino)pyrido[2,3-d]pyrimidine-5(8H)-one;
<23> 6-chloro-4-((1-(8-chloro-1-oxo-2-phenyl-1,2-dihydroisoquinoline-3-yl)ethyl)amino)pyrido[2,3-d]pyrimidine-5(8H)-one;
<24> 6-chloro-4-((1-(4,8-dichloro-1-oxo-2-phenyl-1,2-dihydroisoquinoline-3-yl)ethyl)amino)pyrido[2,3-d]pyrimidine-5(8H)-one;
<25> 2-amino-4-((1-(6-fluoro-3-(pyridine-2-yl)quinoline-2-yl)ethyl)amino)pyrido[2,3-d]pyrimidine-5(8H)-one;
<26> 4-((1-(6-fluoro-3-(pyridine-2-yl)quinoline-2-yl)ethyl)amino)pyrido[2,3-d]pyrimidine-5(8H)-one;
<27> 4-((1-(6-fluoro-3,4-di(pyridine-2-yl)quinoline-2-yl)ethyl)amino)pyrido[2,3-d]pyrimidine-5(8H)-one;
<28> 4-((1-(6-fluoro-3-phenyl-4-(pyridine-2-yl)quinoline-2-yl)ethyl)amino)pyrido[2,3-d]pyrimidine-5(8H)-one;
<29> 4-((1-(6-fluoro-4-oxo-3-(pyridine-3-yl)-3,4-dihydroquinazoline-2-yl)ethyl)amino)pyrido[2,3-d]pyrimidine-5(8H)-one;
<30> 4-((1-(6-fluoro-4-oxo-3-phenyl-3,4-dihydroquinazoline-2-yl)ethyl)amino)pyrido[2,3-d]pyrimidine-5(8H)-one;
<31> 4-((1-(6-fluoro-3-(3-fluorophenyl)-4-oxo-3,4-dihydroquinazoline-2-yl)ethyl)amino)pyrido[2,3-d]pyrimidine-5(8H)-one;
<32> 4-((1-(5-chloro-3-(2-chlorobenzyl)-4-oxo-3,4-dihydroquinazoline-2-yl)ethyl)amino)pyrido[2,3-d]pyrimidine-5(8H)-one;
<33> 4-((1-(6-fluoro-4-oxo-3-(pyridine-2-ylmethyl)-3,4-dihydroquinazoline-2-yl)ethyl)amino)pyrido[2,3-d]pyrimidine-5(8H)-one;
<34> 4-((1-(5-chloro-3-(pyridine-2-yl)quinoline-2-yl)ethyl)amino)pyrido[2,3-d]pyrimidine-5(8H)-one;
<35> 5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one;
<36> 5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one;
<37> 5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one;
<38> 5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one;
<39> 5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one;
<40> 3-methyl-5-((1-(2-phenylquinoline-3-yl)ethyl)amino)-2,3-dihydropyrimido[4,5-d]pyrimidine-4(1H)-one;
<41> 3-methyl-5-((1-(2-phenylquinoline-3-yl)ethyl)amino)-2,3-dihydropyrimido[4,5-d]pyrimidine-4(1H)-one;
<42> 5-((1-(4,8-dichloro-1-oxo-2-phenyl-1,2-dihydroisoquinoline-3-yl)ethyl)amino)-3-methyl-2,3-dihydropyrimido[4,5-d]pyrimidine-4(1H)-one;
<43> 5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one;
<44> 5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one;
<45> 5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one;
<46> 5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one;
<47> 5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one;
<48> 5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one;
<49> 5-(2-(5-chloro-4-oxo-3-phenyl-3,4-dihydropyrrolo[2,1-f][1,2,4]triazine-2-yl)pyrrolidine-1-yl)-3-methyl-2,3-dihydropyrimido[4,5-d]pyrimidine-4(1H)-one;
<50> 7-amino-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one;
<51> 7-amino-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one;
<52> 7-amino-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one;
<53> 7-amino-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one;
<54> 7-amino-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one;

<55> 7-amino-3-methyl-5-((1-(2-phenylquinoline-3-yl)ethyl)amino)-2,3-dihydropyrimido[4,5-d]pyrimidine-4(1H)-one;
<56> 7-amino-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one;
<57> 7-amino-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one;
<58> 7-amino-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one;
<59> 7-amino-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one;
<60> 7-amino-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one;
<61> 7-amino-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one;
<62> 5-(1-(8-chloro-1-oxo-2-phenyl-1,2-dihydroisoquinoline-3-yl)ethylamino)-3-ethyl-2,3-dihydropyrimido[4,5-d]pyrimidine-4(1H)-one;
<63> 5-(1-(8-chloro-1-oxo-2-phenyl-1,2-dihydroisoquinoline-3-yl)ethylamino)-3-propyl-2,3-dihydropyrimido[4,5-d]pyrimidine-4(1H)-one;
<64> 5-(1-(8-chloro-1-oxo-2-phenyl-1,2-dihydroisoquinoline-3-yl)ethylamino)-3-cyclopropyl-2,3-dihydropyrimido[4,5-d]pyrimidine-4(1H)-one;
<65> 5-(1-(8-chloro-1-oxo-2-phenyl-1,2-dihydroisoquinoline-3-yl)ethylamino)-3-cyclopentyl-2,3-dihydropyrimido[4,5-d]pyrimidine-4(1H)-one;
<66> 5-(1-(8-chloro-1-oxo-2-phenyl-1,2-dihydroisoquinoline-3-yl)ethylamino)-3-isopropyl-2,3-dihydropyrimido[4,5-d]pyrimidine-4(1H)-one;
<67> 5-(1-(5-fluoro-4-oxo-3-phenyl-3,4-dihydroquinazoline-2-yl)propylamino)-3-isopropyl-2,3-dihydropyrimido[4,5-d]pyrimidine-4(1H)-one;
<68> 5-((1-(5-chloro-4-oxo-3-phenyl-3,4-dihydroquinazoline-2-yl)ethyl)amino)pyrimido[4,5-d]pyrimidine-4(1H)-one;
<69> 5-((1-(5-chloro-4-oxo-3-(pyridine-3-yl)-3,4-dihydroquinazoline-2-yl)ethyl)amino)pyrimido[4,5-d]pyrimidine-4(1H)-one;
<70> 5-((1-(5-chloro-3-(3-fluorophenyl)-4-oxo-3,4-dihydroquinazoline-2-yl)ethyl)amino)pyrimido[4,5-d]pyrimidine-4(1H)-one;
<71> 5-((1-(5-chloro-4-oxo-3-(m-tolyl)-3,4-dihydroquinazoline-2-yl)ethyl)amino)pyrimido[4,5-d]pyrimidine-4(1H)-one;
<72> 5-((1-(8-chloro-1-oxo-2-phenyl-1,2-dihydroisoquinoline-3-yl)ethyl)amino)pyrimido[4,5-d]pyrimidine-4(1H)-one;
<73> 5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one;
<74> 5-((1-(2-phenylquinoline-3-yl)ethyl)amino)pyrimido[4,5-d]pyrimidine-4(1H)-one;
<75> 5-((1-(5-fluoro-4-oxo-3-phenyl-3,4-dihydroquinazoline-2-yl)propyl)amino)pyrimido[4,5-d]pyrimidine-4(1H)-one;
<76> 5-(2-(5-chloro-4-oxo-3-phenyl-3,4-dihydroquinazoline-2-yl)pyrrolidine-1-yl)pyrimido[4,5-d]pyrimidine-4(1H)-one;
<77> 5-(2-(8-chloro-1-oxo-2-(pyridine-3-yl)-1,2-dihydroisoquinoline-3-yl)pyrrolidine-1-yl)pyrimido[4,5-d]pyrimidine-4(1H)-one;
<78> 5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one;
<79> 5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one;
<80> 5-(2-(5-chloro-4-oxo-3-(m-tolyl)-3,4-dihydroquinazoline-2-yl)pyrrolidine-1-yl)pyrimido[4,5-d]pyrimidine-4(1H)-one;
<81> 5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one;
<82> 5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one;
<83> 7-amino-5-((1-(5-chloro-4-oxo-3-phenyl-3,4-dihydroquinazoline-2-yl)ethyl)amino)pyrimido[4,5-d]pyrimidine-4(1H)-one;
<84> 7-amino-5-((1-(5-chloro-4-oxo-3-(pyridine-3-yl)-3,4-dihydroquinazoline-2-yl)ethyl)amino)pyrimido[4,5-d]pyrimidine-4(1H)-one;
<85> 7-amino-5-((1-(5-chloro-3-(3-fluorophenyl)-4-oxo-3,4-dihydroquinazoline-2-yl)ethyl)amino)pyrimido[4,5-d]pyrimidine-4(1H)-one;
<86> 7-amino-5-((1-(5-chloro-4-oxo-3-(m-tolyl)-3,4-dihydroquinazoline-2-yl)ethyl)amino)pyrimido[4,5-d]pyrimidine-4(1H)-one;
<87> 7-amino-5-(1-(8-chloro-1-oxo-2-phenyl-1,2-dihydroisoquinoline-3-yl)ethylamino)pyrimido[4,5-d]pyrimidine-4(1H)-one;
<88> 7-amino-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one;
<89> 7-amino-5-((1-(5-chloro-3-(3-fluorophenyl)-4-oxo-3,4-dihydropyrrolo[2,1-f][1,2,4]triazine-2-yl)ethyl)amino)pyrimido[4,5-d]pyrimidine-4(1H)-one;
<90> 7-amino-5-((1-(2-phenylquinoline-3-yl)ethyl)amino)pyrimido[4,5-d]pyrimidine-4(1H)-one;
<91> 7-amino-5-((1-(5-fluoro-4-oxo-3-phenyl-3,4-dihydroquinazoline-2-yl)propyl)amino)pyrimido[4,5-d]pyrimidine-4(1H)-one;
<92> 7-amino-5-(2-(5-chloro-4-oxo-3-phenyl-3,4-dihydroquinazoline-2-yl)pyrrolidine-1-yl)pyrimido[4,5-d]pyrimidine-4(1H)-one;
<93> 7-amino-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one;
<94> 7-amino-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one;
<95> 7-amino-5-(2-(5-chloro-4-oxo-3-(m-tolyl)-3,4-dihydroquinazoline-2-yl)pyrrolidine-1-yl)pyrimido[4,5-d]pyrimidine-4(1H)-one;
<96> 7-amino-5-(2-(8-chloro-1-oxo-2-phenyl-1,2-dihydroisoquinoline-3-yl)pyrrolidine-1-yl)pyrimido[4,5-d]pyrimidine-4(1H)-one;
<97> 7-amino-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one;
<98> 7-amino-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one;

<99> 4-((1-(8-chloro-1-oxo-2-phenyl-1,2-dihydroisoquinoline-3-yl)ethyl)amino)-7,8-dihydropyrido[2,3-d]pyrimidine-5(6H)-one;
<100> 4-((1-(4,8-dichloro-1-oxo-2-phenyl-1,2-dihydroisoquinoline-3-yl)ethyl)amino)-7,8-dihydropyrido[2,3-d]pyrimidine-5(6H)-one.

The compound represented by formula 1 of the present invention can be preferably exemplified by the following optical isomer compounds:

<1> (S)-4-((1-(5-chloro-4-oxo-3-phenyl-3,4-dihydroquinazoline-2-yl)ethyl)amino)pyrido[2,3-d]pyrimidine-5(8H)-one;
<2> (S)-4-((1-(5-chloro-4-oxo-3-(pyridine-3-yl)-3,4-dihydroquinazoline-2-yl)ethyl)amino)pyrido[2,3-d]pyrimidine-5(8H)-one;
<3> (S)-4-((1-(5-chloro-4-oxo-3-(pyridine-2-yl)-3,4-dihydroquinazoline-2-yl)ethyl)amino)pyrido[2,3-d]pyrimidine-5(8H)-one;
<4> (S)-4-((1-(5-chloro-3-(3,5-difluorophenyl)-4-oxo-3,4-dihydroquinazoline-2-yl)ethyl)amino)pyrido[2,3-d]pyrimidine-5(8H)-one;
<5> (S)-4-((1-(8-chloro-1-oxo-2-phenyl-1,2-dihydroisoquinoline-3-yl)ethyl)amino)pyrido[2,3-d]pyrimidine-5(8H)-one;
<6> (S)-4-((1-(2-phenylquinoline-3-yl)ethyl)amino)pyrido[2,3-d]pyrimidine-5(8H)-one;
<7> (S)-4-((1-(6-fluoro-3-(pyridine-2-yl)quinoline-2-yl)ethyl)amino)pyrido[2,3-d]pyrimidine-5(8H)-one;
<8> (S)-4-((1-(7-fluoro-2-(3-fluorophenyl)quinoline-3-yl)ethyl)amino)pyrido[2,3-d]pyrimidine-5(8H)-one;
<9> (S)-4-(1-(7-fluoro-2-(pyridine-2-yl)quinoline-3-yl)ethylamino)pyrido[2,3-d]pyrimidine-5(8H)-one;
<10> (S)-4-((1-(4,8-dichloro-1-oxo-2-phenyl-1,2-dihydroisoquinoline-3-yl)ethyl)amino)pyrido[2,3-d]pyrimidine-5(8H)-one;
<11> (S)-4-((1-(8-chloro-4-fluoro-1-oxo-2-phenyl-1,2-dihydroisoquinoline-3-yl)ethyl)amino)pyrido[2,3-d]pyrimidine-5(8H)-one;
<12> (S)-4-((1-(5-fluoro-4-oxo-3-phenyl-3,4-dihydroquinazoline-2-yl)propyl)amino)pyrido[2,3-d]pyrimidine-5(8H)-one;
<13> (S)-4-(2-(5-chloro-4-oxo-3-phenyl-3,4-dihydroquinazoline-2-yl)pyrrolidine-1-yl)pyrido[2,3-d]pyrimidine-5(8H)-one;
<14> (S)-4-(2-(8-chloro-1-oxo-2-phenyl-1,2-dihydroisoquinoline-3-yl)pyrrolidine-1-yl)pyrido[2,3-d]pyrimidine-5(8H)-one;
<15> (S)-2-amino-4-((1-(8-chloro-1-oxo-2-phenyl-1,2-dihydroisoquinoline-3-yl)ethyl)amino)pyrido[2,3-d]pyrimidine-5(8H)-one;
<16> (S)-2-amino-4-(2-(8-chloro-1-oxo-2-phenyl-1,2-dihydroisoquinoline-3-yl)pyrrolidine-1-yl)pyrido[2,3-d]pyrimidine-5(8H)-one;
<17> (S)-4-((1-(8-chloro-1-oxo-2-phenyl-1,2-dihydroisoquinoline-3-yl)ethyl)amino)-6-methylpyrido[2,3-d]pyrimidine-5(8H)-one;
<18> (S)-2-amino-4-((1-(8-chloro-1-oxo-2-phenyl-1,2-dihydroisoquinoline-3-yl)ethyl)amino)-6-methylpyrido[2,3-d]pyrimidine-5(8H)-one;
<19> (S)-4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile;
<20> (S)-4-((1-(8-chloro-1-oxo-2-phenyl-1,2-dihydroisoquinoline-3-yl)ethyl)amino)-6-fluoropyrido[2,3-d]pyrimidine-5(8H)-one;
<21> (S)-4-((1-(5-chloro-4-oxo-3-phenyl-3,4-dihydroquinazoline-2-yl)ethyl)amino)-6-fluoropyrido[2,3-d]pyrimidine-5(8H)-one;
<22> (S)-6-chloro-4-((1-(5-chloro-4-oxo-3-phenyl-3,4-dihydroquinazoline-2-yl)ethyl)amino)pyrido[2,3-d]pyrimidine-5(8H)-one;
<23> (S)-6-chloro-4-((1-(8-chloro-1-oxo-2-phenyl-1,2-dihydroisoquinoline-3-yl)ethyl)amino)pyrido[2,3-d]pyrimidine-5(8H)-one;
<24> (S)-6-chloro-4-((1-(4,8-dichloro-1-oxo-2-phenyl-1,2-dihydroisoquinoline-3-yl)ethyl)amino)pyrido[2,3-d]pyrimidine-5(8H)-one;
<25> (S)-2-amino-4-((1-(6-fluoro-3-(pyridine-2-yl)quinoline-2-yl)ethyl)amino)pyrido[2,3-d]pyrimidine-5(8H)-one;
<26> (S)-4-((1-(6-fluoro-3-(pyridine-2-yl)quinoline-2-yl)ethyl)amino)pyrido[2,3-d]pyrimidine-5(8H)-one;
<27> (S)-4-((1-(6-fluoro-3,4-di(pyridine-2-yl)quinoline-2-yl)ethyl)amino)pyrido[2,3-d]pyrimidine-5(8H)-one;
<28> (S)-4-((1-(6-fluoro-3-phenyl-4-(pyridine-2-yl)quinoline-2-yl)ethyl)amino)pyrido[2,3-d]pyrimidine-5(8H)-one;
<29> (S)-4-((1-(6-fluoro-4-oxo-3-(pyridine-3-yl)-3,4-dihydroquinazoline-2-yl)ethyl)amino)pyrido[2,3-d]pyrimidine-5(8H)-one;
<30> (S)-4-((1-(6-fluoro-4-oxo-3-phenyl-3,4-dihydroquinazoline-2-yl)ethyl)amino)pyrido[2,3-d]pyrimidine-5(8H)-one;
<31> (S)-4-((1-(6-fluoro-3-(3-fluorophenyl)-4-oxo-3,4-dihydroquinazoline-2-yl)ethyl)amino)pyrido[2,3-d]pyrimidine-5(8H)-one;
<32> (S)-4-((1-(5-chloro-3-(2-chlorobenzyl)-4-oxo-3,4-dihydroquinazoline-2-yl)ethyl)amino)pyrido[2,3-d]pyrimidine-5(8H)-one;
<33> (S)-4-((1-(6-fluoro-4-oxo-3-(pyridine-2-ylmethyl)-3,4-dihydroquinazoline-2-yl)ethyl)amino)pyrido[2,3-d]pyrimidine-5(8H)-one;
<34> (S)-4-((1-(5-chloro-3-(pyridine-2-yl)quinoline-2-yl)ethyl)amino)pyrido[2,3-d]pyrimidine-5(8H)-one;
<35> (S)-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one;
<36> (S)-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one;
<37> (S)-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one;
<38> (S)-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one;
<39> (S)-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one;
<40> (S)-3-methyl-5-((1-(2-phenylquinoline-3-yl)ethyl)amino)-2,3-dihydropyrimido[4,5-d]pyrimidine-4(1H)-one;
<41> (S)-3-methyl-5-((1-(2-phenylquinoline-3-yl)ethyl)amino)-2,3-dihydropyrimido[4,5-d]pyrimidine-4(1H)-one;
<42> (S)-5-((1-(4,8-dichloro-1-oxo-2-phenyl-1,2-dihydroisoquinoline-3-yl)ethyl)amino)-3-methyl-2,3-dihydropyrimido[4,5-d]pyrimidine-4(1H)-one;
<43> (S)-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one;

<44> (S)-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one;

<45> (S)-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one;

<46> (S)-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one;

<47> (S)-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one;

<48> (S)-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one;

<49> (S)-5-(2-(5-chloro-4-oxo-3-phenyl-3,4-dihydropyrrolo[2,1-f][1,2,4]triazine-2-yl)pyrrolidine-1-yl)-3-methyl-2,3-dihydropyrimido[4,5-d]pyrimidine-4(1H)-one;

<50> (S)-7-amino-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one;

<51> (S)-7-amino-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one;

<52> (S)-7-amino-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one;

<53> (S)-7-amino-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one;

<54> (S)-7-amino-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one;

<55> (S)-7-amino-3-methyl-5-((1-(2-phenylquinoline-3-yl)ethyl)amino)-2,3-dihydropyrimido[4,5-d]pyrimidine-4(1H)-one;

<56> (S)-7-amino-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one;

<57> (S)-7-amino-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one;

<58> (S)-7-amino-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one;

<59> (S)-7-amino-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one;

<60> (S)-7-amino-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one;

<61> (S)-7-amino-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one;

<62> (S)-5-(1-(8-chloro-1-oxo-2-phenyl-1,2-dihydroisoquinoline-3-yl)ethylamino)-3-ethyl-2,3-dihydropyrimido[4,5-d]pyrimidine-4(1H)-one;

<63> (S)-5-(1-(8-chloro-1-oxo-2-phenyl-1,2-dihydroisoquinoline-3-yl)ethylamino)-3-propyl-2,3-dihydropyrimido[4,5-d]pyrimidine-4(1H)-one;

<64> (S)-5-(1-(8-chloro-1-oxo-2-phenyl-1,2-dihydroisoquinoline-3-yl)ethylamino)-3-cyclopropyl-2,3-dihydropyrimido[4,5-d]pyrimidine-4(1H)-one;

<65> (S)-5-(1-(8-chloro-1-oxo-2-phenyl-1,2-dihydroisoquinoline-3-yl)ethylamino)-3-cyclopentyl-2,3-dihydropyrimido[4,5-d]pyrimidine-4(1H)-one;

<66> (S)-5-(1-(8-chloro-1-oxo-2-phenyl-1,2-dihydroisoquinoline-3-yl)ethylamino)-3-isopropyl-2,3-dihydropyrimido[4,5-d]pyrimidine-4(1H)-one;

<67> (S)-5-(1-(5-fluoro-4-oxo-3-phenyl-3,4-dihydroquinazoline-2-yl)propylamino)-3-isopropyl-2,3-dihydropyrimido[4,5-d]pyrimidine-4(1H)-one;

<68> (S)-5-((1-(5-chloro-4-oxo-3-phenyl-3,4-dihydroquinazoline-2-yl)ethyl)amino)pyrimido[4,5-d]pyrimidine-4(1H)-one;

<69> (S)-5-((1-(5-chloro-4-oxo-3-(pyridine-3-yl)-3,4-dihydroquinazoline-2-yl)ethyl)amino)pyrimido[4,5-d]pyrimidine-4(1H)-one;

<70> (S)-5-((1-(5-chloro-3-(3-fluorophenyl)-4-oxo-3,4-dihydroquinazoline-2-yl)ethyl)amino)pyrimido[4,5-d]pyrimidine-4(1H)-one;

<71> (S)-5-((1-(5-chloro-4-oxo-3-(m-tolyl)-3,4-dihydroquinazoline-2-yl)ethyl)amino)pyrimido[4,5-d]pyrimidine-4(1H)-one;

<72> (S)-5-((1-(8-chloro-1-oxo-2-phenyl-1,2-dihydroisoquinoline-3-yl)ethyl)amino)pyrimido[4,5-d]pyrimidine-4(1H)-one;

<73> (S)-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one;

<74> (S)-5-((1-(2-phenylquinoline-3-yl)ethyl)amino)pyrimido[4,5-d]pyrimidine-4(1H)-one;

<75> (S)-5-((1-(5-fluoro-4-oxo-3-phenyl-3,4-dihydroquinazoline-2-yl)propyl)amino)pyrimido[4,5-d]pyrimidine-4(1H)-one;

<76> (S)-5-(2-(5-chloro-4-oxo-3-phenyl-3,4-dihydroquinazoline-2-yl)pyrrolidine-1-yl)pyrimido[4,5-d]pyrimidine-4(1H)-one;

<77> (S)-5-(2-(8-chloro-1-oxo-2-(pyridine-3-yl)-1,2-dihydroisoquinoline-3-yl)pyrrolidine-1-yl)pyrimido[4,5-d]pyrimidine-4(1H)-one;

<78> (S)-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one;

<79> (S)-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one;

<80> (S)-5-(2-(5-chloro-4-oxo-3-(m-tolyl)-3,4-dihydroquinazoline-2-yl)pyrrolidine-1-yl)pyrimido[4,5-d]pyrimidine-4(1H)-one;

<81> (S)-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one;

<82> (S)-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one;

<83> (S)-7-amino-5-((1-(5-chloro-4-oxo-3-phenyl-3,4-dihydroquinazoline-2-yl)ethyl)amino)pyrimido[4,5-d]pyrimidine-4(1H)-one;

<84> (S)-7-amino-5-((1-(5-chloro-4-oxo-3-(pyridine-3-yl)-3,4-dihydroquinazoline-2-yl)ethyl)amino)pyrimido[4,5-d]pyrimidine-4(1H)-one;

<85> (S)-7-amino-5-((1-(5-chloro-3-(3-fluorophenyl)-4-oxo-3,4-dihydroquinazoline-2-yl)ethyl)amino)pyrimido[4,5-d]pyrimidine-4(1H)-one;

<86> (S)-7-amino-5-((1-(5-chloro-4-oxo-3-(m-tolyl)-3,4-dihydroquinazoline-2-yl)ethyl)amino)pyrimido[4,5-d]pyrimidine-4(1H)-one;

<87> (S)-7-amino-5-(1-(8-chloro-1-oxo-2-phenyl-1,2-dihydroisoquinoline-3-yl)ethylamino)pyrimido[4,5-d]pyrimidine-4(1H)-one;

<88> (S)-7-amino-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one;

<89> (S)-7-amino-5-((1-(5-chloro-3-(3-fluorophenyl)-4-oxo-3,4-dihydropyrrolo[2,1-f][1,2,4]triazine-2-yl)ethyl)amino)pyrimido[4,5-d]pyrimidine-4(1H)-one;

<90> (S)-7-amino-5-((1-(2-phenylquinoline-3-yl)ethyl)amino)pyrimido[4,5-d]pyrimidine-4(1H)-one;

<91> (S)-7-amino-5-((1-(5-fluoro-4-oxo-3-phenyl-3,4-dihydroquinazoline-2-yl)propyl)amino)pyrimido[4,5-d]pyrimidine-4(1H)-one;

<92> (S)-7-amino-5-(2-(5-chloro-4-oxo-3-phenyl-3,4-dihydroquinazoline-2-yl)pyrrolidine-1-yl)pyrimido[4,5-d]pyrimidine-4(1H)-one;

<93> (S)-7-amino-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one;

<94> (S)-7-amino-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one;

<95> (S)-7-amino-5-(2-(5-chloro-4-oxo-3-(m-tolyl)-3,4-dihydroquinazoline-2-yl)pyrrolidine-1-yl)pyrimido[4,5-d]pyrimidine-4(1H)-one;

<96> (S)-7-amino-5-(2-(8-chloro-1-oxo-2-phenyl-1,2-dihydroisoquinoline-3-yl)pyrrolidine-1-yl)pyrimido[4,5-d]pyrimidine-4(1H)-one;

<97> (S)-7-amino-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one;

<98> (S)-7-amino-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one;

<99> (S)-4-((1-(8-chloro-1-oxo-2-phenyl-1,2-dihydroisoquinoline-3-yl)ethyl)amino)-7,8-dihydropyrido[2,3-d]pyrimidine-5(6H)-one;

<100> (S)-4-((1-(4,8-dichloro-1-oxo-2-phenyl-1,2-dihydroisoquinoline-3-yl)ethyl)amino)-7,8-dihydropyrido[2,3-d]pyrimidine-5(6H)-one.

The present invention also provides the intermediate compound represented by formula 1B of the compound represented by formula 1, or the optical isomer of the same.

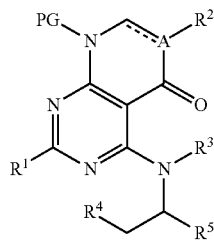

[Formula 1B]

In the formula 1B,

----, A, $R^1$, $R^2$, $R^3$, $R^4$, and $R^5$ are as defined in formula 1; and

PG is an amine protecting group selected from the group consisting of t-butyloxycarbonyl (Boc), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), and aryloxycarbonyl (Alloc).

The compound represented by formula 1B is an intermediate of the compound represented by formula 1 which can be prepared by eliminating the amine protecting group of PG.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the compound represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

The present invention also provides a method for preparing the compound represented by formula 1 comprising the following steps as shown in the below reaction formula 1:

preparing the compound represented by formula 2A by reacting the compound represented by formula 2 and the compound represented by formula 3 (step 1);

preparing the compound represented by formula 5 by reacting the compound represented by formula 2A prepared in step 1 and the compound represented by formula 4 (step 2);

preparing the compound represented by formula 7 by reacting the compound represented by formula 5 prepared in step 2 and the compound represented by formula 6 (step 3);

preparing the compound represented by formula 8 by reacting the compound represented by formula 7 prepared in step 3 and the compound represented by formula 2B under basic condition (step 4);

preparing the compound represented by formula 10 by reacting the compound represented by formula 8 prepared in step 4 and the compound represented by formula 9 (step 5);

preparing the compound represented by formula 11 by reacting the compound represented by formula 10 prepared in step 5 under acidic condition (step 6);

preparing the compound represented by formula 12 by reacting the compound represented by formula 11 prepared in step 6 and the compound represented by formula 2C (step 7); and preparing the compound represented by formula 1a by eliminating the amine protecting group from the compound represented by formula 12 prepared in step 7 under acidic condition (step 8):

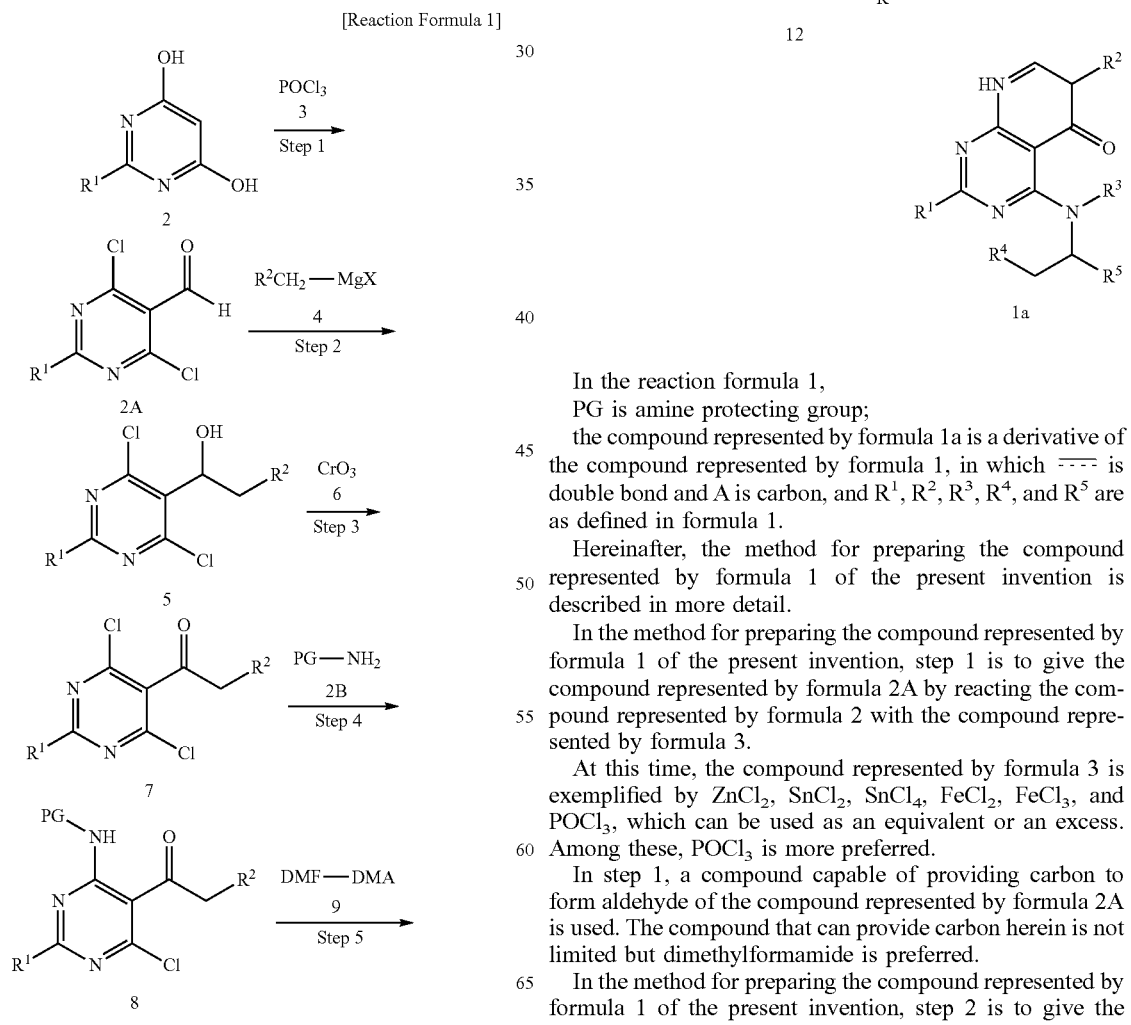

[Reaction Formula 1]

In the reaction formula 1,

PG is amine protecting group;

the compound represented by formula 1a is a derivative of the compound represented by formula 1, in which ---- is double bond and A is carbon, and $R^1$, $R^2$, $R^3$, $R^4$, and $R^5$ are as defined in formula 1.

Hereinafter, the method for preparing the compound represented by formula 1 of the present invention is described in more detail.

In the method for preparing the compound represented by formula 1 of the present invention, step 1 is to give the compound represented by formula 2A by reacting the compound represented by formula 2 with the compound represented by formula 3.

At this time, the compound represented by formula 3 is exemplified by $ZnCl_2$, $SnCl_2$, $SnCl_4$, $FeCl_2$, $FeCl_3$, and $POCl_3$, which can be used as an equivalent or an excess. Among these, $POCl_3$ is more preferred.

In step 1, a compound capable of providing carbon to form aldehyde of the compound represented by formula 2A is used. The compound that can provide carbon herein is not limited but dimethylformamide is preferred.

In the method for preparing the compound represented by formula 1 of the present invention, step 2 is to give the compound represented by formula by reacting the compound represented by formula 2 prepared in step 1 with the compound represented by formula 4, the Grignard reagent.

In the method for preparing the compound represented by formula 1 of the present invention, step 3 is to give the compound represented by formula by reacting the compound represented by formula 5 prepared in step 2 with the compound represented by formula 6.

Particularly, step 3 is to prepare the aldehyde compound represented by formula 7 by reacting the alcohol compound represented by formula 5 with the oxidant represented by formula 6. At this time, the oxidant represented by formula 6 is exemplified by PCC (pyridinium chlorochromate), PDC (pyridinium dichromate), and $CrO_3$, which can be used as an equivalent or an excess. Among these, $CrO_3$ is more preferred.

In the method for preparing the compound represented by formula 1 of the present invention, step 4 is to give the compound represented by formula by reacting the compound represented by formula 7 prepared in step 3 with the compound represented by formula 2B.

At this time, PG in the compound represented by formula 2B is the amine protecting group and the amine protecting group is exemplified by t-butyloxycarbonyl (Boc), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), or aryloxycarbonyl (Alloc), and p-methoxybenzyl (PMB) is more preferred.

In the method for preparing the compound represented by formula 1 of the present invention, step 5 is to give the compound represented by formula 10 by reacting the compound represented by formula 8 prepared in step 4 with DMF-DMA (dimethylformamide-dimethylacetal), the compound represented by formula 9.

In the method for preparing the compound represented by formula 1 of the present invention, step 6 is to give the compound represented by formula 11 by reacting the compound represented by formula 10 prepared in step 5 under acidic condition.

At this time, the acid is exemplified by HCl, $H_2SO_4$, bromic acid, and acetic acid, which can be used as an equivalent or an excess. Among these, acetic acid is more preferred.

In the method for preparing the compound represented by formula 1 of the present invention, step 7 is to give the compound represented by formula 12 by reacting the compound represented by formula 11 prepared in step 6 with the compound represented by formula 2C.

Particularly, step 3 is to prepare the compound represented by formula 1 by dehydration-condensation of the compound represented by formula 11 and the compound represented by formula 2C in the presence of (benzotriazole-1-yloxy)tris(dimethylamino)phosphonium hexafluorophosphate (BOP) and a base.

At this time, the base herein is exemplified by an organic base such as pyridine, triethylamine, N,N-diisopropylethylamine (DIPEA), and 1,8-diazabicyclo[5.4.0]-7-undecene (DBU) or an inorganic base such as sodiumhydroxide, sodiumcarbonate, potassiumcarbonate, cesiumcarbonate, and sodiumhydride, which can be used as an equivalent or an excess independently or mixed together. Among these, 1,8-diazabicyclo[5.4.0]-7-undecene (DBU) is more preferred.

The stereo-selectivity of the compound represented by formula 1 is determined by the stereo-selectivity of the compound represented by formula 2C used in step 7. Thus, the optical isomer of the compound represented by formula 1 can be prepared by using the optical isomer of the compound represented by formula 2C.

In the method for preparing the compound represented by formula 1 of the present invention, step 8 is to give the compound represented by formula 1a by eliminating the amine protecting group of the compound represented by formula 12 prepared in step 7 under acidic condition.

At this time, the acid is exemplified by HCl, H2SO4, acetic acid, and trifluoroacetic acid, which can be used as an equivalent or an excess. Among these, trifluoroacetic acid is more preferred.

In the method for preparing the compound represented by formula 1 of the present invention, each step of the reaction formula 1 can be executed by the conventional method known to those in the art and at this time the usable base is exemplified by such organic bases as pyridine, triethylamine, N,N-diisopropylethylamine (DIPEA), and 1,8-diazabicyclo[5.4.0]-7-undecene (DBU); or such inorganic bases as sodium hydroxide, sodium carbonate, potassium carbonate, cesium carbonate, and sodium hydride, which can be used as an equivalent or an excess independently or as mixed. The acceptable reaction solvent is exemplified by tetrahydrofuran (TFH); dioxane; ether solvents such as ethylether and 1,2-dimethoxyethane; lower alcohols such as methanol, ethanol, propanol, and butanol; dimethylformamide (DMF), dimethylsulfoxide (DMSO), dichloromethane (DCM), dichloroethane, water, acetonagensulfonate, toluenesulfonate, chlorobenzenesulfonate, xylenesulfonate, ethylacetate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate. The reaction solvent can be added independently or as a mixture of those.

As explained hereinbefore, the preparation method represented by the reaction formula 1 of the invention is not only a novel method for preparing easily the compound represented by formula 11, one of the intermediates of the compound represented by formula 1 but also a useful method for preparing various pyrido-pyrimidine derivatives from the compound represented by formula 1 by reacting the compound represented by formula 11 with the compound reacting to hydroxyl group (—OH), the substituent for the compound represented by formula 11.

In the preparation method represented by the reaction formula 1 of the invention, the compound represented by formula 1a can be prepared by the method comprising the following steps as shown in reaction formula 1-a:

preparing the compound represented by formula 13 by reacting the compound represented by formula 8 prepared in step 4 of reaction formula 1 and the compound represented by formula 2C (step 1);

preparing the compound represented by formula 12 by reacting the compound represented by formula 13 prepared in step 1 and the compound represented by formula 9 (step 2); and preparing the compound represented by formula 1a by eliminating the amine protecting group from the compound represented by formula 12 prepared in step 2 under acidic condition (step 3):

[Reaction Formula 1-a]

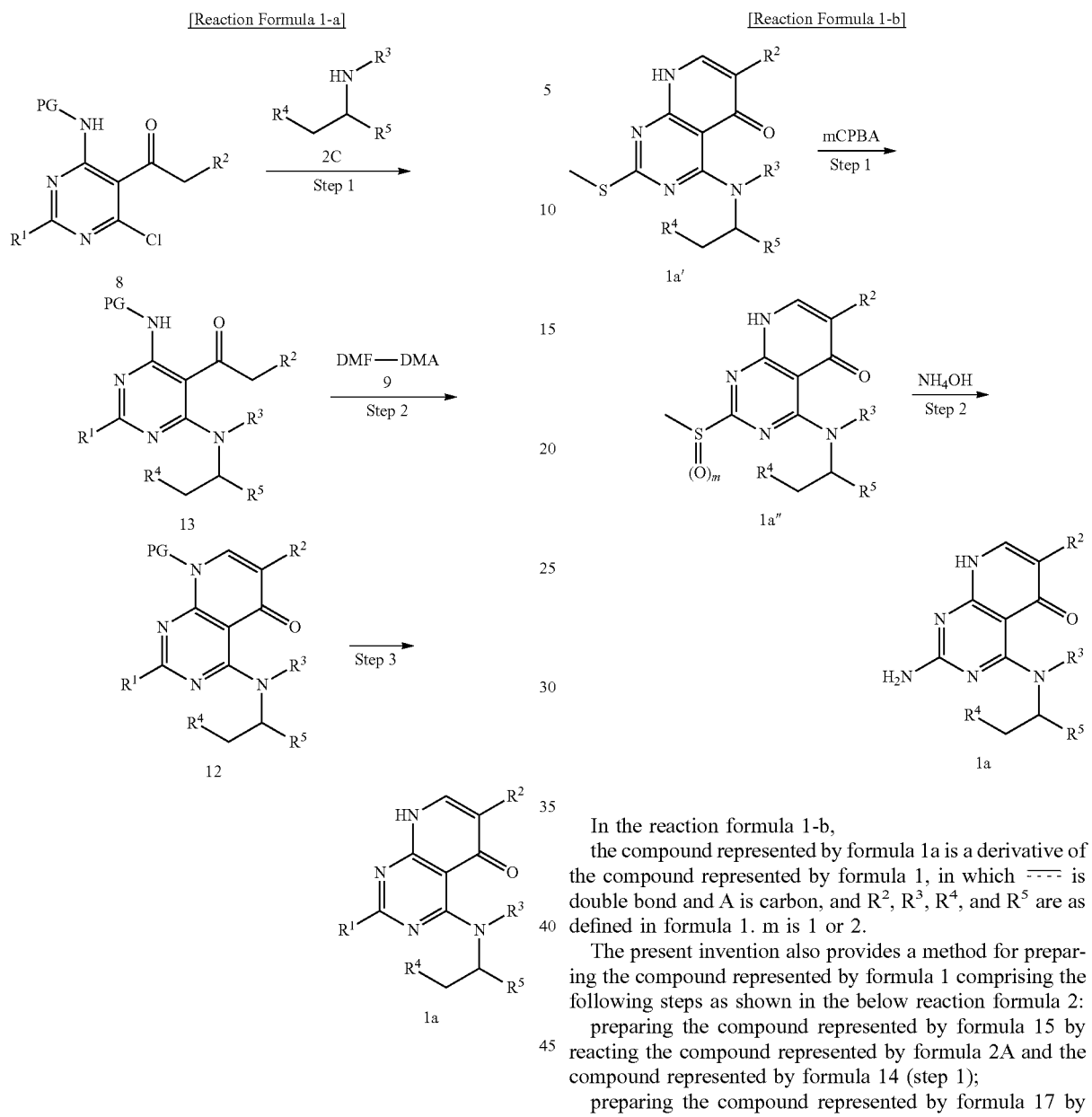

[Reaction Formula 1-b]

In the reaction formula 1-a, the compound represented by formula 1a is a derivative of the compound represented by formula 1, in which ---- is double bond and A is carbon, and $R^1$, $R^2$, $R^3$, $R^4$, and $R^5$ are as defined in formula 1.

Further, in the preparation method represented by the reaction formula 1, the following steps can be added to the method in order to prepare the compound having the substitution of $R^1$ (—$SCH_3$→—$NH_2$), as shown in reaction formula 1-b:

preparing the compound represented by formula 1a″ by reacting the compound represented by formula 1a′ with mCPBA (3-chlorobenzoic acid) (step 1); and preparing the compound represented by formula 1a wherein $R^1$ is —$NH_2$ by reacting the compound represented by formula 1a″ prepared in step 1 in the presence of $NH_4OH$ (step 2):

In the reaction formula 1-b, the compound represented by formula 1a is a derivative of the compound represented by formula 1, in which ---- is double bond and A is carbon, and $R^2$, $R^3$, $R^4$, and $R^5$ are as defined in formula 1. m is 1 or 2.

The present invention also provides a method for preparing the compound represented by formula 1 comprising the following steps as shown in the below reaction formula 2:

preparing the compound represented by formula 15 by reacting the compound represented by formula 2A and the compound represented by formula 14 (step 1);

preparing the compound represented by formula 17 by reacting the compound represented by formula 15 prepared in step 1 and the compound represented by formula 16 (step 2);

preparing the compound represented by formula 18 by reacting the compound represented by formula 17 prepared in step 2 and the compound represented by formula 2B (step 3);

preparing the compound represented by formula 20 by reacting the compound represented by formula 18 prepared in step 3 and the compound represented by formula 19 (step 4);

preparing the compound represented by formula 21 by reacting the compound represented by formula 20 prepared in step 4 and the compound represented by formula 2C under basic condition (step 5); and preparing the compound represented by formula 1b by eliminating the amine protecting group from the compound represented by formula 21 prepared in step 5 under acidic condition (step 6):

[Reaction Formula 2]

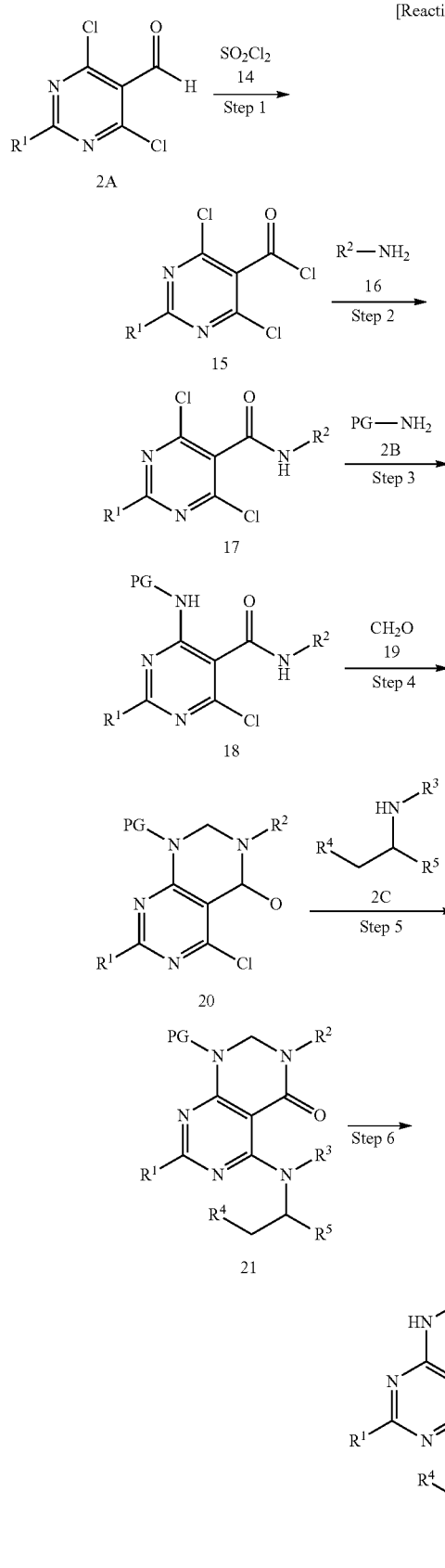

In the reaction formula 2,

PG is amine protecting group;

the compound represented by formula 1b is a derivative of the compound represented by formula 1, in which ---- is single bond and A is nitrogen, and $R^1$, $R^2$, $R^3$, $R^4$, and $R^5$ are as defined in formula 1.

Each step of the preparation method represented by the reaction formula 2 is executed by the same or similar method to the method of reaction formula 1 above or the conventional method known to those in the art.

Therefore, the preparation method represented by the reaction formula 2 of the invention is not only a novel method for preparing easily the compound represented by formula 20, one of the intermediates of the compound represented by formula 1 but also a useful method for preparing diverse dihydro pyrimido-pyrimidine derivatives from the compound represented by formula 1 by reacting the compound represented by formula 20 with the compound reacting to chloride (—Cl), the substituent of the compound.

The present invention also provides a method for preparing the compound represented by formula 1 comprising the following steps as shown in the below reaction formula 3:

preparing the compound represented by formula 15 by reacting the compound represented by formula 2A and the compound represented by formula 14 (step 1);

preparing the compound represented by formula 23 by reacting the compound represented by formula 15 prepared in step 1 and the compound represented by formula 22 (step 2); and preparing the compound represented by formula 1c by reacting the compound represented by formula 23 prepared in step 2 and the compound represented by formula 2C under basic condition (step 3):

[Reaction Formula 3]

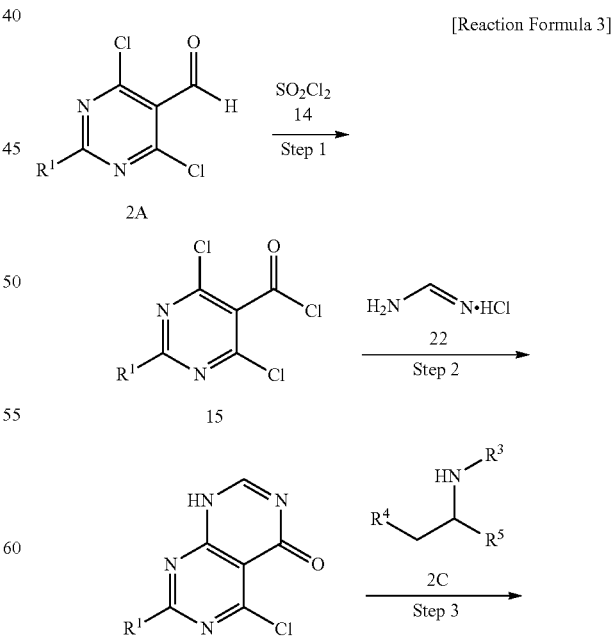

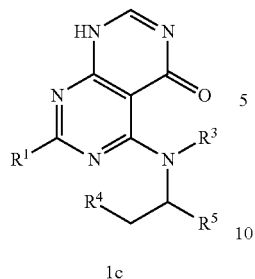

1c

In the reaction formula 3, the compound represented by formula 1c is a derivative of the compound represented by formula 1, in which ---- is double bond and A is nitrogen, and $R^1$, $R^2$, $R^3$, $R^4$, and $R^5$ are as defined in formula 1.

Each step of the preparation method represented by the reaction formula 3 is executed by the same or similar method to the method of reaction formula 1 above or the conventional method known to those in the art.

Therefore, the preparation method represented by the reaction formula 3 of the invention is not only a novel method for preparing easily the compound represented by formula 23, one of the intermediates of the compound represented by formula 1 but also a useful method for preparing diverse pyrimido-pyrimidine derivatives from the compound represented by formula 1 by reacting the compound represented by formula 23 with the compound reacting to chloride (—Cl), the substituent of the compound.

In the preparation method represented by the reaction formula 3, the compound represented by formula 1c can be prepared by the method comprising the following steps as shown in reaction formula 3-a:

preparing the compound represented by formula 25 by reacting the compound represented by formula 15 prepared in step 1 of reaction formula 3 and the compound represented by formula 24 (step 1);

preparing the compound represented by formula 26 by reacting the compound represented by formula 25 prepared in step 1 and the compound represented by formula 2B (step 2);

preparing the compound represented by formula 29 by reacting the compound represented by formula 26 prepared in step 2 and the compound represented by formula 27 (step 3);

preparing the compound represented by formula 30 by reacting the compound represented by formula 29 prepared in step 3 and the compound represented by formula 2C (step 4); and preparing the compound represented by formula 1b by eliminating the amine protecting group from the compound represented by formula 30 prepared in step 4 under acidic condition (step 5):

[Reaction Formula 3-a]

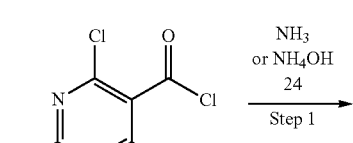

15

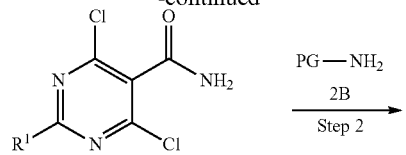

25

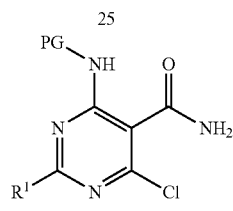

26

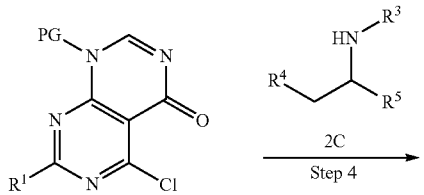

29

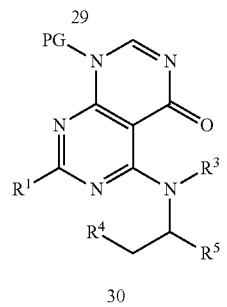

30

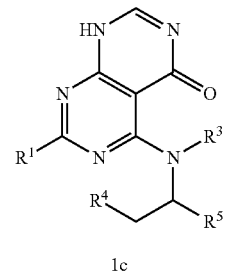

1c

In the reaction formula 3-a,

PG is amine protecting group;

the compound represented by formula 1c is a derivative of the compound represented by formula 1, in which ---- is double bond and A is nitrogen, and $R^1$, $R^2$, $R^3$, $R^4$, and $R^5$ are as defined in formula 1.

The present invention also provides a pharmaceutical composition for the prevention or treatment of PI3 kinase related diseases which comprises the said heteroaryl derivative, the optical isomer thereof, or the pharmaceutically acceptable salt of the same as an active ingredient.

The heteroaryl derivative, the optical isomer thereof, or the pharmaceutically acceptable salt thereof of the invention is characterized by the selective inhibition of PI3 kinase selected from the group consisting of PI3Kα, PI3Kβ, PI3Kδ, and PI3Kγ.

Particularly, the PI3 kinase related disease includes cancer, autoimmune disease, and respiratory disease.

The cancer herein is exemplified by hematological malignance such as myeloid metaplasia, chronic myelomonocytic leukemia, acute lymphoblastic leukemia, acute erythroid leukemia, Hodgikin's/non-Hodgkin's disease, B-cell lymphoma, acute T-cell leukemia, myelodysplastic syndrome, plasma cell dysfunction, hairy cell leukemia, Kaposi's sarcoma, and lymphoma, ovarian cancer, cervical cancer, breast cancer, colorectal cancer, liver cancer, stomach cancer, pancreatic cancer, colon cancer, peritoneal metastasis, skin cancer, bladder cancer, prostate cancer, thyroid cancer, lung cancer, osteosarcoma, fibrous tumor, and brain tumor.

The autoimmune disease herein includes rheumatoid arthritis, systemic lupus erythematosus, multiple sclerosis, type 1 diabetes, hyperthyroidism, myasthenia, Crohn's disease, ankylosing spondylitis, psoriasis, autoimmune pernicious anemia, and Sjogren's syndrome.

The respiratory disease herein includes chronic obstructive pulmonary disease (COPD), rhinitis, asthma, chronic bronchitis, chronic inflammatory lung disease, silicosis, pulmonary sarcoidosis, pleurisy, alveolitis, vasculitis, emphysema, pneumonia, and bronchiectasis.

The present inventors investigated the inhibitory effect of the compound represented by formula 1 of the present invention on PI3K α, β, γ, and δ. As a result, it was confirmed that the compound of the invention was excellent in inhibiting PI3K α, β, γ, and δ. In particular, the inhibitory effect on PI3 kinase γ or δ was more peculiar even at a low concentration (see Experimental Examples 1~4).

Therefore, the compound of the present invention plays a role as a PI3 kinase inhibitor, so that it can be effectively used for the prevention or treatment of PI3 kinase related diseases including cancer such as hematological malignance, ovarian cancer, cervical cancer, breast cancer, colorectal cancer, liver cancer, stomach cancer, pancreatic cancer, colon cancer, peritoneal metastasis, skin cancer, bladder cancer, prostate cancer, thyroid cancer, lung cancer, osteosarcoma, fibrous tumor, and brain tumor; autoimmune disease such as rheumatoid arthritis, systemic lupus erythematosus, multiple sclerosis, type diabetes, hyperthyroidism, myasthenia, Crohn's disease, ankylosing spondylitis, psoriasis, autoimmune pernicious anemia, and Sjogren's syndrome; and respiratory disease such as chronic obstructive pulmonary disease (COPD), rhinitis, asthma, chronic bronchitis, chronic inflammatory lung disease, silicosis, pulmonary sarcoidosis, pleurisy, alveolitis, vasculitis, emphysema, pneumonia, and bronchiectasis.

The compound represented by formula 1, the optical isomer thereof, or the pharmaceutically acceptable salt thereof of the present invention can be prepared for oral or parenteral administration by mixing with generally used diluents or excipients such as fillers, extenders, binders, wetting agents, disintegrating agents and surfactants.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by formula 1, the optical isomer thereof, or the pharmaceutically acceptable salt thereof as an active ingredient can be administered by parenterally and the parenteral administration includes subcutaneous injection, intravenous injection, intramuscular injection, or intrathoracic injection.

To prepare the composition as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by formula 1, the optical isomer thereof, or the pharmaceutically acceptable salt thereof as an active ingredient of the present invention can be determined according to age, weight, gender, administration method, health condition, and severity of disease. The dosage is 0.1~1000 mg/day for an adult patient (70 Kg), preferably 1~500 mg/day, which can be administered several times a day or preferably once a day or a couple of times a day.

The pharmaceutical composition comprising the compound represented by formula 1, the optical isomer thereof, or the pharmaceutically acceptable salt thereof as an active ingredient of the present invention can be administered alone or treated together with surgical operation, hormone therapy, chemo-therapy and biological regulators.

In addition, the present invention provides a health food composition for the prevention or improvement of PI3 kinase related diseases which comprises the said heteroaryl derivative, the optical isomer thereof, or the pharmaceutically acceptable salt of the same as an active ingredient.

The PI3 kinase related disease herein includes cancer such as hematological malignance, ovarian cancer, cervical cancer, breast cancer, colorectal cancer, liver cancer, stomach cancer, pancreatic cancer, colon cancer, peritoneal metastasis, skin cancer, bladder cancer, prostate cancer, thyroid cancer, lung cancer, osteosarcoma, fibrous tumor, and brain tumor, autoimmune disease such as rheumatoid arthritis, systemic lupus erythematosus, multiple sclerosis, type 1 diabetes, hyperthyroidism, myasthenia, Crohn's disease, ankylosing spondylitis, psoriasis, autoimmune pernicious anemia, and Sjogren's syndrome, and respiratory disease such as chronic obstructive pulmonary disease (COPD), rhinitis, asthma, chronic bronchitis, chronic inflammatory lung disease, silicosis, pulmonary sarcoidosis, pleurisy, alveolitis, vasculitis, emphysema, pneumonia, and bronchiectasis.

The compound represented by formula 1 of the present invention acts as a PI3 kinase inhibitor, so that it can be added to a health functional supplement including food and beverages as a health food composition for the prevention or improvement of PI3 kinase related diseases.

The compound represented by formula 1 of the present invention can be used as a food additive. In that case, the compound of the present invention can be added as it is or as mixed with other food components according to the conventional method. The mixing ratio of active ingredients can be regulated according to the purpose of use (prevention or improvement). In general, to produce health food or beverages, the compound of the present invention is added preferably by 0.1~90 weight part. However, if long term administration is required for health and hygiene or regulating health condition, the content can be lower than the above but higher content can be accepted as well since the compound of the present invention has been proved to be very safe.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xylitol, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include fruit flesh addable to natural fruit juice, fruit beverages, and vegetable beverages.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of (S)-2-(1-aminoethyl)-5-chloro-3-phenylquinazoline-4(3H)-one

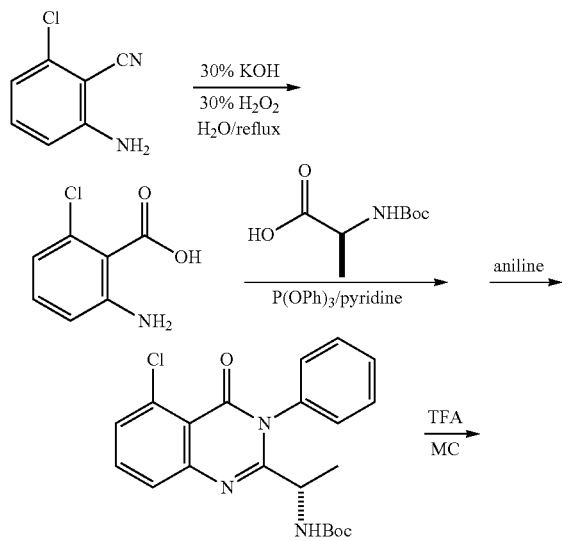

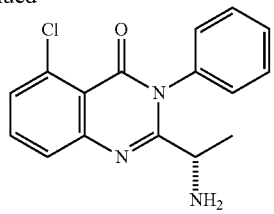

Step 1: Preparation of 2-amino-6-chlorobenzoic acid

The reaction mixture composed of 5 g of 2-amino-6-chlorobenzonitrile (32.77 mmol), 30% potassium hydroxide (50 mL), and 30% hydrogen peroxide aqueous solution (3 mL) was heat-refluxed for 12 hours, which was then cooled down at room temperature. The aqueous layer was separated by using diethyl ether and then acidized with 12 N HCl (pH: 3-4) to separate an organic layer. The organic layer was washed with saturated brine and then separated, dried ($Na_2SO_4$), filtered, and concentrated under reduced pressure. As a result, 5.31 g of the target compound 2-amino-6-chlorobenzoic acid was obtained as a yellow solid (30.95 mmol, yield: 94%).

$^1$H NMR (300 MHz, DMSO-$d_6$) δ 8.24 (s, 2H), 7.00-7.06 (t, J=7.5 Hz, 1H), 6.64 (d, J=8.4 Hz, 1H), 6.56 (d, J=7.8 Hz, 1H).

Step 2: Preparation of tert-butyl (S)-(1-(5-chloro-4-oxo-3-phenyl-3,4-dihydroquinazoline-2-yl)ethyl) carbamate 1.00 g (5.89 mmol) of 2-amino-6-chlorobenzoic acid obtained in step 1 above was mixed with N-Boc-L-alanine (1 equivalent), triphenyl phosphite (1.2 equivalent), and anhydrous pyridine (5 mL). The reaction mixture was stirred at 55° C. for 12 hours, to which aniline (1 equivalent) was added. The mixture was heated for 6 hours, and then cooled down at room temperature. The mixture was concentrated under reduced pressure, followed by acidization with 1N HCl (pH: 5-6). The reaction mixture was extracted by using ethyl acetate to separate an organic layer. The organic layer was washed with saturated brine, separated, dried ($Na_2SO_4$), filtered, and concentrated under reduced pressure. The residue was separated by column chromatography ($SiO_2$, eluent: hexane/ethyl acetate, 10/1→hexane/ethyl acetate, 1/1) to give 1.63 g of the target compound tert-butyl (S)-(1-(5-chloro-4-oxo-3-phenyl-3,4-dihydroquinazoline-2-yl)ethyl) carbamate as a yellow solid (4.09 mmol, yield: 69%).

$^1$H NMR (300 MHz, CDCl$_3$) δ 7.61-7.63 (m, 2H), 7.46-7.57 (m, 4H), 7.36-7.39 (m, 1H), 7.29 (s, 1H), 5.59 (s, 1H), 4.50 (s, 1H), 1.37-1.46 (m, 9H), 1.25 (d, J=6.5 Hz, 3H).

Step 3: Preparation of (S)-2-(1-aminoethyl)-5-chloro-3-phenylquinazoline-4(3H)-one 1.634 g (4.09 mmol) of tert-butyl (S)-(1-(5-chloro-4-oxo-3-phenyl-3,4-dihydroquinazoline-2-yl)ethyl)carbamate prepared in step 2 was dissolved in dichloromethane (15 mL), to which trifluoroacetic acid (TFA, 5 mL) was added. After the reflux at 40° C. for 3 hours, the mixture was cooled down at room temperature, to which saturated NaHCO$_3$ aqueous solution was slowly added to neutralize the mixture. The organic layer was extracted by using ethyl acetate, which was washed with saturated brine, separated, dried (Na$_2$SO$_4$), filtered, and concentrated under reduced pressure. The residue was separated by column chromatography (SiO$_2$, eluent: dichloromethane/methanol, 20/1→dichloromethane/methanol, 5/1) to give 1.046 g of the target compound (S)-2-(1-aminoethyl)-5-chloro-3-phenylquinazoline-4(3H)-one as a white solid (3.49 mmol, yield: 85%).

$^1$H NMR (300 MHz, CDCl$_3$) δ 7.60-7.64 (m, 2H), 7.51-7.59 (m, 3H), 7.44-7.48 (m, 1H), 7.27-7.29 (m, 2H), 3.63-3.70 (m, 1H), 1.83 (s, 2H), 1.27 (d, J=6.5 Hz, 3H).

Preparative Example 2: Preparation of (S)-5-chloro-3-phenyl-2-(pyrrolidine-2-yl)quinazoline-4(3H)-one

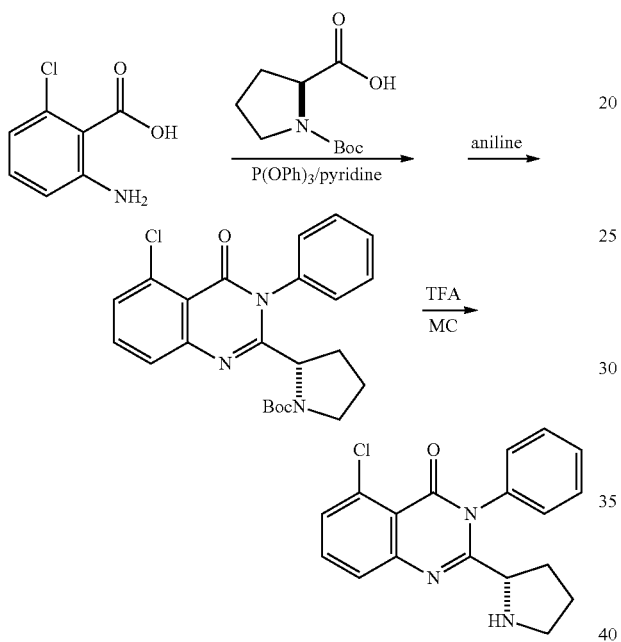

Step 1: Preparation of tert-butyl (S)-2-(5-chloro-4-oxo-3-phenyl-3,4-dihydroquinazoline-2-yl)pyrrolidine-1-carboxylate 5.51 g of tert-butyl (S)-2-(5-chloro-4-oxo-3-phenyl-3,4-dihydroquinazoline-2-yl)pyrrolidine-1-carboxylate was prepared as a beige solid by using 3.76 g (17.47 mmol) of (tert-butoxycarbonyl)-L-proline according to the same manner as described in step 2 of Preparative Example 1 (12.94 mmol, yield: 74%).

$^1$H NMR (300 MHz, CDCl$_3$) δ 7.42-7.61 (m, 6H), 7.32-7.34 (m, 1H), 7.20-7.24 (m, 1H), 4.40-4.43 (m, 1H), 3.41-3.52 (m, 2H), 1.86-2.06 (m, 3H), 1.70-1.76 (m, 1H), 1.30 (s, 9H).

Step 2: Preparation of (S)-5-chloro-3-phenyl-2-(pyrrolidine-2-yl)quinazoline-4(3H)-one 3.3 g of (S)-5-chloro-3-phenyl-2-(pyrrolidine-2-yl)quinazoline-4(3H)-one was prepared as a beige solid by using 5.53 g (12.99 mmol) of tert-butyl (S)-2-(5-chloro-4-oxo-3-phenyl-3,4-dihydroquinazoline-2-yl)pyrrolidine-1-carboxylate prepared in step 1 according to the same manner as described in step 3 of Preparative Example 1 (10.13 mmol, yield: 78%).

$^1$H NMR (300 MHz, CDCl$_3$) δ 7.60-7.62 (m, 2H), 7.47-7.54 (m, 4H), 7.27-7.29 (m, 2H), 3.75-3.79 (m, 1H), 3.22-3.26 (m, 1H), 3.73-3.76 (m, 1H), 1.69-1.77 (m, 4H).

Preparative Example 3: Preparation of (S)-2-(1-aminoethyl)-5-chloro-3-(pyridine-3-yl)quinazoline-4(3H)-one

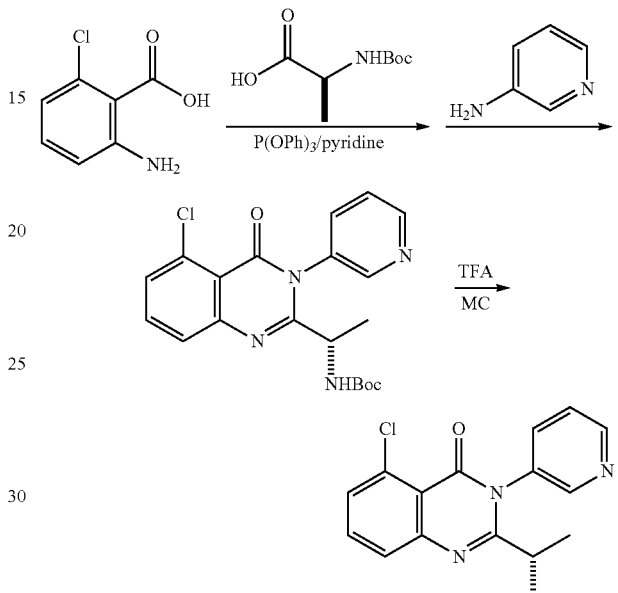

Step 1: Preparation of tert-butyl (S)-(1-(5-chloro-4-oxo-3-(pyridine-3-yl)-3,4-dihydroquinazoline-2-yl)ethyl)carbamate 4.06 g of tert-butyl (S)-(1-(5-chloro-4-oxo-3-(pyridine-3-yl)-3,4-dihydroquinazoline-2-yl)ethyl)carbamate was prepared as an ivory solid by using 1.59 g (16.90 mmol) of 3-aminopyridine according to the same manner as described in step 2 of Preparative Example 1 (10.14 mmol, yield: 60%).

$^1$H NMR (300 MHz, CDCl$_3$) δ 8.77 (s, 1H), 8.57 (s, 1H), 7.45-7.82 (m, 5H), 5.47 (s, 1H), 4.35-4.38 (m, 1H), 1.41 (s, 9H), 1.26-1.31 (m, 3H).

Step 2: Preparation of (S)-2-(1-aminoethyl)-5-chloro-3-(pyridine-3-yl)quinazoline-4(3H)-one 2.6 g of (S)-2-(1-aminoethyl)-5-chloro-3-(pyridine-3-yl)quinazoline-4(3H)-one was prepared as a white solid by using 4.08 g (10.18 mmol) of tert-butyl (S)-(1-(5-chloro-4-oxo-3-(pyridine-3-yl)-3,4-dihydroquinazoline-2-yl)ethyl)carbamate prepared in step 1 according to the same manner as described in step 3 of Preparative Example 1 (8.65 mmol, yield: 85%).

$^1$H NMR (300 MHz, CDCl$_3$) δ 8.78 (s, 1H), 8.58 (s, 1H), 7.65-7.71 (m, 3H), 7.52-7.56 (m, 2H), 3.57-3.64 (m, 1H), 1.29 (dd, J=22.7, 5.9 Hz, 3H).

Preparative Example 4: Preparation of (S)-5-chloro-3-(pyridine-3-yl)-2-(pyrrolidine-2-yl)quinazoline-4(3H)-one

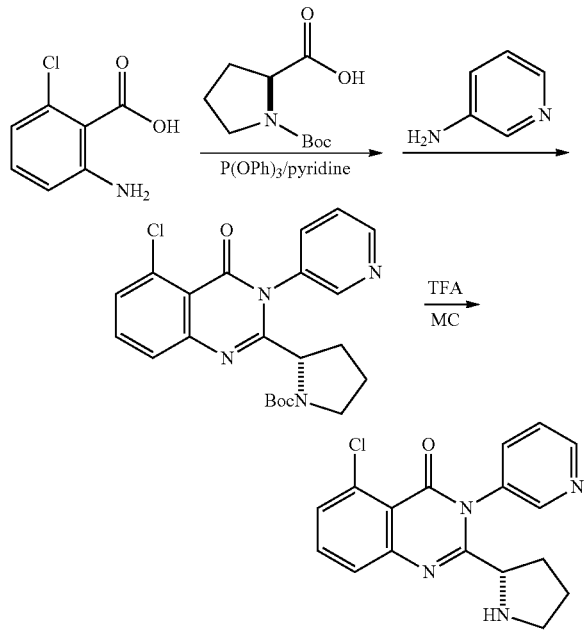

Step 1: Preparation of tert-butyl (S)-2-(5-chloro-4-oxo-3-(pyridine-3-yl)-3,4-dihydroquinazoline-2-yl)pyrrolidine-1-carboxylate 3.82 g of tert-butyl (S)-2-(5-chloro-4-oxo-3-(pyridine-3-yl)-3,4-dihydroquinazoline-2-yl)pyrrolidine-1-carboxylate was prepared as a white solid by using 1.65 g (17.55 mmol) of 3-aminopyridine according to the same manner as described in step 2 of Preparative Example 1 (8.95 mmol, yield: 51%).

$^1$H NMR (300 MHz, CDCl$_3$) δ 8.74-8.77 (m, 1H), 8.51 (s, 1H), 7.45-7.70 (m, 5H), 4.27-4.41 (m, 1H), 3.70-3.83 (m, 1H), 3.45-3.60 (m, 1H), 1.92-1.99 (m, 2H), 1.77-1.87 (m, 2H), 1.31 (d, J=11.3 Hz, 9H).

Step 2: Preparation of (S)-5-chloro-3-(pyridine-3-yl)-2-(pyrrolidine-2-yl)quinazoline-4(3H)-one 2.6 g of (S)-5-chloro-3-(pyridine-3-yl)-2-(pyrrolidine-2-yl)quinazoline-4(3H)-one was prepared as a white solid by using 3.83 g (8.97 mmol) of tert-butyl (S)-2-(5-chloro-4-oxo-3-(pyridine-3-yl)-3,4-dihydroquinazoline-2-yl)pyrrolidine-1-carboxylate prepared in step 1 according to the same manner as described in step 3 of Preparative Example 1 (7.80 mmol, yield: 87%).

$^1$H NMR (300 MHz, CDCl$_3$) δ 8.75 (s, 1H), 8.55-8.59 (d, J=12.2 Hz, 1H), 7.63-7.70 (m, 3H), 7.50-7.52 (m, 2H), 3.63-3.81 (m, 1H), 3.20-3.27 (m, 1H), 2.74-2.79 (m, 1H), 1.65-1.78 (m, 4H).

Preparative Example 5: Preparation of (S)-2-(1-aminoethyl)-5-chloro-3-(m-tolyl)quinazoline-4(3H)-one

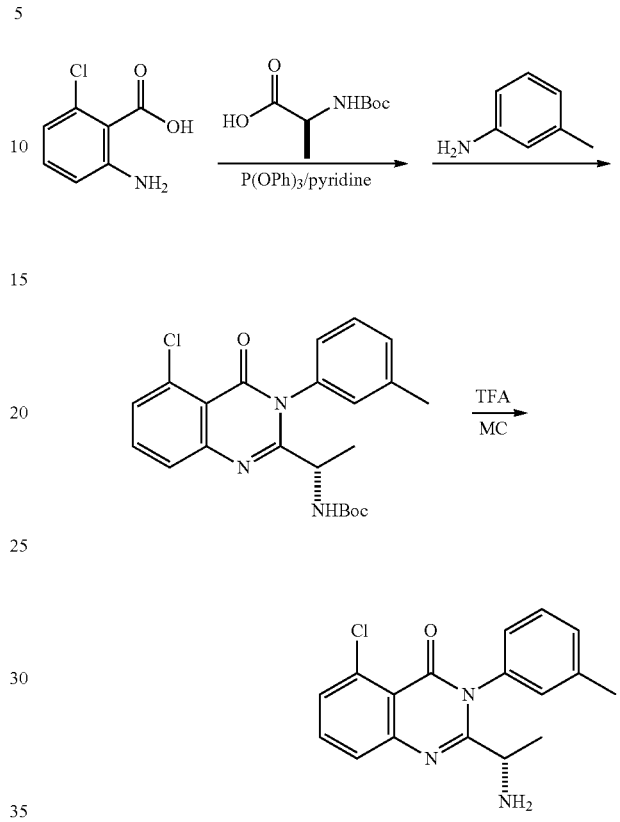

Step 1: Preparation of tert-butyl (S)-(1-(5-chloro-4-oxo-3-(m-tolyl)-3,4-dihydroquinazoline-2-yl)ethyl)carbamate 5.1 g of tert-butyl (S)-(1-(5-chloro-4-oxo-3-(m-tolyl)-3,4-dihydroquinazoline-2-yl)ethyl)carbamate was prepared as a white solid by using 1.88 g (17.56 mmol) of m-toluidine according to the same manner as described in step 2 of Preparative Example 1 (12.29 mmol, yield: 70%).

$^1$H NMR (300 MHz, CDCl$_3$) δ 7.62 (s, 2H), 7.39-7.47 (m, 2H), 7.31-7.33 (m, 1H), 7.15 (s, 1H), 7.08 (s, 1H), 5.61 (s, 1H), 4.50-4.53 (m, 1H), 2.42 (s, 3H), 1.42 (s, 9H), 1.27 (s, 3H).

Step 2: Preparation of (S)-2-(1-aminoethyl)-5-chloro-3-(m-tolyl)quinazoline-4(3H)-one 3.0 g of (S)-2-(1-aminoethyl)-5-chloro-3-(m-tolyl)quinazoline-4(3H)-one was prepared as a white solid by using 5.0 g (12.10 mmol) of tert-butyl (S)-(1-(5-chloro-4-oxo-3-(m-tolyl)-3,4-dihydroquinazoline-2-yl)ethyl)carbamate prepared in step 1 according to the same manner as described in step 3 of Preparative Example 1 (9.56 mmol, yield: 79%).

$^1$H NMR (300 MHz, CDCl$_3$) δ 7.61-7.63 (m, 2H), 7.41-7.48 (m, 2H), 7.30-7.33 (d, J=7.7 Hz, 1H), 7.05-7.08 (m, 2H), 3.66-3.73 (q, J=13.0, 6.5 Hz, 1H), 2.42 (s, 3H), 1.27-1.29 (d, J=6.5 Hz, 3H).

Preparative Example 6: Preparation of (S)-5-chloro-2-(pyrrolidine-2-yl)-3-(m-tolyl)quinazoline-4(3H)-one

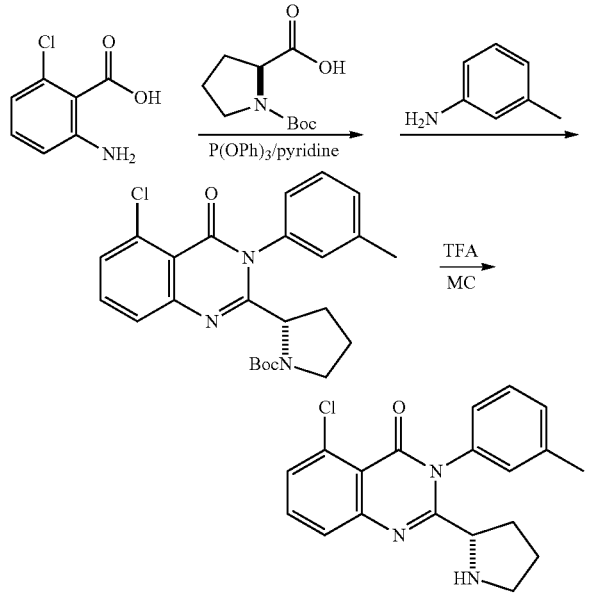

Step 1: Preparation of (S)-tert-butyl 2-(5-chloro-4-oxo-3-(m-tolyl)-3,4-dihydroquinazoline-2-yl)pyrrolidine-1-carboxylate 5.67 g of tert-butyl (S)-2-(5-chloro-4-oxo-3-(m-tolyl)-3,4-dihydroquinazoline-2-yl)pyrrolidine-1-carboxylate was prepared as a yellow solid by using 1.87 g (17.41 mmol) of m-toluidine according to the same manner as described in step 2 of Preparative Example 1 (12.88 mmol, yield: 74%).

$^1$H NMR (300 MHz, CDCl$_3$) δ 7.53-7.58 (m, 2H), 7.45-7.51 (m, 2H), 7.30-7.33 (m, 1H), 7.14 (s, 1H), 7.02 (s, 1H), 4.43-4.51 (m, 1H), 3.63-3.74 (m, 1H), 3.42-3.50 (m, 1H), 2.42 (s, 3H), 1.93-2.04 (m, 3H), 1.73-1.79 (m, 1H), 1.23-1.37 (m, 9H).

Step 2: Preparation of (S)-5-chloro-2-(pyrrolidine-2-yl)-3-(m-tolyl)quinazoline-4(3H)-one 4.0 g of (S)-5-chloro-2-(pyrrolidine-2-yl)-3-(m-tolyl)quinazoline-4(3H)-one was prepared as a white solid by using 5.69 g (12.93 mmol) of tert-butyl (S)-2-(5-chloro-4-oxo-3-(m-tolyl)-3,4-dihydroquinazoline-2-yl)pyrrolidine-1-carboxylate prepared in step 1 according to the same manner as described in step 3 of Preparative Example 1 (11.77 mmol, yield: 91%).

$^1$H NMR (300 MHz, CDCl$_3$) δ 7.42-7.58 (m, 4H), 7.35 (d, J=8.1 Hz, 1H), 7.20-7.24 (m, 1H), 7.05 (s, 1H), 4.44-4.51 (m, 1H), 3.42-3.50 (m, 1H), 3.18-3.24 (m, 1H), 2.44 (d, J=11.7 Hz, 3H), 1.76-1.93 (m, 4H).

Preparative Example 7: Preparation of (S)-2-(1-aminoethyl)-5-chloro-3-(3-fluorophenyl)quinazoline-4(3H)-one

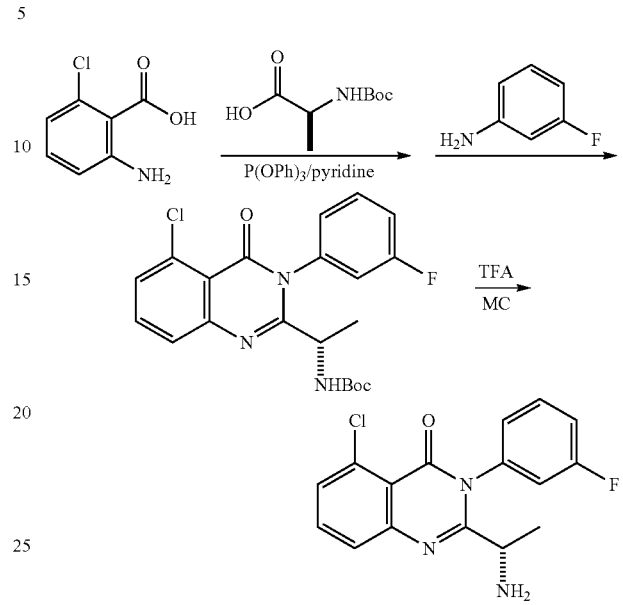

Step 1: Preparation of tert-butyl (S)-(1-(5-chloro-3-(3-fluorophenyl)-4-oxo-3,4-dihydroquinazoline-2-yl)ethyl)carbamate 4.88 g of tert-butyl (S)-(1-(5-chloro-3-(3-fluorophenyl)-4-oxo-3,4-dihydroquinazoline-2-yl)ethyl)carbamate was prepared as a yellow solid by using 1.94 g (17.43 mmol) of 3-fluoroaniline according to the same manner as described in step 2 of Preparative Example 1 (11.68 mmol, yield: 67%).

$^1$H NMR (300 MHz, CDCl$_3$) δ 7.42-7.63 (m, 4H), 7.14-7.23 (m, 1H), 7.03-7.17 (m, 2H), 5.44-5.55 (m, 1H), 4.48-4.52 (m, 1H), 1.42 (s, 9H), 1.18-1.31 (m, 3H).

Step 2: Preparation of (S)-2-(1-aminoethyl)-5-chloro-3-(3-fluorophenyl)quinazoline-4(3H)-one 2.4 g of (S)-2-(1-aminoethyl)-5-chloro-3-(3-fluorophenyl)quinazoline-4(3H)-one was prepared as a white solid by using 4.88 g (11.80 mmol) of tert-butyl (S)-(1-(5-chloro-3-(3-fluorophenyl)-4-oxo-3,4-dihydroquinazoline-2-yl)ethyl)carbamate prepared in step 1 according to the same manner as described in step 3 of Preparative Example 1 (7.55 mmol, yield: 64%).

$^1$H NMR (300 MHz, CDCl$_3$) δ 1.64 (s, 1H), 7.63 (d, J=1.5 Hz, 1H), 7.46-7.60 (m, 2H), 7.22-7.25 (m, 1H), 7.04-7.10 (m, 2H), 3.65-3.71 (m, 1H), 1.31 (dd, J=6.5, 1.3 Hz, 3H).

Preparative Example 8: Preparation of (S)-5-chloro-3-(3-fluorophenyl)-2-(pyrrolidine-2-yl)quinazoline-4(3H)-one

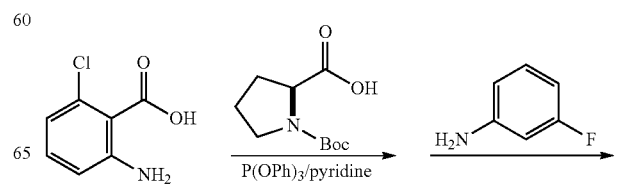

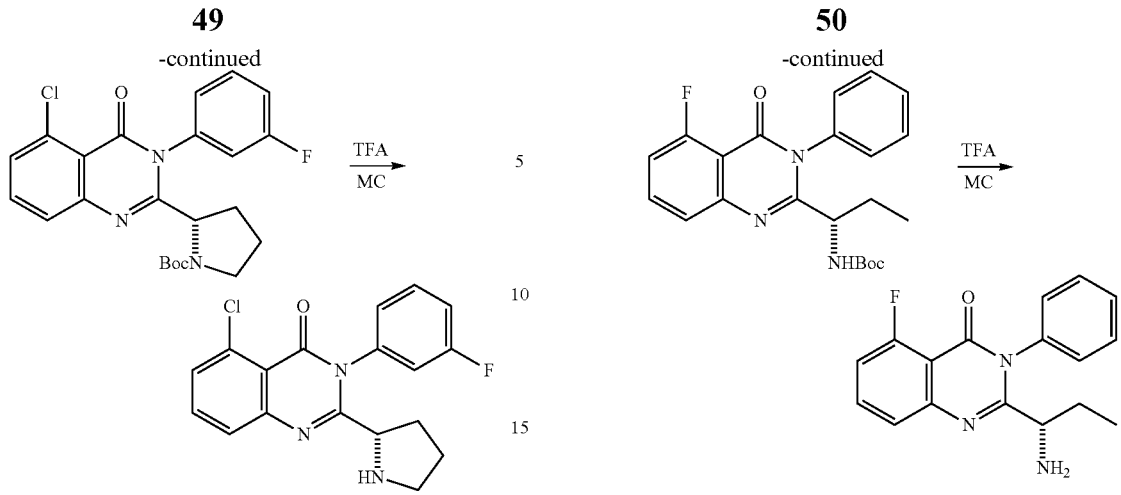

Step 1: Preparation of tert-butyl (S)-2-(5-chloro-3-(3-fluorophenyl)-4-oxo-3,4-dihydroquinazoline-2-yl)pyrrolidine-1-carboxylate 6.33 g of tert-butyl (S)-2-(5-chloro-3-(3-fluorophenyl)-4-oxo-3,4-dihydroquinazoline-2-yl)pyrrolidine-1-carboxylate was prepared as a yellow solid by using 1.93 g (17.39 mmol) of 3-fluoroaniline according to the same manner as described in step 2 of Preparative Example 1 (14.26 mmol, yield: 82%).

$^1$H NMR (300 MHz, CDCl$_3$) δ 7.52-7.65 (m, 3H), 7.34-7.49 (m, 2H), 6.97-7.23 (m, 2H), 4.42-4.51 (m, 1H), 3.65-3.77 (m, 1H), 3.42-3.54 (m, 1H), 1.91-2.11 (m, 3H), 1.79-1.88 (m, 1H), 1.26-1.37 (m, 9H).

Step 2: Preparation of (S)-5-chloro-3-(3-fluorophenyl)-2-(pyrrolidine-2-yl)quinazoline-4(3H)-one 3.82 g of (S)-5-chloro-3-(3-fluorophenyl)-2-(pyrrolidine-2-yl)quinazoline-4(3H)-one was prepared as a white solid by using 6.49 g (14.62 mmol) of tert-butyl (S)-2-(5-chloro-3-(3-fluorophenyl)-4-oxo-3,4-dihydroquinazoline-2-yl)pyrrolidine-1-carboxylate prepared in step 1 according to the same manner as described in step 3 of Preparative Example 1 (11.11 mmol, yield: 76%).

$^1$H NMR (300 MHz, CDCl$_3$) δ 7.62 (s, 1H), 7.61 (s, 1H), 7.44-7.58 (m, 2H), 7.20-7.25 (m, 1H), 7.02-7.12 (m, 2H), 3.78-3.81 (m, 1H), 3.24-3.28 (m, 1H), 3.00 (s, 1H), 2.77-2.80 (m, 1H), 1.72-1.82 (m, 4H).

Preparative Example 9: Preparation of (S)-2-(1-aminopropyl)-5-fluoro-3-phenylquinazoline-4(3H)-one

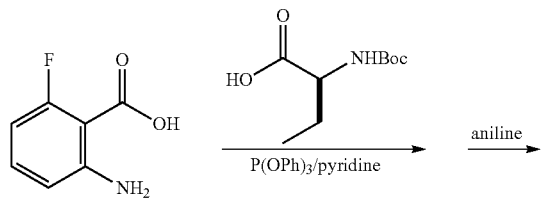

Step 1: Preparation of tert-butyl (S)-(1-(5-fluoro-4-oxo-3-phenyl-3,4-dihydroquinazoline-2-yl)propyl)carbamate 4.42 g of tert-butyl (S)-2-(5-chloro-3-(3-fluorophenyl)-4-oxo-3,4-dihydroquinazoline-2-yl)pyrrolidine-1-carboxylate was prepared as a white solid by using 2.97 g (14.61 mmol) of (S)-2-((tert-butoxycarbonyl)amino)butanoic acid according to the same manner as described in step 2 of Preparative Example 1 (11.11 mmol, yield: 76%).

$^1$H NMR (300 MHz, DMSO-d$_6$) δ 7.39-7.43 (m, 1H), 7.07-7.19 (m, 3H), 6.99-7.02 (m, 2H), 6.72-6.88 (m, 2H), 3.51-3.56 (m, 1H), 2.92 (s, 1H), 1.26-1.31 (m, 1H), 1.10-1.17 (m, 1H), 0.92 (s, 9H), 0.21 (t, J=6.7 Hz, 3H).

Step 2: Preparation of (S)-2-(1-aminopropyl)-5-fluoro-3-phenylquinazoline-4(3H)-one 32.43 g of (S)-2-(1-aminopropyl)-5-fluoro-3-phenylquinazoline-4(3H)-one was prepared as a white solid by using 4.16 g (10.47 mmol) of tert-butyl (S)-2-(5-chloro-3-(3-fluorophenyl)-4-oxo-3,4-dihydroquinazoline-2-yl)pyrrolidine-1-carboxylate prepared in step 1 according to the same manner as described in step 3 of Preparative Example 1 (8.17 mmol, yield: 78%).

$^1$H NMR (300 MHz, CDCl$_3$) δ 7.66-7.73 (m, 1H), 7.50-7.56 (m, 4H), 7.27-7.28 (m, 3H), 7.11 (t, J=5.1 Hz, 1H), 3.40-3.44 (m, 1H), 1.75-1.84 (m, 1H), 1.46-1.55 (m, 1H), 0.79 (t, J=7.4 Hz, 3H).

Preparative Example 10: Preparation of (S)-3-(1-aminoethyl)-4,8-dichloro-2-phenylisoquinoline-1(2H)-one

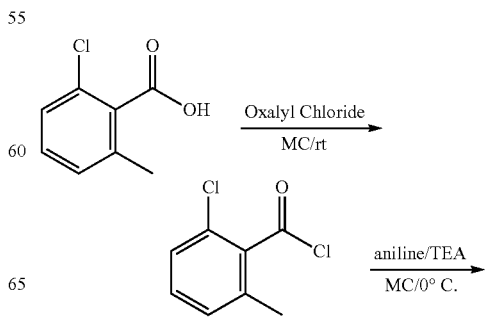

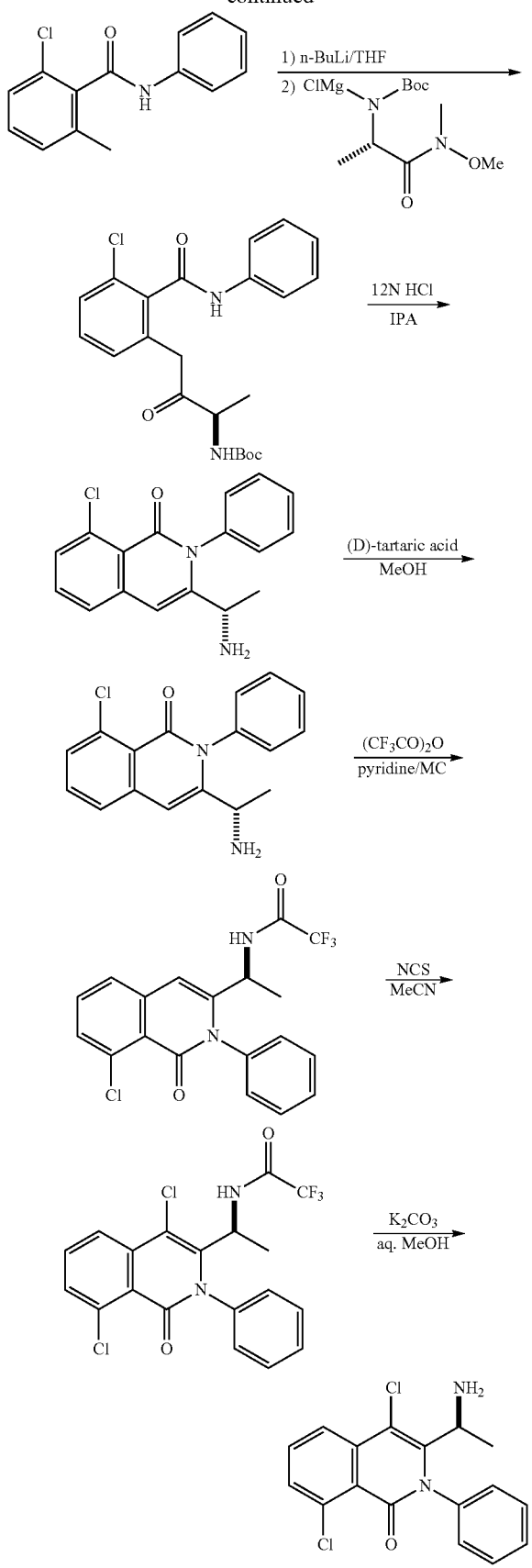

Step 1: Preparation of 2-chloro-6-methylbenzoyl chloride 10.073 g (59.04 mmol) of 2-chloro-6-methylbenzoic acid was mixed with anhydrous dichloromethane (150 mL), to which 10.3 ml (118.09 mmol, 2 equivalents) of oxalylchloride was added. Dimethylformamide was dropped thereto 1-2 drops, and the mixture was stirred at room temperature for 4 hours. The mixture was concentrated under reduced pressure. As a result, 11.479 g of the target compound brown liquid target compound 2-chloro-6-methylbenzoyl chloride was obtained as a brown liquid (59.04 mmol, yield: 100%).

Step 2: Preparation of 2-chloro-6-methyl-N-phenylbenzamide 5.8 mL (63.76 mmol, 1.05 equivalent) of aniline and 14.8 mL (106.26 mmol, 1.75 equivalent) of triethylamine were dissolved in anhydrous dichloromethane (150 mL), to which 11.48 g (60.7 mmol, 1.0 equivalent) of 2-chloro-6-methylbenzoyl chloride prepared in step 1 that had been dissolved in anhydrous dichloromethane (20 mL) was slowly dropped at 0° C. for 10 minutes, followed by stirring for 5 hours. Then, the mixture was washed with 1N HCl, water, and saturated sodiumbicarbonate solution stepwise. The organic layer was separated, dried ($Na_2SO_4$), filtered, and distillated under reduced pressure. The obtained solid was recrystallized with hexane/ethyl acetate to give 13.0 g of the target compound 2-chloro-6-methyl-N-phenylbenzamide as a white solid (52.9 mmol, yield: 87%).

$^1$H NMR (300 MHz, DMSO-$d_6$) δ 10.56 (s, 1H), 7.69-7.72 (d, J=7.7 Hz, 2H), 7.27-7.37 (m, 5H), 7.10 (t, J=7.3 Hz, 1H), 2.31 (s, 3H).

Step 3: Preparation of tert-butyl (S)-(4-(3-chloro-2-(phenylcarbamoyl)phenyl)-3-oxobutane-2-yl)carbamate 6 g (24.42 mmol) of 2-chloro-6-methyl-N-phenylbenzamide prepared in step 2 was dissolved in anhydrous THF (50 mL), to which 24.42 ml (61.05 mmol, 2.5 equivalent) of n-BuLi was slowly added at −30° C. The mixture was stirred for 1 hour. 8.5 g (36.63 mmol, 1.5 equivalent) of tert-butyl (S)-(1-(methoxy(methyl)amino)-1-oxopropane-2-yl)carbamate was dissolved in anhydrous THF (50 mL), to which 56.35 ml (73.26 mmol, 3.0 equivalent) of isopropyl magnesiumchloride was slowly added at −30° C. The reaction mixture was stirred for 1 hour, which was slowly added to the above mixture by using a cannula, followed by stirring at −15° C. for 2 hours. The temperature was maintained at −15° C.~−10° C., while the reaction mixture was added with water and 1N HCl stepwise. PH of the reaction mixture was regulated to be 5 and the mixture was heated at room temperature. The organic layer was extracted by using ethyl acetate, which was washed with saturated brine, separated, dried ($Na_2SO_4$), filtered, and concentrated under reduced pressure. The residue was separated by column chromatography ($SiO_2$, eluent: $CH_2Cl_2$/MeOH, 30/1→$CH_2Cl_2$/MeOH, 10/1) to give 8.8 g of the target compound tert-butyl (S)-(4-(3-chloro-2-(phenylcarbamoyl)phenyl)-3-oxobutane-2-yl)carbamate as a white solid (21.11 mmol, yield: 86%).

$^1$H NMR (300 MHz, CDCl$_3$) δ 7.90 (s, 1H), 7.59 (d, J=7.6 Hz, 2H), 7.29-7.35 (m, 4H), 7.13-7.18 (m, 2H), 5.01 (s, 1H), 4.33-4.37 (m, 1H), 3.91-4.06 (m, 2H), 1.40 (s, 9H), 1.24 (d, J=7.3 Hz, 3H).

Step 4: Preparation of (S)-3-(1-aminoethyl)-8-chloro-2-phenylisoquinoline-1(2H)-one 8.8 g (21.11 mmol) of tert-butyl (S)-(4-(3-chloro-2-(phenylcarbamoyl)phenyl)-3-oxobutane-2-yl)carbamate prepared in step 3 was dissolved in IPA/12 N HCl (5/3, 160 mL), followed by stirring at 65° C. for 2 hours. The mixture was concentrated under reduced pressure, to which saturated sodiumbicarbonate aqueous solution was added. The organic layer was extracted by using dichloromethane, which was separated, dried ($Na_2SO_4$), filtered, and concentrated under reduced pressure. The residue was separated by column chromatography ($SiO_2$, eluent: $CH_2Cl_2$/MeOH, 10/1→$CH_2Cl_2$/MeOH, 5/1) to give 4.871 g of the target compound (S)-3-(1-aminoethyl)-8-chloro-2-phenylisoquinoline-1(2H)-one as a white solid (16.30 mmol, yield: 77%).

Step 5: Preparation of (S)-3-(1-aminoethyl)-8-chloro-2-phenylisoquinoline-1(2H)-one 4.871 g (16.30 mmol) of (S)-3-(1-aminoethyl)-8-chloro-2-phenylisoquinoline-1(2H)-one prepared in step 4 was dissolved in methanol (100 mL), to which 2.45 g (16.30 mmol, 1.0 equivalent) of (D)-tartaric acid was added. The mixture was stirred at room temperature for 30 minutes, followed by reflux for 90 minutes. The reaction mixture was stirred at room temperature for 12 hours and then the generated white solid was filtered. Water was added to the white solid and pH was adjusted to be 8 with saturated sodiumbicarbonate aqueous solution, followed by stirring at room temperature for 30 minutes. The white solid was filtered and dried. As a result, 3.74 g of the target compound (S)-3-(1-aminoethyl)-8-chloro-2-phenylisoquinoline-1(2H)-one was obtained as a white solid (12.50 mmol, yield: 77%).

$^1$H NMR (300 MHz, $CDCl_3$) δ 7.41-7.56 (m, 7H), 7.28 (s, 1H), 6.71 (s, 1H), 3.68-3.74 (q, J=6.5 Hz, 1H), 1.31 (s, 2H), 1.25 (d, J=6.5 Hz, 3H).

Step 6: Preparation of (S)—N-(1-(8-chloro-1-oxo-2-phenyl-1,2-dihydroisoquinoline-3-yl)ethyl)-2,2,2-trifluoroacetamide 2.99 g (10.00 mmol) of (S)-3-(1-aminoethyl)-8-chloro-2-phenylisoquinoline-1(2H)-one prepared in step 5 and anhydrous pyridine (3 equivalent) were added to anhydrous $CH_2Cl_2$ (15 mL), to which trifluoroacetic anhydride [$(CF_3CO)_2O$, 1.2 equivalent] was added at 0° C. 30 minutes later, the reaction mixture was warmed up to room temperature, followed by stirring for 2 hours. The organic layer was extracted by using water and ethyl acetate, which was washed with saturated brine, separated, dried ($Na_2SO_4$), filtered, and concentrated under reduced pressure. The residue was separated by column chromatography ($SiO_2$, eluent: hexane/ethyl acetate, 10/1→hexane/ethyl acetate, 2/1) to give 3.83 g of the target compound (S)—N-(1-(8-chloro-1-oxo-2-phenyl-1,2-dihydroisoquinoline-3-yl)ethyl)-2,2,2-trifluoroacetamide as a white solid (9.70 mmol, yield: 97%).

$^1$H NMR (300 MHz, $CDCl_3$) δ 7.20-7.60 (m, 8H), 6.52 (s, 1H), 6.38 (br d, 1H), 4.64-4.74 (m, 1H), 1.43 (d, J=6.9 Hz, 3H).

Step 7: Preparation of (S)—N-(1-(4,8-dichloro-1-oxo-2-phenyl-1,2-dihydroisoquinoline-3-yl)ethyl)-2,2,2-trifluoroacetamide 3.55 g (9.00 mmol) of (S)—N-(1-(8-chloro-1-oxo-2-phenyl-1,2-dihydroisoquinoline-3-yl)ethyl)-2,2,2-trifluoroacetamide prepared in step 6, N-chlorosuccinimide (NCS, 1.2 equivalent), and anhydrous acetonitrile (25 mL) were mixed together. The reaction mixture was refluxed for 4 hours and then cooled down the temperature to room temperature. Saturated sodiumthiosulfate ($Na_2S_2O_3$) solution (2 mL) and water were added thereto, followed by extraction using ethyl acetate. The organic layer was separated and washed with saturated brine. The organic layer was separated, dried ($Na_2SO_4$), filtered, and concentrated under reduced pressure. The residue was separated by column chromatography ($SiO_2$, eluent:

hexane/ethyl acetate, 10/1→hexane/ethyl acetate, 3/1) to give 3.79 g of the target compound (S)—N-(1-(4,8-dichloro-1-oxo-2-phenyl-1,2-dihydroisoquinoline-3-yl)ethyl)-2,2,2-trifluoroacetamide as a white solid (8.82 mmol, yield: 98%).

$^1$H NMR (300 MHz, $CDCl_3$) δ 7.98 (m, 1H), 7.51-7.69 (m, 6H), 7.15-7.20 (m, 1H), 7.03 (br s, 1H), 4.85-5.00 (m, 1H), 1.58 (d, J=7.2 Hz, 3H).

Step 8: Preparation of (S)-3-(1-aminoethyl)-4,8-dichloro-2-phenylisoquinoline-1(2H)-one 3.78 g (8.8 mmol) of (S)—N-(1-(4,8-dichloro-1-oxo-2-phenyl-1,2-dihydroisoquinoline-3-yl)ethyl)-2,2,2-trifluoroacetamide prepared in step 7, $K_2CO_3$ (5 equivalent), and MeOH/$H_2O$ (10/1, 20 mL) were mixed and the reaction mixture was refluxed for 12 hours. The mixture was cooled down to room temperature. The solvent was eliminated under reduced pressure. Water and ethyl acetate were added thereto, followed by extraction. The organic layer was separated and washed with saturated brine. The organic layer was separated, dried ($Na_2SO_4$), filtered, and concentrated under reduced pressure. The residue was separated by column chromatography ($SiO_2$, eluent: $CH_2Cl_2$/MeOH, 20/1→hexane $CH_2Cl_2$/MeOH, 10/1) to give 2.90 g of the target compound (S)-3-(1-aminoethyl)-4,8-dichloro-2-phenylisoquinoline-1(2H)-one as a white solid (8.7 mmol, yield: 99%).

$^1$H NMR (300 MHz, $CDCl_3$) δ 7.98-8.03 (m, 1H), 7.45-7.65 (m, 5H), 7.17-7.30 (m, 2H), 3.87-4.00 (m, 1H), 1.80 (br s, 2H), 1.46 (d, J=7.1 Hz, 3H).

Preparative Example 11: Preparation of (S)-8-chloro-2-phenyl-3-(pyrrolidine-2-yl)isoquinoline-1(2H)-one

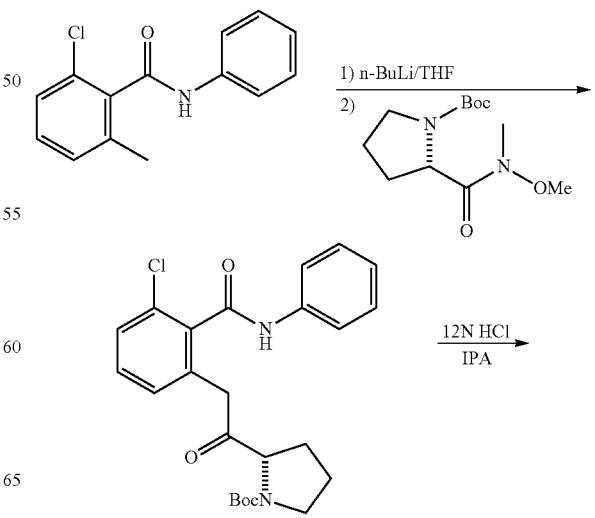

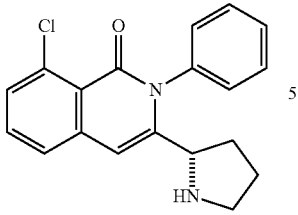

Step 1: Preparation of tert-butyl (S)-2-(2-(3-chloro-2-(phenylcarbamoyl)phenyl)acetyl)pyrrolidine-1-carboxylate 6 g (24.42 mmol) of 2-chloro-6-methyl-N-phenylbenzamide prepared in step 2 of Preparative Example 13 was dissolved in anhydrous THF (50 mL). 24.42 ml (61.05 mmol, 2.5 equivalent) of n-BuLi was slowly added thereto at −30° C., followed by stirring for 1 hour. 9.46 g (36.63 mmol, 1.5 equivalent) of tert-butyl (S)-2-(methoxy(methyl)carbamoyl)pyrrolidine-1-carboxylate was dissolved in anhydrous THF (50 mL), which was slowly added to the reaction mixture above. Then, 5.05 g of the target compound tert-butyl (S)-2-(2-(3-chloro-2-(phenylcarbamoyl)phenyl)acetyl)pyrrolidine-1-carboxylate was obtained as a white solid by the same manner as described in step 3 of Preparative Example (11.41 mmol, yield: 88%).

$^1$H NMR (300 MHz, CDCl$_3$) δ 8.03 (s, 1H), 7.60 (d, J=6.9 Hz, 2H), 7.32-7.38 (m, 3H), 7.16 (d, J=8.6 Hz, 2H), 7.05 (d, J=4.1 Hz, 1H), 4.28-4.39 (m, 1H), 3.98 (s, 1H), 3.41-3.52 (m, 2H), 1.69-1.78 (m, 4H), 1.38 (d, J=12.1 Hz, 9H).

Step 2: Preparation of (S)-8-chloro-2-phenyl-3-(pyrrolidine-2-yl)isoquinoline-1(2H)-one 2.3 g of (S)-8-chloro-2-phenyl-3-(pyrrolidine-2-yl)isoquinoline-1(2H)-one was prepared as a white solid by using 3.34 g (7.53 mmol) of tert-butyl (S)-2-(2-(3-chloro-2-(phenylcarbamoyl)phenyl)acetyl)pyrrolidine-1-carboxylate prepared in step 1 according to the same manner as described in step 4 of Preparative Example (7.08 mmol, yield: 94%).

$^1$H NMR (300 MHz, CDCl$_3$) δ 7.40-7.54 (m, 6H), 7.27-7.30 (m, 1H), 7.21-7.23 (m, 1H), 6.87 (s, 1H), 3.78 (t, J=7.0 Hz, 1H), 3.05-3.12 (m, 1H), 2.82-2.90 (m, 1H), 1.75-1.84 (m, 1H), 1.75 (s, 1H), 1.54-1.66 (m, 3H).

Preparative Example 12: Preparation of (S)-1-(2-phenylquinoline-3-yl)ethaneamine

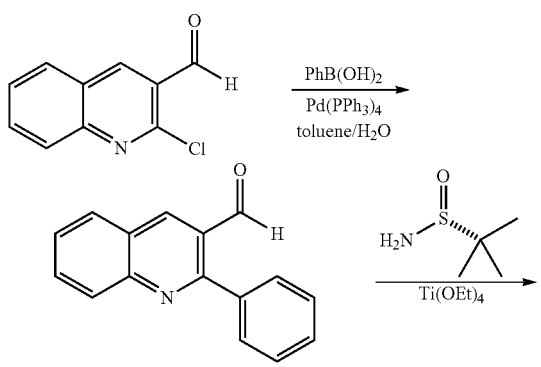

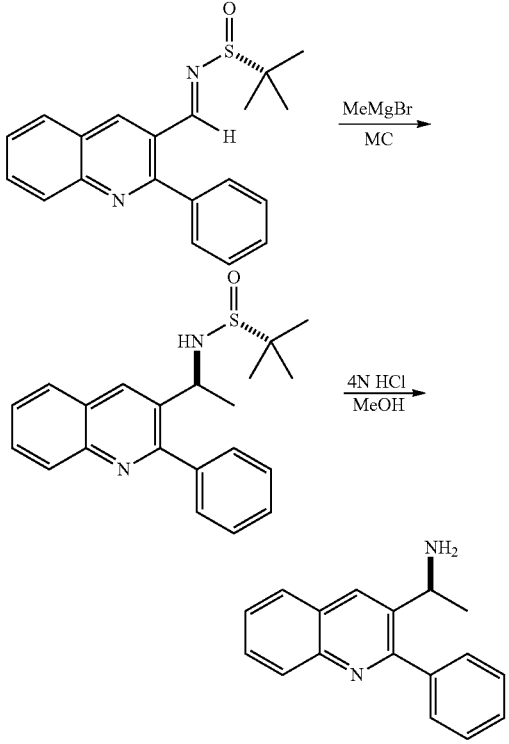

Step 1: Preparation of 2-phenylquinoline-3-carbaldehyde 10 g (52.19 mmol, 1.0 equivalent) of 2-chloro-3-quinolinecarbaldehyde was dissolved in toluene/water (4/1, 150 mL), to which 7 g (57.41 mmol, 1.1 equivalent) of phenylboronic acid, 12.17 g (114.82 mmol, 2.2 equivalent) of Na$_2$CO$_3$, 1.5 g (1.30 mmol, 2.5 mol %) of Pd(PPh$_3$)$_4$, and 7~8 drops of Aliquat 336 were slowly added stepwise. The mixture was refluxed for 12 hours under argon atmosphere. The mixture was then cooled down to room temperature. Water was added thereto, followed by extraction using ethyl acetate. The organic layer was separated, dried (N$_2$SO$^4$), filtered, and concentrated under reduced pressure. The residue was separated by column chromatography (SiO$_2$, eluent: hexane/dichloromethane, 10/1→hexane/dichloromethane, 3/1) to give 12.156 g of the target compound 2-phenylquinoline-3-carbaldehyde as a white solid (52.11 mmol, yield: 94%).

$^1$H NMR (300 MHz, CDCl$_3$) δ 10.19 (s, 1H), 8.86 (s, 1H), 8.22 (d, J=8.4 Hz, 1H), 8.03 (d, J=7.9 Hz, 1H), 7.88 (t, J=7.7 Hz, 1H), 7.64-7.71 (m, 3H), 7.55-7.61 (m, 3H).

Step 2: Preparation of (S,E)-methyl-N-((2-phenylquinoline-3-yl)methylene)propane-2-sulfinamide 3 g (12.89 mmol, 1.1 equivalent) of 2-phenylquinoline-3-carbaldehyde prepared in step 1 was dissolved in THF (100 mL), to which 5 ml (23.43 mmol, 2 equivalent) of Ti(OEt)$_4$ and 1.42 g (11.72 mmol, 1.0 equivalent) of (R)-(+)-2-methyl-2-propanesulfinamide were added, followed by reflux for 12 hours. The reaction mixture was cooled down to room temperature, to which saturated sodiumbicarbonate aqueous solution was added, followed by stirring for 1 hour. The mixture was filtered with celite pad, followed by extraction using ethyl acetate. The organic layer was washed with saturated brine, dried (Na$_2$SO$_4$), filtered, and concentrated under reduced pressure. The residue was separated by column chromatography (SiO$_2$, eluent:
hexane/ethyl acetate, 5/1→hexane/ethyl acetate, 1/1) to give 3.96 g of the target compound (S,E)-2-methyl-N-((2-phenylquinoline-3-yl)methylene)propane-2-sulfinamide as a yellow solid (11.77 mmol, yield: 91%).

$^1$H NMR (300 MHz, CDCl$_3$) δ 8.90 (s, 1H), 8.80 (s, 1H), 8.19 (d, J=8.2 Hz, 1H), 7.97 (d, J=7.8 Hz, 1H), 7.81 (s, 1H), 7.50-7.61 (m, 6H), 1.31 (s, 9H).

Step 3: Preparation of (R)-2-methyl-N—((S)-1-(2-phenylquinoline-3-yl)ethyl)propane-2-sulfinamide 3.96 g (11.76 mmol, 1.0 equivalent) of (S,E)-2-methyl-N-((2-phenylquinoline-3-yl)methylene)propane-2-sulfinamide prepared in step 2 was dissolved in anhydrous dichloromethane (70 mL), to which 11.76 ml (23.53 mmol, 3 equivalent) of 2 M MeMgBr was slowly added at −78° C., followed by stirring for 3 hours. The mixture was further stirred at room temperature for 12 hours, to which saturated NH$_4$Cl aqueous solution was added. The organic layer was separated, dried (Na$_2$SO$_4$), filtered, and concentrated under reduced pressure. The residue was separated by column chromatography (SiO$_2$, eluent: hexane/ethyl acetate, 3/1→hexane/ethyl acetate, 1/2) to give 2.52 g of the target compound (R)-2-methyl-N—((S)-1-(2-phenylquinoline-3-yl)ethyl)propane-2-sulfinamide as a white solid (7.15 mmol, yield: 61%).

$^1$H NMR (300 MHz, CDCl$_3$) δ 8.32 (s, 1H), 8.16 (d, J=8.5 Hz, 1H), 7.84 (d, J=8.2 Hz, 1H), 7.71 (t, J=7.6 Hz, 1H), 7.41-7.58 (m, 6H), 4.90-4.98 (m, 1H), 3.42 (d, J=3.1 Hz, 1H), 1.47 (d, J=6.6 Hz, 3H), 1.20 (s, 9H).

Step 4: Preparation of (S)-1-(2-phenylquinoline-3-yl)ethane-1-amine 2.42 g (7.15 mmol, 1.0 equivalent) of (R)-2-methyl-N—((S)-1-(2-phenylquinoline-3-yl)ethyl)propane-2-sulfinamide prepared in step 3 was dissolved in methanol (50 mL), to which 4 M HCl dioxan solution (15 mL) was added at room temperature. The mixture was stirred at room temperature for 2 hours. Saturated sodiumbicarbonate aqueous solution was added thereto, followed by extraction using ethyl acetate. The organic layer was separated, dried (Na$_2$SO$_4$), filtered, and concentrated under reduced pressure. The residue was separated by column chromatography (SiO$_2$, eluent: dichloromethane/methanol, 20/1→dichloromethane/methanol, 5/1) to give 1.65 g of the target compound (S)-1-(2-phenylquinoline-3-yl)ethane-1-amine as a pale yellow solid (6.64 mmol, yield: 93%).

$^1$H NMR (300 MHz, CDCl$_3$) δ 8.43 (s, 1H), 8.13 (d, J=8.4 Hz, 1H), 7.86 (d, J=8.1 Hz, 1H), 7.68 (t, J=7.6 Hz, 1H), 7.44-7.55 (m, 6H), 4.42-4.48 (q, J=6.5 Hz, 1H), 1.58 (s, 2H), 1.34 (d, J=6.5 Hz, 3H).

Preparative Example 13: Preparation of tert-butyl (S)-(1-(methoxy(methyl)amino)-1-oxopropane-2-yl)carbamate

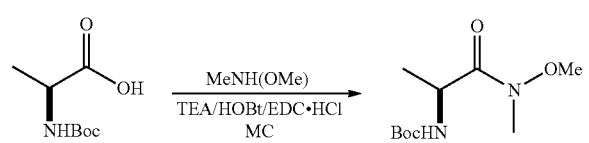 [SMILES: "MeNH(OMe)" ; C[C@H](NC(=O)OC(C)(C)C)C(=O)O ; CON(C)C(=O)[C@H](C)NC(=O)OC(C)(C)C]

10 g (52.85 mmol, 1.0 equivalent) of (S)-2-((tert-butoxycarbonyl)amino)propanoic acid was dissolved in anhydrous dichloromethane (250 ml), to which 29.5 ml (211.40 mmol, 4.0 equivalent) of triethylamine and 7.14 g (52.85 mmol, 1.0 equivalent) of hydroxybenzotriazole (HOBt) were added at 0° C. 20.3 g (105.70 mmol, 2.0 equivalent) of EDCI.HCl was added thereto, followed by stirring at room temperature for 30 minutes. 5.7 g (58.14 mmol, 1.1 equivalent) of N,O-dimethylhydroxylamine was added thereto, followed by stirring at room temperature for hours. Water was added to the reaction mixture, followed by extraction using ethyl acetate. The organic layer was separated, dried (Na$_2$SO$_4$), filtered, and concentrated under reduced pressure. The obtained solid was recrystallized with hexane/ethyl acetate to give 11.7 g of the target compound tert-butyl (S)-(1-(methoxy(methyl)amino)-1-oxopropane-2-yl)carbamate as a white solid (50.37 mmol, yield: 95%).

$^1$H NMR (300 MHz, CDCl$_3$) δ 5.23 (s, 1H), 4.68-4.70 (m, 1H), 3.77 (s, 3H), 3.12 (s, 3H), 1.44 (s, 9H), 1.31 (d, J=3.5 Hz, 3H).

Preparative Example 14: Preparation of 2-((tert-butoxycarbonyl)amino)butanoic Acid

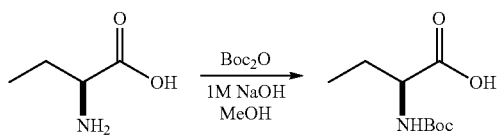

10 g (96.97 mmol, 1.0 eq) of 2-aminobutanoic acid was dissolved in 65 ml of methanol, to which 97 ml of M sodiumhydroxide (NaOH) and 25.4 g (116.37 mmol, 1.2 equivalent) of di-tert-butyl dicarbonate (Boc$_2$O) were added at 0° C. The mixture was stirred at room temperature for 48 hours, followed by concentration under reduced pressure. The reaction mixture was acidized with 1N HCl (pH 2-3), followed by extraction using ethyl acetate. The organic layer was separated, dried (Na$_2$SO$_4$), filtered, and concentrated under reduced pressure. The residue was separated by column chromatography (SiO$_2$, eluent: hexane/ethyl acetate, 10/1→hexane/ethyl acetate, 3/1) to give 18.5 g of the target compound 2-((tert-butoxycarbonyl)amino)butanoic acid as a colorless oil (91.02 mmol, yield: 94%).

$^1$H NMR (300 MHz, CDCl$_3$) δ 6.24 (s, 1H), 5.00-5.03 (d, J=7.6 Hz, 1H), 4.27-4.29 (m, 1H), 1.87-1.94 (m, 1H), 1.66-1.78 (m, 1H), 1.45 (s, 9H), 0.96-1.01 (t, J=7.3 Hz, 3H).

Preparative Example 15: Preparation of pyrrolo[2,1-f][1,2,4]triazine-4(3H)-one derivative

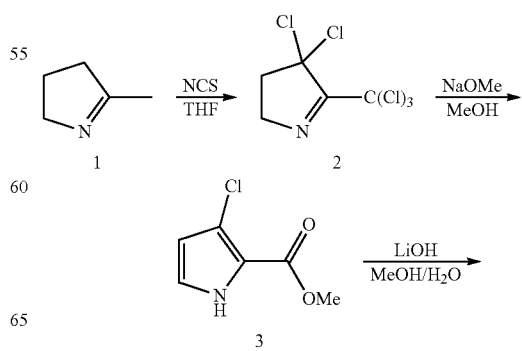

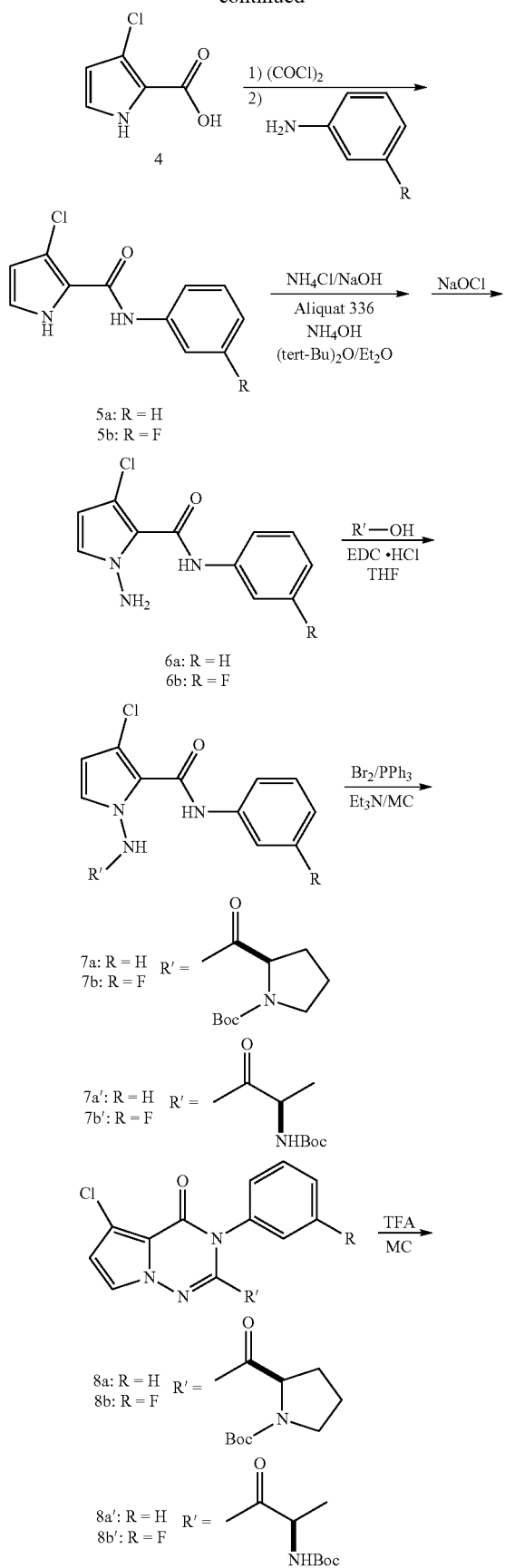
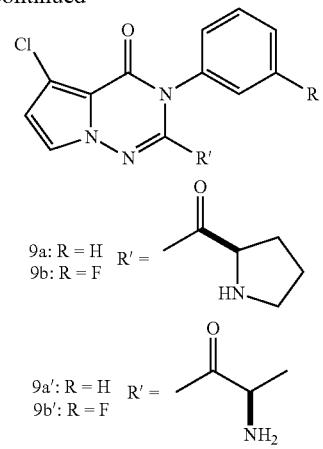

Steps 1 and 2: Preparation of methyl 3-chloro-1H-pyrrole-2-carboxylate (3)

5-methyl-3,4-dihydro-2H-pyrrole(1) (4 g, 0.05 mol) was dissolved in THF (120 ml), to which N-chlorosuccinimide (51.4 g, 0.39 mol) was slowly added at 0° C. The mixture was stirred for 15 minutes, followed by reflux for 2.5 hours. THF was eliminated under reduced pressure. Extraction was performed with dichloromethane. The organic layer was washed with saturated brine, separated, dried (anhydrous $MgSO_4$), filtered, and concentrated under reduced pressure. The obtained compound 4,4-dichloro-5-(trichloromethyl)-3,4-dihydro-2H-pyrrole(2) was used for the next reaction without purification. 4,4-dichloro-5-(trichloromethyl)-3,4-dihydro-2H-pyrrole(2) (12 g, 0.05 mol) was dissolved in methanol (100 ml), to which sodium methoxide (NaOMe) (28 wt % methanol solution) (16 g, 0.29 mol) was slowly added at 0° C., followed by reaction at room temperature for 2 hours. Extraction was performed with ethyl acetate. The organic layer was washed with saturated brine, separated, dried ($MgSO_4$), filtered, and concentrated under reduced pressure. The residue was separated by column chromatography ($SiO_2$, eluent: hexane/ethyl acetate, 5/1) to give 6.5 g of the target compound methyl 3-chloro-1H-pyrrole-2-carboxylate(3) as a brown solid (0.04 mmol, yield: 77%).

$^1$H NMR (300 MHz, $CDCl_3$) δ 9.11 (br s, 1H, NH), 6.87 (t, J=2.7 Hz, 1H), 6.26 (t, J=2.7 Hz, 1H), 3.90 (s, 3H).

Step 3: Preparation of 3-chloro-1H-pyrrole-2-carboxylic acid (4)

Methyl 3-chloro-1H-pyrrole-2-carboxylate (3) (5 g, 0.03 mol) was dissolved in methanol/water (2/1) (30 ml), to which $LiOH \cdot H_2O$ (5.3 g, 0.13 mol) was added, followed by reflux at room temperature for 1.5 hours. 12 N HCl (13 ml) was slowly added thereto at 0° C. The reaction mixture was extracted by using ethyl acetate. The extract was washed with saturated brine, separated, dried (anhydrous ($Na_2SO_4$), filtered, and concentrated under reduced pressure. The obtained solid compound was washed with hexane to give the target compound 3-chloro-1H-pyrrole-2-carboxylic acid (4).

$^1$H NMR (300 MHz, DMSO-$d_6$) δ 12.58 (br s, 1H), 11.92 (br s, 1H), 6.94 (t, J=2.7 Hz, 1H), 6.19 (t, J=2.7 Hz, 1H).

Step 4-1: Preparation of 3-chloro-N-phenyl-1H-pyrrole-2-carboxamide (5a)

3-chloro-1H-pyrrole-2-carboxylic acid (4) (1 g, 6.87 mmol) was dissolved in anhydrous dichloromethane (25 ml), to which oxalyl chloride (1.3 g, 10.31 mmol) and dimethylformamide (2 drops) were slowly added at room temperature. The reaction mixture was refluxed for 1 hour, followed by concentration under reduced pressure. The obtained solid compound was dissolved in anhydrous 1,4-dioxane (8 ml), to which aniline (0.8 g, 8.25 mmol) and N,N-diisopropylethylamine (DIPEA) (2.7 g, 20.61 mmol) were slowly added at 0° C. The mixture was reacted at 60° C. for 1 hour, followed by extraction with ethyl acetate. The extract was washed with saturated brine, separated, dried (anhydrous $Na_2SO_4$), filtered, and concentrated under reduced pressure. The obtained solid compound was washed with hexane to give the target compound 3-chloro-N-phenyl-1H-pyrrole-2-carboxamide (5a) as a dark brown solid.

$^1$H NMR (300 MHz, $CDCl_3$) δ 10.35 (br s, 1H), 8.60 (br s, 1H), 7.64 (d, J=7.2 Hz, 2H), 7.37 (t, J=7.8 Hz, 2H), 7.15 (t, J=7.2 Hz, 1H), 6.91 (s, 1H), 6.27 (s, 1H).

Step 4-2: Preparation of 3-chloro-N-(3-fluorophenyl)-1H-pyrrole-2-carboxamide (5b)

2.6 g of 3-chloro-N-(3-fluorophenyl)-1H-pyrrole-2-carboxamide (5b) was prepared as a pale brown solid by using 3-chloro-1H-pyrrole-2-carboxylic acid (4) (2 g, 13.75 mmol) and 3-fluoroaniline (1.9 g, 17.19 mmol) by the same method to prepare the compound 5a (10.85 mmol, yield: 67%).

$^1$H NMR (300 MHz, $CDCl_3$) δ 9.81 (br s, 1H), 8.61 (br s, 1H), 7.61 (d, J=11.1 Hz, 1H), 7.34-7.21 (m, 2H), 6.93 (t, J=3.0 Hz, 1H), 6.81-6.87 (m, 1H), 6.29 (t, J=3.0 Hz, 1H).

Step 5-1: Preparation of 1-amino-3-chloro-N-phenyl-1H-pyrrole-2-carboxamide (6a)

$NH_4Cl$ (2.1 g, 39 mmol), NaOH (28 wt %) aqueous solution (5.2 g, 130 mmol), $NH_4OH$ (ammoniumhydroxide) (28 wt %) (2.3 g, 65 mmol), and Aliquat 336 (0.3 g, 0.65 mmol) were mixed to prepare a mixed solution. 3-chloro-N-phenyl-1H-pyrrole-2-carboxamide (5a) (1.4 g, 6.50 mmol) was dissolved in t-butylmethyl ether/diethyl ether (1:1) (80 ml), which was slowly added to the mixed solution at 0° C. NaOCl (sodiumhypochloride) aqueous solution (10 wt %) was slowly added thereto at the same temperature, followed by reaction at room temperature for 4 hours. Extraction was performed with ethyl acetate. The organic layer was washed with saturated brine, separated, dried ($MgSO_4$), filtered, and concentrated under reduced pressure. The residue was separated by column chromatography ($SiO_2$, eluent: hexane/ethyl acetate, 5/1) to give 1.1 g of the target compound 1-amino-3-chloro-N-phenyl-1H-pyrrole-2-carboxamide (6a) as a white solid (4.56 mmol, yield: 70%).

$^1$H NMR (300 MHz, $CDCl_3$) δ 8.53 (br s, 1H), 7.59 (d, J=8.4 Hz, 2H), 7.37 (t, J=7.8 Hz, 2H), 7.16 (t, J=7.5 Hz, 1H), 6.91 (d, J=2.7 Hz, 1H), 6.08 (d, J=3.0 Hz, 1H), 5.91 (s, 2H).

Step 5-2: Preparation of 1-amino-3-chloro-N-(3-fluorophenyl)-1H-pyrrole-2-carboxamide (6b)

1.7 g of 1-amino-3-chloro-N-(3-fluorophenyl)-1H-pyrrole-2-carboxamide (6b) was prepared as a white solid by using 3-chloro-N-(3-fluorophenyl)-1H-pyrrole-2-carboxamide (5b) (3.9 g, 0.02 mol) by the same method to prepare the compound 6a (6.78 mmol, yield: 63%).

$^1$H NMR (300 MHz, DMSO-$d_6$) δ 11.03 (br s, 1H), 7.68 (d, J=12 Hz, 1H), 7.36 (s, 2H), 6.98 (d, J=2.7 Hz, 1H), 6.90-6.94 (m, 1H), 6.54 (s, 2H), 6.12 (d, J=3.0 Hz, 1H).

Step 6-1-1: Preparation of tert-butyl (S)-2-((3-chloro-2-(phenylcarbamoyl)-1H-pyrrole-1-yl)carbamoyl)pyrrolidine-1-carboxylate (7a)

1-amino-3-chloro-N-phenyl-1H-pyrrole-2-carboxamide (6a) (150 mg, 0.64 mmol), N-(tert-butoxycarbonyl)-L-proline (192 mg, 0.89 mmol), and EDC.HCl (171 mg, 0.89 mmol) were dissolved in anhydrous THF (1 ml), followed by reaction at room temperature for 20 hours. The reaction mixture was extracted by using ethyl acetate. The organic layer was washed with saturated brine, separated, dried ($MgSO_4$), filtered, and concentrated under reduced pressure. The residue was separated by column chromatography ($SiO_2$, eluent: hexane/ethyl acetate, 5/1) to give 193 mg of the target compound tert-butyl (S)-2-((3-chloro-2-(phenylcarbamoyl)-1H-pyrrole-1-yl)carbamoyl)pyrrolidine-1-carboxylate (7a) as a white solid (0.45 mmol, yield: 70%).

$^1$H NMR (300 MHz, $CDCl_3$) δ 10.61 (br s, 1H), 8.32 (brs, 1H), 7.57 (d, J=7.8 Hz, 2H), 7.34 (t, J=7.8 Hz, 2H), 7.01-7.15 (m, 2H), 6.20 (s, 1H), 4.30-4.56 (m, 1H), 3.30-3.70 (m, 2H), 2.14-2.44 (m, 2H), 1.82-2.08 (m, 2H), 1.49 (s, 9H).

Step 6-1-2: Preparation of tert-butyl (S)-2-((3-chloro-2-((3-fluorophenyl)carbamoyl)-1H-pyrrole-1-yl)carbamoyl)pyrrolidine-1-carboxylate (7b)

Tert-butyl (S)-2-((3-chloro-2-((3-fluorophenyl)carbamoyl)-1H-pyrrole-1-yl)carbamoyl)pyrrolidine-1-carboxylate (7b) was prepared by using 1-amino-3-chloro-N-(3-fluorophenyl)-1H-pyrrole-2-carboxamide (6b) (0.7 g, 2.76 mmol) by the same method to prepare the compound 7a.

$^1$H NMR (300 MHz, $CDCl_3$) δ 10.61 (br s, 1H), 8.38 (br s, 1H), 7.64 (br s, 1H), 7.23-7.31 (m, 2H,), 7.13 (br s, 1H), 6.99 (br s, 1H), 6.79-6.85 (m, 1H), 6.21 (s, 1H), 4.50 (br s, 1H), 3.51 (br s, 1H), 3.42 (br s, 1H), 1.84-2.39 (m, 4H), 1.50 (s, 9H).

Step 6-2-1: Preparation of tert-butyl (S)-(1-((3-chloro-2-(phenylcarbamoyl)-1H-pyrrole-1-yl)amino)-1-oxopropane-2-yl)carbamate (7a')

3.5 g of tert-butyl (S)-(1-((3-chloro-2-(phenylcarbamoyl)-1H-pyrrole-1-yl)amino)-1-oxopropane-2-yl)carbamate (7a') was prepared as a white solid by using 1-amino-3-chloro-N-phenyl-1H-pyrrole-2-carboxamide (6a) (2.3 g, 9.76 mmol) and N-(tert-butoxycarbonyl)-L-aniline (2.6 g, 13.66 mmol) by the same method to prepare the compound 7a (8.56 mmol, yield: 88%).

$^1$H NMR (300 MHz, $CDCl_3$) δ 10.25 (s, 1H), 8.37 (s, 1H), 7.56 (d, J=8.1 Hz, 2H), 7.34 (t, J=7.8 Hz, 2H), 7.14 (t, J=7.5 Hz, 1H), 7.03 (d, J=2.7 Hz, 1H), 6.21 (d, J=2.7 Hz, 1H), 5.06 (d, J=7.2 Hz, 1H), 4.40 (br s, 1H), 1.47 (s, 9H), 1.44 (d, J=7.5 Hz, 3H).

Step 6-2-2: Preparation of tert-butyl (S)-(1-((3-chloro-2-((3-fluorophenyl)carbamoyl)-1H-pyrrole-1-yl)amino)-1-oxopropane-2-yl)carbamate (7b')

Tert-butyl (S)-(1-((3-chloro-2-((3-fluorophenyl)carbamoyl)-1H-pyrrole-1-yl)amino)-1-oxopropane-2-yl)carbamate (7b') was prepared as a white solid by using 1-amino-3-chloro-N-(3-fluorophenyl)-1H-pyrrole-2-carboxamide (6b) (3.1 g, 12.26 mmol) and N-(tert-butoxycarbonyl)-L-alanine (3.3 g, 17.16 mmol) by the same method to prepare the compound 7a (8.56 mmol, yield: 88%).

¹H NMR (300 MHz, CDCl₃) δ 10.16 (s, 1H), 8.42 (s, 1H), 7.61 (d, J=11.1 Hz, 1H), 7.24-7.31 (m, 2H), 7.14-7.11 (m, 1H), 7.02 (d, J=3.3 Hz, 1H), 6.86-6.80 (m, 1H), 6.22 (d, J=3.3 Hz, 1H), 5.00 (d, J=7.8 Hz, 1H) 4.35-4.42 (m, 1H), 1.48 (s, 9H), 1.44 (d, J=7.2 Hz, 3H).

Step 7-1-1: Preparation of tert-butyl (S)-2-(5-chloro-4-oxo-3-phenyl-3,4-dihydropyrrolo[2,1-f][1,2,4]triazine-2-yl)pyrrolidine-1-carboxylate (8a)

Triphenylphosphine (303 mg, 1.16 mmol) was dissolved in dichloromethane (1 ml), to which Br₂ (184 mg, 1.16 mmol) was slowly added at 0° C., followed by stirring at room temperature for 10 minutes. Tert-butyl (S)-2-((3-chloro-2-(phenylcarbamoyl)-1H-pyrrole-1-yl)carbamoyl)pyrrolidine-1-carboxylate (7a) (250 mg, 0.58 mmol) was dissolved in dichloromethane (1 ml), which was slowly added to the mixture above at 0° C. Triethylamine (146 mg, 1.44 mmol) was also added thereto at the same temperature. The reaction mixture was stirred at 0° C. for 10 minutes, followed by extraction using dichloromethane. The organic layer was washed with saturated brine, separated, dried (MgSO₄), filtered, and concentrated under reduced pressure. The residue was separated by column chromatography (SiO₂, eluent: hexane/ethyl acetate, 5/1) to give 82 mg of the target compound tert-butyl (S)-2-(5-chloro-4-oxo-3-phenyl-3,4-dihydropyrrolo[2,1-f][1,2,4]triazine-2-yl)pyrrolidine-1-carboxylate (8a) as a white solid (0.20 mmol, yield: 34%).

¹H NMR (300 MHz, CDCl₃) δ 7.29-7.36 (m, 2H), 7.05-7.13 (m, 3H), 6.36-6.40 (m, 1H), 4.46-4.51 (m, 0.5H), 4.36-4.40 (m, 0.5H), 3.09-3.41 (m, 2H), 2.12-2.25 (m, 1H), 1.86-2.00 (m, 1H), 1.71-1.79 (m, 2H), 1.45 (s, 5H), 1.35 (s, 4H).

Step 7-1-2: Preparation of tert-butyl (S)-2-(5-chloro-3-(3-fluorophenyl)-4-oxo-3,4-dihydropyrrolo[2,1-f][1,2,4]triazine-2-yl)pyrrolidine-1-carboxylate (8b)

45 mg of tert-butyl (S)-2-(5-chloro-3-(3-fluorophenyl)-4-oxo-3,4-dihydropyrrolo[2,1-f][1,2,4]triazine-2-yl)pyrrolidine-1-carboxylate (8b) was prepared as a white solid by using tert-butyl (S)-2-((3-chloro-2-((3-fluorophenyl)carbamoyl)-1H-pyrrole-1-yl)carbamoyl)pyrrolidine-1-carboxylate (7b) (100 mg, 0.22 mmol) by the same method to prepare the compound 8a (0.10 mmol, yield: 47%).

¹H NMR (300 MHz, CDCl₃) δ 7.43-7.57 (m, 1H), 7.18-7.37 (m, 2H), 6.99-7.13 (m, 1H), 6.48 (dd, 1H, J=2.7 Hz, J=12.9 Hz), 4.46-4.53 (m, 0.5H), 4.41 (br s, 0.5H), 3.32-3.70 (m, 2H), 1.80-2.11 (m, 4H), 1.45 (s, 4H), 1.38 (s, 5H).

Step 7-2-1: Preparation of tert-butyl (S)-(1-(5-chloro-4-oxo-3-phenyl-3,4-dihydropyrrolo[2,1-f][1,2,4]triazine-2-yl)ethyl)carbamate (8a')

105 mg of tert-butyl (S)-(1-(5-chloro-4-oxo-3-phenyl-3,4-dihydropyrrolo[2,1-f][1,2,4]triazine-2-yl)ethyl)carbamate (8a') was prepared as a white solid by using tert-butyl (S)-(1-((3-chloro-2-(phenylcarbamoyl)-1H-pyrrole-1-yl)amino)-1-oxopropane-2-yl)carbamate (7a') (500 mg, 1.23 mmol) by the same method to prepare the compound 8a (0.27 mmol, yield: 22%).

¹H NMR (300 MHz, CDCl₃) δ 7.48-7.60 (m, 3H), 7.39-7.41 (m, 1H), 7.28 (brs, 2H), 6.50 (d, J=2.1 Hz, 1H), 5.09 (brs, 1H), 4.48 (br s, 1H), 1.42 (s, 9H), 1.26 (d, J=6.3 Hz, 3H).

Step 7-2-2: Preparation of tert-butyl (S)-(1-(5-chloro-3-(3-fluorophenyl)-4-oxo-3,4-dihydropyrrolo[2,1-f][1,2,4]triazine-2-yl)ethyl)carbamate (8b')

140 mg of tert-butyl (S)-(1-(5-chloro-3-(3-fluorophenyl)-4-oxo-3,4-dihydropyrrolo[2,1-f][1,2,4]triazine-2-yl)ethyl)carbamate (8b') was prepared as a white solid by using tert-butyl (S)-(1-((3-chloro-2-((3-fluorophenyl)carbamoyl)-1H-pyrrole-1-yl)amino)-1-oxopropane-2-yl)carbamate (7b') (500 mg, 1.18 mmol) by the same method to prepare the compound 8a (0.34 mmol, yield: 29%).

¹H NMR (300 MHz, CDCl₃) δ 7.47-7.58 (m, 1H), 7.15-7.30 (m, 3H), 7.02-7.09 (m, 1H), 6.51 (d, J=2.1 Hz, 1H), 4.99-5.10 (m, 1H), 4.48 (br s, 1H), 1.41 (s, 9H), 1.24-1.31 (m, 3H).

Step 8-1-1: Preparation of (S)-5-chloro-3-phenyl-2-(pyrrolidine-2-yl)pyrrolo[2,1-f][1,2,4]triazine-4(3H)-one (9a)

Tert-butyl (S)-2-(5-chloro-4-oxo-3-phenyl-3,4-dihydropyrrolo[2,1-f][1,2,4]triazine-2-yl)pyrrolidine-1-carboxylate (8a) (130 mg, 0.31 mmol) was dissolved in trifluoroacetic acid (50 wt % dichloromethane) (2 ml) at 0° C., followed by stirring at room temperature for 30 minutes. The reaction mixture was neutralized with NaHCO₃ at 0° C., followed by extraction using dichloromethane. The organic layer was washed with saturated brine, separated, dried (MgSO₄), filtered, and concentrated under reduced pressure. As a result, 96 mg of the target compound (S)-5-chloro-3-phenyl-2-(pyrrolidine-2-yl)pyrrolo[2,1-f][1,2,4]triazine-4(3H)-one (9a) was obtained as a white solid (0.30 mmol, yield: 97%).

¹H NMR (300 MHz, CDCl₃) δ 7.47-7.55 (m, 3H), 7.26-7.30 (m, 3H), 6.49 (d, J=2.7 Hz, 1H), 3.81 (t, J=5.7 Hz, 1H), 3.12-3.19 (m, 1H), 2.74-2.81 (m, 1H), 2.02 (br s, 1H), 1.77-1.82 (m, 2H), 1.61-1.73 (m, 2H).

Step 8-1-2: Preparation of (S)-5-chloro-3-(3-fluorophenyl)-2-(pyrrolidine-2-yl)pyrrolo[2,1-f][1,2,4]triazine-4(3H)-one HCl salt (9b)

Conc. HCl (15 wt % methanol) (10 ml) was added to tert-butyl (S)-2-(5-chloro-3-(3-fluorophenyl)-4-oxo-3,4-dihydropyrrolo[2,1-f][1,2,4]triazine-2-yl)pyrrolidine-1-carboxylate (8b) (40 mg, 0.09 mmol) at 0° C., followed by stirring for 1 hour. The solvent was eliminated from the reaction mixture under reduced pressure. As a result, the target compound (S)-5-chloro-3-(3-fluorophenyl)-2-(pyrrolidine-2-yl)pyrrolo[2,1-f][1,2,4]triazine-4(3H)-one hydrochloride salt (9b) was obtained as a white solid.

¹H NMR (300 MHz, DMSO-d₆) δ 9.86 (brs, 1H), 9.08 (brs, 1H), 7.63-7.69 (m, 2H), 7.40-7.54 (m, 3H), 6.78 (s, 1H), 4.23 (br s, 1H), 3.17 (br s, 1H), 2.09-2.14 (m, 1H), 1.90-1.98 (m, 1H), 1.69-1.87 (m, 2H).

Step 8-2-1: Preparation of (S)-2-(1-aminoethyl)-5-chloro-3-phenylpyrrolo[2,1-f][1,2,4]triazine-4(3H)-one (9a')

69 mg of (S)-2-(1-aminoethyl)-5-chloro-3-phenylpyrrolo[2,1-f][1,2,4]triazine-4(3H)-one (9a') was prepared as a white solid by using tert-butyl (S)-(1-(5-chloro-4-oxo-3-phenyl-3,4-dihydropyrrolo[2,1-f][1,2,4]triazine-2-yl)ethyl)carbamate (8a') (105 mg, 0.27 mmol) by the same method to prepare the compound 9a (0.24 mmol, yield: 88%).

¹H NMR (300 MHz, CDCl₃) δ 7.48-7.57 (m, 3H), 7.26-7.30 (m, 3H), 6.50 (d, J=2.4 Hz, 1H), 3.66 (q, J=6.6 Hz, J=13.2 Hz, 1H), 1.29 (d, J=6.6 Hz, 3H).

Step 8-2-2: Preparation of (S)-2-(1-aminoethyl)-5-chloro-3-(3-fluorophenyl)pyrrolo[2,1-f][1,2,4]triazine-4(3H)-one (9b')

103 mg of (S)-2-(1-aminoethyl)-5-chloro-3-(3-fluorophenyl)pyrrolo[2,1-f][1,2,4]triazine-4(3H)-one (9b') was prepared as a white solid by using tert-butyl (S)-(1-(5-chloro-3-(3-fluorophenyl)-4-oxo-3,4-dihydropyrrolo[2,1-f][1,2,4]-triazin-2-yl)ethyl)carbamate (8b') (140 mg, 0.34 mmol) by the same method to prepare the compound 9a (0.33 mmol, yield: 97%).

¹H NMR (300 MHz, CDCl₃) δ 7.48-7.56 (m, 1H), 7.22-7.29 (m, 2H), 7.02-7.14 (m, 2H), 6.50 (d, J=2.7 Hz, 1H), 3.76 (q, J=6.3 Hz, J=12.8 Hz, 1H), 2.22 (br s, 2H), 1.34 (d, J=6.6 Hz, 3H).

Preparative Example 16: Preparation of (S)-1-(7-fluoro-2-(3-fluorophenyl)quinoline-3-yl)ethane-1-amine

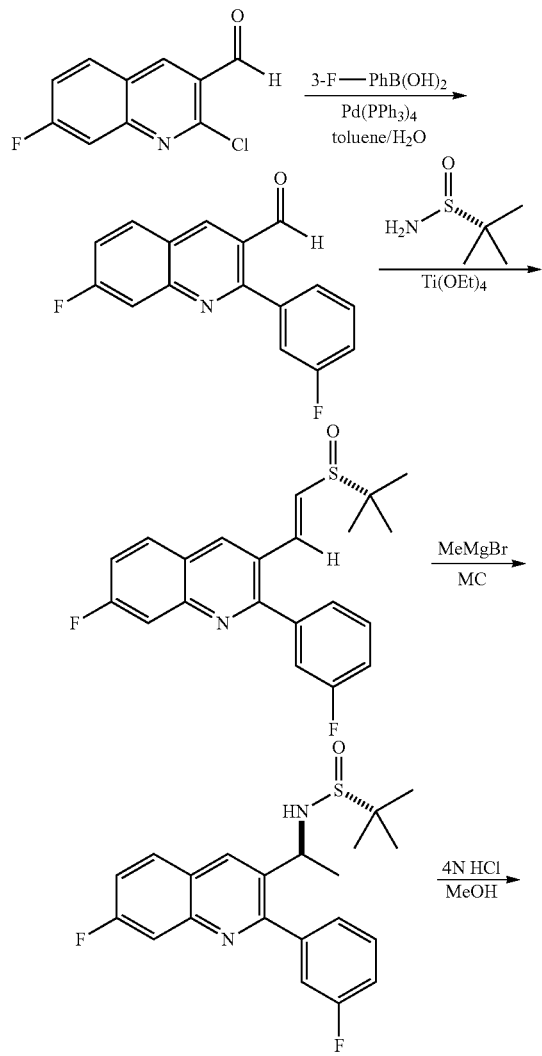

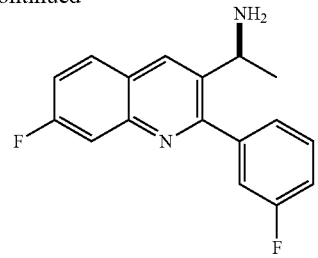

Step 1: Preparation of 7-fluoro-2-(3-fluorophenyl)quinoline-3-carbaldehyde 2.48 g of 7-fluoro-2-(3-fluorophenyl)quinoline-3-carbaldehyde was prepared as a pale yellow solid by using 2.10 g (10.0 mmol) of 2-chloro-7-fluoroquinoline-3-carbaldehyde by the same manner as described in step 1 of Preparative Example 12 (9.2 mmol, yield: 92%).
MS [m/z; (M+1)⁺]:270.

Step 2: Preparation of (R,E)-N-((7-fluoro-2-(3-fluorophenyl)quinoline-3-yl)methylene)-2-methylpropane-2-sulfinamide 1.3 g of (R,E)-N-((7-fluoro-2-(3-fluorophenyl)quinoline-3-yl)methylene)-2-methylpropane-2-sulfinamide was prepared as a yellow solid by using 1.0 g (3.71 mmol, 1.0 equivalent) of 7-fluoro-2-(3-fluorophenyl)quinoline-3-carbaldehyde prepared in step 1 by the same manner as described in step 2 of Preparative Example 12 (3.49 mmol, yield: 94%).

¹H NMR (300 MHz, CDCl₃) δ 1.31 (s, 9H), 7.18-7.54 (m, 5H), 7.79-7.83 (m, 1H), 7.98-8.03 (m, 1H), 8.76 (s, 1H), 8.91 (s, 1H).

Step 3: Preparation of (R)—N—((S)-1-(7-fluoro-2-(3-fluorophenyl)quinoline-3-yl)ethyl)-2-methylpropane-2-sulfinamide 1.30 g of (R)—N—((S)-1-(7-fluoro-2-(3-fluorophenyl)quinoline-3-yl)ethyl)-2-methylpropane-2-sulfinamide was prepared as a pale yellow solid by using 1.3 g (3.49 mmol) of (R,E)-N-((7-fluoro-2-(3-fluorophenyl)quinoline-3-yl)methylene)-2-methylpropane-2-sulfinamide prepared in step 2 by the same manner as described in step 3 of Preparative Example 12 (3.35 mmol, yield: 96%)

¹H NMR (500 MHz, CDCl₃) δ 1.23 (s, 9H), 1.51-1.53 (d, J=10.0, 3H), 3.38-3.39 (d, J=5.0, 1H), 4.92-4.94 (m, 1H), 7.17-7.21 (m, 1H), 7.29-7.32 (m, 1H), 7.38-7.41 (m, 2H), 7.49-7.53 (m, 1H), 7.78-7.80 (m, 1H), 7.85-7.88 (m, 1H), 8.35 (s, 1H).

Step 4: Preparation of (S)-1-(7-fluoro-2-(3-fluorophenyl)quinoline-3-yl)ethane-1-amine 0.37 g of (S)-1-(7-fluoro-2-(3-fluorophenyl)quinoline-3-yl)ethane-1-amine was prepared as a pale yellow solid by using 0.52 g (1.34 mmol) of (R)—N—((S)-1-(7-fluoro-2-(3-fluorophenyl)quinoline-3-yl)ethyl)-2-methylpropane-2-sulfinamide prepared in step 3 by the same manner as described in step 4 of Preparative Example 12 (1.30 mmol, yield: 97%)

¹H NMR (300 MHz, CDCl₃) δ 1.35 (d, J=9.0, 3H), 1.53 (br s, 2H), 4.43 (t, J=6.0, 1H), 4.92-4.94 (m, 1H), 7.16 (t,

J=9.0, 1H), 7309-7.36 (m, 3H), 7.42-7.49 (m, 1H), 7.73 (d, J=12.0, 1H), 7.82-7.87 (m, 1H), 8.47 (s, 1H).

Preparative Example 17: Preparation of (S)-1-(7-fluoro-2-(pyridine-2-yl)quinoline-3-yl)ethane-1-amine

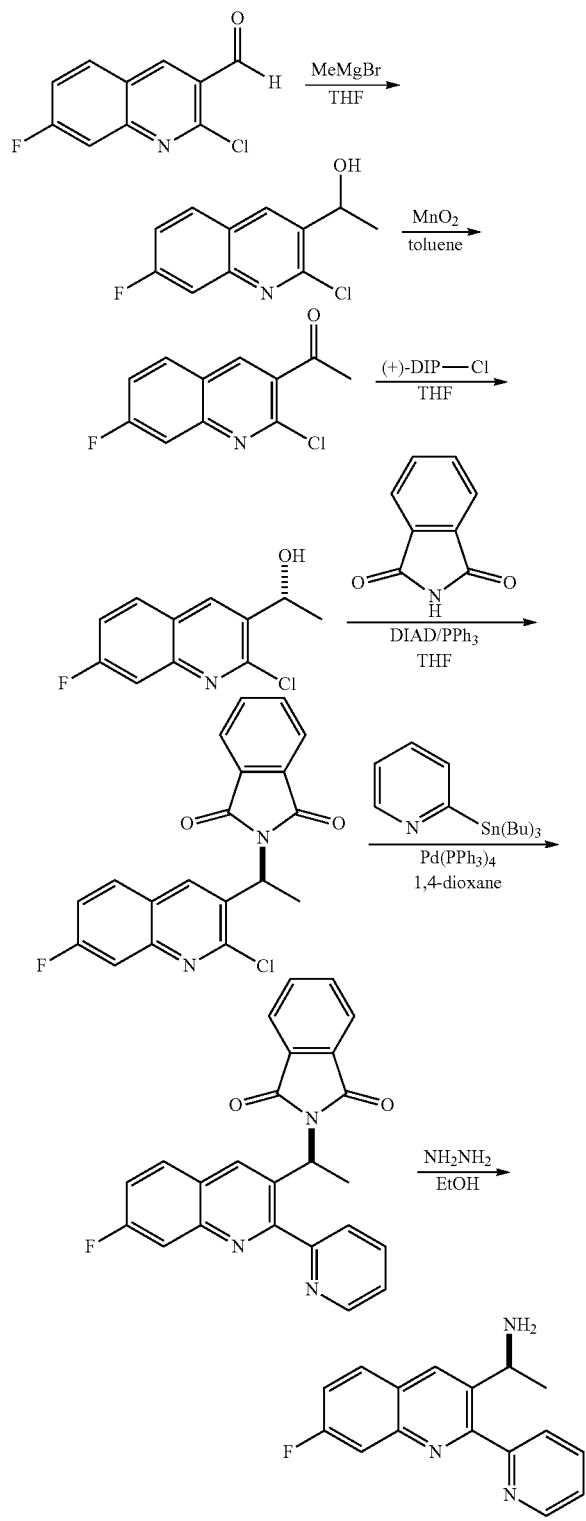

Step 1: Preparation of 1-(2-chloro-7-fluoroquinoline-3-yl)ethane-1-ol 2.5 g (11.927 mmol) of 2-chloro-7-fluoroquinoline-3-carbaldehyde was dissolved in anhydrous THF (30 mL), to which 4.77 mL (14.312 mmol) of 3 M MeMgBr (Et$_2$O) solution was added at −78° C., followed by stirring at −78° C.~10° C. for 2 hours. The temperature was adjusted at −20° C. After adding saturated NH$_4$Cl aqueous solution, the reaction mixture was heated at room temperature, followed by extraction using ethyl acetate. The organic layer was separated, dried (Na$_2$SO$_4$), filtered, and concentrated under reduced pressure. The residue was separated by column chromatography (SiO$_2$, eluent: hexane/ethyl acetate, 3/1) to give 2.4 g of the target compound 1-(2-chloro-7-fluoroquinoline-3-yl)ethane-1-ol as a yellow solid (10.636 mmol, yield: 89%).

$^1$H NMR (300 MHz, CDCl$_3$) δ 8.38 (s, 1H), 7.79~7.87 (m, 1H), 7.63 (dd, J=9.6, 2.2 Hz, 1H), 7.35 (td, J=8.6, 2.4 Hz, 1H), 5.32~5.41 (m, 1H), 2.31 (d, J=2.9 Hz, 1H), 1.61 (d, J=7.1 Hz, 3H).

Step 2: Preparation of 1-(2-chloro-7-fluoroquinoline-3-yl)ethane-1-one 2.4 g (10.636 mmol) of 1-(2-chloro-7-fluoroquinoline-3-yl)ethane-1-ol prepared in step 1 was dissolved in 30 mL of anhydrous toluene, to which 9.2 g (106.36 mmol) of manganese dioxide (MnO$_2$) was added, followed by reflux for 10 hours. The reaction mixture was cooled down at room temperature, filtered with celite pad, concentrated under reduced pressure. The residue was separated by column chromatography (SiO$_2$, eluent: hexane/ethyl acetate, 3/1) to give 1.8 g of the target compound 1-(2-chloro-7-fluoroquinoline-3-yl)ethane-1-one as a yellow solid (8.049 mmol, yield: 76%).

$^1$H NMR (300 MHz, CDCl$_3$) δ 8.42 (s, 1H), 7.88~7.95 (m, 1H), 7.68 (dd, J=9.8, 2.2 Hz, 1H), 7.41 (td, J=8.4, 2.4 Hz, 1H), 2.79 (s, 3H).

Step 3: Preparation of (R)-1-(2-chloro-7-fluoroquinoline-3-yl) ethane-1-ol 5 g (15.588 mmol) of B-chlorodiisopinocampheolborane ((+)DIP-Cl) was dissolved in anhydrous THF (10 ml), which was frozen at −47° C. 1.8 g (8.049 mmol) of 1-(2-chloro-7-fluoroquinoline-3-yl)ethane-1-one prepared in step 2 was dissolved in anhydrous THF (20 ml), which was added to the mixture above, followed by stirring at room temperature for 12 hours. The reaction mixture was cooled down at 0° C., to which 1 ml of acetone and 1 ml of 10% Na$_2$CO$_3$ were added, followed by stirring at room temperature for 1 hour. Ethyl acetate and water were added to the reaction mixture. The separated organic layer was dried (Na$_2$SO$_4$), filtered, and concentrated under reduced pressure. The residue was separated by column chromatography (SiO$_2$, eluent: hexane/ethyl acetate, 4/1) to give 1.4 g of the target compound (R)-1-(2-chloro-7-fluoroquinoline-3-yl)ethane-1-ol as a white solid (6.204 mmol, yield: 77%).

$^1$H NMR (300 MHz, CDCl$_3$) δ 8.39 (s, 1H), 7.81~7.88 (m, 1H), 7.65 (dd, J=9.9, 2.6 Hz, 1H), 7.36 (td, J=8.9, 2.8 Hz, 1H), 5.31~5.41 (m, 1H), 2.15 (d, J=3.8 Hz, 1H), 1.61 (d, J=6.4 Hz, 3H).

Step 4: Preparation of (S)-2-(1-(2-chloro-7-fluoro-quinoline-3-yl)ethyl)isoindoline-1,3-dione 1.4 g (6.204 mmol) of (R)-1-(2-chloro-7-fluoroquinoline-3-yl)ethane-1-ol prepared in step 3 was dissolved in anhydrous THF (30 mL), to which 1.95 g (7.445 mmol) of triphenylphosphine (PPh₃) and 1.1 g (7.445 mmol) of phthalimide were added. The mixture was cooled down at 0° C., to which 1.47 mL (7.445 mmol) of diisopropyl azodicarboxylate (DIAD) was added, followed by stirring at room temperature for 15 hours. Water and ethyl acetate were added to the reaction mixture, followed by extraction. The separated organic layer was dried (Na₂SO₄), filtered, and concentrated under reduced pressure. The residue was separated by column chromatography (SiO₂, eluent: hexane/ethyl acetate, 4/1) to give 2 g of the target compound (S)-2-(1-(2-chloro-7-fluoroquinoline-3-yl)ethyl)isoindoline-1,3-dione as a white solid (5.637 mmol, yield: 91%).

¹H NMR (300 MHz, CDCl₃) δ 8.56 (s, 1H), 7.87~7.94 (m, 1H), 7.77~7.83 (m, 2H), 7.68~7.74 (m, 2H), 7.61 (dd, J=9.7, 2.2 Hz, 1H), 7.37 (td, J=8.4, 2.4 Hz, 1H), 5.95 (q, J=7.1, 6.9 Hz, 1H), 1.97 (d, J=7.1 Hz, 3H).

Step 5: Preparation of (S)-2-(1-(7-fluoro-2-(pyridine-2-yl)quinoline-3-yl)ethyl)isoindoline-1,3-dione 1 g (2.819 mmol) of (S)-2-(1-(2-chloro-7-fluoroquinoline-3-yl)ethyl)isoindoline-1,3-dione prepared in step 4 was dissolved in 1,4-dioxane (5 mL), to which 163 mg (0.141 mmol) of Pd(PPh₃)₄ and 1.25 g (3.383 mmol) of 2-(tributylstanyl)-pyridine were added, followed by reflux at 100° C. for 3 days under argon atmosphere. Water and ethyl acetate were added to the reaction mixture, followed by extraction. The extracted organic layer was dried (Na₂SO₄), filtered, and concentrated under reduced pressure. The residue was separated by column chromatography (SiO₂, eluent: hexane/ethyl acetate, 4/1) to give 500 mg of the target compound (S)-2-(1-(7-fluoro-2-(pyridine-2-yl)quinoline-3-yl)ethyl)isoindoline-1,3-dione as a white solid (1.258 mmol, yield: 91%).

¹H NMR (300 MHz, CDCl₃) δ 8.69 (s, 1H), 8.65 (d, J=5.0 Hz, 1H), 7.90~7.97 (m, 1H), 7.60-7.76 (m, 7H), 7.28~7.42 (m, 2H), 6.31 (q, J=7.4, 7.1 Hz, 1H), 1.98 (d, J=7.5 Hz, 3H).

Step 6: Preparation of (S)-1-(7-fluoro-2-(pyridine-2-yl)quinoline-3-yl)ethane-1-amine 500 mg (1.258 mmol) of (S)-2-(1-(7-fluoro-2-(pyridine-2-yl)quinoline-3-yl)ethyl)isoindoline-1,3-dione prepared in step 5 was dissolved in ethanol (20 mL), to which 612 µL (12.58 mmol) of hydrazine hydrate was added, followed by reflux for 2 hours. The reaction mixture was cooled down at room temperature, and then filtered. The filtrate was added with ethyl acetate and water, followed by extraction. The extracted organic layer was dried (Na₂SO₄), filtered, and concentrated under reduced pressure. The residue was separated by column chromatography (SiO₂, eluent: dichloromethane/methanol, 20/1→dichloromethane/methanol, 10/1) to give 312 mg of the target compound (S)-1-(7-fluoro-2-(pyridine-2-yl)quinoline-3-yl)ethane-1-amine as a yellow liquid (1.167 mmol, yield: 93%).

¹H NMR (300 MHz, CDCl₃) δ 8.70 (d, J=4.6 Hz, 1H), 8.43 (s, 1H), 7.82~7.95 (m, 3H), 7.75 (dd, J=9.7, 2.4 Hz, 1H), 7.31~7.41 (m, 2H), 4.63 (q, J=6.7, 6.7 Hz, 1H), 2.01 (br s, 2H), 1.43 (d, J=6.8 Hz, 3H).

Preparative Example 18: Preparation of 1-(6-fluoro-3-(pyridine-2-yl)quinoline-2-yl)ethane-1-amine

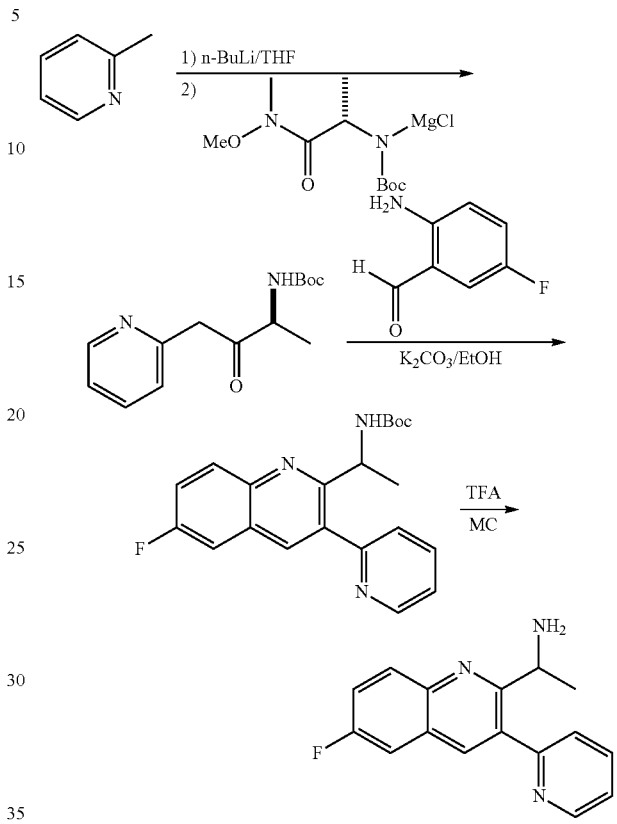

Step 1: Preparation of tert-butyl (S)-(3-oxo-4-(pyridine-2-yl)butane-2-yl)carbamate 5 g (21.526 mmol) of tert-butyl (S)-(1-(methoxy(methyl)amino)-1-oxopropane-2-yl)carbamate was dissolved in anhydrous THF (40 mL), to which 16.6 mL (21.526 mmol) of isopropylmagnesium chloride lithium chloride solution was added at −40° C., followed by stirring at −30° C. for 30 minutes. The reaction mixture was cooled down to −40° C. 2.6 g (27.984 mmol) of 2-picoline was dissolved in anhydrous THF (20 mL), to which 11 mL (27.984 mmol) of 2.5 M n-BuLi was added at −40° C., followed by stirring at −20° C. for 1 hour.

This solution was added to the reaction mixture above, followed by stirring at −20° C.~−10° C., for 3 hours. The reaction mixture was frozen at −78° C., to which saturated ammoniumchloride aqueous solution was added. Ethyl acetate and water were added thereto, followed by extraction. The extracted organic layer was dried (Na₂SO₄), filtered, and concentrated under reduced pressure. The residue was separated by column chromatography (SiO₂, eluent: hexane/ethyl acetate, 4/1) to give 5 g of the target compound tert-butyl (S)-(3-oxo-4-(pyridine-2-yl)butane-2-yl)carbamate as a yellow liquid (18.916 mmol, yield: 99%).

¹H NMR (300 MHz, CDCl₃) δ 8.55 (d, J=4.0 Hz, 1H), 7.66 (td, J=7.8, 1.8 Hz, 1H), 7.16~7.24 (m, 2H), 5.37 (br s, 1H), 4.39~4.49 (m, 1H), 3.95~4.11 (m, 2H), 1.45 (s, 9H), 1.37 (d, J=7.2 Hz, 3H).

Step 2: Preparation of tert-butyl(1-(6-fluoro-3-(pyridine-2-yl)quinoline-2-yl)ethyl)carbamate 254 mg (0.916 mmol) of tert-butyl (S)-(3-oxo-4-(pyridine-2-yl)butane-2-yl)carbamate prepared in step 1, 134 mg (0.961 mmol) of 2-amino-5-fluorobenzaldehyde, and 398 mg (2.883 mmol) of potassiumcarbonate ($K_2CO_3$) were dissolved in ethanol (3 mL), followed by stirring at 90° C. for 2 hours. The reaction mixture was added with ethyl acetate and water, followed by extraction. The extracted organic layer was dried ($Na_2SO_4$), filtered, and concentrated under reduced pressure. The residue was separated by column chromatography ($SiO_2$, eluent: hexane/ethyl acetate, 5/1) to give 250 mg of the target compound tert-butyl(1-(6-fluoro-3-(pyridine-2-yl)quinoline-2-yl)ethyl)carbamate as a yellow solid (0.680 mmol, yield: 71%).

$^1$H NMR (300 MHz, CDCl$_3$) δ 8.76 (d, J=4.5 Hz, 1H), 8.08~8.15 (m, 2H), 7.84 (td, J=7.9, 1.9 Hz, 1H), 7.41~7.60 (m, 3H), 7.35 (t, J=4.5 Hz, 1H), 6.34 (d, J=7.6 Hz, 1H), 5.37~5.48 (m, 1H), 1.45 (s, 9H), 1.33 (d, J=6.3 Hz, 3H).

Step 3: Preparation of 1-(6-fluoro-3-(pyridine-2-yl)quinoline-2-yl)ethane-1-amine 250 mg (0.680 mmol) of tert-butyl(1-(6-fluoro-3-(pyridine-2-yl)quinoline-2-yl)ethyl)carbamate prepared in step 2 was dissolved in dichloromethane (3 mL), to which 1 mL of TFA was added, followed by stirring at room temperature for 3 hours. The reaction mixture was filtered under reduced pressure and neutralized with NaHCO$_3$ aqueous solution. The reaction mixture was added with dichloromethane and water, followed by extraction. The extracted organic layer was separated, dried (Na$_2$SO$_4$), filtered, and concentrated under reduced pressure. The residue was separated by column chromatography (SiO$_2$, eluent: hexane/ethyl acetate, 5/1) to give 120 mg of the target compound 1-(6-fluoro-3-(pyridine-2-yl)quinoline-2-yl)ethane-1-amine as a yellow oil (0.449 mmol, yield: 66%).

$^1$H NMR (500 MHz, CDCl$_3$) δ 8.75 (d, J=4.1 Hz, 1H), 8.01~8.15 (m, 2H), 7.84 (td, J=7.8, 1.5 Hz, 1H), 7.40~7.50 (m, 3H), 7.33~7.39 (m, 1H), 4.49 (br s, 1H), 2.11 (br s, 2H), 1.39 (d, J=5.6 Hz, 3H).

Preparative Example 19: Preparation of (S)-3-(1-aminoethyl)-8-chloro-4-fluoro-2-phenylisoquinoline-1(2H)-one

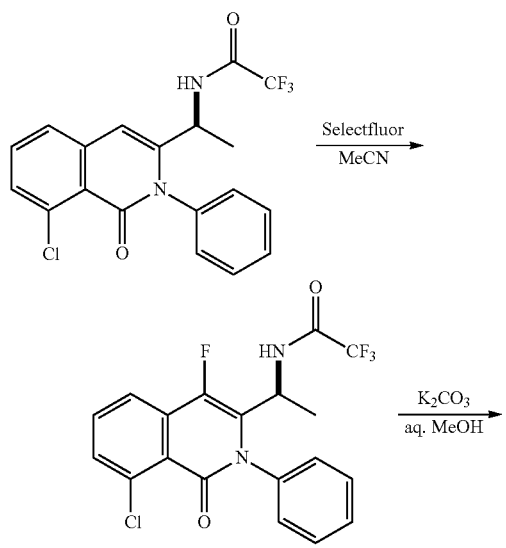

Step 1: Preparation of (S)—N-(1-(8-chloro-4-fluoro-1-oxo-2-phenyl-1,2-dihydroisoquinoline-3-yl)ethyl)-2,2,2-trifluoroacetamide

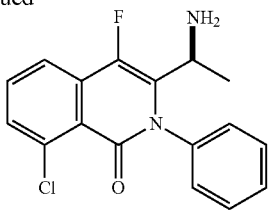

1.97 g (5.0 mmol, 1 equivalent) of (S)—N-(1-(8-chloro-1-oxo-2-phenyl-1,2-dihydroisoquinoline-3-yl)ethyl)-2,2,2-trifluoroacetamide prepared in step 6 of Preparative Example 10, Selectfluor (1.5 equivalent), and anhydrous CH$_3$CN (30 mL) were mixed, which was refluxed for 12 hours. The reaction mixture was cooled down at room temperature. Water and ethyl acetate were added thereto, followed by extraction. The extracted organic layer was washed with saturated NaHCO$_3$ aqueous solution, separated, dried (Na$_2$SO$_4$), filtered, and concentrated under reduced pressure. The residue was separated by column chromatography (SiO$_2$, eluent: hexane/ethyl acetate, 10/1→hexane/ethyl acetate, 3/1) to give 1.61 g of the target compound (S)—N-(1-(8-chloro-4-fluoro-1-oxo-2-phenyl-1,2-dihydroisoquinoline-3-yl)ethyl)-2,2,2-trifluoroacetamide as a white solid (3.9 mmol, yield: 78%).

$^1$H NMR (500 MHz, CDCl$_3$) δ 10.99 (br d, J=5.4 Hz, 1H), 7.77-7.85 (m, 2H), 7.64-7.71 (m, 1H), 7.50-7.61 (m, 3H), 7.42-7.46 (m, 2H), 4.17-4.24 (m, 1H), 1.47 (d, J=7.1 Hz, 3H).

Step 2: Preparation of (S)-3-(1-aminoethyl)-8-chloro-4-fluoro-2-phenylisoquinoline-1(2H)-one 1.20 g of (S)-3-(1-aminoethyl)-8-chloro-4-fluoro-2-phenylisoquinoline-1(2H)-one was prepared as a white solid by using 1.65 g (4.0 mmol) of (S)—N-(1-(8-chloro-4-fluoro-1-oxo-2-phenyl-1,2-dihydroisoquinoline-3-yl)ethyl)-2,2,2-trifluoroacetamide prepared in step 1 by the same manner as described in step 8 of Preparative Example 10 (3.8 mmol, yield: 95%).

$^1$H NMR (500 MHz, CDCl$_3$) δ 7.74 (d, j=8.0 hz, 1H), 7.64 (t, J=7.9 Hz, 1H), 7.54-7.60 (m, 3H), 7.47-7.53 (m, 1H), 7.32-7.35 (m, 1H), 7.22-7.25 (m, 1H), 3.57-3.64 (m, 1H), 1.85 (br s, 2H), 1.46 (d, J=6.9 Hz, 3H).

Preparative Example 20: Preparation of 4-chloro-8-(4-methoxybenzyl)-7,8-dihydropyrido[2,3-d]pyrimidine-5(6H)-one

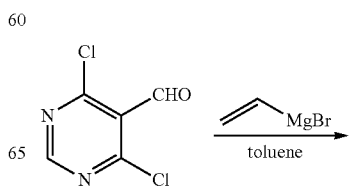

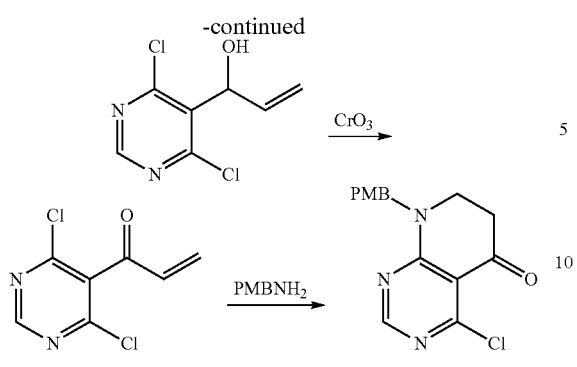

Step 1: Preparation of 1-(4,6-dichloropyrimidine-5-yl)propene-2-en-1-ol 200 mg (2.8 mmol) of 4,6-dichloropyrimidine-5-carbaldehyde was dissolved in anhydrous toluene (15 mL), to which 2.1 mL (1.2 equivalent) of vinylmagnesium chloride (1.6 M in THF) was slowly added at −20° C., followed by stirring for 1 hour. Saturated NH$_4$Cl aqueous solution (10 mL) was added thereto. The reaction mixture was extracted by using ethyl acetate. The extracted organic layer was washed with saturated brine, separated, dried (Na$_2$SO$_4$), filtered, and concentrated under reduced pressure. The residue was separated by column chromatography (SiO$_2$, eluent: hexane/ethyl acetate, 10/1) to give 475 mg of the target compound 1-(4,6-dichloropyrimidine-5-yl)propene-2-en-1-ol as a yellow oil (2.3 mmol, yield: 82%).

$^1$H NMR (300 MHz, CDCl$_3$) δ 8.72 (s, 1H), 6.23-6.12 (m, 1H), 5.90 (s, —OH), 5.43-5.34 (m, 2H).

Step 2: Preparation of 1-(4,6-dichloropyrimidine-5-yl)propene-2-en-1-one 323 mg of 1-(4,6-dichloropyrimidine-5-yl)propene-2-en-1-one was prepared as a colorless oil by using 394 mg (1.9 mmol) of 1-(4,6-dichloropyrimidine-5-yl)propene-2-en-1-ol prepared in step 1 by the same manner as described in step 3 of Example 1 (1.57 mmol, yield: 83%).

$^1$H NMR (300 MHz, CDCl$_3$) δ 8.87 (s, 1H), 6.69-6.59 (m, 1H), 6.31 (d, J=10.6 Hz, 1H), 6.08 (d, J=17.9 Hz, 1H).

Step 3: Preparation of 4-chloro-8-(4-methoxybenzyl)-7,8-dihydropyrido[2,3-d]pyrimidine-5(6H)-one 4-methoxybenzylamine (1.1 equivalent) was dissolved in anhydrous CH$_2$CL$_2$ (5 mL), which was slowly added to the reaction mixture comprising 300 mg (1.48 mmol) of 1-(4,6-dichloropyrimidine-5-yl)propene-2-en-1-one prepared in step 2, DIPEA (1.1 equivalent), and anhydrous CH$_2$CL$_2$ (15 mL) at 0° C. The mixture was heated at room temperature, followed by stirring for 1 hour. The reaction mixture was added with 1N HCl (5 mL), followed by extraction with ethyl acetate. The extracted organic layer was washed with saturated NaHCO$_3$ aqueous solution, separated, dried (Na$_2$SO$_4$), filtered, and concentrated under reduced pressure. The residue was separated by column chromatography (SiO$_2$, eluent: hexane/ethyl acetate, 2/1) to give 413 mg of the target compound 4-chloro-8-(4-methoxybenzyl)-7,8-dihydropyrido[2,3-d]pyrimidine-5(6H)-one as a pale yellow solid (1.36 mmol, yield: 92%).

$^1$H NMR (300 MHz, CDCl$_3$) δ 8.72 (s, 1H), 6.23-6.12 (m, 1H), 5.90

$^1$H NMR (300 MHz, CDCl$_3$) δ 8.40 (s, 1H), 7.22 (d, J=8.5 Hz, 2H), 6.87 (d, J=8.5 Hz, 2H), 4.92 (s, 2H), 3.80 (s, 3H), 3.56 (m, 2H), 2.96 (m, 2H).

Preparative Example 21: Preparation of (S)-1-(6-fluoro-3-(pyridine-2-yl)quinoline-2-yl)ethane-1-amine

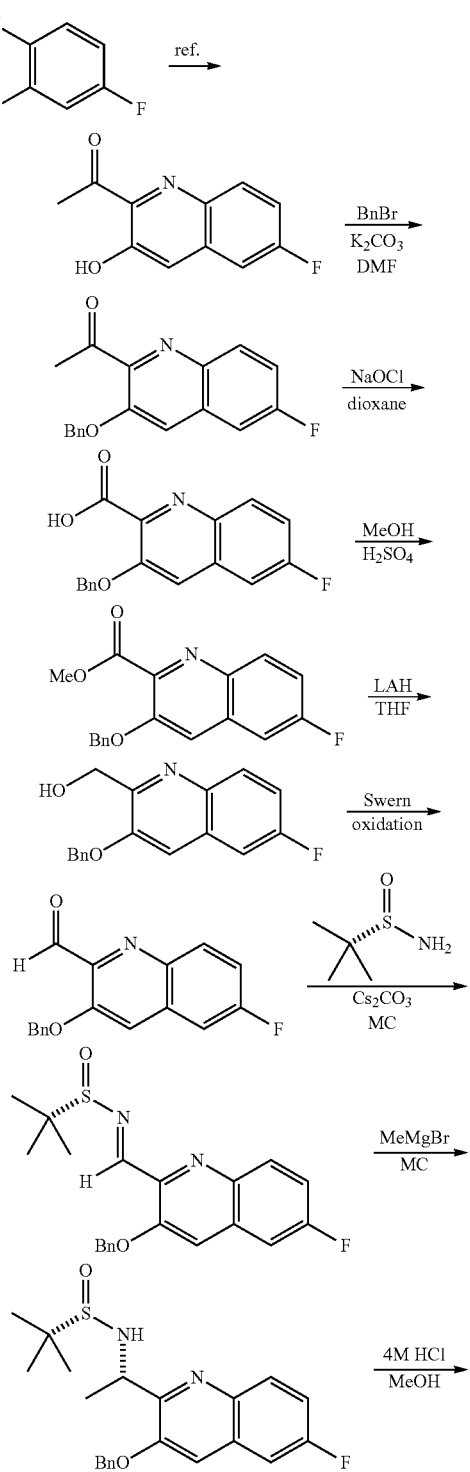

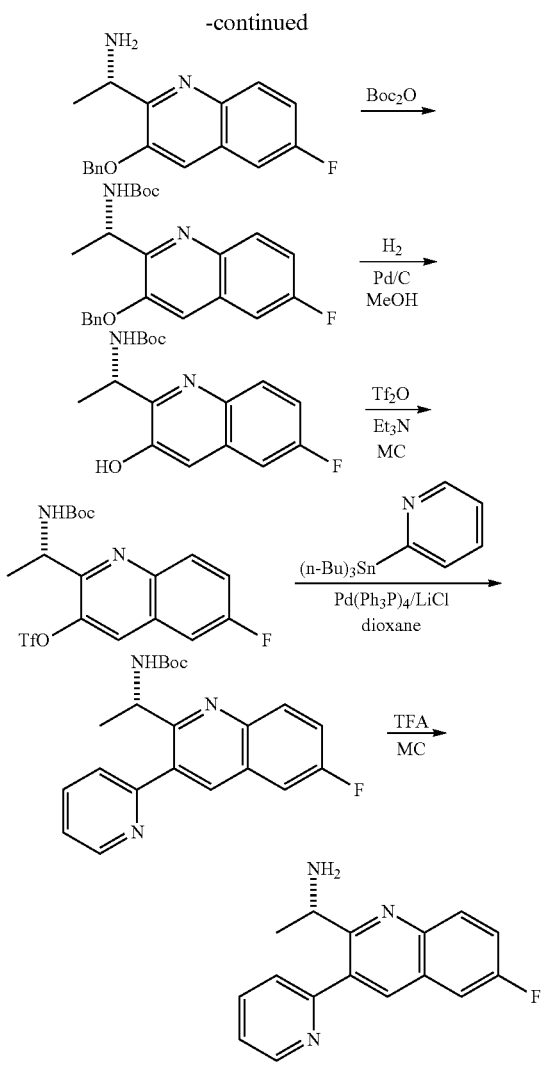

Step 1: Preparation of 1-(3-(benzyloxy)-6-fluoro-quinoline-2-yl)ethane-1-one 20.52 g (100.0 mmol) of 1-(6-fluoro-3-hydroxyquinoline-2-yl)ethane-1-one [reference: WO 2010-151740], BnBr (1.1 equivalent), and K₂CO₃ (3 equivalent) were dissolved in anhydrous DMF (150 mL), followed by stirring at room temperature for 6 hours. The reaction solvent was eliminated under reduced pressure. Water and ethyl acetate were added to the reaction mixture, followed by extraction. The extracted organic layer was washed with saturated brine, separated, dried (Na₂SO₄), filtered, and concentrated under reduced pressure. The residue was separated by column chromatography (SiO₂, eluent: hexane/ethyl acetate, 10/1→hexane/ethyl acetate, 3/1) to give 29.53 g of the target compound 1-(3-(benzyloxy)-6-fluoroquinoline-2-yl)ethane-1-one as a pale brown oil (100.0 mmol, yield: 100%).

$^1$H NMR (300 MHz, CDCl₃) δ 8.00-8.10 (m, 1H), 7.28-7.57 (m, 8H), 5.26 (s, 2H), 2.76 (s, 3H).

Step 2: Preparation of 3-(benzyloxy)-6-fluoroquinoline-2-carboxylic Acid 28.06 g (95.0 mmol) of 1-(3-(benzyloxy)-6-fluoroquinoline-2-yl)ethane-1-one prepared in step 1 was dissolved in dioxane/H₂O (4/1, 300 mL), to which NaOCl aqueous solution (12%, 5 equivalent) was slowly added at room temperature for 30 minutes, followed by stirring for 5 hours. PH of the reaction mixture was adjusted (pH=4) with saturated 2 N HCl solution. The reaction mixture was extracted by using ethyl acetate. The extracted organic layer was washed with saturated brine, separated, dried (Na₂SO₄), filtered, and concentrated under reduced pressure. The residue was separated by column chromatography (SiO₂, eluent: hexane/ethyl acetate, 1/1→ethylacetate) to give 27.96 g of the target compound 3-(benzyloxy)-6-fluoroquinoline-2-carboxylic acid as a pale yellow oil (94.1 mmol, yield: 99%).

$^1$H NMR (300 MHz, CDCl₃) δ 8.05-8.12 (m, 1H), 7.67 (s, 1H), 7.28-7.60 (m, 7H), 5.37 (s, 2H).

Step 3: Preparation of methyl 3-(benzyloxy)-6-fluoroquinoline-2-carboxylate 26.76 g (90.0 mmol) of 3-(benzyloxy)-6-fluoroquinoline-2-carboxylic acid prepared in step 2, anhydrous MeOH (200 mL), CH(OMe)₃ (50 mL), and conc H₂SO₄ (2 mL) were mixed, followed by heating at 45° C. for 12 hours. The reaction mixture was slowly added to cold saturated NaHCO₃ aqueous solution, followed by extraction with ethyl acetate. The extracted organic layer was washed with saturated brine, separated, dried (Na₂SO₄), filtered, and concentrated under reduced pressure. The residue was separated by column chromatography (SiO₂, eluent: hexane/ethyl acetate, 10/1→hexane/ethylacetate, 3/1) to give 27.46 g of the target compound methyl 3-(benzyloxy)-6-fluoro-quinoline-2-carboxylate as a pale yellow solid (88.2 mmol, yield: 98%).

$^1$H NMR (300 MHz, CDCl₃) δ 8.07-8.14 (m, 1H), 7.50 (s, 1H), 7.28-7.49 (m, 7H), 5.28 (s, 2H), 4.04 (s, 3H).

Step 4: Preparation of (3-(benzyloxy)-6-fluoroquinoline-2-yl)methanol 14.17 g (50.0 mmol) of methyl 3-(benzyloxy)-6-fluoroquinoline-2-carboxylate prepared in step 3 was dissolved in anhydrous THF (200 mL). The reaction mixture was cooled down to 0° C., to which LiAlH₄ (1 equivalent) was slowly added for 10 minutes, followed by stirring for 1 hour. The reaction mixture was heated at room temperature, followed by stirring for 5 hours. The reaction mixture was added with diethylether (200 mL) and distilled water (10 mL) slowly to degrade LiAlH₄, followed by stirring for 1 hour. The mixture was added with anhydrous MgSO₄, dried, filtered, and concentrated. The obtained compound was separated by column chromatography (SiO₂, eluent: hexane/ethyl acetate, 10/1→hexane/ethylacetate, 1/1) to give 12.04 g of the target compound (3-(benzyloxy)-6-fluoroquinoline-2-yl)methanol as a pale yellow solid (42.5 mmol, yield: 85%).

$^1$H NMR (300 MHz, CDCl₃) δ 7.97-8.05 (m, 1H), 7.27-7.46 (m, 8H), 5.22 (s, 2H), 4.93 (d, J=4.6 Hz, 2H), 4.54 (t, J=4.6 Hz, 1H, OH).

Step 5: Preparation of 3-(benzyloxy)-6-fluoroquinoline-2-carbaldehyde 11.91 g of 3-(benzyloxy)-6-fluoroquinoline-2-carbaldehyde was prepared as a pale yellow solid by Swern oxidation using 12.00 g (42.4 mmol) of (3-(benzyloxy)-6-fluoroqui-noline-2-yl)methanol prepared in step 4 (42.3 mmol, yield: 100%).

¹H NMR (300 MHz, CDCl₃) δ 10.53 (s, 1H), 8.20 (m, 1H), 7.59 (s, 1H), 7.25-7.58 (m, 7H), 5.32 (s, 2H).

Step 6: Preparation of (S)-(E)-((3-(benzyloxy)-6-fluoroquinoline-2-yl)methylene)-2-methylpropane-2-sulfinamide 5.63 g (20.00 mmol) of 3-(benzyloxy)-6-fluoroquinoline-2-carbaldehyde prepared in step 5, (S)-(−)-2-methyl-2-propanesulfinamide (1.1 equivalent), and Cs₂CO₃ (1.2 equivalent) were dissolved in anhydrous CH₂Cl₂ (30 mL), followed by stirring at room temperature for 12 hours. The reaction mixture was filtered and concentrated. The obtained compound was separated by column chromatography (SiO₂, eluent: hexane/ethyl acetate, 7/1→hexane/ethylacetate, 3/1) to give 7.30 g of the target compound (S)-(E)-((3-(benzyloxy)-6-fluoroquinoline-2-yl)methylene)-2-methylpropane-2-sulfinamide as a pale yellow solid (18.99 mmol, yield: 95%).
¹H NMR (300 MHz, CDCl₃) δ 9.22 (s, 1H), 8.14-8.20 (m, 1H), 7.53 (s, 1H), 7.28-7.50 (m, 7H), 5.30 (s, 2H), 1.28 (s, 9H).

Step 7: Preparation of (S)—N—((S)-1-(3-(benzyloxy)-6-fluoroquinoline-2-yl)ethyl)-2-methylpropane-2-sulfinamide 3.85 g (10.00 mmol) of (S)-(E)-((3-(benzyloxy)-6-fluoroquinoline-2-yl)methylene)-2-methylpropane-2-sulfinamide prepared in step 6 was dissolved in anhydrous CH₂Cl₂ (50 mL), which was frozen at −78° C. MeMgBr (3 M diethylether solution, 3 equivalent) was slowly added thereto for 10 minutes. 2 hours later, the reaction mixture was slowly heated to −20° C., followed by stirring for 1 hour. Saturated NH₄Cl aqueous solution (50 mL) was added thereto. The reaction mixture was heated at room temperature, followed by extraction with ethyl acetate. The extracted organic layer was washed with saturated brine, separated, dried (Na₂SO₄), filtered, and concentrated under reduced pressure. The residue was separated by column chromatography (SiO₂, eluent: hexane/ethyl acetate, 3/1→hexane/ethylacetate, 1/2) to give 3.00 g of the target compound (S)—N—((S)-1-(3-(benzyloxy)-6-fluoroquinoline-2-yl)ethyl)-2-methylpropane-2-sulfinamide as a pale yellow solid (7.40 mmol, yield: 74%).
¹H NMR (500 MHz, CDCl₃) δ 7.97-8.01 (m, 1H), 7.45-7.52 (m, 4H), 7.38-7.44 (m, 2H), 7.28-7.33 (m, 2H), 5.60 (d, J=6.5 Hz, 1H), 5.24 (s, 2H), 5.08-5.13 (m, 1H), 1.53 (d, J=6.7 Hz, 3H), 1.32 (s, 9H).

Step 8: Preparation of (S)-1-(3-(benzyloxy)-6-fluoroquinoline-2-yl)ethane)-1-amine 2.81 g (7.02 mmol) of (S)—N—((S)-1-(3-(benzyloxy)-6-fluoroquinoline-2-yl)ethyl)-2-methylpropane-2-sulfinamide prepared in step 7 was dissolved in anhydrous MeOH (10 mL), to which 4M HCl (dioxane solution) was added at room temperature, followed by stirring for 1 hour. The solvent was eliminated under reduced pressure. The mixture was added slowly with saturated NaHCO₃ aqueous solution, followed by extraction with ethyl acetate. The extracted organic layer was washed with saturated brine, separated, dried (Na₂SO₄), filtered, and concentrated under reduced pressure. The obtained compound was separated by column chromatography (SiO₂, eluent: MeOH/CH₂Cl₂, 1/20→MeOH/CH₂Cl₂, 1/10) to give 2.00 g of the target compound (S)-1-(3-(benzyloxy)-6-fluoroquinoline-2-yl)ethane)-1-amine as a pale white solid (6.75 mmol, yield: 96%).
¹H NMR (300 MHz, CDCl₃) δ 7.96-8.02 (m, 1H), 7.25-7.50 (m, 8H), 5.21 (s, 2H), 4.60-4.70 (m, 1H), 2.04 (br s, 2H), 1.47 (d, J=6.6 Hz, 3H).

Step 9: Preparation of tert-butyl (S)-1-(3-(benzyloxy)-6-fluoroquinoline-2-yl)ethyl)carbamate 1.90 g (6.41 mmol) of (S)-1-(3-(benzyloxy)-6-fluoroquinoline-2-yl)ethane)-1-amine prepared in step 8 was dissolved in anhydrous CH₂Cl₂ (15 mL), to which Boc₂O (1.3 equivalent) was added at room temperature, followed by stirring for 2 hours. The reaction mixture was concentrated under reduced pressure. The obtained compound was separated by column chromatography (SiO₂, eluent: hexane/ethyl acetate, 10/1→hexane/ethylacetate, 3/1) to give 2.52 g of the target compound tert-butyl (S)-1-(3-(benzyloxy)-6-fluoroquinoline-2-yl)ethyl)carbamate as a white solid (6.36 mmol, yield: 99%).
¹H NMR (300 MHz, CDCl₃) δ 8.00-8.04 (m, 1H), 7.30-7.52 (m, 8H), 6.44 (br d, J=7.6 Hz, 1H), 5.38-5.45 (m, 1H), 5.20-5.27 (m, 2H), 1.47-1.56 (m, 12H).

Step 10: Preparation of tert-butyl (S)-(1-(6-fluoro-3-hydroxyquinoline-2-yl)ethyl)carbamate 1.98 g (4.99 mmol) of tert-butyl (S)-1-(3-(benzyloxy)-6-fluoroquinoline-2-yl)ethyl)carbamate prepared in step 9 was dissolved in MeOH (20 mL), to which 200 mg of 10% Pd/C was added, followed by hydrogenation at room temperature for 1 hour under 1 atm H₂. The reaction mixture was filtered with celite pad and concentrated under reduced pressure. The obtained compound was separated by column chromatography (SiO₂, eluent: hexane/ethyl acetate, 3/1→hexane/ethylacetate, 1/1) to give 1.53 g of the target compound tert-butyl (S)-(1-(6-fluoro-3-hydroxyquinoline-2-yl)ethyl)carbamate as a white solid (4.99 mmol, yield: 100%).
¹H NMR (300 MHz, CDCl₃) δ 9.47 (br s, 1H), 7.87-7.90 (m, 1H), 7.18-7.23 (m, 1H), 7.00-7.04 (m, 1H), 6.84-6.89 (m, 1H), 5.52 (br s, 1H), 5.29-5.36 (m, 1H), 1.62 (d, J=6.8 Hz, 3H), 1.53 (s, 9H).

Step 11: Preparation of (S)-2-(1-((tert-butoxycarbonyl)amino)ethyl)-6-fluoroquinoline-3-yl trifluoromethanesulfonate 1.50 g (4.90 mmol) of tert-butyl (S)-(1-(6-fluoro-3-hydroxyquinoline-2-yl)ethyl)carbamate prepared in step 10 and anhydrous Et₃N (3 equivalent) were dissolved in anhydrous CH₂Cl₂ (15 mL), to which Tf₂O (1.2 equivalent) was slowly added at 0° C. for 5 minutes, followed by stirring for 2 hours. The solvent was eliminated under reduced pressure. The reaction mixture was added with water, followed by extraction with ethyl acetate. The extracted organic layer was washed with saturated brine, separated, dried (Na₂SO₄), filtered, and concentrated under reduced pressure. The obtained compound was separated by column chromatography (SiO₂, eluent: hexane/ethyl acetate, 10/1→hexane/ethylacetate, 5/1) to give 2.15 g of the target compound (S)-2-(1-((tert-butoxycarbonyl)amino)ethyl)-6-fluoroquinoline-3-yl trifluoromethanesulfonate as a colorless oil (4.90 mmol, yield: 100%).
¹H NMR (300 MHz, CDCl₃) δ 8.11-8.17 (m, 1H), 8.08 (s, 1H), 7.53-7.62 (m, 1H), 7.47-7.52 (m, 1H), 7.98 (br s, 1H), 5.30-5.40 (m, 1H), 1.54 (d, J=6.7 Hz, 3H), 1.48 (s, 9H).

Step 12: Preparation of tert-butyl (S)-(1-(6-fluoro-3-(pyridine-2-yl)quinoline-2-yl)ethyl)carbamate 438 mg (1.00 mmol) of (S)-2-(1-((tert-butoxycarbonyl)amino)ethyl)-6-fluoroquinoline-3-yl trifluoromethanesulfonate prepared in step 11, 2-(tributylstanyl)pyridine (2.0 equivalent), LiCl (3 equivalent), Pd(Ph$_3$P)$_4$ (0.1 equivalent), and anhydrous dioxane (13 mL) were mixed, which was heated at 100° C. for 24 hours under argon atmosphere. The reaction mixture was cooled down at room temperature and filtered with celite pad. The filtrate was added with water, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 3/1) to give 286 mg of the target compound tert-butyl (S)-(1-(6-fluoro-3-(pyridine-2-yl)quinoline-2-yl)ethyl)carbamate as a pale yellow solid (0.78 mmol, yield: 78%).

$^1$H NMR (300 MHz, CDCl$_3$) δ 8.76 (d, J=4.5 Hz, 1H), 8.08-8.15 (m, 2H), 7.84 (td, J=7.9, 1.9 Hz, 1H), 7.41-7.60 (m, 3H), 7.35 (t, J=4.5 Hz, 1H), 6.34 (d, J=7.6 Hz, 1H), 5.37-5.48 (m, 1H), 1.45 (s, 9H), 1.33 (d, J=6.3 Hz, 3H).

Step 13: Preparation of (S)-1-(6-fluoro-3-(pyridine-2-yl)quinoline-2-yl)ethane-1-amine (S)-1-(6-fluoro-3-(pyridine-2-yl)quinoline-2-yl)ethane-1-amine was prepared by using tert-butyl (S)-(1-(6-fluoro-3-(pyridine-2-yl)quinoline-2-yl)ethyl)carbamate prepared in step 12 by the same manner as described in step 3 of Preparative Example 18.

Preparative Example 22: Preparation of 1-(6-fluoro-3,4-di(pyridine-2-yl)quinoline-2-yl)ethane-1-amine

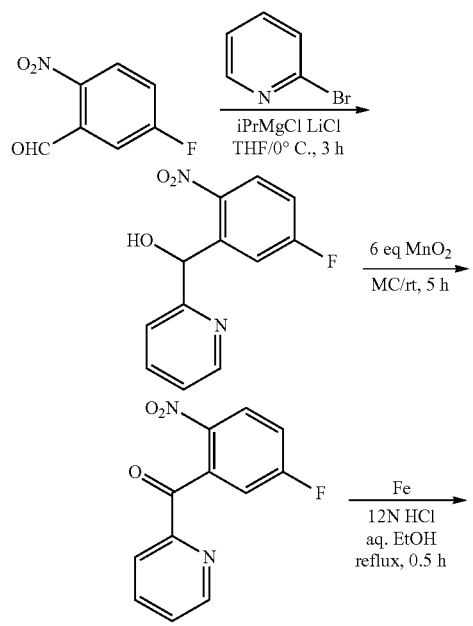

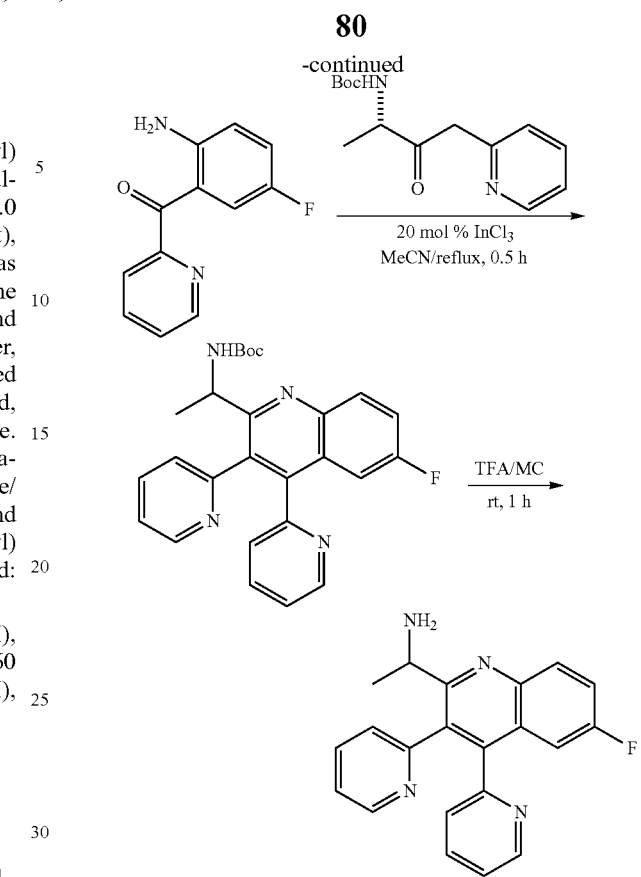

Step 1: Preparation of (5-fluoro-2-nitrophenyl)(pyridine-2-yl)methanol 1.90 g (12.0 mmol) of 2-bromopyridine was dissolved in anhydrous THF (20 mL), which was cooled down to 0° C. Isopropylmagnesium chloride lithium chloride complex solution (1.3M THF solution, 1.2 equivalent) was slowly added thereto for 5 minutes, followed by stirring for 1 hour. 1.69 g (10.0 mmol) of 3-fluoro-6-nitrobenzaldehyde was dissolved in anhydrous THF (10 mL), which was slowly added to the mixture above for 10 minutes, followed by stirring for 1 hour. The reaction mixture was heated to room temperature, followed by stirring for 2 hours. Saturated NH$_4$Cl solution (20 mL) was added thereto, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 5/1) to give 1.61 g of the target compound (5-fluoro-2-nitrophenyl)(pyridine-2-yl)methanol as a pale yellow solid (6.5 mmol, yield: 65%).

$^1$H NMR (300 MHz, CDCl$_3$) δ 8.56-8.60 (m, 1H), 8.01-8.06 (m, 1H), 7.65-7.72 (m, 1H), 7.32-7.41 (m, 2H), 7.23-7.30 (m, 1H), 7.05-7.13 (m, 1H), 6.51 (s, 1H), 5.44 (br s, 1H).

Step 2: Preparation of (5-fluoro-2-nitrophenyl)(pyridine-2-yl)methanone 1.50 g (6.04 mmol) of (5-fluoro-2-nitrophenyl)(pyridine-2-yl)methanol prepared in step 1 was dissolved in anhydrous CH$_2$Cl$_2$ (30 mL), to which MnO$_2$ (6 equivalent) was added, followed by stirring at room temperature for 5 hours. The reaction mixture was filtered with celite pad and concentrated under reduced pressure. The obtained compound was separated by column chromatography (SiO$_2$, eluent: hexane/ethyl acetate, 10/1→hexane/ethylacetate, 4/1) to give 1.48 g of the target compound (5-fluoro-2-니트로 phenyl) (pyridine-2-yl)methanone as a pale brown solid (6.01 mmol, yield: 100%).

$^1$H NMR (300 MHz, CDCl$_3$) δ 8.49-8.52 (m, 1H), 8.22-8.29 (m, 2H), 7.88-7.96 (m, 1H), 7.43-7.48 (m, 1H), 7.23-7.36 (m, 2H).

Step 3: Preparation of (2-amino-5-fluorophenyl) (pyridine-2-yl)methanone 1.40 g (5.69 mmol) of (5-fluoro-2-nitrophenyl) (pyridine-2-yl)methanone and Fe (5 equivalent) were dissolved in EtOH/H$_2$O (4/1, 30 mL), to which 2~3 drops of conc HCl were added. The reaction mixture was heated at 85° C. for 30 minutes and cooled down to room temperature. The reaction mixture was filtered with celite pad, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 4/1) to give 1.23 g of the target compound (2-amino-5-fluorophenyl) (pyridine-2-yl)methanone as a pale yellow solid (5.69 mmol, yield: 100%).

$^1$H NMR (300 MHz, CDCl$_3$) δ 8.71 (d, J=4.7 Hz, 1H), 7.92-7.80 (m, 2H), 7.52-7.43 (m, 2H), 7.12-7.05 (m, 1H), 6.66-6.72 (m, 1H), 6.13 (br s, 2H).

Step 4: Preparation of tert-butyl (1-(6-fluoro-3,4-di (pyridine-2-yl)quinoline-2-yl)ethyl)carbamate 1.08 g (5.0 mmol) of (2-amino-5-fluorophenyl) (pyridine-2-yl)methanone prepared in step 3, tert-butyl (S)-3-oxo-4-(pyridine-2-yl)carbamate (1.0 equivalent), and InCl$_3$(0.2 equivalent) were added to anhydrous CH$_3$CN (10 mL), which was heated at 80° C. for 15 minutes and cooled down to room temperature. The reaction mixture was filtered with celite pad, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 3/1) to give 2.22 g of the target compound tert-butyl (1-(6-fluoro-3,4-di(pyridine-2-yl)quinoline-2-yl)ethyl)carbamate as a white solid (4.99 mmol, yield: 100%).

$^1$H NMR (300 MHz, CDCl$_3$) δ 8.60-8.67 (m, 2H), 8.15-8.21 (m, 1H), 7.45-7.55 (m, 3H), 7.10-7.21 (m, 3H), 7.05 (br t, J=6.8 Hz, 2H), 6.35 (br s, 1H), 5.03 (br s, 1H), 1.44 (s, 9H).

Step 5: Preparation of 1-(6-fluoro-3,4-di(pyridine-2-yl)quinoline-2-yl)ethane-1-amine 133 mg (0.3 mmol) of tert-butyl (1-(6-fluoro-3,4-di(pyridine-2-yl)quinoline-2-yl)ethyl)carbamate prepared in step 4 was dissolved in CH$_2$Cl$_2$ (10 mL), to which TFA (1.0 mL) was added, followed by stirring at room temperature for 1 hour. The reaction mixture was added with saturated NaHCO$_3$ aqueous solution (25 mL), followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: MeOH/CH$_2$Cl$_2$, 1/20→MeOH/CH$_2$Cl$_2$, 1/10) to give 117 mg of the target compound 1-(6-fluoro-3,4-di(pyridine-2-yl)quinoline-2-yl)ethane-1-amine as a white solid (0.3 mmol, yield: 100%).

$^1$H NMR (300 MHz, CDCl$_3$) δ 8.66 (dd, J=12.0, 4.1 Hz, 2H), 8.11 (dd, J=9.0, 5.5 Hz, 1H), 7.61-7.46 (m, 3H), 7.24-7.16 (m, 3H), 7.04-6.95 (m, 2H), 4.78 (br s, 1H), 2.54 (br s, 2H), 1.51 (d, J=6.1 Hz, 3H).

Preparative Example 23: Preparation of (S)-1-(6-fluoro-3-phenyl-4-(pyridine-2-yl)quinoline-2-yl) ethane-1-amine

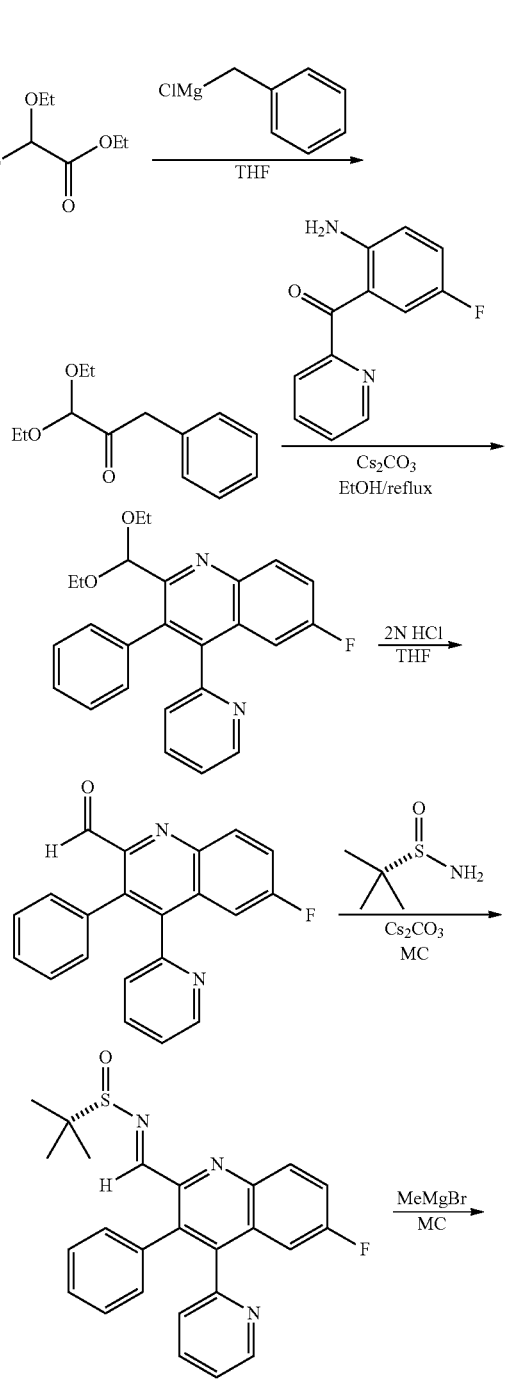

-continued

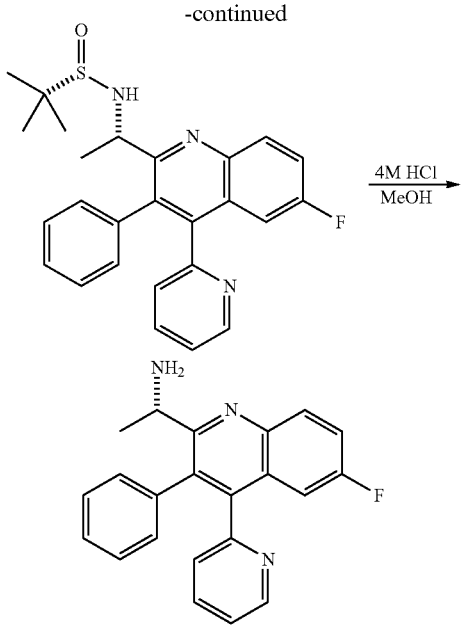

Step 1: Preparation of 1,1-diethoxy-3-phenylpropane-2-one 5.29 g (30.0 mmol) of ethyl diethoxyacetate was dissolved in anhydrous THF (50 mL), which was frozen at −78° C. PhMgCl (2M THF solution, 1.5 equivalent) was added slowly thereto for 5 minutes, followed by stirring for 12 hours. While cooling the reaction mixture with ice water, saturated NH$_4$Cl aqueous solution (50 mL) was slowly added thereto. The reaction mixture was extracted by using ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 20/1→hexane/ethylacetate, 5/1) to give 6.21 g of the target compound 1,1-diethoxy-3-phenylpropane-2-one as a colorless oil (27.9 mmol, yield: 93%).

$^1$H NMR (300 MHz, CDCl$_3$) δ 7.18-7.35 (m, 5H), 4.63 (s, 1H), 3.89 (s, 2H), 3.63-3.71 (m, 2H), 3.47-3.61 (m, 2H), 1.19-1.27 (m, 6H).

Step 2: Preparation of 2-(diethoxymethyl)-6-fluoro-3-phenyl-4-(pyridine-2-yl)quinoline 3.33 g (15.0 mmol) of 1,1-diethoxy-3-phenylpropane-2-one prepared in step 1, 1.62 g (7.49 mmol) of (2-amino-5-fluorophenyl) (pyridine-2-yl)methanone, and Cs$_2$CO$_3$ (30.0 mmol) were added to EtOH (40 mL), followed by reflux for 12 hours. The reaction mixture was cooled down to room temperature. The reaction mixture was added with water, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 3/1) to give 3.02 g of the target compound 2-(diethoxymethyl)-6-fluoro-3-phenyl-4-(pyridine-2-yl)quinoline as a white solid (7.50 mmol, yield: 100%).

$^1$H NMR (300 MHz, CDCl$_3$) δ 8.64-8.67 (m, 1H), 8.32-8.38 (m, 1H), 7.44-7.54 (m, 2H), 7.14-7.26 (m, 6H), 7.03-7.08 (m, 1H), 6.93-6.97 (m, 1H), 5.37 (s, 1H), 3.55-3.80 (m, 2H), 3.39-3.46 (m, 2H), 1.17 (t, J=7.0 Hz, 6H).

Step 3: Preparation of 6-fluoro-3-phenyl-4-(pyridine-2-yl)quinoline-2-carbaldehyde 2.01 g (4.99 mmol) of 2-(diethoxymethyl)-6-fluoro-3-phenyl-4-(pyridine-2-yl)quinoline prepared in step 2 was dissolved in THF (20 mL), to which 2N HCl aqueous solution (20 mL) was added, followed by stirring at room temperature for 3 hours. Saturated NaHCO$_3$ aqueous solution was slowly added thereto, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 10/1→hexane/ethylacetate, 3/1) to give 1.64 g of the target compound 6-fluoro-3-phenyl-4-(pyridine-2-yl)quinoline-2-carbaldehyde as a pale yellow solid (4.99 mmol, yield: 100%).

$^1$H NMR (300 MHz, CDCl$_3$) δ 10.14 (s, 1H), 8.69-8.72 (m, 1H), 8.38-8.44 (m, 1H), 7.53-7.64 (m, 2H), 7.11-7.27 (m, 7H), 6.96-7.00 (m, 1H).

Step 4: Preparation of (S,E)-N-((6-fluoro-3-phenyl-4-(pyridine-2-yl)quinoline-2-yl)methylene)-2-methylpropane-2-sulfinamide 328 mg (1.0 mmol) of 6-fluoro-3-phenyl-4-(pyridine-2-yl)quinoline-2-carbaldehyde prepared in step 3 was reacted by the same manner as described in step 6 of Preparative Example 21. The obtained compound was separated by column chromatography (SiO$_2$, eluent: hexane/ethyl acetate, 4/1→hexane/ethylacetate, 1/1) to give 418 mg of the target compound (S,E)-N-((6-fluoro-3-phenyl-4-(pyridine-2-yl)quinoline-2-yl)methylene)-2-methylpropane-2-sulfinamide as a pale yellow solid (0.97 mmol, yield: 97%).

$^1$H NMR (500 MHz, CDCl$_3$) δ 8.70-8.72 (m, 2H), 8.38-8.40 (m, 1H), 7.56-7.58 (m, 2H), 6.95-7.28 (m, 8H), 1.18 (s, 9H).

Step 5: Preparation of (S)—N—((S)-1-(6-fluoro-3-phenyl-4-(pyridine-2-yl)quinoline-2-yl)ethyl)-2-methylpropane-2-sulfinamide 388 mg (0.90 mmol) of (S,E)-N-((6-fluoro-3-phenyl-4-(pyridine-2-yl)quinoline-2-yl)methylene)-2-methylpropane-2-sulfinamide prepared in step 4 was reacted by the same manner as described in step 7 of Preparative Example 21. The obtained compound was separated by column chromatography (SiO$_2$, eluent: CH$_2$Cl$_2$/ethyl acetate, 4/1→CH$_2$Cl$_2$/ethylacetate, 1/1) to give 306 mg of the target compound (S)—N—((S)-1-(6-fluoro-3-phenyl-4-(pyridine-2-yl)quinoline-2-yl)ethyl)-2-methylpropane-2-sulfinamide as a pale white solid (0.68 mmol, yield: 76%).

$^1$H NMR (300 MHz, CDCl$_3$) δ 8.62-8.67 (m, 1H), 8.08-8.15 (m, 1H), 7.35-7.56 (m, 4H), 7.11-7.25 (m, 3H), 7.01-7.07 (m, 1H), 6.90-7.00 (m, 2H), 5.61-5.92 (m, 1H), 4.66-4.80 (m, 1H), 1.29 (s, 9H), 1.20 (d, J=6.6 Hz, 3H).

Step 6: Preparation of (S)-1-(6-fluoro-3-phenyl-(pyridine-2-yl)quinoline-2-yl)ethane-1-amine 224 mg (0.5 mmol) of (S)—N—((S)-1-(6-fluoro-3-phenyl-4-(pyridine-2-yl)quinoline-2-yl)ethyl)-2-methylpropane-2-sulfinamide prepared in step 5 was reacted by the same manner as described in step 8 of Preparative Example 21. The obtained compound was separated by column chromatography (SiO$_2$, eluent: MeOH/CH$_2$Cl$_2$, 1/20→MeOH/CH$_2$Cl$_2$, 1/10) to give 163 mg of the target compound (S)-1-(6-fluoro-3-phenyl-4-(pyridine-2-yl)quinoline-2-yl)ethane-1-amine as a yellow oil (0.47 mmol, yield: 95%).

$^1$H NMR (300 MHz, CDCl$_3$) δ 8.62-8.67 (m, 1H), 8.10-8.17 (m, 1H), 7.41-7.55 (m, 2H), 6.91-7.32 (m, 8H), 4.40-4.50 (m, 1H), 3.50 (br s, 2H), 1.23-1.30 (m, 3H).

Preparative Example 24: Preparation of (S)-2-(1-aminoethyl)-6-fluoro-3-(pyridine-3-yl)quinazoline-4(3H)-one

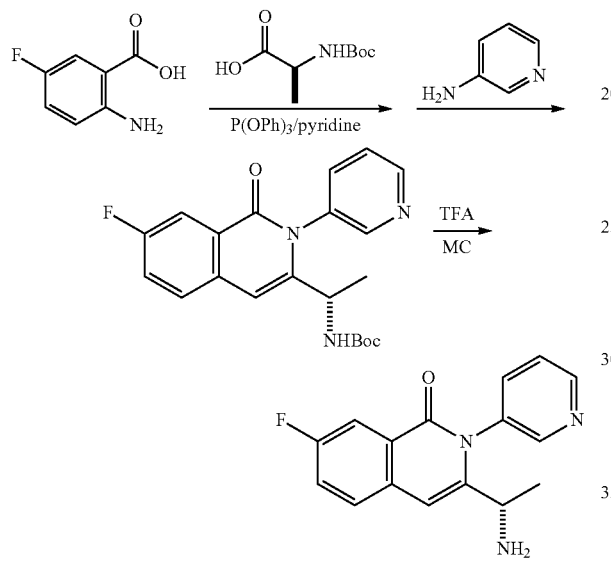

Step 1: Preparation of tert-butyl (S)-(1-(6-fluoro-4-oxo-3-(pyridine-3-yl)-3,4-dihydroquinazoline-2-yl)ethyl)carbamate Tert-butyl (S)-(1-(6-fluoro-4-oxo-3-(pyridine-3-yl)-3,4-dihydroquinazoline-2-yl)ethyl)carbamate was prepared by using 2-amino-5-fluorobenzoic acid and 3-aminopyridine according to the same manner as described in step 2 of Preparative Example 1.

$^1$H NMR (300 MHz, CDCl$_3$) δ 8.79 (t, J=3.2 Hz, 2H), 7.92-7.72 (m, 2H), 7.60-7.48 (m, 2H), 5.46 (d, J=8.3 Hz, 2H), 4.45-4.37 (m, 1H), 1.41 (m, 9H), 1.28 (t, J=6.8 Hz, 3H).

Step 2: Preparation of (S)-2-(1-aminoethyl)-6-fluoro-3-(pyridine-3-yl)quinazoline-4(3H)-one (S)-2-(1-aminoethyl)-6-fluoro-3-(pyridine-3-yl)quinazoline-4(3H)-one was prepared by using the compound prepared in step 1 according to the same manner as described in step 3 of Preparative Example 1.

$^1$H NMR (300 MHz, CDCl$_3$) δ 8.79 (d, J=4.0 Hz, 1H), 7.90 (d, J=8.1 Hz, 1H), 7.74 (d, J=6.5 Hz, 1H), 7.53 (d, J=7.7 Hz, 2H), 7.31-7.11 (m, 2H), 3.80-3.73 (m, 1H), 2.80 (s, 2H), 1.32 (dd, J=21, 6.3 Hz, 3H).

Preparative Example 25: Preparation of (S)-2-(1-aminoethyl)-6-fluoro-3-phenylquinazoline-4(3H)-one

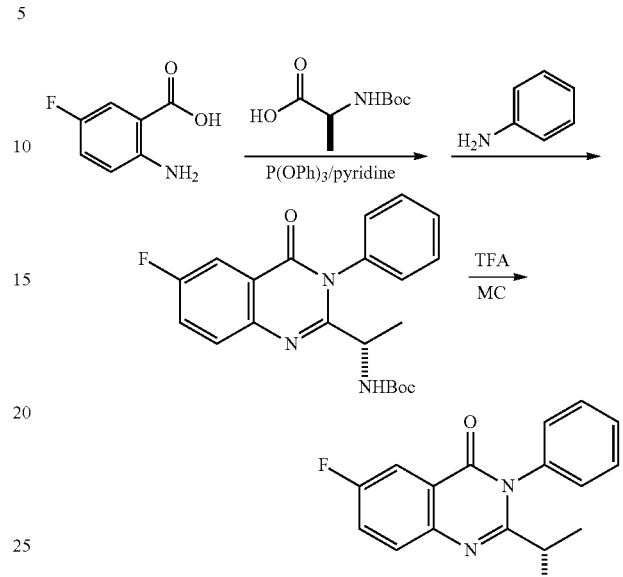

Step 1: Preparation of tert-butyl (S)-(1-(6-fluoro-4-oxo-3-phenyl-3,4-dihydroquinazoline-2-yl)ethyl)carbamate The target compound was prepared by using 2-amino-5-fluorobenzoic acid and aniline according to the same manner as described in step 2 of Preparative Example 1.

$^1$H NMR (300 MHz, CDCl$_3$) δ 7.88 (d, J=8.0 Hz, 1H), 7.70-7.74 (m, 1H), 7.60-7.39 (m, 3H), 7.28 (d, J=6.8 Hz, 1H), 5.66 (d, J=6.7 Hz, 1H), 4.54 (t, J=6.3 Hz, 1H), 1.41 (s, 9H), 1.26 (d, J=6.3 Hz, 3H).

Step 2: Preparation of (S)-2-(1-aminoethyl)-6-fluoro-3-phenylquinazoline-4(3H)-one The target compound was prepared by using the compound prepared in step 1 according to the same manner as described in step 3 of Preparative Example 1.

$^1$H NMR (300 MHz, CDCl$_3$) δ 7.87 (d, J=7.6 Hz, 1H), 7.66 (dd, J=8.5, 5.0 Hz, 1H), 7.57-7.29 (m, 2H), 4.03-4.09 (m, 1H), 1.36 (d, J=6.4 Hz, 3H).

Preparative Example 26: Preparation of (S)-2-(1-aminoethyl)-6-fluoro-3-(3-fluorophenyl)quinazoline-4(3H)-one

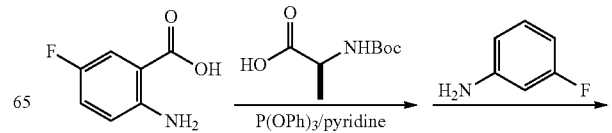

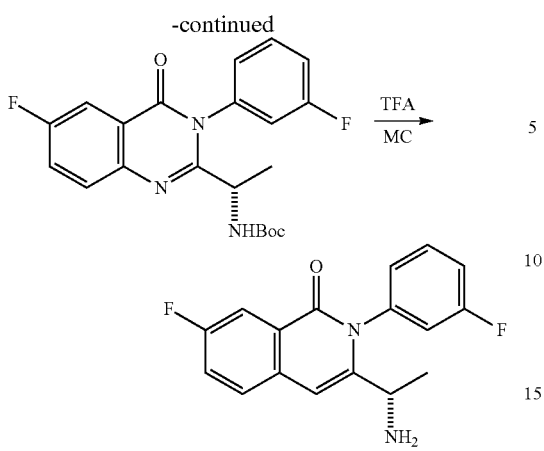

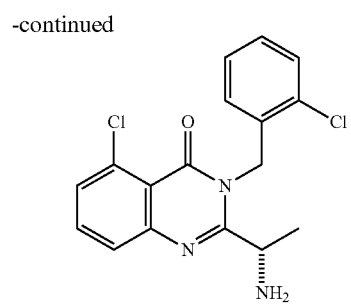

Step 1: Preparation of tert-butyl (S)-(1-(5-chloro-3-(2-chlorobenzyl)-4-oxo-3,4-dihydroquinazoline-2-yl)ethyl)carbamate The target compound was prepared by using 2-amino-6-chlorobenzoic acid and 2-chlorobenzylamine according to the same manner as described in step 2 of Preparative Example 1.

$^1$H NMR (500 MHz, CDCl$_3$) δ 7.60-7.67 (m, 2H), 7.48-7.54 (m, 1H), 7.42-7.46 (m, 1H), 7.14-7.27 (m, 2H), 6.82 (d, J=7.3 Hz, 1H), 5.63 (s, 2H), 5.39-5.44 (m, 1H), 4.82-4.85 (m, 1H), 1.49 (s, 9H), 1.37 (d, J=6.6 Hz, 3H).

Step 1: Preparation of tert-butyl (S)-(1-(6-fluoro-3-(3-fluorophenyl)-4-oxo-3,4-dihydroquinazoline-2-yl)ethyl)carbamate The target compound was prepared by using 2-amino-5-fluorobenzoic acid and 3-fluoroaniline according to the same manner as described in step 2 of Preparative Example 1.

$^1$H NMR (300 MHz, CDCl$_3$) δ 7.88 (d, J=8.0 Hz, 1H), 7.73 (dd, J=8.4, 4.6 Hz, 1H), 7.62-7.47 (m, 2H), 7.28-7.03 (m, 3H), 5.55-5.50 (m, 1H), 4.56-4.49 (m, 1H), 1.41 (s, 9H). 1.30 (t, J=4.4 Hz, 3H).

Step 2: Preparation of (S)-2-(1-aminoethyl)-5-chloro-3-(2-chlorobenzyl)quinazoline-4(3H)-one The target compound was prepared by using the compound prepared in step 1 according to the same manner as described in step 3 of Preparative Example 1.

$^1$H NMR (300 MHz, CDCl$_3$) δ 7.57-7.65 (m, 2H), 7.39-7.52 (m, 2H), 7.13-7.26 (m, 2H), 6.75-6.85 (m, 1H), 5.75 (d, J=17.1 Hz, 1H), 5.27 (d, J=17.1 Hz, 1H), 3.83-3.91 (m, 1H), 1.40 (d, J=6.5 Hz, 3H).

Step 2: Preparation of (S)-2-(1-aminoethyl)-6-fluoro-3-(3-fluorophenyl)quinazoline-4(3H)-one The target compound was prepared by using the compound prepared in step 1 according to the same manner as described in step 3 of Preparative Example 1.

$^1$H NMR (300 MHz, CDCl$_3$) δ 7.89 (d, J=8.3 Hz, 1H), 7.74 (dd, J=8.5, 4.4 Hz, 1H), 7.59-7.48 (m, 2H), 7.29-7.24 (m, 1H), 7.12-7.03 (m, 2H), 3.75-3.67 (m, 1H), 1.85 (s, 2H), 1.31 (d, J=6.4 Hz, 3H).

Preparative Example 27: Preparation of (S)-2-(1-aminoethyl)-5-chloro-3-(2-chlorobenzyl)quinazoline-4(3H)-one

Preparative Example 28: Preparation of (S)-2-(1-aminoethyl)-6-fluoro-3-(pyridine-2-ylmethyl)quinazoline-4(3H)-one

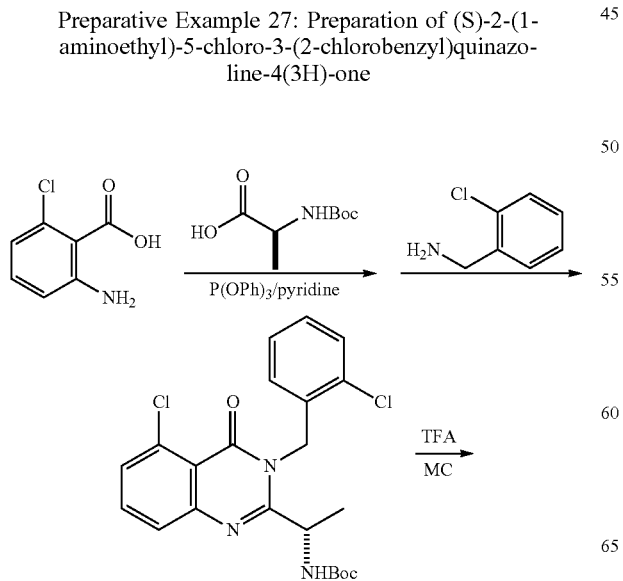

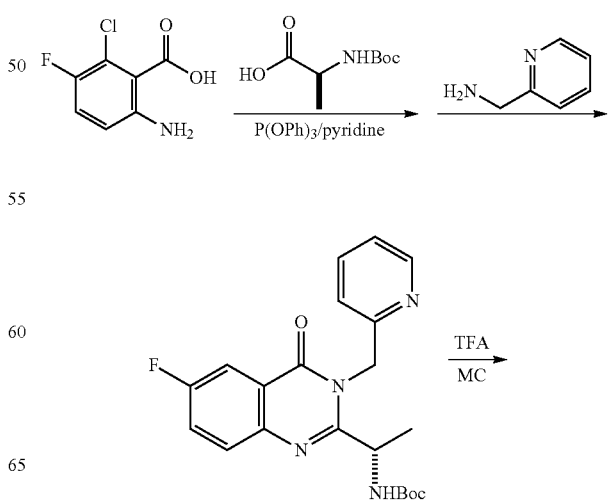

89

-continued

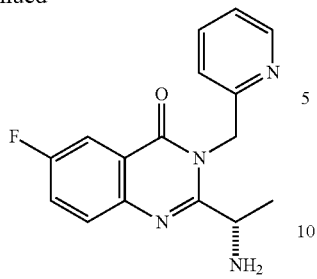

Step 1: Preparation of tert-butyl (S)-(1-(6-fluoro-4-oxo-3-(pyridine-2-ylmethyl)-3,4-dihydroquinazoline-2-yl)ethyl)carbamate The target compound was prepared by using 2-amino-6-fluorobenzoic acid and pyridine-2-ylmethaneamine according to the same manner as described in step 2 of Preparative Example 1.

$^1$H NMR (300 MHz, CDCl$_3$) δ 8.48 (d, J=4.0 Hz, 1H), 7.89 (dd, J=8.5, 3.0 Hz, 1H), 7.71-7.62 (m, 2H), 7.46 (td, J=8.6, 2.9 Hz, 1H), 7.19-7.15 (m, 2H), 5.61 (s, 2H), 5.22-5.13 (m, 1H), 1.44 (s, 3H), 1.41 (s, 9H).

Step 2: Preparation of (S)-2-(1-aminoethyl)-6-fluoro-3-(pyridine-2-ylmethyl)quinazoline-4(3H)-one The target compound was prepared by using the compound prepared in step 1 according to the same manner as described in step 3 of Preparative Example 1.

$^1$H NMR (300 MHz, CDCl$_3$) δ 8.48 (d, J=4.5 Hz, 1H), 7.83 (dd, J=8.4, 2.9 Hz, 1H), 7.71-7.63 (m, 2H), 7.42-7.33 (m, 2H), 7.19 (dd, J=7.1, 5.1 Hz, 1H), 8.48 (d, J=4.5 Hz, 1H), 5.73 (d, J=15.8 Hz, 1H), 5.21 (d, J=15.8 Hz, 1H), 4.72 (q, J=6.5 Hz, 1H), 4.45 (s, 2H), 1.53 (d, J=6.6 Hz, 3H)

Preparative Example 29: Preparation of 1-(5-chloro-3-(pyridine-2-yl)quinoline-2-yl)ethane-1-amine

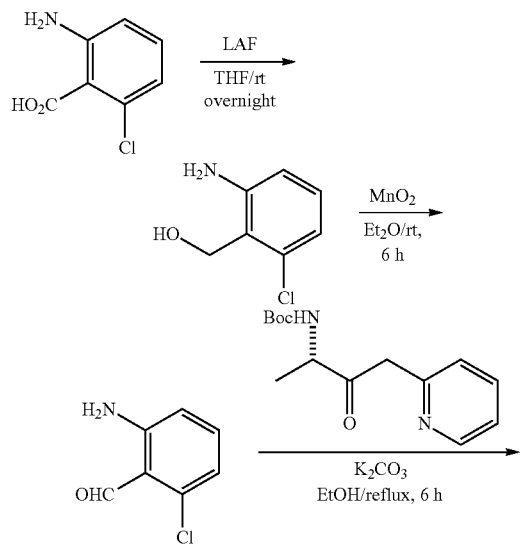

90

-continued

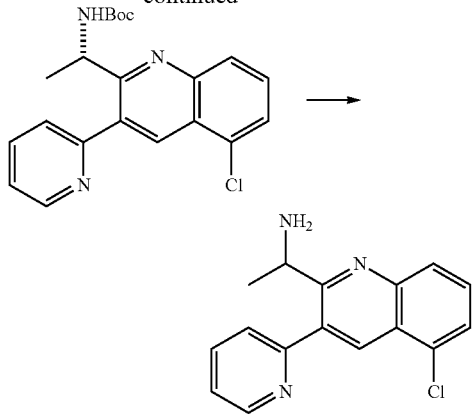

Step 1: Preparation of (2-amino-6-chlorophenyl)methanol 3.43 g (20.0 mmol) of 2-amino-6-chlorobenzoic acid was dissolved in anhydrous THF 30 mL), to which LiAlH$_4$ (1.5 equivalent) was slowly added at room temperature for 10 minutes, followed by stirring for 12 hours. Diethylether (40 mL) and water (5 mL) were added thereto. The reaction mixture was dried (MgSO$_4$) and concentrated under reduced pressure. The residue was separated by column chromatography (SiO$_2$, eluent: CH$_2$Cl$_2$/ethyl acetate, 5/1→CH$_2$Cl$_2$/ethylacetate, 2/1) to give 2.36 g of the target compound (2-amino-6-chlorophenyl)methanol as a pale yellow solid (15.0 mmol, yield: 75%).

$^1$H NMR (300 MHz, CDCl$_3$) δ 7.01 (t, J=8.0 Hz, 1H), 6.76 (d, J=7.9 Hz, 1H), 6.58 (d, J=8.0 Hz, 1H), 4.89 (s, 2H), 4.30 (br s, 2H), 1.66 (br s, 1H).

Step 2: Preparation of 2-amino-6-chlorobenzaldehyde 2.30 g (14.6 mmol) of (2-amino-6-chlorophenyl)methanol prepared in step 1, MnO$_2$ (10 equivalent), and diethylether (50 mL) were mixed together, which was stirred at room temperature for 6 hours. The reaction mixture was filtered with celite pad, and concentrated under reduced pressure. The residue was separated by column chromatography (SiO$_2$, eluent: hexane/CH$_2$Cl$_2$, 5/1→CH$_2$Cl$_2$) to give 2.27 g of the target compound 2-amino-6-chlorobenzaldehyde as a yellow solid (14.6 mmol, yield: 10%).

$^1$H NMR (300 MHz, CDCl$_3$) δ 10.48 (s, 1H), 7.17 (t, J=8.2 Hz, 1H), 6.67 (d, J=7.7 Hz, 1H), 6.54 (d, J=8.4 Hz, 1H), 6.48 (br s, 2H).

Step 3: Preparation of tert-butyl (1-(5-chloro-3-(pyridine-2-yl)quinoline-2-yl)ethylcarbamate 793 mg (3.0 mmol) of 2-amino-6-chlorobenzaldehyde (1.2 equivalent) prepared in step 2, tert-butyl (S)-(3-oxo-4-(pyridine-2-yl)butane-2-yl)carbamate, K$_2$CO$_3$ (3 equivalent), and ethanol (15 mL) were mixed together, which was refluxed for 6 hours. The reaction mixture was cooled down to room temperature. Water was added thereto, followed by extraction with ethyl acetate. The extracted organic layer was washed with saturated brine, separated, dried (Na$_2$SO$_4$), and concentrated under reduced pressure. The obtained compound was separated by column chromatography (SiO$_2$, eluent: hexane/ethyl acetate, 8/1→hexane/ethylacetate, 3/1)

to give 1.16 g of the target compound tert-butyl (1-(5-chloro-3-(pyridine-2-yl)quinoline-2-yl)ethylcarbamate as a white solid (3.0 mmol, yield: 100%).

$^1$H NMR (300 MHz, CDCl$_3$) δ 8.77 (br d, J=4.1 Hz, 1H), 8.53 (s, 1H), 8.05 (d, J=8.6 Hz, 1H), 7.83-7.89 (m, 1H), 7.59-7.68 (m, 3H), 7.34-7.39 (m, 1H), 6.33 (br d, J=6.6 Hz, 1H), 5.43-5.52 (m, 1H), 1.45 (s, 9H), 1.34 (d, J=6.5 Hz, 3H).

Step 4: Preparation of 1-(5-chloro-3-(pyridine-2-yl)quinoline-2-yl)ethane-1-amine 739 mg of 1-(5-chloro-3-(pyridine-2-yl)quinoline-2-yl)ethane-1-amine was prepared by using 1.0 g (2.60 mmol) of tert-butyl (1-(5-chloro-3-(pyridine-2-yl)quinoline-2-yl)ethylcarbamate prepared in step 3 according to the same manner as described in step 3 of Preparative Example 1 (2.60 mmol, yield: 100%).

$^1$H NMR (300 MHz, CDCl$_3$) δ 8.64 (d, J=2.7 Hz, 1H), 8.60 (s, 1H), 8.05-7.99 (m, 1H), 8.05-7.99 (m, 1H), 7.88 (td, J=7.7, 1.3 Hz, 1H), 7.70-7.63 (m, 3H), 7.36-7.32 (m, 1H), 5.18-5.24 (m, 1H), 1.58 (d, J=6.6 Hz, 3H).

The following examples 1~33 were performed by the method represented by the reaction formula 1A.

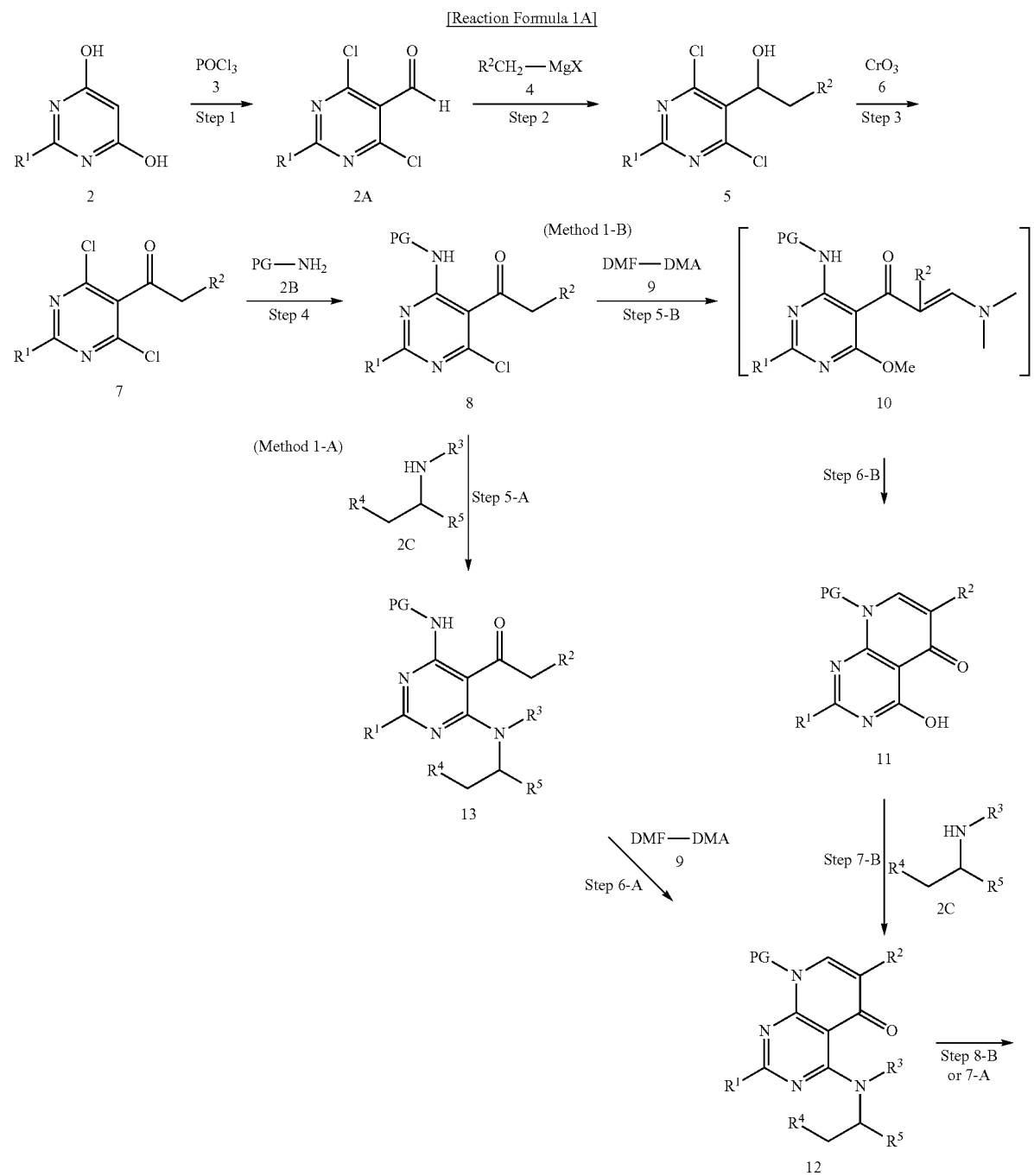

[Reaction Formula 1A]

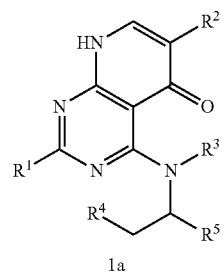

1a

Example 1: Preparation of (S)-4-((1-(5-chloro-4-oxo-3-phenyl-3,4-dihydroquinazoline-2-yl)ethyl)amino)pyrido[2,3-d]pyrimidine-5(8H)-one

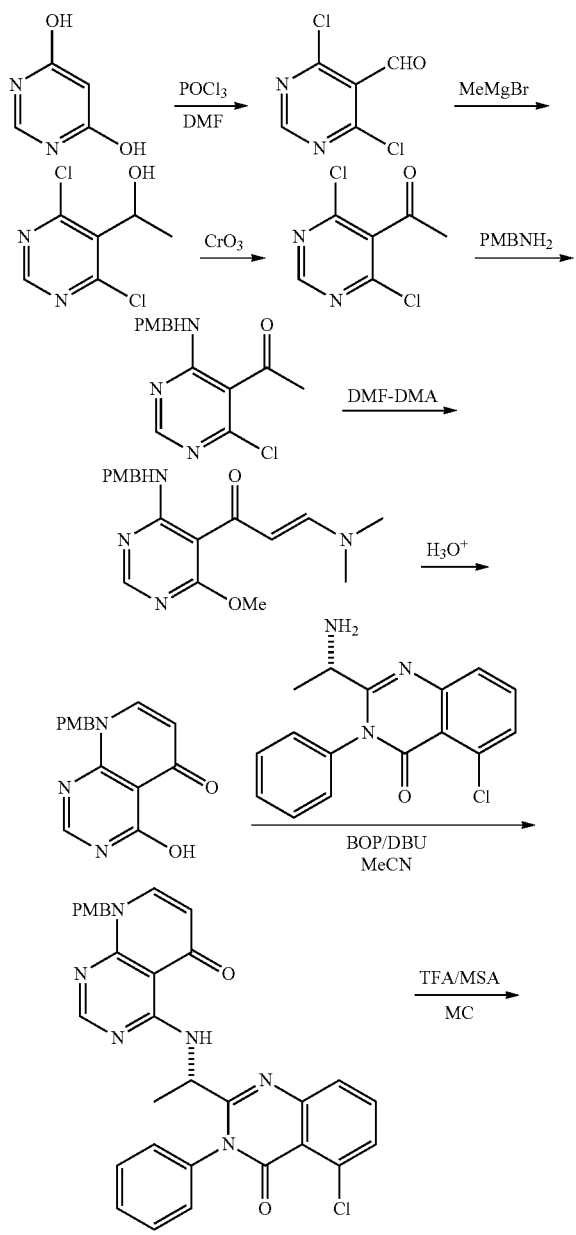

Step 1: Preparation of 4,6-dichloropyrimidine-5-carbaldehyde 30 mL of phosphorylchloride ($POCl_3$) was cooled down to 0° C., to which 9.6 mL of anhydrous dimethylformamide (DMF) was slowly added. 1 hour later, 7.85 g (70.0 mmol) of 4,6-dihydroxypyrimidine was added thereto. The reaction mixture was heated at room temperature, followed by stirring at room temperature for 30 minutes. The reaction mixture was refluxed for 3 hours. The mixture was cooled down to room temperature. The reaction mixture was slowly added to ice water, followed by extraction with ethylacetate. The extracted organic layer was dried over $Na_2SO_4$, filtered, and concentrated under reduced pressure. The obtained solid was washed with hexane/diethyl ether (5/1, v/v) to give 10.5 g of 4,6-dichloropyrimidine-5-carbaldehyde as a white solid (5.95 mmol, yield: 85%).

$^1$H NMR (300 MHz, $CDCl_3$) δ 10.47 (s, 1H), 8.90 (s, 1H).

Step 2: preparation of 1-(4,6-dichloropyrimidine-5-yl)ethane-1-ol 1.2 g (6.8 mmol) of 4,6-dichloropyrimidine-5-carbaldehyde was dissolved in THF (25 mL), to which 8.14 mL (8.14 mmol, 1.2 equivalent) of methylmagnesium bromide (18% in THF) was slowly added at 0° C. Saturated ammoniumchloride aqueous solution (10 mL) was slowly added thereto, followed by extraction with ethyl acetate. The extracted organic layer was dried over $Na_2SO_4$, filtered, and concentrated under reduced pressure. The residue was separated by column chromatography ($SiO_2$, eluent: hexane/ethylacetate, 4/1) to give 1.1 g of the target compound 1-(4,6-dichloropyrimidine-5-yl)ethane-1-ol as a white solid (5.7 mmol, yield: 80%).

$^1$H NMR (300 MHz, $CDCl_3$) δ 8.69 (s, 1H), 5.57-5.47 (m, 1H), 2.64 (d, J=9.3 Hz, 1H), 1.68 (d, J=6.8 Hz, 3H).

Step 3: Preparation of 1-(4,6-dichloropyrimidine-5-yl)ethane-1-one 980 mg (5.08 mmol) of 1-(4,6-dichloropyrimidine-5-yl) ethane-1-ol prepared in step 2 was dissolved in 30 mL of acetone, to which 1.0 g (10.2 mmol, 2.0 eq) of chromium trioxide was slowly added, followed by stirring at room temperature for 2 hours. 2 mL of Isopropylalcohol was added thereto, followed by stirring for 10 minutes. 20 mL of saturated sodiumbicarbonate aqueous solution was added to the reaction mixture, followed by extraction with ethylacetate. The extracted organic layer was dried over $Na_2SO_4$, filtered, and concentrated under reduced pressure. The residue was separated by column chromatography ($SiO_2$, eluent: hexane/ethylacetate, 6/1) to give 823 mg of the target compound 1-(4,6-dichloropyrimidine-5-yl)ethane-1-one as a white solid (4.3 mmol, yield: 85%).

$^1$H NMR (300 MHz, $CDCl_3$) δ 8.84 (s, 1H), 2.63 (s, 3H).

Step 4: Preparation of 1-(4-chloro-6-((4-methoxybenzyl)amino)pyrimidine-5-yl)ethane-1-one 3.82 g (20.0 mmol) of 1-(4,6-dichloropyrimidine-5-yl) ethane-1-one was dissolved in 30 mL of dichloromethane, which was cooled down to 0° C., to which 3.88 g (30.0 mmol) of diisopropylethylamine and 3.29 g (24.0 mmol) of p-methoxybenzylamine ($PMBNH_2$) were added stepwise. 1 hour later, the reaction mixture was heated to room temperature, followed by stirring at room temperature for 6 hours. Water and ethylacetate were added to the reaction mixture, followed by extraction. The extracted organic layer was dried over $Na_2SO_4$, filtered, and concentrated under reduced pressure. The residue was separated by column chromatography ($SiO_2$, eluent: hexane/ethylacetate, 3/1) to give 5.54 g of the target compound 1-(4-chloro-6-((4-methoxybenzyl)amino)pyrimidine-5-yl)ethane-1-one as a white solid (19.0 mmol, yield: 95%).

$^1$H NMR (300 MHz, $CDCl_3$) δ 9.07 (br s, 1H, NH), 8.38 (s, 1H), 7.25 (d, J=8.1 Hz, 2H), 6.88 (d, J=8.1 Hz, 2H), 4.67 (d, J=4.8 Hz, 2H), 3.81 (s, 3H), 2.74 (s, 3H).

Steps 5 and 6: Preparation of 4-hydroxy-8-(4-methoxybenzyl)pyrido[2,3-d]pyrimidine-5(8H)-one 5.83 g (20.0 mmol) of 1-(4-chloro-6-((4-methoxybenzyl) amino)pyrimidine-5-yl)ethane-1-one prepared in step 4 and 3.57 g (30.0 mmol) of N,N-dimethylformamide dimethyl acetal (DMF-DMA) were dissolved in 30 mL of anhydrous toluene, which was heated at 100° C. for 3 hours. The reaction mixture was cooled down to room temperature. The solvent and DMF-DMA were eliminated under reduced pressure. The obtained intermediate compound was added with 100 mL of acetic acid and 20 mL of water, followed by reflux for 4 days. The reaction mixture was cooled down to room temperature. The solvent was eliminated under reduced pressure. The obtained yellow product was washed with water/isopropanol (IPA) (1/1) to give 4.53 g of the target compound 4-hydroxy-8-(4-methoxybenzyl)pyrido[2,3-d]pyrimidine-5(8H)-one as a white solid (16.0 mmol, yield: 80%).

$^1$H NMR (300 MHz, DMSO-d6) δ 8.78 (br s, 1H, NH), 7.76 (d, J=4.7 Hz, 1H), 7.28 (d, J=5.2 Hz, 2H), 6.93 (d, J=5.2 Hz, 2H), 6.47 (d, J=4.7 Hz, 1H), 5.48 (s, 3H), 3.83 (s, 3H).

Step 7: Preparation of (S)-4-((1-(5-chloro-4-oxo-3-phenyl-3,4-dihydroquinazoline-2-yl)ethyl)amino)-8-(4-methoxybenzyl)pyrido[2,3-d]pyrimidine-5(8H)-one 50 mg (0.176 mmol) of 4-hydroxy-8-(4-methoxybenzyl) pyrido[2,3-d]pyrimidine-5(8H)-one prepared in step 5 and step 6 was dissolved in 2 mL of anhydrous acetonitrile, to which 101 mg (0.229 mmol) of (benzotriazole-1-yloxy)tris (dimethylamino)phosphonium hexafluorophosphate (BOP) and 39 μL (0.264 mmol) of 1,8-diazabicyclo[5.4.0]-7-undecene (DBU) were added, followed by stirring for 30 minutes. 58 mg (0.194 mmol) of (S)-2-(1-aminoethyl)-5-chloro-3-phenylquinazoline-4(3H)-one was added thereto, followed by stirring at 60° C. for 12 hours. The reaction mixture was filtered under reduced pressure. Ethyl acetate and water were added thereto, followed by extraction. The extracted organic layer was dried ($Na_2SO_4$), filtered, and concentrated under reduced pressure. The residue was separated by column chromatography ($SiO_2$, eluent: hexane/ethylacetate, 6/1→hexane/ethylacetate, 1/1) to give 72 mg of the target compound (S)-4-((1-(5-chloro-4-oxo-3-phenyl-3,4-dihydroquinazoline-2-yl)ethyl)amino)-8-(4-methoxybenzyl)pyrido[2,3-d]pyrimidine-5(8H)-one as a yellow solid (0.127 mmol, yield: 50%).

$^1$H NMR (300 MHz, $CDCl_3$) δ 11.02 (d, J=7.7 Hz, 1H), 8.28 (s, 1H), 7.7.71 (d, J=8.1 Hz, 1H), 7.54-7.62 (m, 2H), 7.40-7.53 (m, 5H), 7.33 (d, J=7.9 Hz, 1H), 7.20 (d, J=8.6 Hz, 2H), 6.85 (d, J=8.6 Hz, 2H), 6.30 (d, J=7.9 Hz, 1H), 5.33 (s, 2H), 5.01 (q, J=6.9 Hz, 6.9 Hz, 1H), 3.78 (s, 3H), 1.49 (d, J=6.7 Hz, 3H).

Step 8: Preparation of (S)-4-((1-(5-chloro-4-oxo-3-phenyl-3,4-dihydroquinazoline-2-yl)ethyl)amino) pyrido[2,3-d]pyrimidine-5(8H)-one 72 mg (0.127 mmol) of (S)-4-((1-(5-chloro-4-oxo-3-phenyl-3,4-dihydroquinazoline-2-yl)ethyl)amino)-8-(4-methoxybenzyl)pyrido[2,3-d]pyrimidine-5(8H)-one prepared in step 7 was dissolved in 1 mL of dichloromethane, to which 1 mL of trifluoroacetic acid (TFA) and 0.5 mL of methanesulfonic acid were added, followed by stirring at 70° C. for 10 hours. Saturated sodiumbicarbonate aqueous solution was added thereto, followed by neutralization. Dichloromethane and water were added thereto, followed by extraction. The extracted organic layer was dried ($Na_2SO_4$), filtered, and concentrated under reduced pressure. The residue was separated by column chromatography ($SiO_2$, eluent: dichloromethane/methanol, 30/1) to give 51 mg of the target compound (S)-4-((1-(5-chloro-4-oxo-3-phenyl-3,4-dihydroquinazoline-2-yl)ethyl)amino)pyrido[2,3-d]pyrimidine-5 (8H)-one as a pale yellow solid (0.115 mmol, yield: 90%).

$^1$H NMR (500 MHz, $CDCl_3$) δ 11.06 (d, J=7.0 Hz, 1H), 8.24 (s, 1H), 7.73 (d, J=8.2 Hz, 1H), 7.58-7.64 (m, 2H), 7.51-7.57 (m, 3H), 7.46-7.51 (m, 2H), 7.37 (d, J=7.6 Hz, 1H), 6.38 (d, J=7.6 Hz, 1H), 5.12 (q, J=6.8 Hz, 6.8 Hz, 1H), 1.53 (d, J=6.4 Hz, 3H).

Example 2: Preparation of (S)-4-((1-(5-chloro-4-oxo-3-(pyridine-3-yl)-3,4-dihydroquinazoline-2-yl) ethyl)amino)pyrido[2,3-d]pyrimidine-5(8H)-one

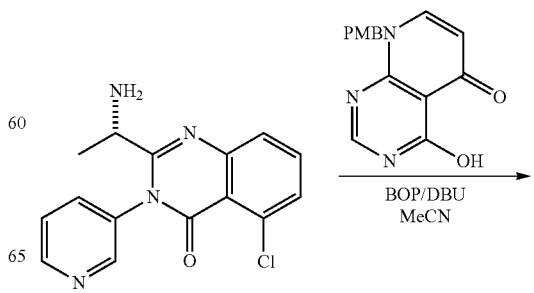

97

-continued

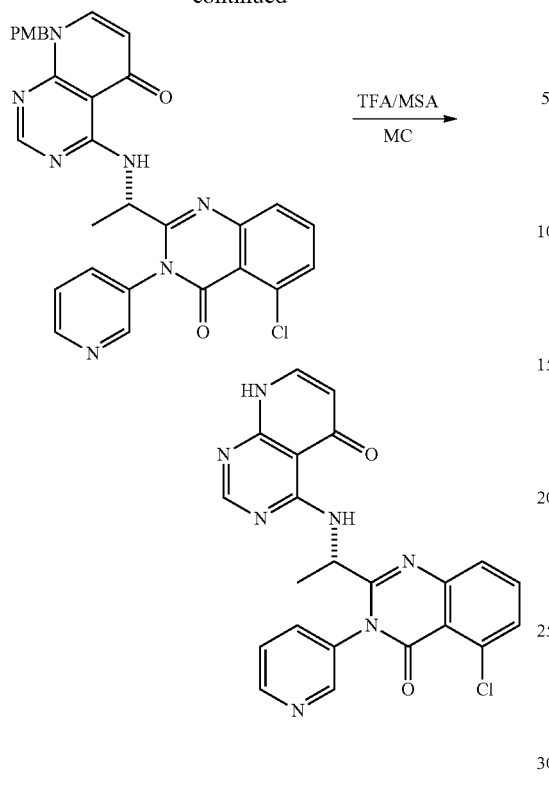

Step 1: Preparation of (S)-4-((1-(5-chloro-4-oxo-3-(pyridine-3-yl)-3,4-dihydroquinazoline-2-yl)ethyl)amino)-8-(4-methoxybenzyl)pyrido[2,3-d]pyrimidine-5(8H)-one 30 mg of (S)-4-((1-(5-chloro-4-oxo-3-(pyridine-3-yl)-3,4-dihydroquinazoline-2-yl)ethyl)amino)-8-(4-methoxybenzyl)pyrido[2,3-d]pyrimidine-5(8H)-one was prepared as a yellow solid by using 58 mg (0.194 mmol) of (S)-2-(1-aminoethyl)-5-chloro-3-(pyridine-3-yl)quinazoline-4(3H)-one according to the same manner as described in step 7 of Example 1 (0.053 mmol, yield: 30%).

MS [m/z; (M+1)$^+$]: 567.

Step 2: Preparation of (S)-4-((1-(5-chloro-4-oxo-3-(pyridine-3-yl)-3,4-dihydroquinazoline-2-yl)ethyl)amino)pyrido[2,3-d]pyrimidine-5(8H)-one 14 mg of (S)-4-((1-(5-chloro-4-oxo-3-(pyridine-3-yl)-3,4-dihydroquinazoline-2-yl)ethyl)amino)pyrido[2,3-d]pyrimidine-5(8H)-one was prepared as a pale yellow solid by using 30 mg (0.053 mmol) of (S)-4-((1-(5-chloro-4-oxo-3-(pyridine-3-yl)-3,4-dihydroquinazoline-2-yl)ethyl)amino)-8-(4-methoxybenzyl)pyrido[2,3-d]pyrimidine-5(8H)-one prepared in step 1 according to the same manner as described in step 8 of Example 1 (0.031 mmol, yield: 59%).

$^1$H NMR (300 MHz, CDCl$_3$) δ 10.78 (t, J=6.5 Hz, 1H), 8.76 (s, 1H), 8.20 (d, J=4.6 Hz, 1H), 7.44-7.77 (m, 6H), 6.33 (d, J=7.4 Hz, 1H), 4.93-4.50 (m, 1H), 1.49-1.60 (m, 3H).

98

Example 3: Preparation of (S)-4-((1-(5-chloro-4-oxo-3-(pyridine-2-yl)-3,4-dihydroquinazoline-2-yl)ethyl)amino)pyrido[2,3-d]pyrimidine-5(8H)-one

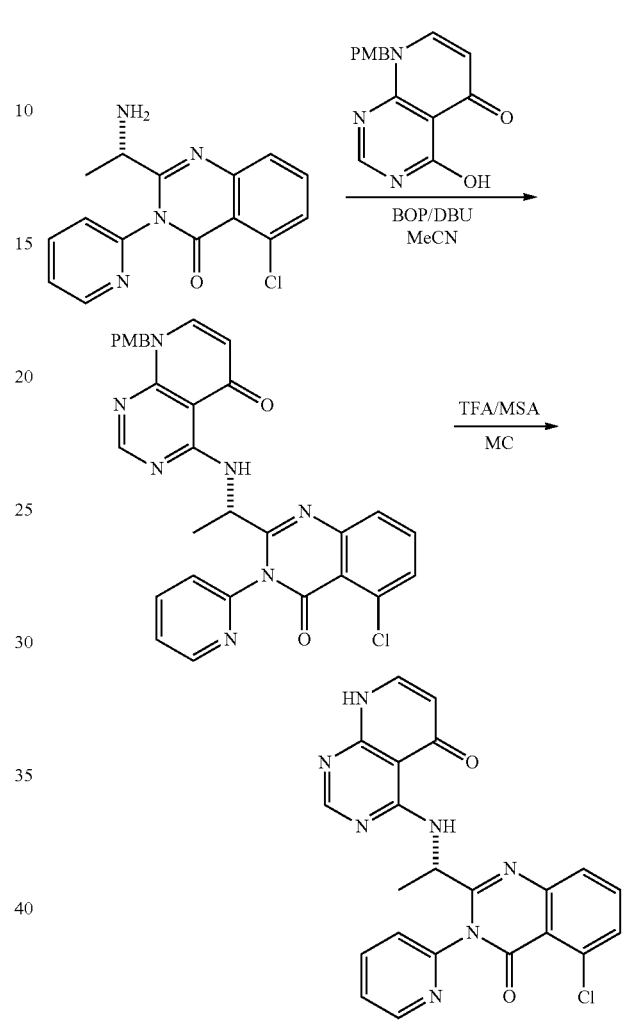

Step 1: Preparation of (S)-4-((1-(5-chloro-4-oxo-3-(pyridine-2-yl)-3,4-dihydroquinazoline-2-yl)ethyl)amino)-8-(4-methoxybenzyl)pyrido[2,3-d]pyrimidine-5(8H)-one 50 mg of (S)-4-((1-(5-chloro-4-oxo-3-(pyridine-2-yl)-3,4-dihydroquinazoline-2-yl)ethyl)amino)-8-(4-methoxybenzyl)pyrido[2,3-d]pyrimidine-5(8H)-one was prepared as a pale yellow solid by using 58 mg (0.194 mmol) of (S)-2-(1-aminoethyl)-5-chloro-3-(pyridine-2-yl)quinazoline-4(3H)-one according to the same manner as described in step 7 of Example 1 (0.112 mmol, yield: 64%).

$^1$H NMR (300 MHz, CDCl$_3$) δ 10.97 (d, J=4.6 Hz, 1H), 8.68 (d, J=4.6 Hz, 1H), 8.23 (s, 1H), 7.85 (t, J=7.9 Hz, 1H), 7.72 (d, J=7.9 Hz, 1H), 7.59 (t, J=7.9 Hz, 1H), 7.38-7.53 (m, 4H), 7.19 (d, J=8.5 Hz, 2H), 6.85 (d, J=8.6 Hz, 2H), 6.27 (d, J=7.9 Hz, 1H), 5.32 (s, 2H), 4.20-5.03 (m, 1H), 3.78 (s, 3H), 1.60 (d, J=6.6 Hz, 3H).

Step 2: Preparation of (S)-4-((1-(5-chloro-4-oxo-3-(pyridine-2-yl)-3,4-dihydroquinazoline-2-yl)ethyl)amino)pyrido[2,3-d]pyrimidine-5(8H)-one 14 mg of (S)-4-((1-(5-chloro-4-oxo-3-(pyridine-2-yl)-3,4-dihydroquinazoline-2-yl)ethyl)amino)pyrido[2,3-d]pyrimidine-5(8H)-one was prepared as a pale yellow solid by using 50 mg (0.112 mmol) of (S)-4-((1-(5-chloro-4-oxo-3-(pyridine-2-yl)-3,4-dihydroquinazoline-2-yl)ethyl)amino)-8-(4-methoxybenzyl)pyrido[2,3-d]pyrimidine-5(8H)-one prepared in step 1 according to the same manner as described in step 8 of Example 1 (0.031 mmol, yield: 28%).
$^1$H NMR (300 MHz, CDCl$_3$) δ 11.20 (brs, 1H), 10.92 (d, J=6.1 Hz, 1H), 8.70 (d, J=4.7 Hz, 1H), 8.16 (s, 1H), 7.90 (t, J=7.7 Hz, 1H), 7.72 (d, J=7.7 Hz, 1H), 7.61 (t, J=8.3 Hz, 1H), 7.41-7.55 (m, 4H), 6.33 (d, J=7.7 Hz, 1H), 4.92-5.03 (m, 1H), 1.60 (d, J=7.0 Hz, 3H).

Example 4: Preparation of (S)-4-((1-(5-chloro-3-(3,5-difluorophenyl)-4-oxo-3,4-dihydroquinazoline-2-yl)ethyl)amino)pyrido[2,3-d]pyrimidine-5(8H)-one

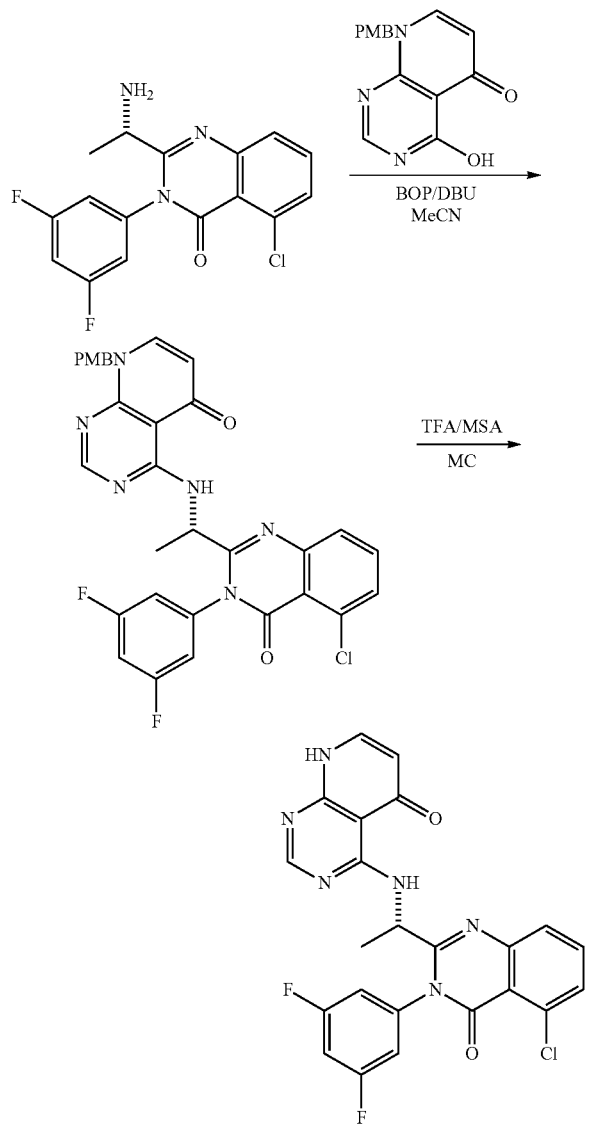

Step 1: Preparation of (S)-4-((1-(5-chloro-3-(3,5-difluorophenyl)-4-oxo-3,4-dihydroquinazoline-2-yl)ethyl)amino)-8-(4-methoxybenzyl)pyrido[2,3-d]pyrimidine-5(8H)-one 50 mg of (S)-4-((1-(5-chloro-3-(3,5-difluorophenyl)-4-oxo-3,4-dihydroquinazoline-2-yl)ethyl)amino)-8-(4-methoxybenzyl)pyrido[2,3-d]pyrimidine-5(8H)-one was prepared as a white solid by using 65 mg (0.194 mmol) of (S)-2-(1-aminoethyl)-5-chloro-3-(3,5-difluorophenyl)quinazoline-4(3H)-one according to the same manner as described in step 7 of Example 1 (0.083 mmol, yield: 47%).
$^1$H NMR (500 MHz, CDCl$_3$) δ 10.94 (d, J=7.2 Hz, 1H), 8.33 (s, 1H), 7.70 (d, J=8.1 Hz, 1H), 7.63 (t, J=8.1 Hz, 1H), 7.51 (t, J=8.0 Hz, 2H), 7.23 (d, J=8.5 Hz, 2H), 7.11 (d, J=7.1 Hz, 1H), 6.02-7.00 (m, 2H), 6.89 (d, J=8.5 Hz, 2H), 6.33 (d, J=8.0 Hz, 1H), 5.37 (d, J=3.1 Hz, 2H), 5.09-5.15 (m, 1H), 3.82 (s, 3H), 1.58 (d, J=7.2 Hz, 3H).

Step 2: Preparation of S)-4-((1-(5-chloro-3-(3,5-difluorophenyl)-4-oxo-3,4-dihydroquinazoline-2-yl)ethyl)amino)pyrido[2,3-d]pyrimidine-5(8H)-one 35 mg of (S)-4-((1-(5-chloro-3-(3,5-difluorophenyl)-4-oxo-3,4-dihydroquinazoline-2-yl)ethyl)amino)pyrido[2,3-d]pyrimidine-5(8H)-one was prepared as a pale yellow solid by using 50 mg (0.083 mmol) of (S)-4-((1-(5-chloro-3-(3,5-difluorophenyl)-4-oxo-3,4-dihydroquinazoline-2-yl)ethyl)amino)-8-(4-methoxybenzyl)pyrido[2,3-d]pyrimidine-5(8H)-one prepared in step 1 according to the same manner as described in step 8 of Example 1 (0.073 mmol, yield: 87%).
$^1$H NMR (300 MHz, CDCl$_3$) δ 10.84 (br s, 1H), 10.81 (d, J=6.3 Hz, 1H), 8.24 (s, 1H), 7.58-7.71 (m, 2H), 7.46-7.56 (m, 2H), 7.07-7.13 (m, 1H), 6.89-7.03 (m, 2H), 6.36 (d, J=8.0 Hz, 1H), 5.09 (q, J=5.5 Hz, 6.8 Hz, 1H), 1.56 (t, J=6.6 Hz, 3H).

Example 5: Preparation of (S)-4-((1-(8-chloro-1-oxo-2-phenyl-1,2-dihydroisoquinoline-3-yl)ethyl)amino)pyrido[2,3-d]pyrimidine-5(8H)-one

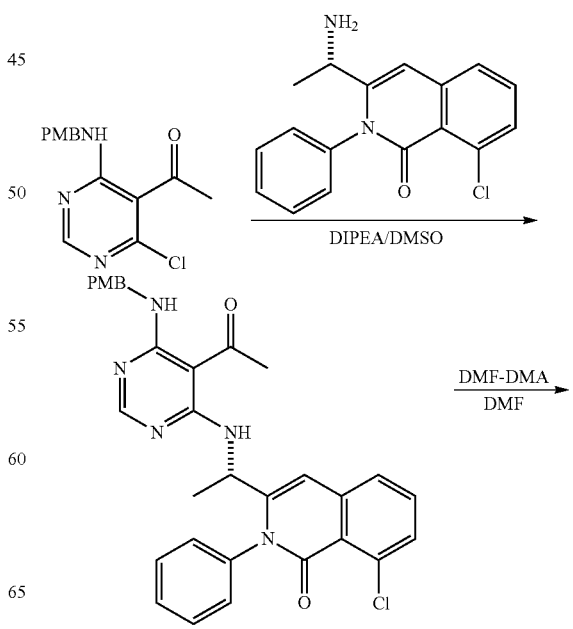

-continued

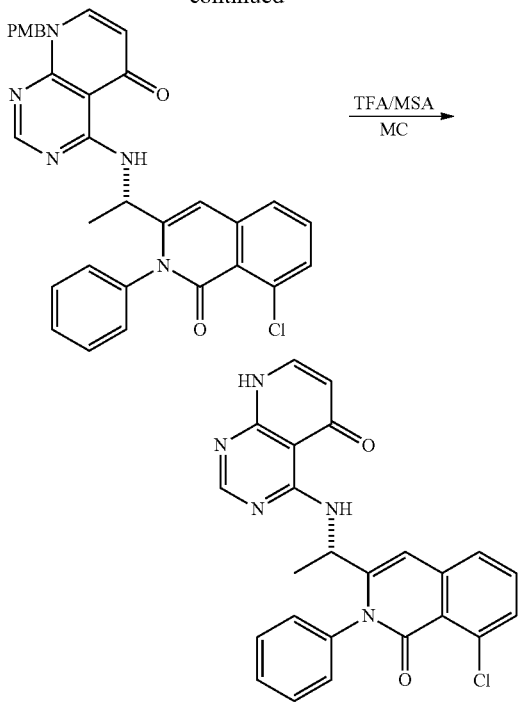

Step 1: Preparation of (S)-3-(1-((5-acetyl-6-((4-methoxybenzyl)amino)pyrimidine-4-yl)amino)ethyl)-8-chloro-2-phenylisoquinoline-1(2H)-one 292 mg (1.0 mmol, 1 equivalent) of 1-(4-chloro-6-((4-methoxybenzyl)amino)pyrimidine-5-yl)ethane-1-one prepared in step 4 of Example 1 and (S)-3-(1-aminoethyl)-8-chloro-2-phenylisoquinoline-1(2H)-one (1.1 equivalent) were dissolved in 10 mL of anhydrous dimethylsulfoxide (DMSO), to which diisopropylethylamine (DIPEA) (3 equivalent) was added, followed by stirring at 80° C. for 10 hours. Ethyl acetate and water was added to the reaction mixture, followed by extraction. The extracted organic layer was dried (Na$_2$SO$_4$), filtered, and concentrated under reduced pressure. The residue was separated by column chromatography (SiO$_2$, eluent: hexane/ethyl acetate, 3/1→hexane/ethyl acetate, 1/1) to give 482 mg of the target compound (S)-3-(1-((5-acetyl-6-((4-methoxybenzyl)amino)pyrimidine-4-yl)amino)ethyl)-8-chloro-2-phenylisoquinoline-1(2H)-one as a white solid (0.87 mmol, yield: 87%).

$^1$H NMR (300 MHz, CDCl$_3$) δ 8.56 (br d, J=6.3 Hz, 1H), 8.02 (s, 1H), 7.20-7.55 (m, 10H), 6.87 (d, J=8.7 Hz, 2H), 6.48 (s, 1H), 6.44 (br t, 1H), 4.84-4.95 (m, 1H), 4.66 (d, J=4.8 Hz, 2H), 3.79 (s, 3H), 2.52 (s, 3H), 1.38 (d, J=6.6 Hz, 3H).

Step 2: Preparation of (S)-4-((1-(8-chloro-1-oxo-2-phenyl-1,2-dihydroisoquinoline-3-yl)ethyl)amino)-8-(4-methoxybenzyl)pyrido[2,3-d]pyrimidine-5(8H)-one 200 mg (0.361 mmol) of (S)-3-(1-((5-acetyl-6-((4-methoxybenzyl)amino)pyrimidine-4-yl)amino)ethyl)-8-chloro-2-phenylisoquinoline-1(2H)-one prepared in step 1 was dissolved in 3 mL of anhydrous dimethylformamide (DMF), to which 0.24 mL (1.805 mmol) of N,N-dimethylformamide dimethyl acetal was added, followed by stirring at 130° C. for 15 hours. Ethyl acetate and water was added to the reaction mixture, followed by extraction. The extracted organic layer was dried (Na$_2$SO$_4$), filtered, and concentrated under reduced pressure. The residue was separated by column chromatography (SiO$_2$, eluent: dichloromethane/ethyl acetate, 10/1→dichloromethane/ethyl acetate, 1/1) to give 90 mg of the target compound (S)-4-((1-(8-chloro-1-oxo-2-phenyl-1,2-dihydroisoquinoline-3-yl)ethyl)amino)-8-(4-methoxybenzyl)pyrido[2,3-d]pyrimidine-5(8H)-one as a white solid (0.160 mmol, yield: 44%).

$^1$H NMR (300 MHz, CDCl$_3$) δ 10.71 (d, J=6.9 Hz, 1H), 8.30 (s, 1H), 7.47-7.57 (m, 3H), 7.29-7.47 (m, 6H), 7.23 (d, J=8.3 Hz, 2H), 6.87 (d, J=8.3 Hz, 2H), 6.59 (s, 1H), 6.30 (d, J=8.3 Hz, 1H), 5.35 (s, 2H), 4.93 (t, J=6.9 Hz, 1H), 3.78 (s, 3H), 1.45 (d, J=6.9 Hz, 3H).

Step 3: Preparation of (S)-4-((1-(8-chloro-1-oxo-2-phenyl-1,2-dihydroisoquinoline-3-yl)ethyl)amino)pyrido[2,3-d]pyrimidine-5(8H)-one 67 mg of (S)-4-((1-(8-chloro-1-oxo-2-phenyl-1,2-dihydroisoquinoline-3-yl)ethyl)amino)pyrido[2,3-d]pyrimidine-5(8H)-one was prepared as a white solid by using 90 mg (0.160 mmol) of (S)-4-((1-(8-chloro-1-oxo-2-phenyl-1,2-dihydroisoquinoline-3-yl)ethyl)amino)-8-(4-methoxybenzyl)pyrido[2,3-d]pyrimidine-5(8H)-one prepared in step 2 according to the same manner as described in step 8 of Example 1 (0.151 mmol, yield: 95%).

$^1$H NMR (300 MHz, DMSO-d$_6$) δ 12.14 (s, 1H), 10.48 (d, J=7.2 Hz, 1H), 8.19 (s, 1H), 7.75-7.82 (m, 1H), 7.58-7.69 (m, 2H), 7.46-7.54 (m, 2H), 7.28-7.45 (m, 4H), 6.77 (s, 1H), 6.15 (d, J=8.6 Hz, 1H), 4.71 (t, J=7.1 Hz, 1H), 1.40 (d, J=8.6 Hz, 3H).

Example 6: Preparation of (S)-4-((1-(2-phenylquinoline-3-yl)ethyl)amino)pyrido[2,3-d]pyrimidine-5(8H)-one

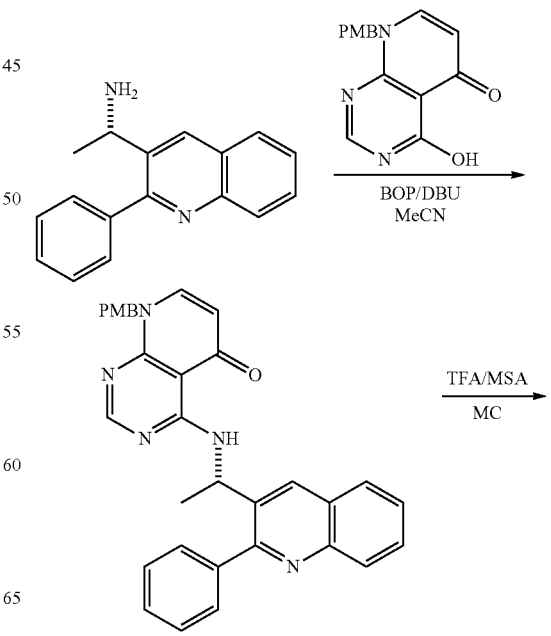

-continued

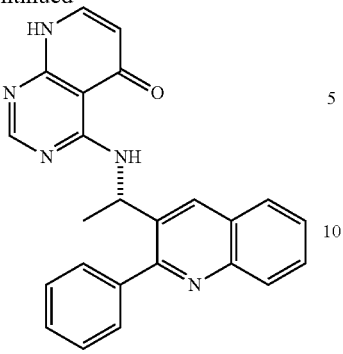

Step 1: Preparation of (S)-8-(4-methoxybenzyl)-4-((1-(2-phenylquinoline-3-yl)ethyl)amino)pyrido[2,3-d]pyrimidine-5(8H)-one 30 mg of (S)-8-(4-methoxybenzyl)-4-((1-(2-phenylquinoline-3-yl)ethyl)amino)pyrido[2,3-d]pyrimidine-5(8H)-one was prepared as a pale yellow solid by using 29 mg (0.117 mmol) of (S)-1-(2-phenylquinoline-3-yl)ethane-1-amine according to the same manner as described in step 7 of Example 1 (0.058 mmol, yield: 55%).

$^1$H NMR (300 MHz, CDCl$_3$) δ 10.94 (d, J=6.5 Hz, 1H), 8.42-8.56 (m, 1H), 8.28 (d, J=12.7 Hz, 2H), 7.38-8.17 (m, 9H), 7.21 (d, J=8.6 Hz, 2H), 6.85 (d, J=8.6 Hz, 2H), 6.30 (d, J=7.6 Hz, 1H), 5.64-5.75 (m, 1H), 5.34 (d, J=7.6 Hz, 2H), 3.78 (s, 3H), 1.49 (d, J=7.1 Hz, 3H).

Step 2: Preparation of (S)-4-((1-(2-phenylquinoline-3-yl)ethyl)amino)pyrido[2,3-d]pyrimidine-5(8H)-one 20 mg of (S)-4-((1-(2-phenylquinoline-3-yl)ethyl)amino)pyrido[2,3-d]pyrimidine-5(8H)-one was prepared as a pale yellow solid by using 30 mg (0.058 mmol) of (S)-8-(4-methoxybenzyl)-4-((1-(2-phenylquinoline-3-yl)ethyl)amino)pyrido[2,3-d]pyrimidine-5(8H)-one prepared in step 1 according to the same manner as described in step 8 of Example 1 (0.051 mmol, yield: 87%).

$^1$H NMR (300 MHz, CDCl$_3$) δ 10.78 (d, J=8.0 Hz, 1H), 10.55 (brs, 1H), 8.24 (d, J=6.7 Hz, 2H), 8.14 (d, J=6.7 Hz, 1H), 7.64-7.84 (m, 4H), 7.41-7.55 (m, 5H), 6.34 (d, J=7.4 Hz, 1H), 5.71 (q, J=5.3 Hz, 6.6 Hz, 1H), 1.50 (d, J=7.4 Hz, 3H).

Example 7: Preparation of 4-((1-(6-fluoro-3-(pyridine-2-yl)quinoline-2-yl)ethyl)amino)pyrido[2,3-d]pyrimidine-5(8H)-one

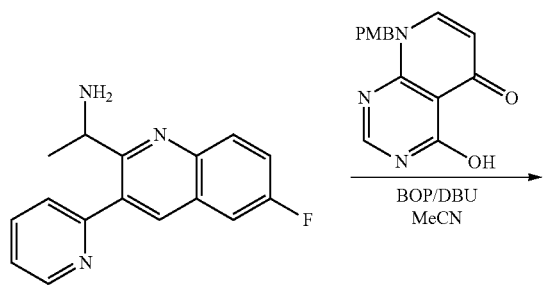

-continued

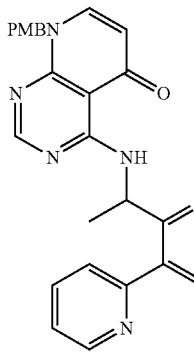

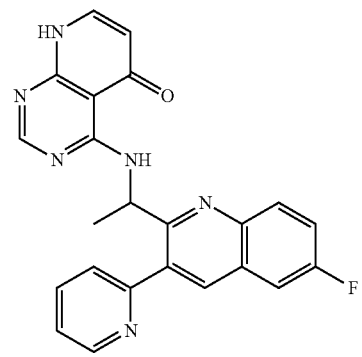

Step 1: Preparation of 4-((1-(6-fluoro-3-(pyridine-2-yl)quinoline-2-yl)ethyl)amino)-8-(4-methoxybenzyl)pyrido[2,3-d]pyrimidine-5(8H)-one 30 mg of 4-((1-(6-fluoro-3-(pyridine-2-yl)quinoline-2-yl)ethyl)amino)-8-(4-methoxybenzyl)pyrido[2,3-d]pyrimidine-5(8H)-one was prepared as a pale yellow solid by using 52 mg (0.194 mmol) of 1-(6-fluoro-3-(pyridine-2-yl)quinoline-2-yl)ethane-1-amine according to the same manner as described in step 7 of Example 1 (0.031 mmol, yield: 59%).

$^1$H NMR (300 MHz, CDCl$_3$) δ 11.61 (d, J=6.7 Hz, 1H), 8.79 (d, J=3.6 Hz, 1H), 8.27-8.36 (m, 2H), 8.10 (s, 1H), 7.82 (t, J=6.5 Hz, 1H), 7.40-7.62 (m, 4H), 7.32-7.39 (m, 1H), 7.19 (d, J=7.9 Hz, 2H), 6.85 (d, J=8.6 Hz, 2H), 6.29 (d, J=7.8 Hz, 1H), 6.03-6.14 (m, 1H), 5.33 (s, 2H), 3.78 (s, 3H), 1.57 (d, J=6.5 Hz, 3H).

Step 2: 4-((1-(6-fluoro-3-(pyridine-2-yl)quinoline-2-yl)ethyl)amino)pyrido[2,3-d]pyrimidine-5(8H)-one 22 mg of 4-((1-(6-fluoro-3-(pyridine-2-yl)quinoline-2-yl)ethyl)amino)pyrido[2,3-d]pyrimidine-5(8H)-one was prepared as a pale yellow solid by using mg (0.056 mmol) of 4-((1-(6-fluoro-3-(pyridine-2-yl)quinoline-2-yl)ethyl)amino)-8-(4-methoxybenzyl)pyrido[2,3-d]pyrimidine-5(8H)-one prepared in step 1 according to the same manner as described in step 8 of Example 1 (0.053 mmol, yield: 95%).

$^1$H NMR (500 MHz, CDCl$_3$) δ 11.54 (d, J=7.1 Hz, 1H), 8.79 (d, J=4.7 Hz, 1H), 8.30-8.35 (m, 1H), 8.21 (s, 1H), 8.12 (s, 1H), 7.86 (t, J=8.7 Hz, 1H), 7.59 (d, J=8.1 Hz, 1H), 7.53 (t, J=8.1 Hz, 1H), 7.46 (d, J=7.6 Hz, 2H), 7.39 (t, J=6.4 Hz, 1H), 6.32 (d, J=7.6 Hz, 1H), 6.02-6.08 (m, 1H), 1.54 (d, J=6.9 Hz, 3H).

Example 7-1

Preparation of (S)-4-((1-(6-fluoro-3-(pyridine-2-yl)quinoline-2-yl)ethyl)amino)pyrido[2,3-d]pyrimidine-5(8H)-one

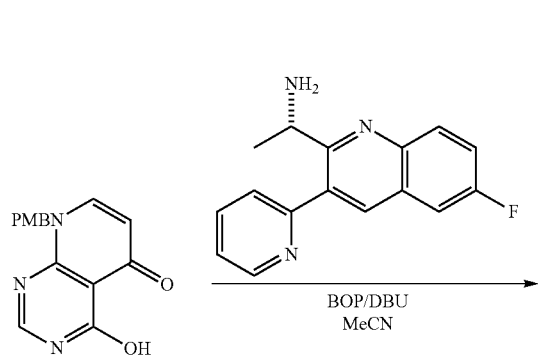

The target compound (S)-4-((1-(6-fluoro-3-(pyridine-2-yl)quinoline-2-yl)ethyl)amino)pyrido[2,3-d]pyrimidine-5(8H)-one was prepared by using tert-butyl (S)-1-(6-fluoro-3-(pyridine-2-yl)quinoline-2-yl)ethane-1-amine prepared in Preparative Example 21 according to the same manner as described in step 7 and step 8 of Example 1.

$^1$H NMR (500 MHz, CDCl$_3$) δ 11.54 (d, J=7.1 Hz, 1H), 8.79 (d, J=4.7 Hz, 1H), 8.30-8.35 (m, 1H), 8.21 (s, 1H), 8.12 (s, 1H), 7.86 (t, J=8.7 Hz, 1H), 7.59 (d, J=8.1 Hz, 1H), 7.53 (t, J=8.1 Hz, 1H), 7.46 (d, J=7.6 Hz, 2H), 7.39 (t, J=6.4 Hz, 1H), 6.32 (d, J=7.6 Hz, 1H), 6.02-6.08 (m, 1H), 1.54 (d, J=6.9 Hz, 3H).

Example 8: Preparation of (S)-4-((1-(7-fluoro-2-(3-fluorophenyl)quinoline-3-yl)ethyl)amino)pyrido[2,3-d]pyrimidine-5(8H)-one

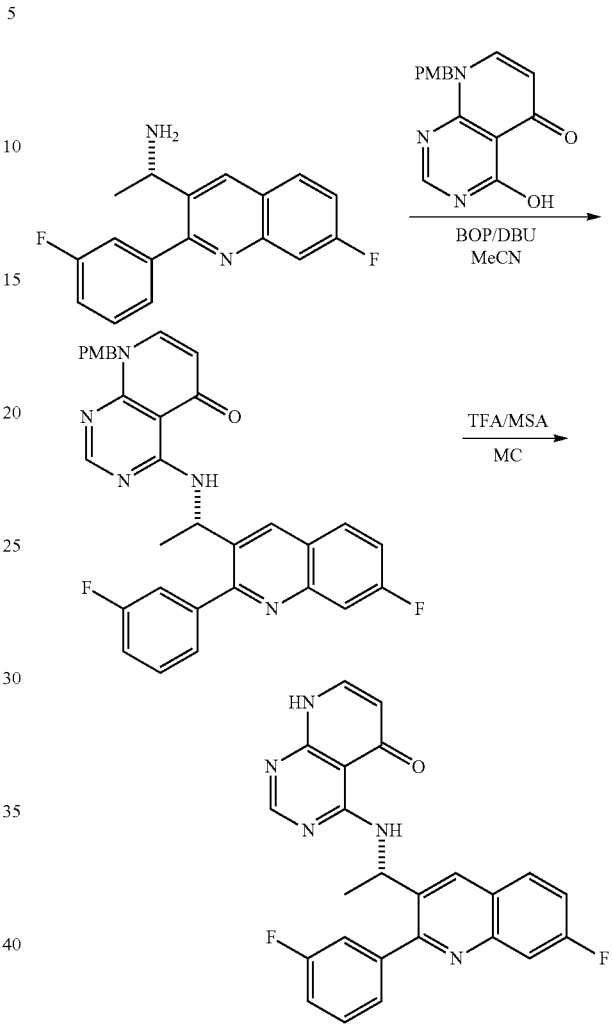

Step 1: Preparation of (S)-4-((1-(7-fluoro-2-(3-fluorophenyl)quinoline-3-yl)ethyl)amino)-8-(4-methoxybenzyl)pyrido[2,3-d]pyrimidine-5(8H)-one 40 mg of (S)-4-((1-(7-fluoro-2-(3-fluorophenyl)quinoline-3-yl)ethyl)amino)-8-(4-methoxybenzyl)pyrido[2,3-d]pyrimidine-5(8H)-one was prepared as a yellow solid by using 55 mg (0.194 mmol) of (S)-1-(7-fluoro-2-(3-fluorophenyl)quinoline-3-yl)ethane-1-amine according to the same manner as described in step 7 of Example 1 (0.073 mmol, yield: 40%).

$^1$H NMR (300 MHz, CDCl$_3$) δ 10.94 (d, J=5.3 Hz, 1H), 8.32 (s, 1H), 8.27 (s, 1H), 7.71-7.84 (m, 2H), 7.40-7.55 (m, 4H), 7.27-7.36 (m, 1H), 7.21 (d, J=8.7 Hz, 2H), 7.08-7.17 (m, 1H), 6.85 (d, J=8.5 Hz, 2H), 6.31 (d, J=7.5 Hz, 1H), 5.61-5.73 (m, 1H), 5.34 (d, J=6.8 Hz, 2H), 3.78 (s, 3H), 1.49 (d, J=6.9 Hz, 3H).

Step 2: Preparation of (S)-4-((1-(7-fluoro-2-(3-fluorophenyl)quinoline-3-yl)ethyl)amino)pyrido[2,3-d]pyrimidine-5(8H)-one 25 mg of (S)-4-((1-(7-fluoro-2-(3-fluorophenyl)quinoline-3-yl)ethyl)amino)pyrido[2,3-d]pyrimidine-5(8H)-one was prepared as a white solid by using 40 mg (0.073 mmol) of (S)-4-((1-(7-fluoro-2-(3-fluorophenyl)quinoline-3-yl)ethyl)amino)-8-(4-methoxybenzyl)pyrido[2,3-d]pyrimidine-5(8H)-one prepared in step 1 according to the same manner as described in step 8 of Example 1 (0.058 mmol, yield: 80%).

$^1$H NMR (300 MHz, CDCl$_3$) δ 11.25 (brs, 1H), 10.84 (d, J=7.2 Hz, 1H), 8.25 (d, J=3.3 Hz, 2H), 7.71-7.84 (m, 2H), 7.42-7.56 (m, 4H), 7.28-7.36 (m, 1H), 7.11-7.19 (m, 1H), 6.35 (d, J=7.2 Hz, 1H), 5.61-5.72 (m, 1H), 1.51 (d, J=6.9 Hz, 3H).

Example 9: Preparation of (S)-4-(1-(7-fluoro-2-(pyridine-2-yl)quinoline-3-yl)ethylamino)pyrido[2,3-d]pyrimidine-5(8H)-one

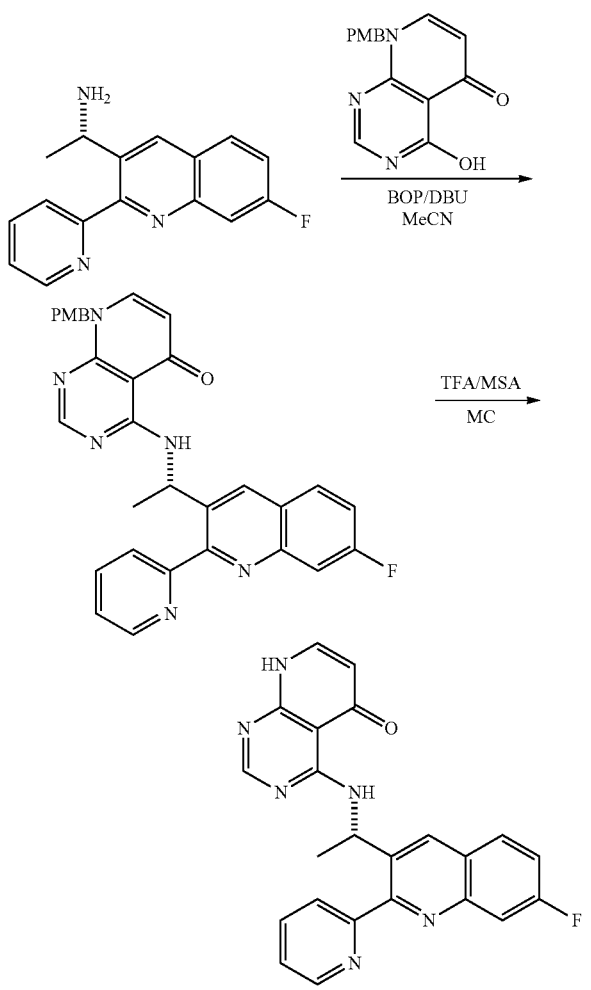

Step 1: Preparation of (S)-4-(1-(7-fluoro-2-(pyridine-2-yl)quinoline-3-yl)ethyl)amino)-8-(4-methoxybenzyl)pyrido[2,3-d]pyrimidine-5(8H)-one 245 mg of (S)-4-(1-(7-fluoro-2-(pyridine-2-yl)quinoline-3-yl)ethyl)amino)-8-(4-methoxybenzyl)pyrido[2,3-d]pyrimidine-5(8H)-one was prepared as a pale yellow solid by using 212 mg (0.793 mmol) of (S)-1-(7-fluoro-2-(pyridine-2-yl)quinoline-3-yl)ethane-1-amine according to the same manner as described in step 7 of Example 1 (0.460 mmol, yield: 58%).

$^1$H NMR (300 MHz, CDCl$_3$) δ 10.99 (d, J=7.3 Hz, 1H), 8.75 (d, J=4.7 Hz, 1H), 8.33 (s, 1H), 8.22 (s, 1H), 7.99 (d, J=7.6 Hz, 1H), 7.72~7.88 (m, 3H), 7.46 (d, J=7.6 Hz, 1H), 7.27~7.37 (m, 2H), 7.18 (d, J=8.5 Hz, 2H), 6.83 (d, J=8.8 Hz, 2H), 6.27 (d, J=8.0 Hz, 1H), 6.07 (q, J=7.2 Hz, 6.4 Hz, 1H), 5.31 (q, J=14.8 Hz, 5.9 Hz, 2H), 3.76 (s, 3H), 1.66 (d, J=6.7 Hz, 3H).

Step 2: Preparation of (S)-4-(1-(7-fluoro-2-(pyridine-2-yl)quinoline-3-yl)ethylamino)pyrido[2,3-d]pyrimidine-5(8H)-one 187 mg of (S)-4-(1-(7-fluoro-2-(pyridine-2-yl)quinoline-3-yl)ethylamino)pyrido[2,3-d]pyrimidine-5(8H)-one was prepared as a pale yellow solid by using 245 mg (0.460 mmol) of (S)-4-(1-(7-fluoro-2-(pyridine-2-yl)quinoline-3-yl)ethyl)amino)-8-(4-methoxybenzyl)pyrido[2,3-d]pyrimidine-5(8H)-one according to the same manner as described in step 8 of Example 1 (0.453 mmol, yield: 99%).

$^1$H NMR (500 MHz, CDCl$_3$) δ 11.26 (br s, 1H), 10.93 (d, J=7.0 Hz, 1H), 8.82 (d, J=4.6 Hz, 1H), 8.35 (s, 1H), 8.17 (s, 1H), 8.03 (d, J=7.7 Hz, 1H), 7.86-7.93 (m, 1H), 7.83~7.87 (m, 1H), 7.77~7.81 (m, 1H), 7.44 (d, J=7.7 Hz, 1H), 7.33~7.42 (m, 2H), 6.31 (d, J=7.0 Hz, 1H), 6.12 (q, J=7.0 Hz, 7.0 Hz, 1H), 1.68 (d, J=6.8 Hz, 3H).

Example 10: Preparation of (S)-4-((1-(4,8-dichloro-1-oxo-2-phenyl-1,2-dihydroisoquinoline-3-yl)ethyl)amino)pyrido[2,3-d]pyrimidine-5(8H)-one

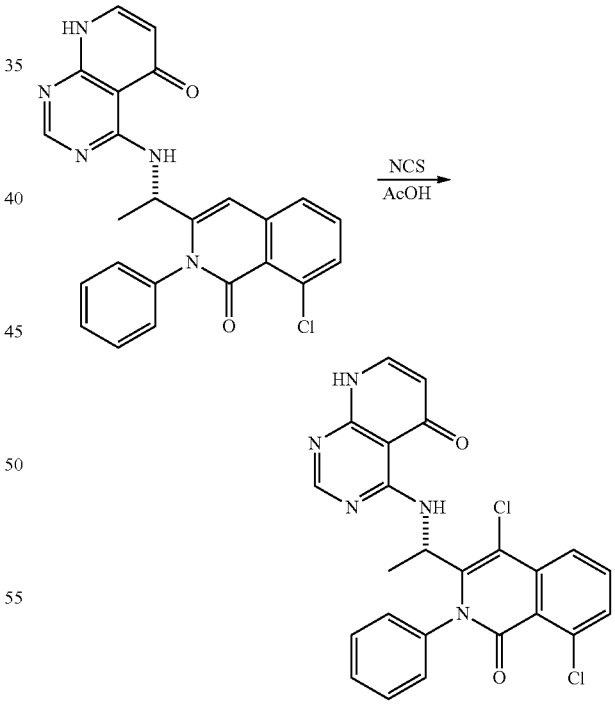

50 mg (0.113 mmol) of (S)-4-((1-(8-chloro-1-oxo-2-phenyl-1,2-dihydroisoquinoline-3-yl)ethyl)amino)pyrido[2,3-d]pyrimidine-5(8H)-one prepared in Example 5 was dissolved in 2 mL of acetic acid, to which 17 mg (0.124 mmol) of N-chlorosuccinimide (NCS) was added, followed by stirring at 50° C. for 15 hours. The reaction mixture was filtered under reduced pressure. Saturated sodiumbicarbonate aqueous solution was added thereto, followed by neutralization. Dichloromethane and water were added thereto, followed by extraction. The extracted organic layer was dried (Na₂SO₄), filtered, and concentrated under reduced pressure. The residue was separated by column chromatography (SiO₂, eluent: dichloromethane/methanol, 30/1→dichloromethane/methanol, 10/1) to give 25 mg of the target compound (S)-4-((1-(4,8-dichloro-1-oxo-2-phenyl-1,2-dihydroisoquinoline-3-yl)ethyl)amino)pyrido[2,3-d]pyrimidine-5(8H)-one as a pale yellow solid (0.052 mmol, yield: 46%).

¹H NMR (300 MHz, CDCl₃) δ 10.99 (d, J=4.8 Hz, 1H), 8.25 (s, 1H), 7.95 (dd, J=1.9 Hz, J=7.5 Hz, 1H), 7.75 (d, J=7.8 Hz, 1H), 7.46-7.62 (m, 6H), 7.20 (d, J=6.7 Hz, 1H), 6.3 (d, J=7.5 Hz, 1H), 5.04 (t, J=67.2 Hz, 1H), 1.67 (d, J=7.2 Hz, 3H).

Example 11: Preparation of (S)-4-((1-(8-chloro-4-fluoro-1-oxo-2-phenyl-1,2-dihydroisoquinoline-3-yl)ethyl)amino)pyrido[2,3-d]pyrimidine-5(8H)-one

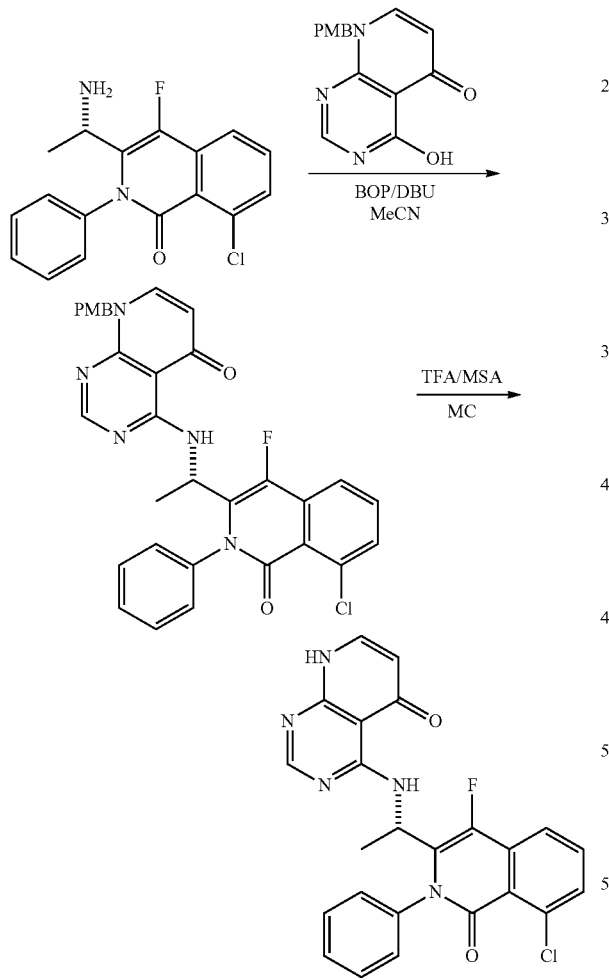

Step 1: Preparation of (S)-4-((1-(8-chloro-4-fluoro-1-oxo-2-phenyl-1,2-dihydroisoquinoline-3-yl)ethyl)amino)-8-(4-methoxybenzyl)pyrido[2,3-d]pyrimidine-5(8H)-one 5 mg of (S)-4-((1-(8-chloro-4-fluoro-1-oxo-2-phenyl-1,2-dihydroisoquinoline-3-yl)ethyl)amino)-8-(4-methoxybenzyl)pyrido[2,3-d]pyrimidine-5(8H)-one was prepared as a white solid by using 25 mg (0.079 mmol) of (S)-3-(1-aminoethyl)-8-chloro-4-fluoro-2-phenylisoquinoline-1(2H)-one according to the same manner as described in step 7 of Example 1 (0.009 mmol, yield: 11%).

¹H NMR (300 MHz, CDCl₃) δ 10.96 (d, J=7.8 Hz, 1H), 8.32 (s, 1H), 7.7.68 (t, J=6.5 Hz, 2H), 7.43-7.62 (m, 7H), 7.19 (d, J=8.8 Hz, 2H), 6.84 (d, J=9.0 Hz, 2H), 6.27 (d, J=7.8 Hz, 1H), 5.33 (q, J=12.6 Hz, J=9.1 Hz, 2H), 4.95 (q, J=5.2 Hz, 6.5 Hz, 1H), 3.77 (s, 3H), 1.60 (d, J=6.5 Hz, 3H).

Step 2: Preparation of (S)-4-((1-(8-chloro-4-fluoro-1-oxo-2-phenyl-1,2-dihydroisoquinoline-3-yl)ethyl)amino)pyrido[2,3-d]pyrimidine-5(8H)-one 2 mg of (S)-4-((1-(8-chloro-4-fluoro-1-oxo-2-phenyl-1,2-dihydroisoquinoline-3-yl)ethyl)amino)pyrido[2,3-d]pyrimidine-5(8H)-one was prepared as a white solid by using 5 mg (0.009 mmol) of (S)-4-((1-(8-chloro-4-fluoro-1-oxo-2-phenyl-1,2-dihydroisoquinoline-3-yl)ethyl)amino)-8-(4-methoxybenzyl)pyrido[2,3-d]pyrimidine-5(8H)-one prepared in step 1 according to the same manner as described in step 8 of Example 1 (0.004 mmol, yield: 50%).

¹H NMR (500 MHz, CDCl₃) δ 10.82 (d, J=6.2 Hz, 1H), 8.22 (s, 1H), 7.71 (d, J=6.2 Hz, 1H), 7.46-7.66 (m, 7H), 7.21-7.24 (m, 1H), 6.31 (d, J=7.3 Hz, 1H), 4.96 (q, J=4.9 Hz, 6.2 Hz, 1H), 1.61 (d, J=7.3 Hz, 3H).

Example 12: Preparation of (S)-4-((1-(5-fluoro-4-oxo-3-phenyl-3,4-dihydroquinazoline-2-yl)propyl)amino)pyrido[2,3-d]pyrimidine-5(8H)-one

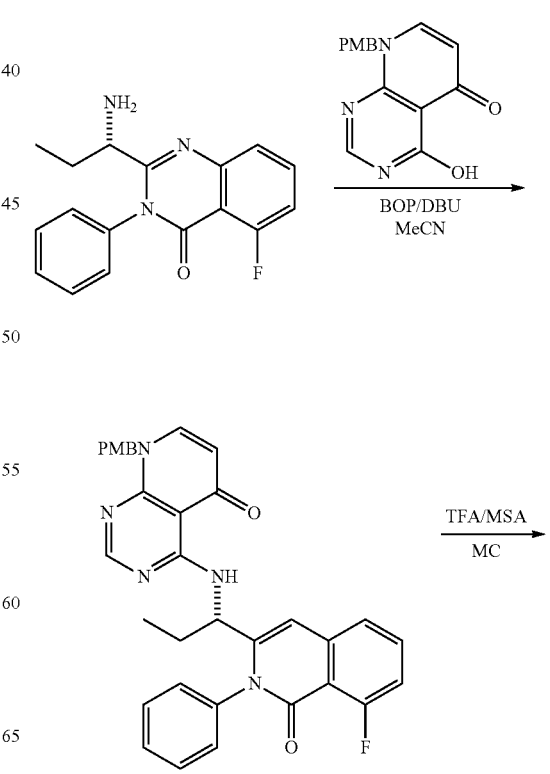

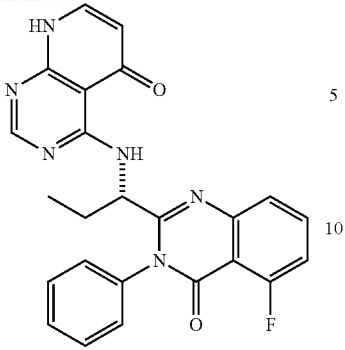

Step 1: Preparation of (S)-4-((1-(5-fluoro-4-oxo-3-phenyl-3,4-dihydroquinazoline-2-yl)propyl)amino)-8-(4-methoxybenzyl)pyrido[2,3-d]pyrimidine-5(8H)-one 60 mg of (S)-4-((1-(5-fluoro-4-oxo-3-phenyl-3,4-dihydroquinazoline-2-yl)propyl)amino)-8-(4-methoxybenzyl)pyrido[2,3-d]pyrimidine-5(8H)-one was prepared as a white solid by using 58 mg (0.194 mmol) of (S)-2-(1-aminopropyl)-5-fluoro-3-phenylquinazoline-4(3H)-one according to the same manner as described in step 7 of Example 1 (0.107 mmol, yield: 60%).

$^1$H NMR (300 MHz, CDCl$_3$) δ 10.96 (d, J=5.9 Hz, 1H), 8.28 (s, 1H), 7.43-7.73 (m, 8H), 7.32 (d, J=6.5 Hz, 1H), 7.21 (d, J=8.3 Hz, 2H), 7.15 (d, J=9.7 Hz, 1H), 6.85 (d, J=7.6 Hz, 2H), 6.23-6.37 (m, 1H), 5.34 (s, 2H), 4.96-5.07 (m, 1H), 3.77 (s, 3H), 1.75-1.99 (m, 2H), 0.88 (t, J=7.0 Hz, 3H).

Step 2: Preparation of (S)-4-((1-(5-fluoro-4-oxo-3-phenyl-3,4-dihydroquinazoline-2-yl)propyl)amino)pyrido[2,3-d]pyrimidine-5(8H)-one 33 mg of (S)-4-((1-(5-fluoro-4-oxo-3-phenyl-3,4-dihydroquinazoline-2-yl)propyl)amino)pyrido[2,3-d]pyrimidine-5(8H)-one was prepared as a pale brown solid by using 60 mg (0.107 mmol) of (S)-4-((1-(5-fluoro-4-oxo-3-phenyl-3,4-dihydroquinazoline-2-yl)propyl)amino)-8-(4-methoxybenzyl)pyrido[2,3-d]pyrimidine-5(8H)-one prepared in step 1 according to the same manner as described in step 8 of Example 1 (0.075 mmol, yield: 88%).

$^1$H NMR (300 MHz, CDCl$_3$) δ 11.88 (brs, 1H), 10.90 (d, J=7.3 Hz, 1H), 8.20 (s, 1H), 7.41-7.70 (m, 7H), 7.33 (d, J=7.0 Hz, 1H), 7.09 (t, J=8.2 Hz, 1H), 6.34 (d, J=7.6 Hz, 1H), 4.99-5.09 (m, 1H), 1.78-2.00 (m, 2H), 0.89 (t, J=7.6 Hz, 3H).

Example 13: Preparation of (S)-4-(2-(5-chloro-4-oxo-3-phenyl-3,4-dihydroquinazoline-2-yl)pyrrolidine-1-yl)pyrido[2,3-d]pyrimidine-5(8H)-one

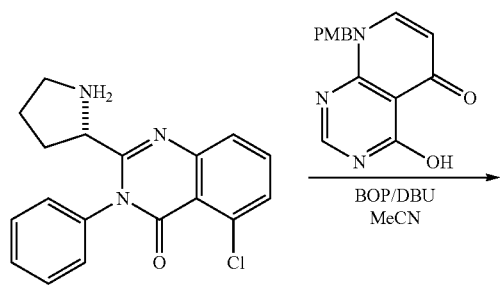

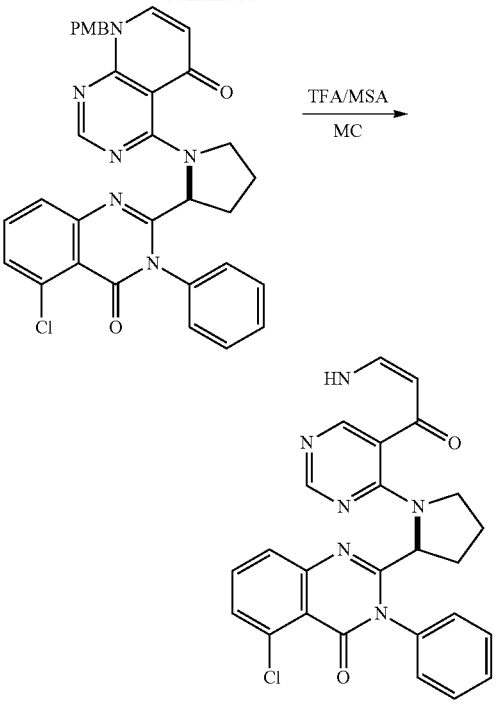

Step 1: Preparation of (S)-4-(2-(5-chloro-4-oxo-3-phenyl-3,4-dihydroquinazoline-2-yl)pyrrolidine-1-yl)-8-(4-methoxybenzyl)pyrido[2,3-d]pyrimidine-5(8H)-one 60 mg of (S)-4-(2-(5-chloro-4-oxo-3-phenyl-3,4-dihydroquinazoline-2-yl)pyrrolidine-1-yl)-8-(4-methoxybenzyl)pyrido[2,3-d]pyrimidine-5(8H)-one was prepared as a pale yellow solid by using 63 mg (0.194 mmol) of (S)-5-chloro-3-phenyl-2-(pyrrolidine-2-yl)quinazoline-4(3H)-one according to the same manner as described in step 7 of Example 1 (0.102 mmol, yield: 58%).

$^1$H NMR (300 MHz, CDCl$_3$) δ 8.21 (s, 1H), 7.71-7.78 (m, 1H), 7.45-7.65 (m, 8H), 7.37-7.44 (m, 3H), 7.19 (d, J=6.8 Hz, 2H), 6.83 (d, J=8.3 Hz, 2H), 6.23 (d, J=7.5 Hz, 1H), 5.39 (d, J=15.0 Hz, 1H), 5.23 (d, J=14.3 Hz, 1H), 4.74-4.83 (m, 1H), 3.82-3.95 (m, 1H), 3.63-3.74 (m, 1H), 2.23-2.36 (m, 1H), 2.06-2.16 (m, 2H), 1.71-1.86 (m, 1H).

Step 2: Preparation of (S)-4-(2-(5-chloro-4-oxo-3-phenyl-3,4-dihydroquinazoline-2-yl)pyrrolidine-1-yl)pyrido[2,3-d]pyrimidine-5(8H)-one 36 mg of (S)-4-(2-(5-chloro-4-oxo-3-phenyl-3,4-dihydroquinazoline-2-yl)pyrrolidine-1-yl)pyrido[2,3-d]pyrimidine-5(8H)-one was prepared as a pale yellow solid by using 60 mg (0.102 mmol) of (S)-4-(2-(5-chloro-4-oxo-3-phenyl-3,4-dihydroquinazoline-2-yl)pyrrolidine-1-yl)-8-(4-methoxybenzyl)pyrido[2,3-d]pyrimidine-5(8H)-one prepared in step 1 according to the same manner as described in step 8 of Example 1 (0.076 mmol, yield: 75%).

$^1$H NMR (500 MHz, CDCl$_3$) δ 10.28 (br s, 1H), 8.15 (s, 1H), 7.75 (d, J=8.1 Hz, 1H), 7.49-7.65 (m, 5H), 7.41-7.47 (m, 3H), 6.28 (d, J=7.8 Hz, 1H), 4.87 (t, J=6.5 Hz, 1H), 3.90-3.97 (m, 1H), 3.81-3.87 (m, 1H), 2.32-2.41 (m, 1H), 2.09-2.16 (m, 2H), 1.86-1.92 (m, 1H).

Example 14: Preparation of (S)-4-(2-(8-chloro-1-oxo-2-phenyl-1,2-dihydroisoquinoline-3-yl)pyrrolidine-1-yl)pyrido[2,3-d]pyrimidine-5(8H)-one

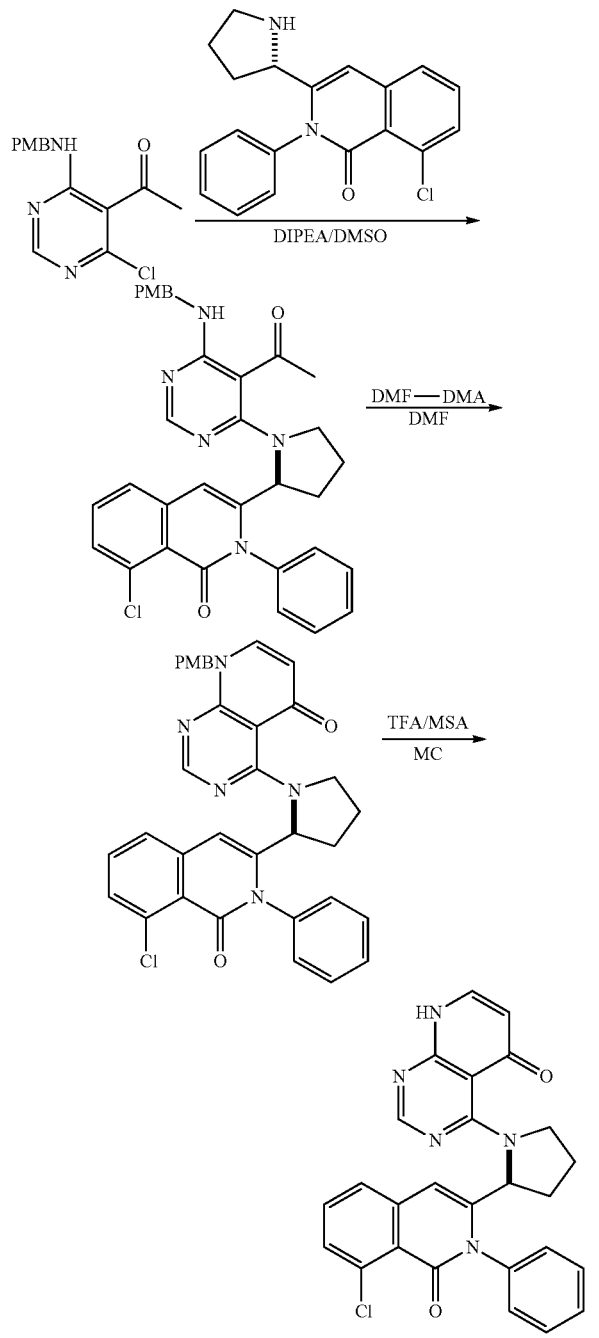

Step 1: Preparation of (S)-3-(1-(5-acetyl-6-((4-methoxybenzyl)amino)pyrimidine-4-yl)pyrrolidine-2-yl)-8-chloro-2-phenylisoquinoline-1(2H)-one 180 mg of (S)-3-(1-(5-acetyl-6-((4-methoxybenzyl)amino)pyrimidine-4-yl)pyrrolidine-2-yl)-8-chloro-2-phenylisoquinoline-1(2H)-one was prepared as a pale yellow solid by using 100 mg (0.343 mmol) of 1-(4-chloro-6-((4-methoxybenzyl)amino)pyrimidine-5-yl)ethane-1-one prepared in step 4 of Example 1 and 122 mg (0.377 mmol) of (S)-8-chloro-2-phenyl-3-(pyrrolidine-2-yl)isoquinoline-1(2H)-one according to the same manner as described in step 1 of Example 5 (0.310 mmol, yield: 91%).

¹H NMR (300 MHz, CDCl₃) δ 8.61 (t, J=3.4 Hz, 1H), 8.10 (s, 1H), 7.72 (d, J=5.2 Hz, 1H), 7.38-7.63 (m, 5H), 7.27-7.33 (m, 2H), 7.23 (d, J=8.3 Hz, 2H), 6.84 (d, J=8.3 Hz, 2H), 6.49 (s, 1H), 4.82-4.90 (m, 1H), 4.63-4.72 (m, 1H), 4.46-4.55 (m, 1H), 3.78 (s, 3H), 3.70-3.76 (m, 1H), 3.25 (t, J=9.0 Hz, 1H), 2.53 (s, 3H), 2.03-2.14 (m, 1H), 1.87-2.01 (m, 1H), 1.75-1.87 (m, 1H), 1.57 (m, 1H).

Step 2: Preparation of (S)-4-(2-(8-chloro-1-oxo-2-phenyl-1,2-dihydroisoquinoline-3-yl)pyrrolidine-1-yl)-8-(4-methoxybenzyl)pyrido[2,3-d]pyrimidine-5(8H)-one 70 mg of (S)-4-(2-(8-chloro-1-oxo-2-phenyl-1,2-dihydroisoquinoline-3-yl)pyrrolidine-1-yl)-8-(4-methoxybenzyl)pyrido[2,3-d]pyrimidine-5(8H)-one was prepared as a pale yellow solid by using 180 mg (0.310 mmol) of (S)-3-(1-(5-acetyl-6-((4-methoxybenzyl)amino)pyrimidine-4-yl)pyrrolidine-2-yl)-8-chloro-2-phenylisoquinoline-1 (2H)-one prepared in step 1 according to the same manner as described in step 2 of Example 5 (0.119 mmol, yield: 38%).

¹H NMR (300 MHz, CDCl₃) δ 8.36 (s, 1H), 7.71 (t, J=6.6 Hz, 1H), 7.43-7.65 (m, 6H), 7.30-7.42 (m, 4H), 7.23 (d, J=7.3 Hz, 2H), 6.71 (brs, 1H), 6.25 (d, J=7.3 Hz, 1H), 5.26-5.42 (m, 2H), 4.97 (t, J=7.3 Hz, 1H), 4.30-4.43 (m, 1H), 2.94-3.06 (m, 1H), 1.82-2.12 (m, 4H).

Step 3: Preparation of (S)-4-(2-(8-chloro-1-oxo-2-phenyl-1,2-dihydroisoquinoline-3-yl)pyrrolidine-1-yl)pyrido[2,3-d]pyrimidine-5(8H)-one 48 mg of (S)-4-(2-(8-chloro-1-oxo-2-phenyl-1,2-dihydroisoquinoline-3-yl)pyrrolidine-1-yl)pyrido[2,3-d]pyrimidine-5(8H)-one was prepared as a pale yellow solid by using 70 mg (0.119 mmol) of (S)-4-(2-(8-chloro-1-oxo-2-phenyl-1,2-dihydroisoquinoline-3-yl)pyrrolidine-1-yl)-8-(4-methoxybenzyl)pyrido[2,3-d]pyrimidine-5(8H)-one prepared in step 2 according to the same manner as described in step 8 of Example 1 (0.102 mmol, yield: 86%).

¹H NMR (300 MHz, CDCl₃) δ 11.17 (brs, 1H), 8.29 (s, 1H), 7.43-7.73 (m, 5H), 7.29-7.42 (m, 4H), 6.66 (s, 1H), 6.29 (d, J=8.6 Hz, 1H), 4.98 (t, J=7.3 Hz, 1H), 4.34-4.49 (m, 1H), 3.05-3.18 (m, 1H), 1.82-2.15 (m, 3H), 1.74 (brs, 1H).

Example 15: Preparation of (S)-2-amino-4-((1-(8-chloro-1-oxo-2-phenyl-1,2-dihydroisoquinoline-3-yl)ethyl)amino)pyrido[2,3-d]pyrimidine-5(8H)-one

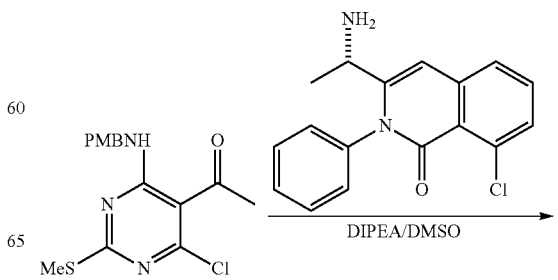

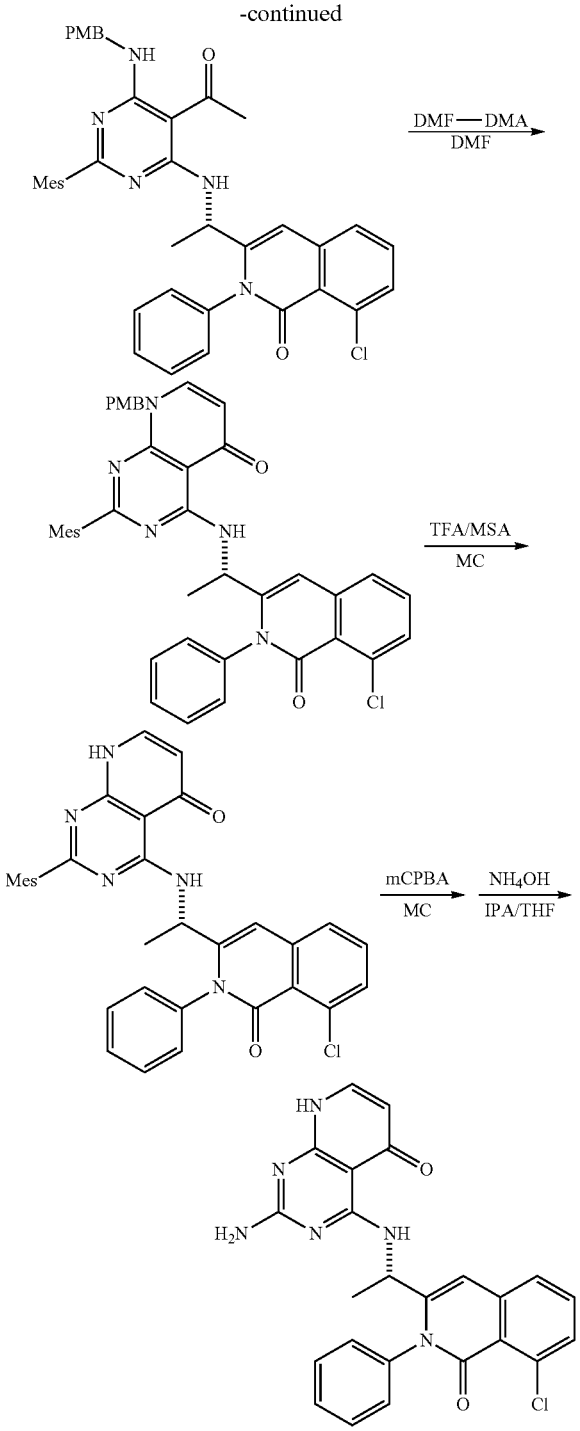

Step 1: Preparation of (S)-3-(1-((5-acetyl-6-((4-methoxybenzyl)amino)-2-(methylthio)pyrimidine-4-yl)amino)ethyl)-8-chloro-2-phenylisoquinoline-1(2H)-one 1.5 g of (S)-3-(1-((5-acetyl-6-((4-methoxybenzyl)amino)-2-(methylthio)pyrimidine-4-yl)amino)ethyl)-8-chloro-2-phenylisoquinoline-1(2H)-one was prepared as a pale yellow solid by using 920 mg (2.723 mmol) of 1-(4-chloro-6-((4-methoxybenzyl)amino)-2-(methylthio)pyrimidine-5-yl)ethane-1-one and 895 mg (2.996 mmol) of (S)-3-(1-aminoethyl)-8-chloro-2-phenylisoquinoline-1(2H)-one according to the same manner as described in step 1 of Example 5 (2.199 mmol, yield: 92%).

$^1$H NMR (300 MHz, CDCl$_3$) δ 8.71 (d, J=6.7 Hz, 1H), 7.56-7.63 (m, 1H), 7.38-7.55 (m, 6H), 7.27-7.38 (m, 2H), 7.20-7.26 (m, 2H), 6.87 (d, J=8.9 Hz, 2H), 6.53 (brs, 1H), 6.47 (s, 1H), 4.91 (t, J=7.7 Hz, 1H), 4.67 (d, J=4.5 Hz, 2H), 3.80 (s, 3H), 3.51 (s, 3H), 3.37 (s, 3H), 1.35 (d, J=6.7 Hz, 3H).

Step 2: Preparation of (S)-4-((1-(8-chloro-1-oxo-2-phenyl-1,2-dihydroisoquinoline-3-yl)ethyl)amino)-8-(4-methoxybenzyl)-2-(methylthio)pyrido[2,3-d]pyrimidine-5(8H)-one 90 mg of (S)-4-((1-(8-chloro-1-oxo-2-phenyl-1,2-dihydroisoquinoline-3-yl)ethyl)amino)-8-(4-methoxybenzyl)pyrido[2,3-d]pyrimidine-5(8H)-one was prepared as a white solid by using 700 mg (1.166 mmol) of (S)-3-(1-((5-acetyl-6-((4-methoxybenzyl)amino)-2-(methylthio)pyrimidine-4-yl)amino)ethyl)-8-chloro-2-phenylisoquinoline-1(2H)-one prepared in step 1 according to the same manner as described in step 2 of Example 5 (0.160 mmol, yield: 44%).

$^1$H NMR (300 MHz, CDCl$_3$) δ 10.71 (d, J=6.9 Hz, 1H), 8.30 (s, 1H), 7.47-7.57 (m, 3H), 7.29-7.47 (m, 6H), 7.23 (d, J=8.3 Hz, 2H), 6.87 (d, J=8.3 Hz, 2H), 6.59 (s, 1H), 6.30 (d, J=8.3 Hz, 1H), 5.35 (s, 2H), 4.93 (t, J=6.9 Hz, 1H), 3.78 (s, 3H), 1.45 (d, J=6.9 Hz, 3H).

Step 3: Preparation of (S)-4-((1-(8-chloro-1-oxo-2-phenyl-1,2-dihydroisoquinoline-3-yl)ethyl)amino)-2-(methylthio)pyrido[2,3-d]pyrimidine-5(8H)-one 195 mg of (S)-4-((1-(8-chloro-1-oxo-2-phenyl-1,2-dihydroisoquinoline-3-yl)ethyl)amino)-2-(methylthio)pyrido[2,3-d]pyrimidine-5(8H)-one was prepared as a white solid by using 249 mg (0.408 mmol) of (S)-4-((1-(8-chloro-1-oxo-2-phenyl-1,2-dihydroisoquinoline-3-yl)ethyl)amino)-8-(4-methoxybenzyl)-2-(methylthio)pyrido[2,3-d]pyrimidine-5(8H)-one prepared in step 2 according to the same manner as described in step 8 of Example 1 (0.398 mmol, yield: 98%).

$^1$H NMR (300 MHz, DMSO-d$_6$) δ 10.56 (d, J=6.6 Hz, 1H), 7.58-7.72 (m, 3H), 7.47-7.57 (m, 2H), 7.34-7.46 (m, 2H), 7.29 (d, J=3.2 Hz, 2H), 6.77 (s, 1H), 6.07 (d, J=6.6 Hz, 1H), 4.74 (t, J=7.7 Hz, 1H), 2.34 (s, 3H), 1.39 (d, J=6.6 Hz, 3H).

Step 4: Preparation of (S)-2-amino-4-((1-(8-chloro-1-oxo-2-phenyl-1,2-dihydroisoquinoline-3-yl)ethyl)amino)pyrido[2,3-d]pyrimidine-5(8H)-one 100 mg (0.204 mmol) of (S)-4-((1-(8-chloro-1-oxo-2-phenyl-1,2-dihydroisoquinoline-3-yl)ethyl)amino)-2-(methylthio)pyrido[2,3-d]pyrimidine-5(8H)-one prepared in step 3 was dissolved in 7 mL of dichloromethane:methanol (2:5), to which 70 mg (0.408 mmol) of 3-chloroperoxybenzoic acid (mCPBA) was added at 0° C., followed by stirring at room temperature for 30 minutes. Water was added to the reaction mixture, followed by extraction with ethyl acetate. The extract was washed with saturated sodiumbicarbonate solution. The organic layer was separated, dried (Na$_2$SO$_4$), and concentrated. The obtained compound was dissolved in 5 mL of tetrahydrofuran:isopropanol (1:1), to which 2 mL of 28% ammonia water was added, followed by stirring at 50° C. for 10 hours. The reaction mixture was cooled down to room temperature. Water was added to the reaction mixture, followed by extraction with ethyl acetate. The extracted organic layer was dried (Na$_2$SO$_4$) and concentrated. The obtained compound was separated by column chromatography (SiO$_2$, eluent: 2% methanol dichloromethane/methanol, 50/1→dichloromethane/methanol, 20/1) to give 49 mg of the target compound (S)-2-amino-4-((1-(8-chloro-1-oxo-2-phenyl-1,2-dihydroisoquinoline-3-yl)ethyl)amino)pyrido[2,3-d]pyrimidine-5(8H)-one as a white solid (0.107 mmol, yield: 52%).

$^1$H NMR (300 MHz, CDCl$_3$) δ 10.48 (d, J=5.9 Hz, 1H), 7.28-7.55 (m, 8H), 7.22 (d, J=7.3 Hz, 1H), 6.60 (s, 1H), 6.07 (d, J=7.3 Hz, 1H), 4.99 (brs, 2H), 4.83 (t, J=7.3 Hz, 1H), 1.40 (d, J=7.3 Hz, 3H).

Example 16: Preparation of (S)-2-amino-4-(2-(8-chloro-1-oxo-2-phenyl-1,2-dihydroisoquinoline-3-yl)pyrrolidine-1-yl)pyrido[2,3-d]pyrimidine-5(8H)-one

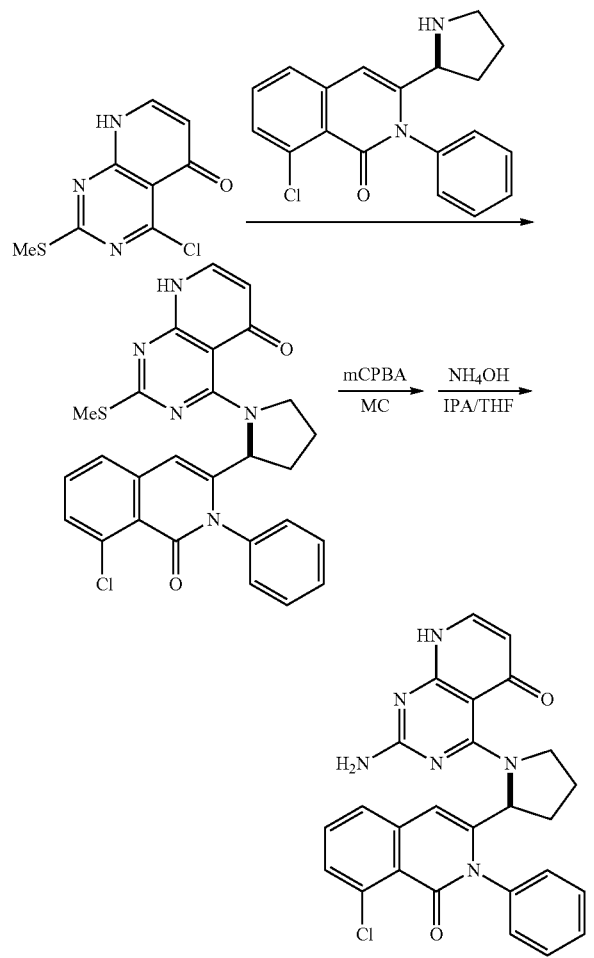

Step 1: Preparation of (S)-4-(2-(8-chloro-1-oxo-2-phenyl-1,2-dihydroisoquinoline-3-yl)pyrrolidine-1-yl)-2-(methylthio)pyrido[2,3-d]pyrimidine-5(8H)-one 42 mg of (S)-4-(2-(8-chloro-1-oxo-2-phenyl-1,2-dihydroisoquinoline-3-yl)pyrrolidine-1-yl)-2-(methylthio)pyrido[2,3-d]pyrimidine-5(8H)-one was prepared as a white solid by using 25 mg (0.11 mmol, 1.1 equivalent) of 4-chloro-2-(methylthio)pyrido[2,3-d]pyrimidine-5(8H)-one and 33 mg (0.10 mmol) of (S)-8-chloro-2-phenyl-3-(pyrrolidine-2-yl)isoquinoline-1(2H)-one according to the same manner as described in step 1 of Example 15 (0.081 mmol, yield: 81%).

$^1$H NMR (300 MHz, CDCl$_3$) δ 11.55 (s, —NH), 8.08 (s, 1H), 7.85-7.83 (m, 1H), 7.69-7.64 (m, 1H), 7.69-7.33 (m, 7H), 6.63 (s, 1H), 5.02-4.96 (m, 1H), 4.40-4.31 (m, 1H), 3.18-3.12 (m, 1H), 2.57 (s, 3H), 2.12-1.98 (m, 2H), 1.87-1.81 (m, 1H), 1.64-1.55 (m, 1H).

Step 2: Preparation of (S)-2-amino-4-(2-(8-chloro-1-oxo-2-phenyl-1,2-dihydroisoquinoline-3-yl)pyrrolidine-1-yl)pyrido[2,3-d]pyrimidine-5(8H)-one 23 mg of (S)-2-amino-4-(2-(8-chloro-1-oxo-2-phenyl-1,2-dihydroisoquinoline-3-yl)pyrrolidine-1-yl)pyrido[2,3-d]pyrimidine-5(8H)-one was prepared as a white solid by using 35 mg (0.068 mmol) of (S)-4-(2-(8-chloro-1-oxo-2-phenyl-1,2-dihydroisoquinoline-3-yl)pyrrolidine-1-yl)-2-(methylthio)pyrido[2,3-d]pyrimidine-5(8H)-one according to the same manner as described in step 4 of Example 15 (0.047 mmol, yield: 70%).

$^1$H NMR (300 MHz, CDCl$_3$) δ 8.76 (br s, 1H), 7.81-7.20 (m, 9H), 6.73 (s, 1H), 6.19 (d, J=7.5 Hz, 1H), 5.02-4.95 (m, 1H), 4.75 (br s, 2H), 4.44-4.31 (m, 1H), 3.20-3.10 (m, 1H), 2.57 (s, 3H), 2.10-1.40 (m, 4H).

Example 17: Preparation of (S)-4-((1-(8-chloro-1-oxo-2-phenyl-1,2-dihydroisoquinoline-3-yl)ethyl)amino)-6-methylpyrido[2,3-d]pyrimidine-5(8H)-one

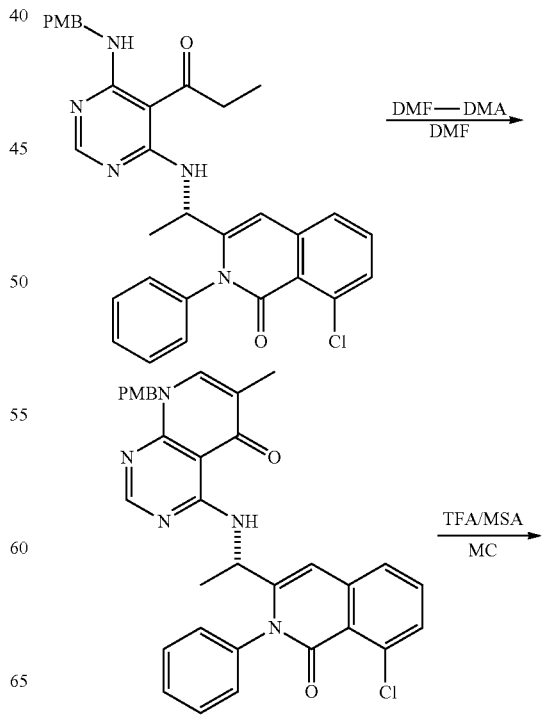

119

-continued

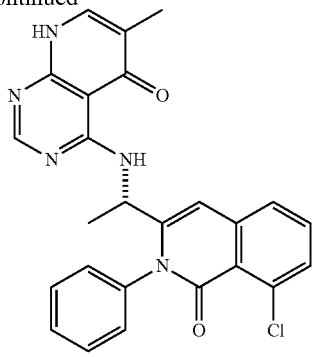

Step 1: Preparation of (S)-4-((1-(8-chloro-1-oxo-2-phenyl-1,2-dihydroisoquinoline-3-yl)ethyl)amino)-8-(4-methoxybenzyl)-6-methylpyrido[2,3-d]pyrimidine-5(8H)-one 168 mg of (S)-4-((1-(8-chloro-1-oxo-2-phenyl-1,2-dihydroisoquinoline-3-yl)ethyl)amino)-8-(4-methoxybenzyl)-6-methylpyrido[2,3-d]pyrimidine-5(8H)-one was prepared as a white solid by using 300 mg (0.528 mmol) of (S)-8-chloro-3-(1-((6-((4-methoxybenzyl)amino)-5-propionylpyrimidine-4-yl)amino)ethyl)-2-phenylisoquinoline-1(2H)-one according to the same manner as described in step 2 of Example 5 (0.291 mmol, yield: 55%).

¹H NMR (300 MHz, CDCl₃) δ 10.87 (d, J=7.3 Hz, 1H), 8.28 (s, 1H), 7.29-7.57 (m, 9H), 7.22 (d, J=8.3 Hz, 2H), 6.86 (d, J=8.3 Hz, 2H), 6.60 (s, 1H), 5.36 (s, 2H), 4.93 (t, J=6.3 Hz, 1H), 3.79 (s, 3H), 2.06 (s, 3H), 1.46 (d, J=7.3 Hz, 3H).

Step 2: Preparation of (S)-4-((1-(8-chloro-1-oxo-2-phenyl-1,2-dihydroisoquinoline-3-yl)ethyl)amino)-6-methylpyrido[2,3-d]pyrimidine-5(8H)-one 120 mg of (S)-4-((1-(8-chloro-1-oxo-2-phenyl-1,2-dihydroisoquinoline-3-yl)ethyl)amino)-6-methylpyrido[2,3-d]pyrimidine-5(8H)-one was prepared as a white solid by using 168 mg (0.291 mmol) of (S)-4-((1-(8-chloro-1-oxo-2-phenyl-1,2-dihydroisoquinoline-3-yl)ethyl)amino)-8-(4-methoxybenzyl)-6-methylpyrido[2,3-d]pyrimidine-5(8H)-one prepared in step 1 according to the same manner as described in step 8 of Example 1 (0.262 mmol, yield: 90%).

¹H NMR (300 MHz, DMSO-d₆) δ 10.69 (d, J=5.0 Hz, 1H), 8.15 (s, 1H), 7.77 (s, 1H), 7.57-7.69 (m, 2H), 7.30-7.56 (m, 7H), 6.76 (s, 1H), 4.64-4.73 (m, 1H), 1.92 (s, 3H), 1.40 (d, J=6.0 Hz, 3H).

Example 18: Preparation of (S)-2-amino-4-((1-(8-chloro-1-oxo-2-phenyl-1,2-dihydroisoquinoline-3-yl)ethyl)amino)-6-methylpyrido[2,3-d]pyrimidine-5(8H)-one

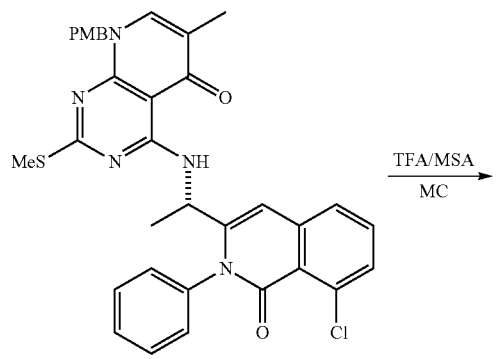

120

-continued

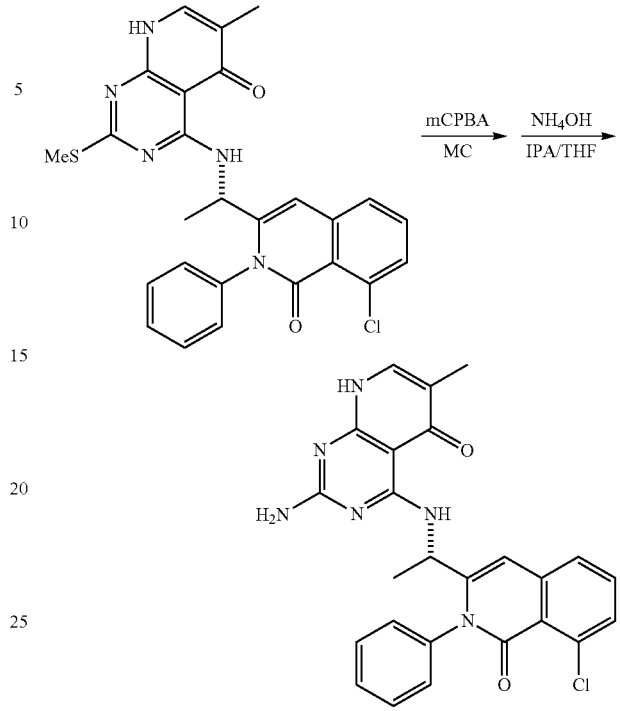

Step 1: Preparation of (S)-4-((1-(8-chloro-1-oxo-2-phenyl-1,2-dihydroisoquinoline-3-yl)ethyl)amino)-6-methyl-2-(methylthio)pyrido[2,3-d]pyrimidine-5(8H)-one 110 mg of (S)-4-((1-(8-chloro-1-oxo-2-phenyl-1,2-dihydroisoquinoline-3-yl)ethyl)amino)-6-methyl-2-(methylthio)pyrido[2,3-d]pyrimidine-5(8H)-one was prepared as a white solid by using 150 mg (0.240 mmol) of (S)-4-((1-(8-chloro-1-oxo-2-phenyl-1,2-dihydroisoquinoline-3-yl)ethyl)amino)-8-(4-methoxybenzyl)-6-methyl-2-(methylthio)pyrido[2,3-d]pyrimidine-5(8H)-one according to the same manner as described in step 8 of Example 1 (0.218 mmol, yield: 91%).

¹H NMR (300 MHz, CDCl₃) δ 10.97 (brs, 1H), 10.82 (d, J=7.4 Hz, 1H), 7.28-7.60 (m, 9H), 6.67 (s, 1H), 5.11 (t, J=7.4 Hz, 1H), 2.38 (s, 3H), 2.06 (s, 3H), 1.48 (d, J=7.4 Hz, 3H).

Step 2: Preparation of (S)-2-amino-4-((1-(8-chloro-1-oxo-2-phenyl-1,2-dihydroisoquinoline-3-yl)ethyl)amino)-6-methylpyrido[2,3-d]pyrimidine-5(8H)-one 84 mg of (S)-2-amino-4-((1-(8-chloro-1-oxo-2-phenyl-1,2-dihydroisoquinoline-3-yl)ethyl)amino)-6-methylpyrido[2,3-d]pyrimidine-5(8H)-one was prepared as a white solid by using 110 mg (0.218 mmol) of (S)-4-((1-(8-chloro-1-oxo-2-phenyl-1,2-dihydroisoquinoline-3-yl)ethyl)amino)-6-methyl-2-(methylthio)pyrido[2,3-d]pyrimidine-5(8H)-one prepared in step 1 according to the same manner as described in step 4 of Example 15 (0.178 mmol, yield: 81%).

¹H NMR (300 MHz, CDCl₃) δ 10.67 (d, J=5.9 Hz, 1H), 7.29-7.59 (m, 8H), 7.20 (s, 1H), 6.61 (s, 1H), 4.78-4.93 (m, 3H), 1.99 (s, 3H), 1.41 (d, J=7.3 Hz, 3H).

Example 19: Preparation of (S)-4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile

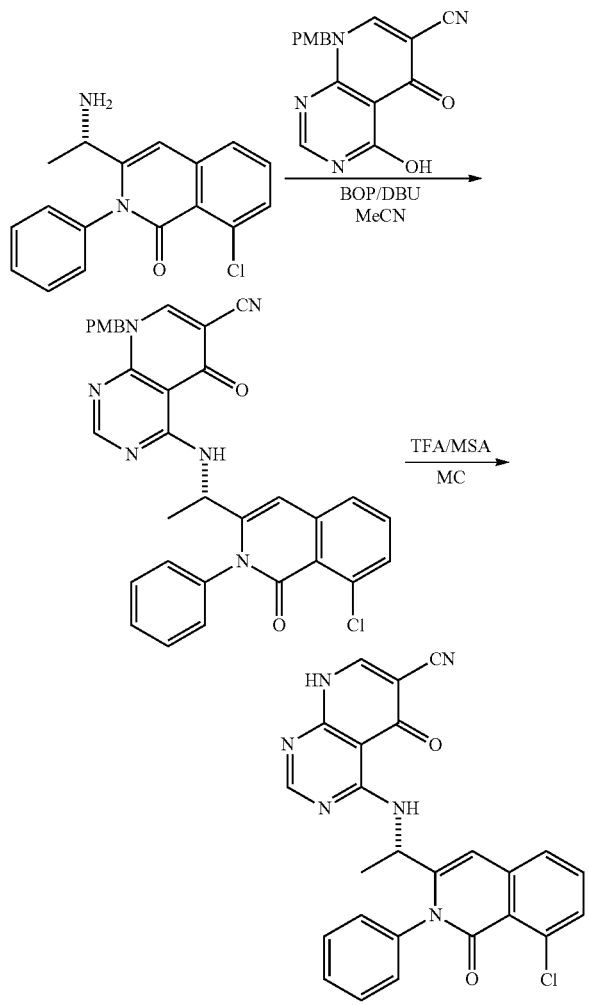

Step 1: Preparation of (S)-4-(1-(8-chloro-1-oxo-2-phenyl-1,2-dihydroisoquinoline-3-yl)ethylamino)-8-(4-methoxybenzyl)-5-oxo-5,8-dihydropyrido[2,3-d]pyrimidine-6-carbonitrile (S)-4-(1-(8-chloro-1-oxo-2-phenyl-1,2-dihydroisoquinoline-3-yl)ethylamino)-8-(4-methoxybenzyl)-5-oxo-5,8-dihydropyrido[2,3-d]pyrimidine-6-carbonitrile was prepared by using 4-hydroxy-8-(4-methoxybenzyl)-5-oxo-5,8-dihydropyrido[2,3-d]pyrimidine-6-carbonitrile and (S)-3-(1-aminoethyl)-8-chloro-2-phenylisoquinoline-1(2H)-one according to the same manner as described in step 7 of Example 1.

MS[m/z; (M+1)+]: 590.

Step 2: Preparation of (S)-4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile (S)-4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile was prepared by using (S)-4-(1-(8-chloro-1-oxo-2-phenyl-1,2-dihydroisoquinoline-3-yl)ethylamino)-8-(4-methoxybenzyl)-5-oxo-5,8-dihydropyrido[2,3-d]pyrimidine-6-carbonitrile prepared in step 1 according to the same manner as described in step 8 of Example 1.

MS[m/z; (M+1)+]: 470.

Example 20: Preparation of (S)-4-((1-(8-chloro-1-oxo-2-phenyl-1,2-dihydroisoquinoline-3-yl)ethyl)amino)-6-fluoropyrido[2,3-d]pyrimidine-5(8H)-one

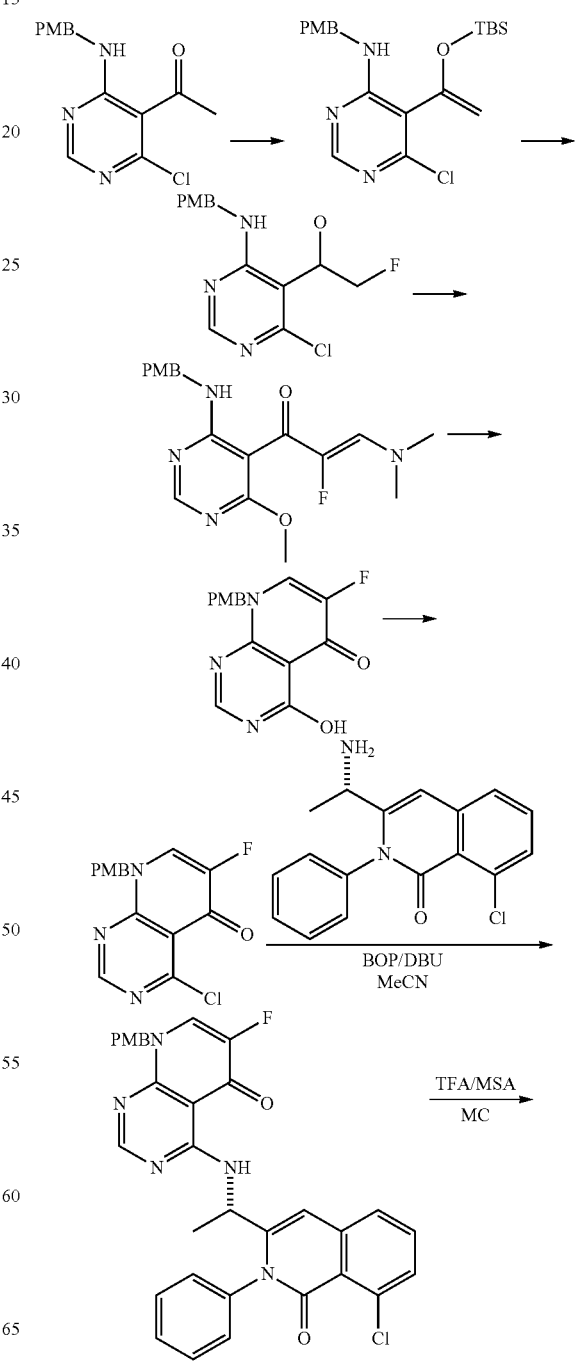

-continued

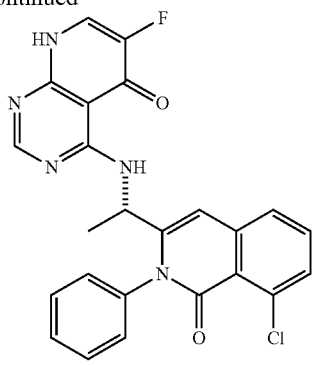

Step 1: Preparation of 5-(1-((tert-butyldimethylsylyl)oxy)vinyl)-6-chloro-N-(4-methoxybenzyl)pyrimidine-4-amine 2.8 g (9.598 mmol) of 1-(4-chloro-6-((4-methoxybenzyl)amino)pyrimidine-5-yl)ethane-1-one prepared in step 4 of Example 1 was dissolved in 15 mL anhydrous dichloromethane, to which 2 mL (14.397 mmol) of $Et_3N$ was added, followed by stirring at room temperature for 30 minutes. 3.09 mL (13.437 mmol) of TBS-OTf was added thereto, followed by stirring at room temperature for 12 hours. Then, the reaction mixture was concentrated under reduced pressure. The residue was separated by column chromatography ($SiO_2$, eluent: hexane/ethyl acetate, 10/1) to give 3.8 g of the target compound 5-(1-((tert-butyldimethylsylyl)oxy)vinyl)-6-chloro-N-(4-methoxybenzyl)pyrimidine-4-amine as a white liquid (9.360 mmol, yield: 98%).

$^1$H NMR (300 MHz, $CDCl_3$) δ 8.34 (s, 1H), 7.35 (d, J=8.6 Hz, 2H), 6.99 (d, J=8.4 Hz, 2H), 5.93 (br s, 1H), 4.97 (d, J=1.4 Hz, 1H), 4.81 (d, J=1.4 Hz, 1H), 4.73 (d, J=5.4 Hz, 2H), 3.83 (s, 3H), 0.91 (s, 9H), 0.12 (m, 6H).

Step 2: Preparation of 1-(4-chloro-6-((4-methoxybenzyl)amino)pyrimidine-5-yl)-2-fluoroethane-1-one 3.8 g (9.360 mmol) of 5-(1-((tert-butyldimethylsylyl)oxy)vinyl)-6-chloro-N-(4-methoxybenzyl)pyrimidine-4-amine prepared in step 1 was dissolved in 40 mL of anhydrous acetonitrile, to which 3.65 g (10.300 mmol) of 1-chloromethyl-4-fluoro-1,4-diazoniabicyclo[2.2.2]octanebis(tetrafluoroborate) (selectfluor) was added, followed by stirring at room temperature for 15 hours. Ethyl acetate and water was added to the reaction mixture, followed by extraction. The extracted organic layer was dried ($Na_2SO_4$), filtered, and concentrated under reduced pressure. The residue was separated by column chromatography ($SiO_2$, eluent: hexane/ethylacetate, 4/1) to give 2.5 g of the target compound 1-(4-chloro-6-((4-methoxybenzyl)amino)pyrimidine-5-yl)-2-fluoroethane-1-one as a white liquid (8.072 mmol, yield: 86%).

$^1$H NMR (300 MHz, $CDCl_3$) δ 9.55 (br s, 1H), 8.44 (s, 1H), 7.28 (d, J=7.9 Hz, 2H), 6.91 (d, J=8.4 Hz, 2H), 5.60 (s, 1H), 5.51 (s, 1H), 4.73 (d, J=5.0 Hz, 2H), 3.83 (s, 3H).

Step 3: Preparation of 3-(dimethylamino)-2-fluoro-1-(4-methoxy-6-((4-methoxybenzyl)amino)pyrimidine-5-yl)prop-2-en-1-one 2.5 g (8.072 mmol) of 1-(4-chloro-6-((4-methoxybenzyl)amino)pyrimidine-5-yl)-2-fluoroethane-1-one prepared in step 2 was dissolved in 50 mL of anhydrous toluene, to which 10.76 mL (80.720 mmol) of N,N-dimethylformamide dimethyl acetal (DMF-DMA) was added, followed by stirring at 90° C. for 1 hour. The reaction mixture was cooled down to room temperature. Ethyl acetate and water was added to the reaction mixture, followed by extraction. The extracted organic layer was dried ($Na_2SO_4$), filtered, and concentrated under reduced pressure. The residue was separated by column chromatography ($SiO_2$, eluent: hexane/ethyl acetate, 3/1,→hexane/ethyl acetate, 1/1) to give 2.1 g of the target compound 3-(dimethylamino)-2-fluoro-1-(4-methoxy-6-((4-methoxybenzyl)amino)pyrimidine-5-yl)prop-2-en-1-one as a yellow liquid (5.827 mmol, yield: 72%).

$^1$H NMR (500 MHz, $CDCl_3$) δ 8.19 (s, 1H), 7.28 (d, J=8.4 Hz, 2H), 6.86 (d, J=8.4 Hz, 2H), 4.64 (d, J=5.5 Hz, 2H), 3.91 (s, 3H), 3.80 (s, 3H), 3.12 (s, 6H).

Step 4: Preparation of 6-fluoro-4-hydroxy-8-(4-methoxybenzyl)pyrido[2,3-d]pyrimidine-5(8H)-one 2.1 g (5.827 mmol) of (Z)-3-(dimethylamino)-2-fluoro-1-(4-methoxy-6-((4-methoxybenzyl)amino)pyrimidine-5-yl)prop-2-en-1-one prepared in step 3 was dissolved in 120 mL of acetic acid:water (5:1), which was stirred at 90~150° C. for 2 days. The reaction mixture was cooled down to room temperature and filtered under reduced pressure. Isopropanol and ether were added thereto, followed by filtration to give 1.5 g of the target compound 6-fluoro-4-hydroxy-8-(4-methoxybenzyl)pyrido[2,3-d]pyrimidine-5(8H)-one as a pale yellow solid (4.978 mmol, yield: 85%).

$^1$H NMR (500 MHz, DMSO-$d_6$) δ 8.39 (d, J=7.7 Hz, 1H), 8.27 (s, 1H), 7.28 (d, J=8.5 Hz, 2H), 6.90 (d, J=8.8 Hz, 2H), 5.34 (s, 2H), 3.73 (s, 3H).

Step 5: Preparation of 4-chloro-6-fluoro-8-(4-methoxybenzyl)pyrido[2,3-d]pyrimidine-5(8H)-one 50 mg (0.166 mmol) of 6-fluoro-4-hydroxy-8-(4-methoxybenzyl)pyrido[2,3-d]pyrimidine-5(8H)-one prepared in step 4 was dissolved in 2 mL of anhydrous toluene, to which 131 mg (0.498 mmol) of triphenylphosphine ($PPh_3$) and 50 μL (0.498 mmol) of trichloroacetonitrile ($CCl_3CN$) were added, followed by stirring at 120° C. for 4 hours. The reaction mixture was cooled down to room temperature. Ethyl acetate and water were added thereto, followed by extraction. The extracted organic layer was dried ($Na_2SO_4$), filtered, and concentrated under reduced pressure. The residue was separated by column chromatography ($SiO_2$, eluent: hexane/ethyl acetate, 5/1→hexane/ethyl acetate, 3/1) to give 4 mg of the target compound 4-chloro-6-fluoro-8-(4-methoxybenzyl)pyrido[2,3-d]pyrimidine-5(8H)-one as a pale yellow solid (0.013 mmol, yield: 8%).

$^1$H NMR (300 MHz, $CDCl_3$) δ 8.87 (s, 1H), 7.71 (d, J=7.1 Hz, 1H), 7.24 (d, J=8.8 Hz, 2H), 6.90 (d, J=8.8 Hz, 2H), 5.47 (s, 2H), 3.81 (s, 3H).

Step 6: Preparation of (S)-4-((1-(8-chloro-1-oxo-2-phenyl-1,2-dihydroisoquinoline-3-yl)ethyl)amino)-6-fluoro-8-(4-methoxybenzyl)pyrido[2,3-d]pyrimidine-5(8H)-one 4 mg (0.013 mmol) of 4-chloro-6-fluoro-8-(4-methoxybenzyl)pyrido[2,3-d]pyrimidine-5(8H)-one prepared in step 5 and 4 mg (0.014 mmol) of (S)-3-(1-aminoethyl)-8-chloro-2-phenylisoquinoline-1(2H)-one were dissolved in 1 mL of anhydrous dimethylsulfoxide (DMSO), to which 6.6 μL (0.039 mmol) of diisopropylethylamine (DIPEA) was added, followed by stirring at 70° C. for 5 hours. The reaction mixture was cooled down to room temperature. Ethyl acetate and water were added thereto, followed by extraction. The extracted organic layer was dried ($Na_2SO_4$), filtered, and concentrated under reduced pressure. The residue was separated by column chromatography ($SiO_2$, eluent: hexane/ethyl acetate, 4/1→hexane/ethyl acetate, 1/1) to give 6 mg of the target compound (S)-4-((1-(8-chloro-1-oxo-2-phenyl-1,2-dihydroisoquinoline-3-yl)ethyl)amino)-6-fluoro-8-(4-methoxybenzyl)pyrido[2,3-d]pyrimidine-5(8H)-one as a pale yellow solid (0.010 mmol, yield: 82%).

$^1$H NMR (300 MHz, $CDCl_3$) δ 10.53 (d, J=6.6 Hz, 1H), 8.31 (s, 1H), 7.61 (d, J=6.9 Hz, 1H), 7.47-7.57 (m, 2H), 7.30-7.47 (m, 6H), 7.22 (d, J=8.2 Hz, 2H), 7.88 (d, J=8.2 Hz, 2H), 6.58 (s, 1H), 5.38 (s, 2H), 4.95 (q, J=4.2 Hz, 5.2 Hz, 1H), 3.79 (s, 3H), 1.46 (d, J=6.9 Hz, 3H).

Step 7: Preparation of (S)-4-((1-(8-chloro-1-oxo-2-phenyl-1,2-dihydroisoquinoline-3-yl)ethyl)amino)-6-fluoropyrido[2,3-d]pyrimidine-5(8H)-one 3 mg of (S)-4-((1-(8-chloro-1-oxo-2-phenyl-1,2-dihydroisoquinoline-3-yl)ethyl)amino)-6-fluoropyrido[2,3-d]pyrimidine-5(8H)-one was prepared as a pale yellow solid by using 6 mg (0.010 mmol) of (S)-4-((1-(8-chloro-1-oxo-2-phenyl-1,2-dihydroisoquinoline-3-yl)ethyl)amino)-6-fluoro-8-(4-methoxybenzyl)pyrido[2,3-d]pyrimidine-5(8H)-one prepared in step 6 according to the same manner as described in step 8 of Example 1 (0.006 mmol, yield: 63%).

$^1$H NMR (500 MHz, $CD_3OD$) δ8.19 (s, 1H), 8.07 (d, J=6.5 Hz, 1H), 7.62 (t, J=4.7 Hz, 2H), 7.53-7.60 (m, 2H), 7.39-7.45 (m, 3H), 7.34 (t, J=7.9 Hz, 1H), 6.90 (s, 1H), 4.99-5.05 (m, 1H), 1.56 (d, J=6.6 Hz, 3H).

Example 21: Preparation of (S)-4-((1-(5-chloro-4-oxo-3-phenyl-3,4-dihydroquinazoline-2-yl)ethyl)amino)-6-fluoropyrido[2,3-d]pyrimidine-5(8H)-one

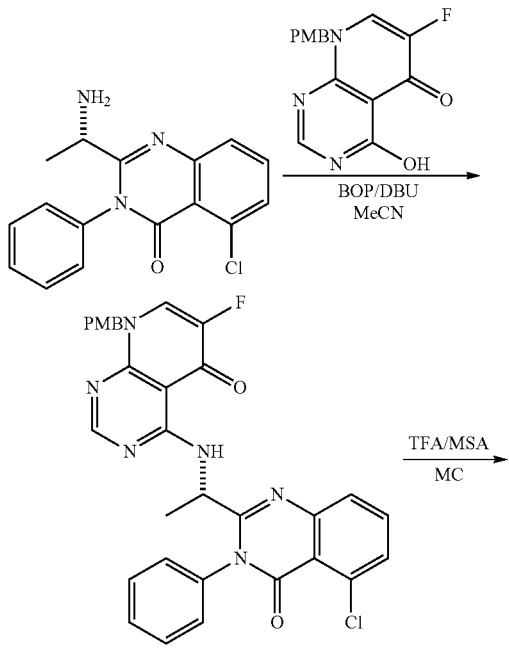

Step 1: Preparation of (S)-4-((1-(5-chloro-4-oxo-3-phenyl-3,4-dihydroquinazoline-2-yl)ethyl)amino)-6-fluoro-8-(4-methoxybenzyl)pyrido[2,3-d]pyrimidine-5(8H)-one

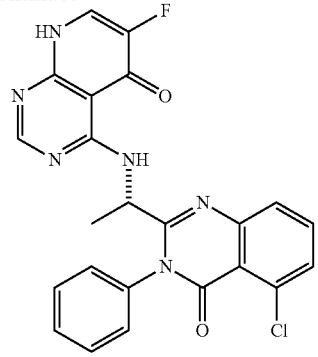 [SMILES: C[C@H](Nc1ncnc2[nH]cc(F)c(=O)c12)c1cc2cccc(Cl)c2c(=O)n1-c1ccccc1]

50 mg (0.166 mmol) of 6-fluoro-4-hydroxy-8-(4-methoxybenzyl)pyrido[2,3-d]pyrimidine-5(8H)-one was dissolved in 2 mL of anhydrous dimethylformamide, to which 95 mg (0.216 mmol) of (benzotriazole-1-yloxy)tris(dimethylamino)phosphonium hexafluorophosphate (BOP) and 81 mg (0.249 mmol) of cesiumcarbonate ($Cs_2CO_3$) were added, followed by stirring at room temperature for 30 minutes. 55 mg (0.183 mmol) of (S)-2-(1-aminoethyl)-5-chloro-3-phenylquinazoline-4(3H)-one was added thereto, followed by stirring at 60~80° C. for 2 hours. Ethyl acetate and water were added to the reaction mixture, followed by extraction. The extracted organic layer was dried ($Na_2SO_4$), filtered, and concentrated under reduced pressure. The residue was separated by column chromatography ($SiO_2$, eluent: hexane/ethyl acetate, 5/1→hexane/ethyl acetate, 1/1) to give 10 mg of the target compound (S)-4-((1-(5-chloro-4-oxo-3-phenyl-3,4-dihydroquinazoline-2-yl)ethyl)amino)-6-fluoro-8-(4-methoxybenzyl)pyrido[2,3-d]pyrimidine-5(8H)-one as a pale yellow solid (0.017 mmol, yield: 10%).

$^1$H NMR (300 MHz, $CDCl_3$) δ 10.87 (d, J=7.0 Hz, 1H), 8.29 (s, 1H), 7.72 (d, J=7.8 Hz, 1H), 7.44-7.62 (m, 7H), 7.33 (d, J=7.3 Hz, 1H), 7.21 (d, J=8.6 Hz, 2H), 6.87 (d, J=8.6 Hz, 2H), 5.32 (s, 2H), 5.11 (q, J=5.4 Hz, 6.8 Hz, 1H), 3.79 (s, 3H), 1.50 (d, J=7.1 Hz, 3H).

Step 2: Preparation of (S)-4-((1-(5-chloro-4-oxo-3-phenyl-3,4-dihydroquinazoline-2-yl)ethyl)amino)-6-fluoropyrido[2,3-d]pyrimidine-5(8H)-one 6 mg of (S)-4-((1-(5-chloro-4-oxo-3-phenyl-3,4-dihydroquinazoline-2-yl)ethyl)amino)-6-fluoropyrido[2,3-d]pyrimidine-5(8H)-one was prepared as a pale yellow solid by using 10 mg (0.017 mmol) of (S)-4-((1-(5-chloro-4-oxo-3-phenyl-3,4-dihydroquinazoline-2-yl)ethyl)amino)-6-fluoro-8-(4-methoxybenzyl)pyrido[2,3-d]pyrimidine-5(8H)-one prepared in step 1 according to the same manner as described in step 8 of Example 1 (0.013 mmol, yield: 76%).

$^1$H NMR (300 MHz, $CDCl_3$) δ 10.84 (d, J=8.1 Hz, 1H), 8.22 (s, 1H), 7.72 (d, J=7.9 Hz, 1H), 7.52-7.64 (m, 6H), 7.42-7.49 (m, 2H), 7.35 (d, J=7.3 Hz, 1H), 5.12 (q, J=5.5 Hz, 6.7 Hz, 1H), 1.51 (d, J=6.7 Hz, 3H).

Example 22: Preparation of (S)-6-chloro-4-((1-(5-chloro-4-oxo-3-phenyl-3,4-dihydroquinazoline-2-yl)ethyl)amino)pyrido[2,3-d]pyrimidine-5(8H)-one

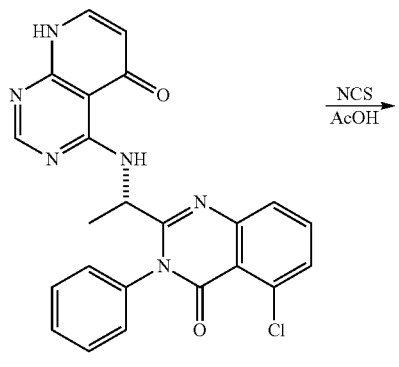

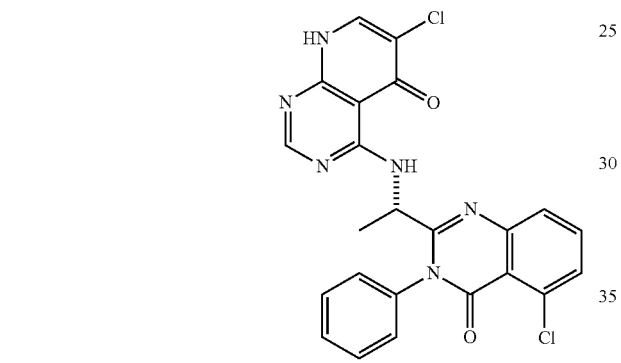

10 mg (0.022 mmol) of (S)-4-((1-(5-chloro-4-oxo-3-phenyl-3,4-dihydroquinazoline-2-yl)ethyl)amino)pyrido[2,3-d]pyrimidine-5(8H)-one prepared in Example 1 was dissolved in 1 mL of acetic acid, to which 3.3 mg (0.025 mmol) of N-chlorosuccinimide (NCS) was added, followed by stirring at 50~60° C. for 12 hours. The reaction mixture was cooled down to room temperature and filtered under reduced pressure. Saturated sodiumbicarbonate aqueous solution was added thereto, followed by neutralization. Dichloromethane and water were added thereto, followed by extraction. The extracted organic layer was dried ($Na_2SO_4$), filtered, and concentrated under reduced pressure. The residue was separated by column chromatography ($SiO_2$, eluent: dichloromethane/methanol, 50/1→dichloromethane/methanol, 20/1) to give 3 mg of the target compound (S)-6-chloro-4-((1-(5-chloro-4-oxo-3-phenyl-3,4-dihydroquinazoline-2-yl)ethyl)amino)pyrido[2,3-d]pyrimidine-5(8H)-one as a pale yellow solid (0.006 mmol, yield: 28%).

$^1$H NMR (300 MHz, $CDCl_3$) δ 9.62 (d, J=8.1 Hz, 1H), 8.07 (s, 1H), 7.74 (d, J=7.3 Hz, 1H), 7.46-7.67 (m, 6H), 7.29-7.40 (m, 2H), 5.08-5.18 (m, 1H), 1.45 (d, J=5.7 Hz, 3H).

Example 23: Preparation of (S)-6-chloro-4-((1-(8-chloro-1-oxo-2-phenyl-1,2-dihydroisoquinoline-3-yl)ethyl)amino)pyrido[2,3-d]pyrimidine-5(8H)-one

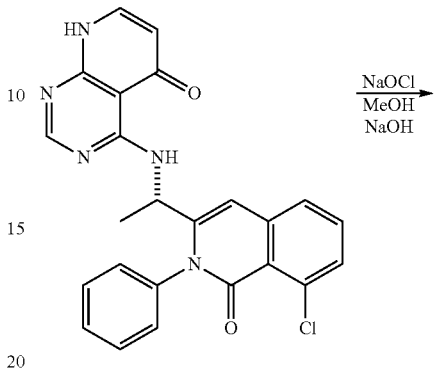

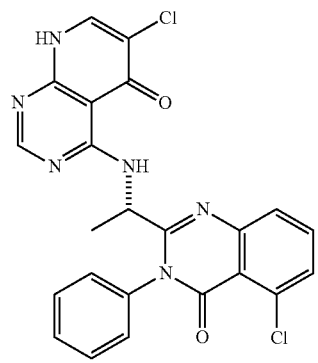

10 mg (0.023 mmol) of (S)-4-((1-(8-chloro-1-oxo-2-phenyl-1,2-dihydroisoquinoline-3-yl)ethyl)amino)pyrido[2,3-d]pyrimidine-5(8H)-one prepared in Example 5 was dissolved in 2 mL of methanol:water (1:1), to which 34 μL (0.068 mmol) of 2N sodiumhydroxide and 34 μL of 12% sodiumhypochloride at 0° C., followed by stirring at room temperature for 1 hour. The reaction mixture was filtered under reduced pressure, followed by neutralization with 1N HCl. Dichloromethane and water were added thereto, followed by extraction. The extracted organic layer was dried ($Na_2SO_4$), filtered, and concentrated under reduced pressure. The residue was separated by column chromatography ($SiO_2$, eluent: dichloromethane/methanol, 50/1→dichloromethane/methanol, 20/1) to give 2 mg of the target compound (S)-6-chloro-4-((1-(8-chloro-1-oxo-2-phenyl-1,2-dihydroisoquinoline-3-yl)ethyl)amino)pyrido[2,3-d]pyrimidine-5(8H)-one as a yellow solid (0.004 mmol, yield: 19%).

$^1$H NMR (300 MHz, $CDCl_3$) δ 10.53 (d, J=5.6 Hz, 1H), 8.25 (s, 1H), 7.84 (s, 1H), 7.49-7.57 (m, 2H), 7.40-7.47 (m, 4H), 7.30-7.39 (m, 2H), 6.58 (s, 1H), 4.95 (t, J=6.7 Hz, 1H), 1.47 (d, J=6.6 Hz, 3H).

Example 24: Preparation of (S)-6-chloro-4-((1-(4,8-dichloro-1-oxo-2-phenyl-1,2-dihydroisoquinoline-3-yl)ethyl)amino)pyrido[2,3-d]pyrimidine-5(8H)-one Example 25: Preparation of (S)-2-amino-4-((1-(6-fluoro-3-(pyridine-2-yl)quinoline-2-yl)ethyl)amino)pyrido[2,3-d]pyrimidine-5(8H)-one

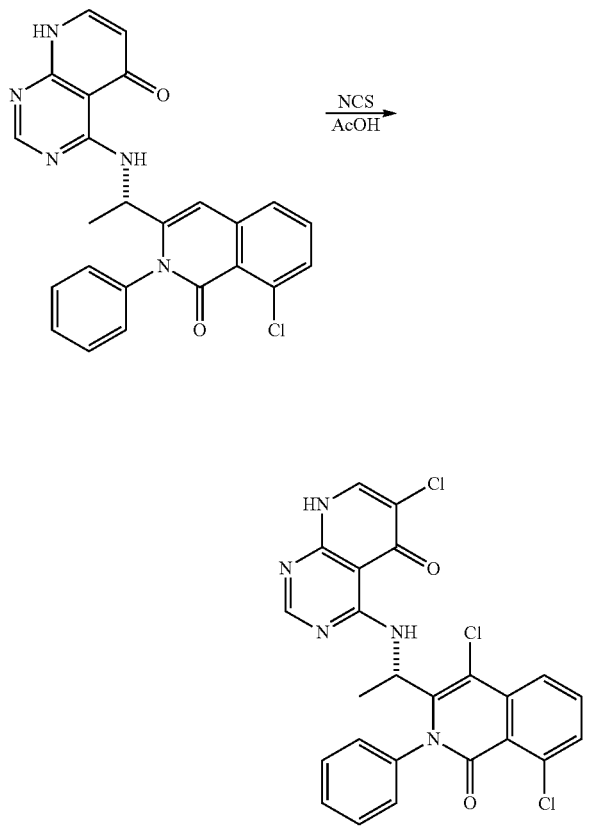

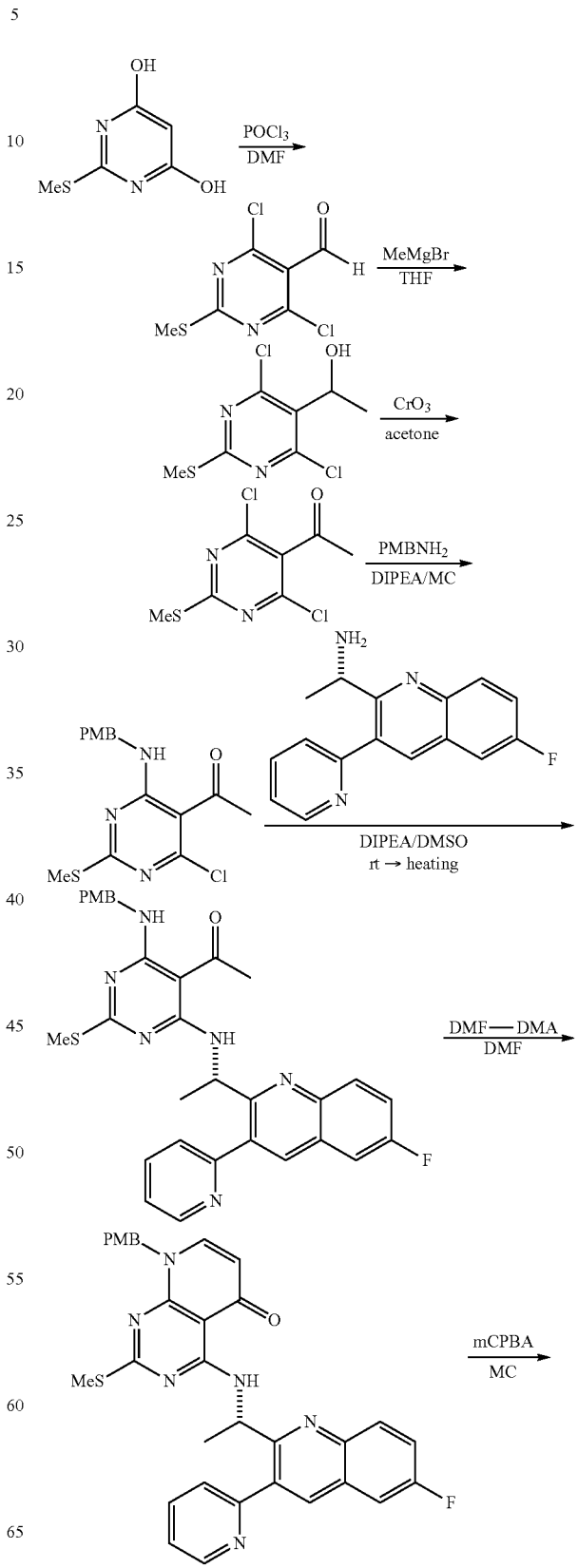

50 mg (0.113 mmol) of (S)-4-((1-(8-chloro-1-oxo-2-phenyl-1,2-dihydroisoquinoline-3-yl)ethyl)amino)pyrido[2,3-d]pyrimidine-5(8H)-one prepared in Example 5 was dissolved in 2 mL of acetic acid, to which 17 mg (0.124 mmol) of N-chlorosuccinimide (NCS) was added, followed by stirring at 50° C. for 15 hours. The reaction mixture was filtered under reduced pressure. Saturated sodiumbicarbonate aqueous solution was added thereto, followed by neutralization. Dichloromethane and water were added thereto, followed by extraction. The extracted organic layer was dried ($Na_2SO_4$), filtered, and concentrated under reduced pressure. The residue was separated by column chromatography ($SiO_2$, eluent: dichloromethane/methanol, 50/1→dichloromethane/methanol, 20/1) to give 17 mg of the target compound (S)-6-chloro-4-((1-(4,8-dichloro-1-oxo-2-phenyl-1,2-dihydroisoquinoline-3-yl)ethyl)amino)pyrido[2,3-d]pyrimidine-5(8H)-one as a pale yellow solid (0.036 mmol, yield: 29%).

$^1$H NMR (300 MHz, $CDCl_3$) δ 10.92 (d, J=4.4 Hz, 1H), 8.28 (s, 1H), 7.91-7.98 (m, 1H), 7.70-7.79 (m, 2H), 7.48-7.64 (m, 5H), 7.20 (d, J=6.2 Hz, 1H), 5.04 (t, J=7.12 Hz, 1H), 1.68 (d, J=7.1 Hz, 3H).

-continued

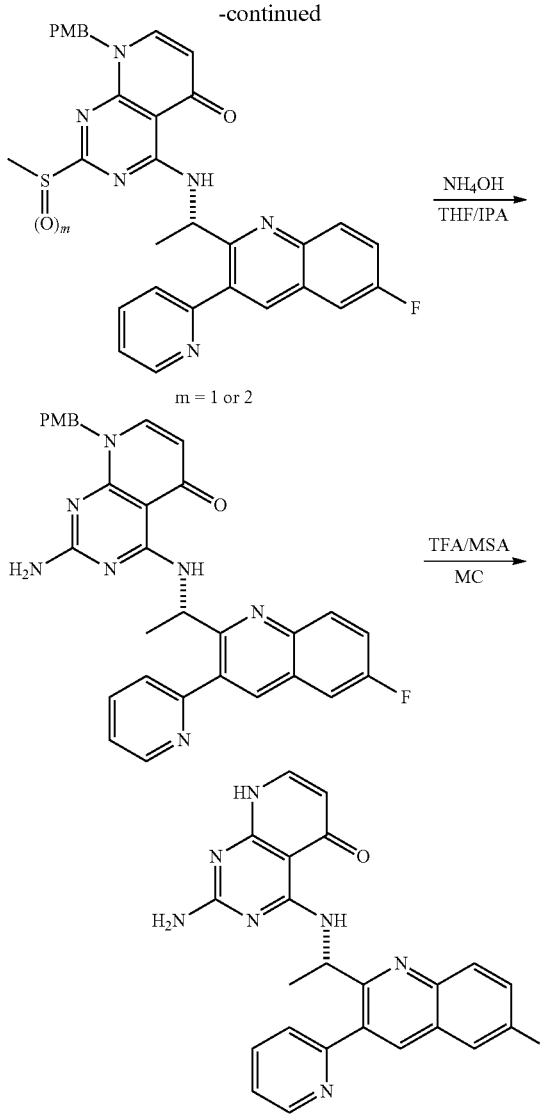

m = 1 or 2

Step 1: Preparation of 4,6-dichloro-2-methylmer-captopyrimidine-5-carbaldehyde 8.36 g of 4,6-dichloro-2-methylmercaptopyrimidine-5-carbaldehyde was prepared as a white solid by using 7.91 g (50.0 mmol) of 4,6-dihydroxy-2-methylmercaptopyrimidine according to the same manner as described in step 1 of Example 1 (37.5 mmol, yield: 75%).

$^1$H NMR (300 MHz, CDCl$_3$) δ 10.38 (s, 1H), 2.64 (s, 3H).

Step 2: Preparation of 1-(4,6-dichloro-2-methylmer-captopyrimidine-5-yl)ethane-1-ol 2.27 g of 1-(4,6-dichloro-2-methylmercaptopyrimidine-5-yl)ethane-1-ol was prepared as a white solid by using 2.23 g (10.0 mmol) of 4,6-dichloro-2-methylmercaptopyrimidine-5-carbaldehyde prepared in step 1 according to the same manner as described in step 2 of Example 1 (9.5 mmol, yield: 95%).

$^1$H NMR (300 MHz, CDCl$_3$) δ 5.40-5.47 (m, 1H), 2.57 (s, 3H), 2.52 (d, J=9.2 Hz, 1H), 1.64 (d, J=6.8 Hz, 3H).

Step 3: Preparation of 1-(4,6-dichloro-2-methylmer-captopyrimidine-5-yl)ethane-1-one 1.09 g of 1-(4,6-dichloro-2-methylmercaptopyrimidine-5-yl)ethane-1-one was prepared as a white solid by using 1.20 g (5.0 mmol) of 1-(4,6-dichloro-2-methylmercaptopyrimidine-5-yl)ethane-1-ol prepared in step 2 according to the same manner as described in step 3 of Example 1 (4.6 mmol, yield: 92%).

$^1$H NMR (300 MHz, CDCl$_3$) δ 2.62 (s, 3H), 2.61 (s, 3H).

Step 4: Preparation of 1-(4-chloro-2-methylmer-capto-6-((4-methoxybenzyl)amino)pyrimidine-5-yl)ethane-1-one 1.014 g of 1-(4-chloro-2-methylmercapto-6-((4-methoxy-benzyl)amino)pyrimidine-5-yl)ethane-1-one was prepared as a colorless oil by using 712 mg (3.0 mmol) of 1-(4,6-dichloro-2-methylmercaptopyrimidine-5-yl)ethane-1-one prepared in step 3 according to the same manner as described in step 4 of Example 1 (3.0 mmol, yield: 100%).

$^1$H NMR (300 MHz, CDCl$_3$) δ 9.53 (br s, 1H, NH), 7.25 (d, J=8.7 Hz, 2H), 6.87 (d, J=8.7 Hz, 2H), 4.66 (d, J=5.6 Hz, 2H), 3.80 (s, 3H), 2.71 (s, 3H), 2.50 (s, 3H).

Step 5: Preparation of (S)-1-(4-((1-(6-fluoro-3-(pyridine-2-yl)quinoline-2-yl)ethyl)amino)-6-((4-methoxybenzyl)amino)-2-(methylmercapto)pyrimi-dine-5-yl)ethane-1-one 376 mg of (S)-1-(4-((1-(6-fluoro-3-(pyridine-2-yl)quino-line-2-yl)ethyl)amino)-6-((4-methoxybenzyl)amino)-2-(methylmercapto)pyrimidine-5-yl)ethane-1-one was prepared as a colorless oil by using 338 mg (1.0 mmol) of 1-(4-chloro-2-methylmercapto-6-((4-methoxybenzyl) amino)pyrimidine-5-yl)ethane-1-one prepared in step 4 and 267 mg (1.0 mmol) of (S)-1-(6-fluoro-3-(pyridine-2-yl)eth-ane-1-amine according to the same manner as described in step 1 of Example 5 (0.66 mmol, yield: 66%).

$^1$H NMR (300 MHz, CDCl$_3$) δ 9.71 (br t, J=5.4 Hz, 1H, NH), 7.79 (d, J=4.7 Hz, 1H), 8.16 (s, 1H), 8.04 (m, 1H), 7.86-7.93 (m, 2H), 7.61-7.64 (m, 1H), 7.30-7.60 (m, 3H), 7.24 (m, 2H), 6.84 (m, 2H), 6.28 (m, 1H), 4.64 (d, J=5.4 Hz, 2H), 3.78 (s, 3H), 2.77 (s, 3H), 2.37 (s, 3H), 1.27 (d, J=7.2 Hz, 3H).

Step 6: Preparation of (S)-4-((1-(6-fluoro-3-(pyri-dine-2-yl)quinoline-2-yl)ethyl)amino)-8-(4-methoxybenzyl)-2-(methylmercapto)pyrido[2,3-d] pyrimidine-5(8H)-one 168 mg of (S)-4-((1-(6-fluoro-3-(pyridine-2-yl)quinoline-2-yl)ethyl)amino)-8-(4-methoxybenzyl)-2-(methylmer-capto)pyrido[2,3-d]pyrimidine-5(8H)-one was prepared as a white solid by using 285 mg (0.5 mmol) of (S)-1-(4-((1-(6-fluoro-3-(pyridine-2-yl)quinoline-2-yl)ethyl)amino)-6-((4-methoxybenzyl)amino)-2-(methylmercapto)pyrimidine-5-yl)ethane-1-one prepared in step 5 according to the same manner as described in step 2 of Example 5 (0.29 mmol, yield: 58%).

$^1$H NMR (300 MHz, CDCl$_3$) δ 11.42 (br d, J=7.6 Hz, 1H, NH), 8.77 (br d, J=4.8 Hz, 1H), 8.27 (m, 1H), 8.11 (s, 1H), 7.82 (m, 1H), 7.61 (d, J=7.8 Hz, 1H), 7.20-7.60 (m, 4H), 7.18 (d, J=8.6 Hz, 2H), 6.84 (d, J=8.6 Hz, 2H), 6.21 (d, J=7.9 Hz, 1H), 6.14 (m, 1H), 5.26 (s, 2H), 3.78 (s, 3H), 2.36 (s, 3H), 1.56 (d, J=6.6 Hz, 3H).

Steps 7 and 8: Preparation of (S)-2-amino-4-((1-(6-fluoro-3-(pyridine-2-yl)quinoline-2-yl)ethyl)amino)-8-(4-methoxybenzyl)pyrido[2,3-d]pyrimidine-5(8H)-one 145 mg (0.25 mmol) of (S)-4-((1-(6-fluoro-3-(pyridine-2-yl)quinoline-2-yl)ethyl)amino)-8-(4-methoxybenzyl)-2-(methylmercapto)pyrido[2,3-d]pyrimidine-5(8H)-one prepared in step 6 was dissolved in 5 mL of dichloromethane, to which 3-chloroperoxybenzoic acid (mCPBA) (2 equivalent) was added, followed by stirring at room temperature for 30 minutes. Water was added to the reaction mixture, followed by extraction with ethyl acetate. The extracted organic layer was washed with saturated sodiumbicarbonate solution, separated, dried ($Na_2SO_4$), and concentrated. The obtained compound was dissolved in 5 mL of tetrahydrofuran:isopropanol (1:1), to which 2 mL of 28% ammonia water was added, followed by stirring at 50° C. for 10 hours. The reaction mixture was cooled down to room temperature. Water was added thereto, followed by extraction with ethyl acetate. The extracted organic layer was separated, dried ($Na_2SO_4$), and concentrated. The obtained compound was separated by column chromatography ($SiO_2$, eluent: hexane/ethyl acetate, 2/1→ethyl acetate) to give 78 mg of the target compound (S)-2-amino-4-((1-(6-fluoro-3-(pyridine-2-yl)quinoline-2-yl)ethyl)amino)-8-(4-methoxybenzyl)pyrido[2,3-d]pyrimidine-5(8H)-one as a white solid (0.14 mmol, yield: 57%).

$^1$H NMR (300 MHz, $CDCl_3$) δ 11.20 (br d, J=7.2 Hz, 1H, NH), 8.79 (m, 1H), 8.25 (m, 1H), 8.08 (s, 1H), 7.80 (m, 1H), 7.30-7.55 (m, 4H), 7.10-7.26 (m, 3H), 6.83 (m, 2H), 6.08 (d, J=7.9 Hz, 1H), 5.85 (m, 1H), 5.16 (s, 2H), 4.84 (s, 2H), 3.77 (s, 3H), 1.62 (d, J=6.6 Hz, 3H).

Step 9: Preparation of (S)-2-amino-4-((1-(6-fluoro-3-(pyridine-2-yl)quinoline-2-yl)ethyl)amino)pyrido[2,3-d]pyrimidine-5(8H)-one 54 mg of (S)-2-amino-4-((1-(6-fluoro-3-(pyridine-2-yl)quinoline-2-yl)ethyl)amino)pyrido[2,3-d]pyrimidine-5(8H)-one was prepared as a white solid by using 70 mg (0.128 mmol) of (S)-2-amino-4-((1-(6-fluoro-3-(pyridine-2-yl)quinoline-2-yl)ethyl)amino)-8-(4-methoxybenzyl)pyrido[2,3-d]pyrimidine-5(8H)-one prepared in step 8 according to the same manner as described in step 8 of Example 1 (0.126 mmol, yield: 99%).

$^1$H NMR (300 MHz, $CDCl_3$) δ 11.39 (s, 1H), 8.77 (d, J=4.5 Hz, 1H), 8.22 (dd, J=9.0, 5.5 Hz, 1H), 8.03 (s, 1H), 7.86 (td, J=1.5, 7.6 Hz, 1H), 7.54-7.36 (m, 4H), 7.19 (d, J=7.6 Hz, 1H), 6.08 (d, J=7.6 Hz, 1H), 5.93-5.84 (m, 1H), 5.59 (br s, 2H), 1.55 (d, J=6.5 Hz, 3H).

Example 26: Preparation of 4-((1-(6-fluoro-3,4-di(pyridine-2-yl)quinoline-2-yl)ethyl)amino)pyrido[2,3-d]pyrimidine-5(8H)-one

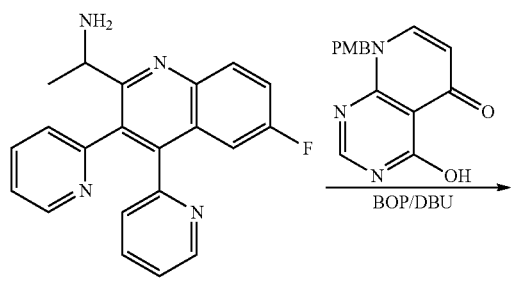

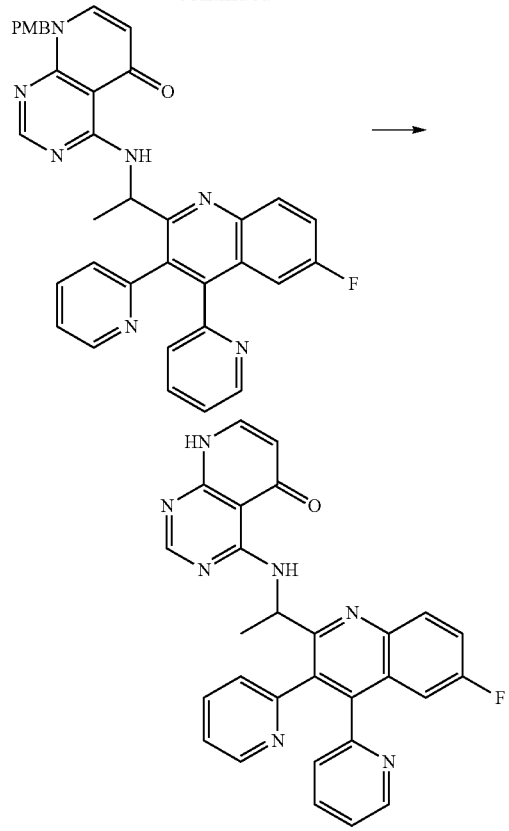

Step 1: Preparation of 4-((1-(6-fluoro-3,4-di(pyridine-2-yl)quinoline-2-yl)ethyl)amino)-8-(4-methoxybenzyl)pyrido[2,3-d]pyrimidine-5(8H)-one 99 mg of 4-((1-(6-fluoro-3,4-di(pyridine-2-yl)quinoline-2-yl)ethyl)amino)-8-(4-methoxybenzyl)pyrido[2,3-d]pyrimidine-5(8H)-one was prepared as a beige solid by using 100 mg (0.29 mmol) of 1-(6-fluoro-3,4-di(pyridine-2-yl)quinoline-2-yl)ethane-1-amine prepared in Preparative Example 22 according to the same manner as described in step 7 of Example 1 (0.16 mmol, yield: 56%).

$^1$H NMR (300 MHz, $CDCl_3$) δ 8.69 (s, 2H), 8.39-8.34 (m, 2H), 7.65-7.42 (m, 4H), 7.24-7.19 (m, 3H), 7.13-7.05 (m, 2H), 6.91-6.84 (m, 2H), 6.32 (s, 1H), 5.61 (s, 1H), 5.34 (s, 2H), 3.77 (s, 3H), 3.57-3.50 (m, 1H), 3.46 (s, 1H), 1.59 (d, J=2.1 Hz, 3H).

Step 2: Preparation of 4-((1-(6-fluoro-3,4-di(pyridine-2-yl)quinoline-2-yl)ethyl)amino)pyrido[2,3-d]pyrimidine-5(8H)-one 54 mg of 4-((1-(6-fluoro-3,4-di(pyridine-2-yl)quinoline-2-yl)ethyl)amino)pyrido[2,3-d]pyrimidine-5(8H)-one was prepared as a beige solid by using 90 mg (0.15 mmol) of 4-((1-(6-fluoro-3,4-di(pyridine-2-yl)quinoline-2-yl)ethyl)amino)-8-(4-methoxybenzyl)pyrido[2,3-d]pyrimidine-5(8H)-one prepared in step 1 according to the same manner as described in step 8 of Example 1 (0.11 mmol, yield: 75%).

$^1$H NMR (300 MHz, $CDCl_3$) δ 11.48 (br s, 1H), 10.69 (s, 1H), 8.67 (t, J=5.7 Hz, 2H), 8.67 (t, J=5.7 Hz, 2H), 8.37 (dd, J=9.2, 5.6 Hz, 1H), 8.17 (s, 2H), 7.54-7.44 (m, 3H), 7.34 (d,

J=7.7 Hz, 1H), 7.21-7.13 (m, 3H), 7.08-7.02 (m, 2H), 6.29 (d, J=7.6 Hz, 1H), 5.70 (br s, 1H), 1.54 (d, J=2.3 Hz, 3H).

Example 27: Preparation of (S)-4-((1-(6-fluoro-3-phenyl-4-(pyridine-2-yl)quinoline-2-yl)ethyl)amino)pyrido[2,3-d]pyrimidine-5(8H)-one

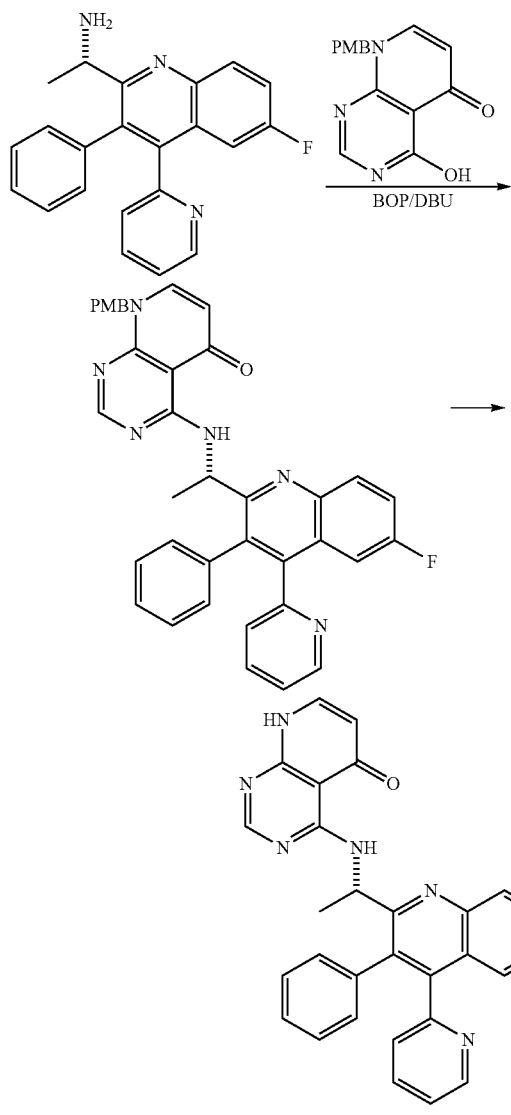

Step 1: Preparation of (S)-4-((1-(6-fluoro-3-phenyl-4-(pyridine-2-yl)quinoline-2-yl)ethyl)amino)-8-(4-methoxybenzyl)pyrido[2,3-d]pyrimidine-5(8H)-one (S)-4-((1-(6-fluoro-3-phenyl-4-(pyridine-2-yl)quinoline-2-yl)ethyl)amino)-8-(4-methoxybenzyl)pyrido[2,3-d]pyrimidine-5(8H)-one was prepared as a pale beige solid by using 120 mg (0.35 mmol) of (S)-1-(6-fluoro-3-phenyl-4-(pyridine-2-yl)quinoline-2-yl)ethane-1-amine prepared in Preparative Example 23 according to the same manner as described in step 7 of Example 1.

$^1$H NMR (300 MHz, CDCl$_3$) δ 8.64 (br d, J=4.9 Hz, 1H), 8.29-8.35 (m, 2H), 7.42-7.55 (m, 3H), 7.13-7.34 (m, 7H), 6.91-7.09 (m, 3H), 6.82-6.89 (m, 2H), 6.30-6.32 (m, 1H), 5.65-5.69 (m, 1H), 5.30 (s, 2H), 3.78 (s, 3H), 1.47 (d, J=6.3 Hz, 3H).

Step 2: Preparation of (S)-4-((1-(6-fluoro-3-phenyl-4-(pyridine-2-yl)quinoline-2-yl)ethyl)amino)pyrido[2,3-d]pyrimidine-5(8H)-one (S)-4-((1-(6-fluoro-3-phenyl-4-(pyridine-2-yl)quinoline-2-yl)ethyl)amino)pyrido[2,3-d]pyrimidine-5(8H)-one was prepared as a pale beige solid by using 95 mg (0.16 mmol) of (S)-4-((1-(6-fluoro-3-phenyl-4-(pyridine-2-yl)quinoline-2-yl)ethyl)amino)-8-(4-methoxybenzyl)pyrido[2,3-d]pyrimidine-5(8H)-one prepared in step 1 according to the same manner as described in step 8 of Example 1.

$^1$H NMR (300 MHz, CDCl$_3$) δ 11.58 (br s, 1H), 11.32 (br s, 1H), 8.65 (br d, J=4.2 Hz, 1H), 8.32-8.38 (m, 1H), 8.23 (s, 1H), 7.43-7.54 (m, 3H), 7.13-7.36 (m, 6H), 6.94-7.10 (m, 3H), 6.36 (d, J=7.6 Hz, 1H), 5.65-6.75 (m, 1H), 1.45 (d, J=6.3 Hz, 3H).

Example 28: Preparation of (S)-4-((1-(6-fluoro-4-oxo-3-(pyridine-3-yl)-3,4-dihydroquinazoline-2-yl)ethyl)amino)pyrido[2,3-d]pyrimidine-5(8H)-one

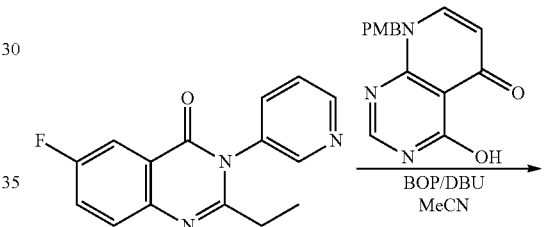

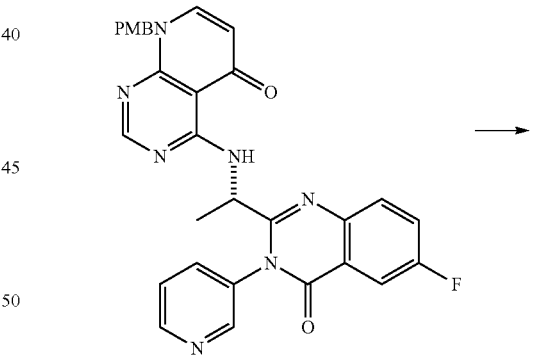

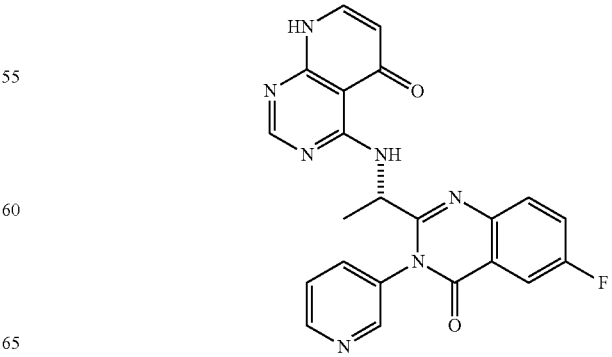

Step 1: Preparation of (S)-4-((1-(6-fluoro-4-oxo-3-(pyridine-3-yl)-3,4-dihydroquinazoline-2-yl)ethyl)amino)-8-(4-methoxybenzyl)pyrido[2,3-d]pyrimidine-5(8H)-one The target compound was prepared by using the compound prepared in Preparative Example 24 according to the same manner as described in step 7 of Example 1.

$^1$H NMR (300 MHz, CDCl$_3$) δ 10.91 (s, 1H), 8.75-8.62 (m, 1H), 8.37-8.26 (m, 1H), 7.89-7.71 (m, 2H), 7.89-7.71 (m, 2H), 7.57-7.40 (m, 3H), 7.21 (d, J=7.2 Hz, 2H), 6.31 (d, J=7.7 Hz, 2H), 5.41-5.26 (m, 2H), 5.13-4.99 (m, 1H), 3.78 (s, 3H), 1.53 (dd, J=11.3, 6.7 Hz, 3H).

Step 2: Preparation of (S)-4-((1-(6-fluoro-4-oxo-3-(pyridine-3-yl)-3,4-dihydroquinazoline-2-yl)ethyl)amino)pyrido[2,3-d]pyrimidine-5(8H)-one The target compound was prepared by using the compound prepared in step 1 according to the same manner as described in step 8 of Example 1.

$^1$H NMR (300 MHz, CDCl$_3$) δ 10.89 (d, J=6.7 Hz, 1H), 8.77 (s, 1H), 8.68 (d, J=7.4 Hz, 1H), 8.17 (d, J=3.2 Hz, 1H), 7.90-7.73 (m, 3H), 7.59-7.47 (m, 3H), 6.35 (t, J=4.9 Hz, 2H), 5.13-5.03 (m, 1H), 1.55 (t, J=8.0 Hz, 3H).

Example 29: Preparation of (S)-4-((1-(6-fluoro-4-oxo-3-phenyl-3,4-dihydroquinazoline-2-yl)ethyl)amino)pyrido[2,3-d]pyrimidine-5(8H)-one

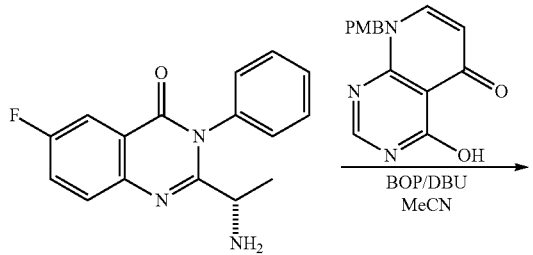

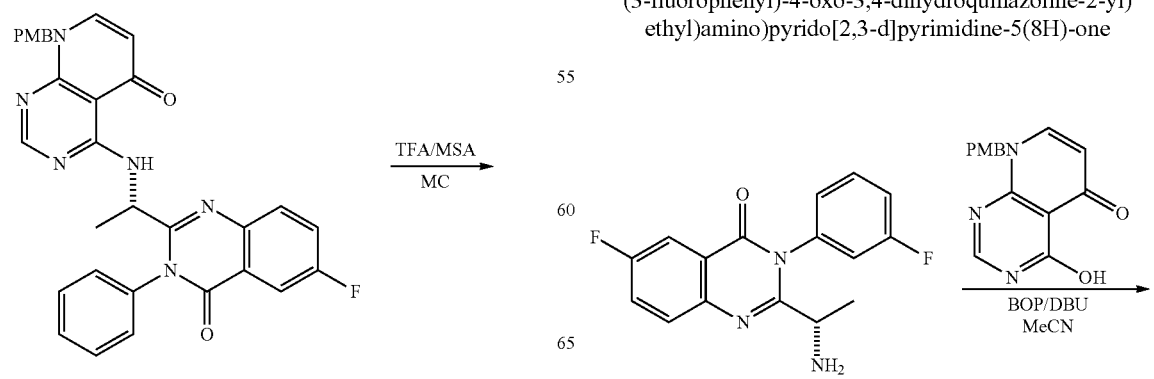

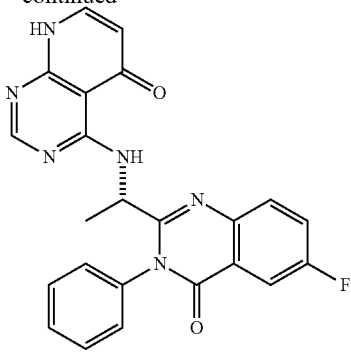

Step 1: Preparation of (S)-4-((1-(6-fluoro-4-oxo-3-phenyl-3,4-dihydroquinazoline-2-yl)ethyl)amino)-8-(4-methoxybenzyl)pyrido[2,3-d]pyrimidine-5(8H)-one The target compound was prepared by using the compound prepared in Preparative Example 25 according to the same manner as described in step 7 of Example 1.

$^1$H NMR (300 MHz, CDCl$_3$) δ 11.01 (d, J=6.8 Hz, 1H), 8.27 (s, 1H), 7.90-7.88 (m, 2H), 7.90-7.88 (m, 2H), 7.58-7.44 (m, 6H), 7.33 (d, J=6.8 Hz, 1H), 7.20 (d, J=7.8 Hz, 1H), 6.85 (d, J=8.0 Hz, 2H), 6.32 (d, J=7.8 Hz, 1H), 5.34 (s, 1H), 5.18-5.09 (m, 1H), 3.78 (s, 3H), 1.50 (d, J=6.5 Hz, 3H).

Step 2: Preparation of (S)-4-((1-(6-fluoro-4-oxo-3-phenyl-3,4-dihydroquinazoline-2-yl)ethyl)amino)pyrido[2,3-d]pyrimidine-5(8H)-one The target compound was prepared by using the compound prepared in step 1 according to the same manner as described in step 8 of Example 1.

$^1$H NMR (300 MHz, CDCl$_3$) δ 11.05 (d, J=6.9 Hz, 1H), 8.17 (s, 1H), 7.90 (d, J=8.3 Hz, 1H), 7.85-7.80 (m, 1H), 7.60-7.41 (m, 6H), 6.36 (d, J=7.6 Hz, 1H), 5.20-5.11 (m, 1H), 1.51 (d, J=6.4 Hz, 3H).

Example 30: Preparation of (S)-4-((1-(6-fluoro-3-(3-fluorophenyl)-4-oxo-3,4-dihydroquinazoline-2-yl)ethyl)amino)pyrido[2,3-d]pyrimidine-5(8H)-one

139

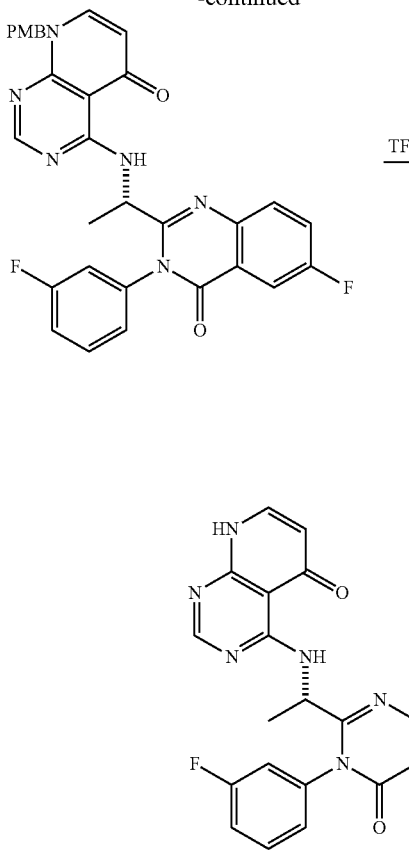

Step 1: Preparation of (S)-4-((1-(6-fluoro-3-(3-fluorophenyl)-4-oxo-3,4-dihydroquinazoline-2-yl)ethyl)amino)-8-(4-methoxybenzyl)pyrido[2,3-d]pyrimidine-5(8H)-one The target compound was prepared by using the compound prepared in Preparative Example 26 according to the same manner as described in step 7 of Example 1.

$^1$H NMR (300 MHz, CDCl$_3$) δ 10.97-10.91 (m, 1H), 8.28 (s, 1H), 7.90-7.72 (m, 3H), 7.59-7.50 (m, 4H), 7.24-7.20 (m, 3H), 6.86 (d, J=7.8 Hz 2H), 6.32 (d, J=7.8 Hz, 1H), 5.35 (s, 2H), 5.17-5.10 (m, 1H), 3.78 (s, 3H), 1.53 (d, J=6.5 Hz, 3H).

Step 2: Preparation of (S)-4-((1-(6-fluoro-3-(3-fluorophenyl)-4-oxo-3,4-dihydroquinazoline-2-yl)ethyl)amino)pyrido[2,3-d]pyrimidine-5(8H)-one The target compound was prepared by using the compound prepared in step 1 according to the same manner as described in step 8 of Example 1.

$^1$H NMR (300 MHz, CDCl$_3$) δ 10.84-10.78 (m, 1H), 8.20 (d, J=5.4 Hz, 1H), 7.91-7.77 (m, 2H), 7.59-7.46 (m, 3H), 7.22-7.08 (m, 2H), 6.34 (d, J=7.4 Hz, 1H), 5.18-5.09 (m, 1H), 1.53 (d, J=6.5 Hz, 3H).

140

Example 31: Preparation of (S)-4-((1-(5-chloro-3-(2-chlorobenzyl)-4-oxo-3,4-dihydroquinazoline-2-yl)ethyl)amino)pyrido[2,3-d]pyrimidine-5(8H)-one

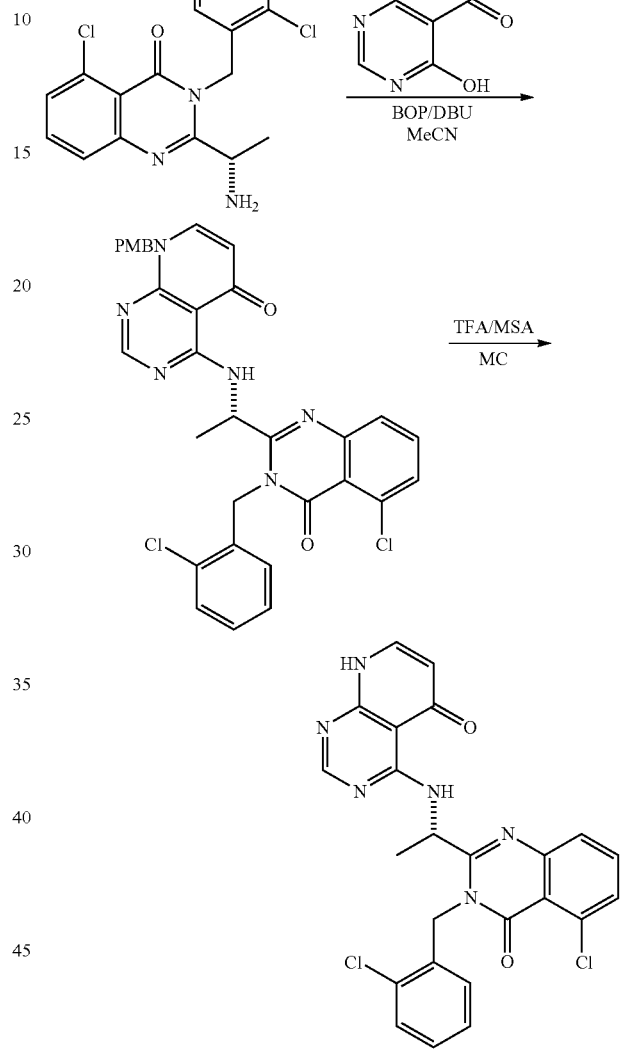

단계 1: (S)-4-((1-(5-chloro-3-(2-chlorobenzyl)-4-oxo-3,4-dihydroquinazoline-2-yl)ethyl)amino)-8-(4-methoxybenzyl)pyrido[2,3-d]pyrimidine-5(8H)-one의 제조

The target compound was prepared by using the compound prepared in Preparative Example 27 according to the same manner as described in step 7 of Example 1.

$^1$H NMR (300 MHz, CDCl$_3$) δ 10.84 (d, J=7.8 Hz, 1H), 8.32 (s, 1H), 7.71-7.58 (m, 2H), 7.47 (t, J=8.3 Hz, 2H), 7.26-7.18 (m, 3H), 7.01 (s, 2H), 6.87 (d, J=7.7 Hz, 2H), 6.79 (d, J=5.2 Hz, 1H), 6.23 (d, J=7.8 Hz, 1H), 5.79-5.73 (m, 1H), 5.63-5.54 (m, 1H), 5.46-5.36 (m, 3H), 3.80 (s, 3H), 1.56 (d, J=6.2 Hz, 3H).

Step 2: Preparation of ((S)-4-((1-(5-chloro-3-(2-chlorobenzyl)-4-oxo-3,4-dihydroquinazoline-2-yl)ethyl)amino)pyrido[2,3-d]pyrimidine-5(8H)-one The target compound was prepared by using the compound prepared in step 1 according to the same manner as described in step 8 of Example 1.

$^1$H NMR (300 MHz, CDCl$_3$) δ 10.84 (d, J=7.9 Hz, 1H), 8.22 (s, 1H), 7.72 (dd, J=7.9, 0.8 Hz, 1H), 7.62 (t, J=7.8 Hz, 2H), 7.51-7.46 (m, 2H), 7.33-7.30 (m, 1H), 7.13-7.04 (m, 2H), 6.83-6.80 (m, 1H), 6.29 (d, J=7.7 Hz, 1H), 5.78 (d, J=17.1 Hz, 1H), 5.61-5.52 (m, 1H), 5.49-5.41 (m, 1H), 1.57 (d, J=6.6 Hz, 1H). (m, 1H), 5.46-5.36 (m, 3H), 3.80 (s, 3H), 1.56 (d, J=6.2 Hz, 3H).

Example 32: Preparation of (S)-4-((1-(6-fluoro-4-oxo-3-(pyridine-2-ylmethyl)-3,4-dihydroquinazoline-2-yl)ethyl)amino)pyrido[2,3-d]pyrimidine-5(8H)-one

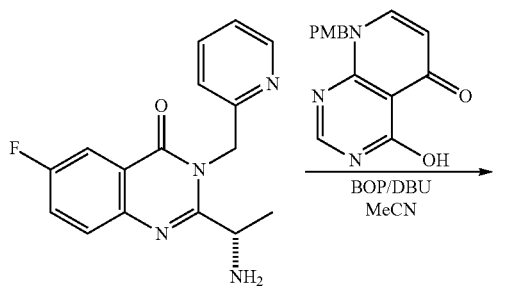

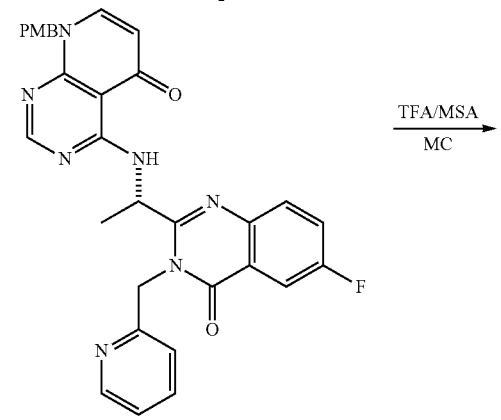

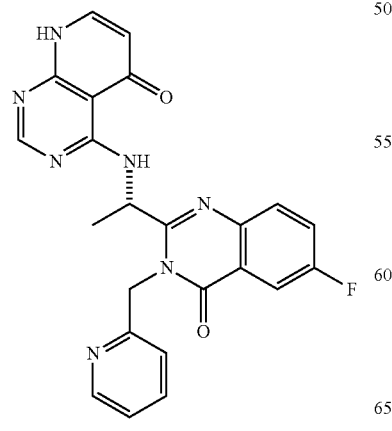

Step 1: Preparation of (S)-4-((1-(6-fluoro-4-oxo-3-(pyridine-2-ylmethyl)-3,4-dihydroquinazoline-2-yl)ethyl)amino)-8-(4-methoxybenzyl)pyrido[2,3-d]pyrimidine-5(8H)-one The target compound was prepared by using the compound prepared in Preparative Example 28 according to the same manner as described in step 7 of Example 1.

$^1$H NMR (300 MHz, CDCl$_3$) δ 11.02 (d, J=7.7 Hz, 1H), 8.41 (d, J=4.4 Hz, 1H), 8.40 (s, 1H), 7.89 (dd, J=8.5, 2.9 Hz, 1H), 7.78 (dd, J=9.0, 4.9 Hz, 1H), 7.81-7.39 (m, 2H), 7.21 (d, J=8.6 Hz, 2H), 7.09 (dd, J=7.0, 5.3 Hz, 1H), 6.86 (d, J=8.6 Hz, 2H), 6.29 (d, J=7.9 Hz, 1H), 5.89-5.80 (m, 2H), 5.59 (d, J=16.2 Hz, 1H), 5.33 (dd, J=14.6, 16.1 Hz, 2H), 3.78 (s, 3H), 1.59 (d, J=6.5 Hz, 3H).

Step 2: Preparation of (S)-4-((1-(6-fluoro-4-oxo-3-(pyridine-2-ylmethyl)-3,4-dihydroquinazoline-2-yl)ethyl)amino)pyrido[2,3-d]pyrimidine-5(8H)-one The target compound was prepared by using the compound prepared in step 1 according to the same manner as described in step 8 of Example 1.

$^1$H NMR (300 MHz, CDCl$_3$) δ 11.19 (d, J=7.6 Hz, 1H), 8.46 (d, J=4.3 Hz, 1H), 8.23 (s, 1H), 7.90 (dd, J=8.5, 3.0 Hz, 1H), 7.81 (dd, J=9.0, 4.9 Hz, 1H), 7.63 (td, J=1.7, 7.7 Hz, 1H), 7.51-7.43 (m, 2H), 7.31 (d, J=7.9 Hz, 1H), 7.15 (dd, J=7.0, 5.0 Hz, 1H), 6.34 (d, J=7.7 Hz, 1H), 5.95-5.81 (m 2H), 5.54 (d, J=16.1 Hz, 1H), 1.61 (d, J=6.5 Hz, 3H).

Example 33: Preparation of 4-((1-(5-chloro-3-(pyridine-2-yl)quinoline-2-yl)ethyl)amino)pyrido[2,3-d]pyrimidine-5(8H)-one

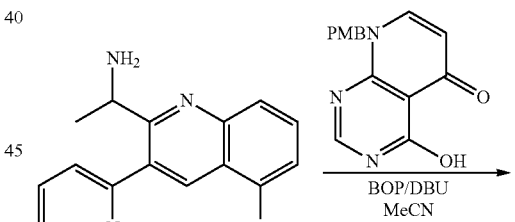

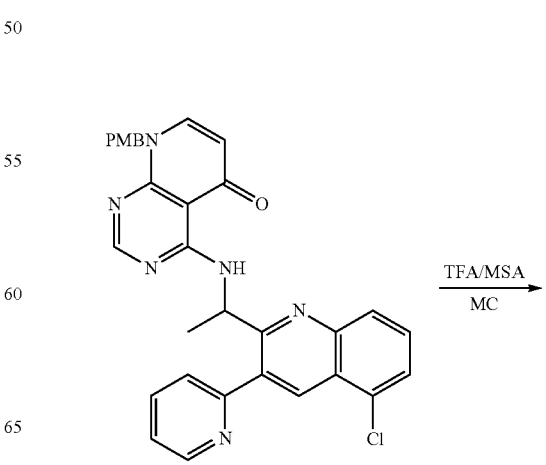

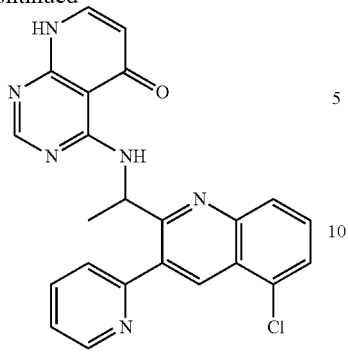

Step 1: Preparation of 4-((1-(5-chloro-3-(pyridine-2-yl)quinoline-2-yl)ethyl)amino)-8-(4-methoxybenzyl)pyrido[2,3-d]pyrimidine-5(8H)-one 4-((1-(5-chloro-3-(pyridine-2-yl)quinoline-2-yl)ethyl)amino)-8-(4-methoxybenzyl)pyrido[2,3-d]pyrimidine-5(8H)-one was prepared as a pale yellow solid by using 1-(5-chloro-3-(pyridine-2-yl)quinoline-2-yl)ethane-1-amine prepared in Preparative Example 29 according to the same manner as described in step 7 of Example 1.

$^1$H NMR (300 MHz, CDCl$_3$) δ 11.6 (d, J=7.4 Hz, 1H), 8.81 (d, J=4.8 Hz, 1H), 8.51 (s, 1H), 8.32 (s, 1H), 8.81 (d, J=4.8 Hz, 1H), 8.23 (d, J=8.0 Hz, 1H), 7.87-7.82 (m, 1H), 7.67-7.60 (m, 3H), 7.44 (d, J=7.9 Hz, 1H), 7.40-7.35 (m, 1H), 7.19 (d, J=8.6 Hz, 2H), 6.85 (d, J=8.6 Hz, 2H), 6.31 (d, J=7.9 Hz, 1H), 6.16-6.07 (m, 1H), 5.33 (s, 2H), 3.78 (s, 3H), 1.56 (d, J=6.6 Hz, 2H).

Step 2: Preparation of 4-((1-(5-chloro-3-(pyridine-2-yl)quinoline-2-yl)ethyl)amino)pyrido[2,3-d]pyrimidine-5(8H)-one 4-((1-(5-chloro-3-(pyridine-2-yl)quinoline-2-yl)ethyl)amino)pyrido[2,3-d]pyrimidine-5(8H)-one was prepared as a white solid by using 4-((1-(5-chloro-3-(pyridine-2-yl)quinoline-2-yl)ethyl)amino)-8-(4-methoxybenzyl)pyrido[2,3-d]pyrimidine-5(8H)-one prepared in step 1 according to the same manner as described in step 8 of Example 1.

$^1$H NMR (300 MHz, CDCl$_3$) δ 11.54 (d, J=7.1 Hz, 1H), 10.86 (s, 1H), 8.83 (d, J=4.7 Hz, 1H), 8.54 (s, 1H), 8.26 (s, 1H), 8.24 (s, 1H), 7.87 (t, J=7.7 Hz, 1H), 7.69-7.61 (m, 3H), 7.44-7.37 (m, 2H), 6.32 (d, J=6.8 Hz, 1H), 6.20-6.12 (m, 1H), 1.57 (d, J=6.3 Hz, 3H).

The following examples 34~65 were performed by the method represented by the reaction formula 2.

[Reaction Formula 2]

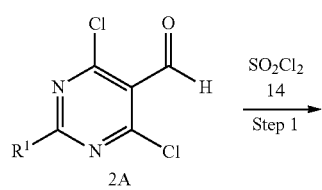

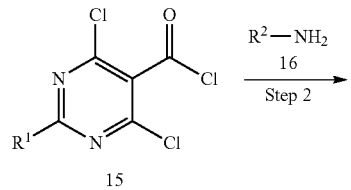

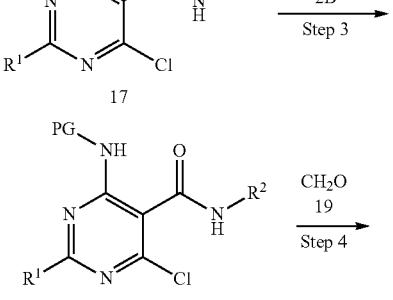

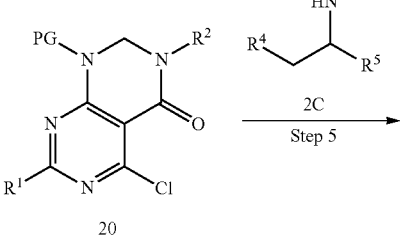

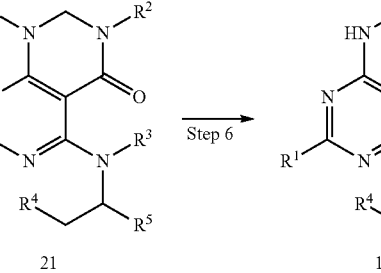

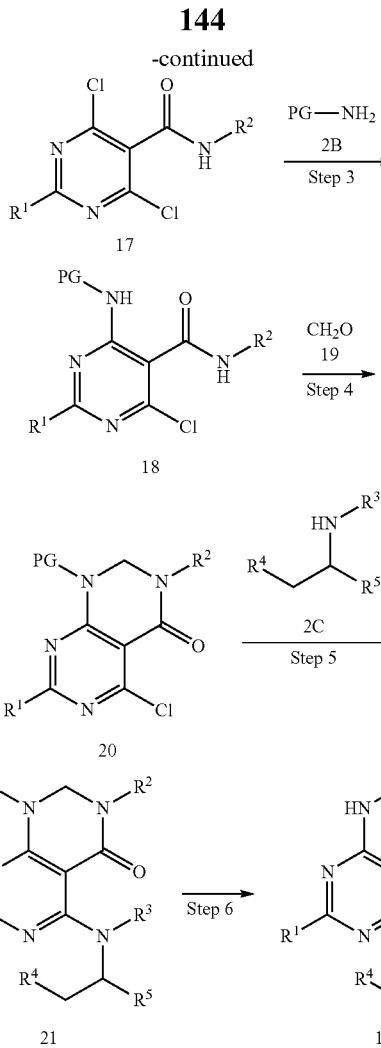

Example 34: Preparation of (S)-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one

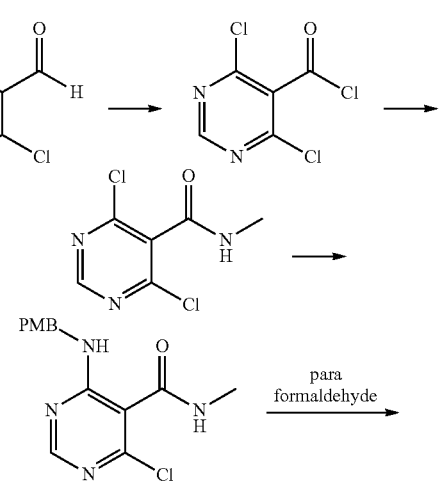

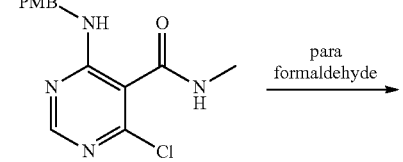

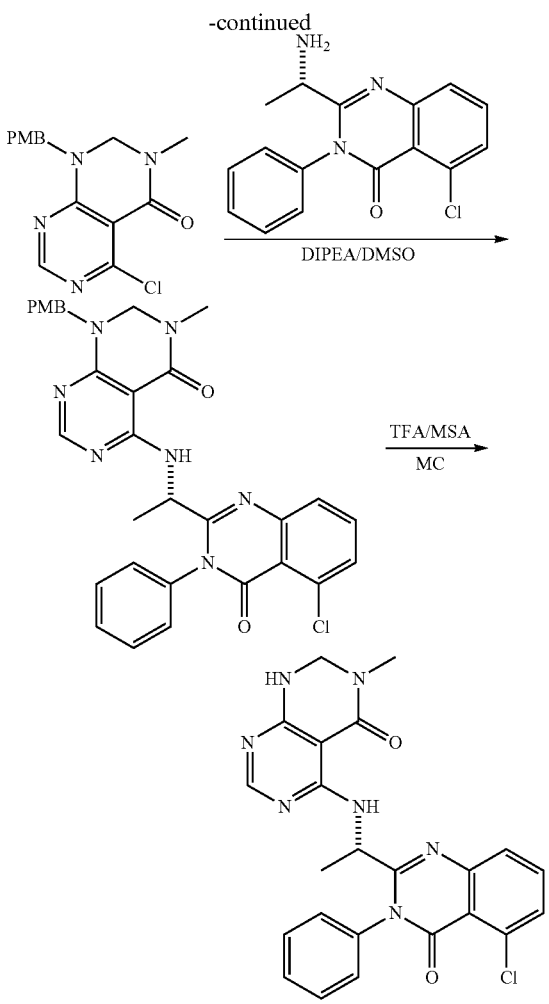

Steps 1 and 2: Preparation of 4,6-dichloro-N-methylpyrimidine-5-carboxamide 1.00 g (5.65 mmol) of 4,6-dichloropyrimidine-5-carboxaldehyde was dissolved in 15 mL of CCl$_4$, to which 0.78 mL (9.61 mmol) of sulfuryl chloride and 46 mg (0.28 mmol) of 2-2-azobis(2-methyl propionitrile) were added, followed by stirring at 80° C. for 3 hours. The reaction mixture was cooled down to room temperature and filtered under reduced pressure. 5 mL of anhydrous toluene was added thereto, followed by filtration under reduced pressure. The resultant product was dissolved in 15 mL of anhydrous tetrahydrofuran, to which 4.73 mL of 2.0 M methylamine/tetrahydrofuran solution was added at −20° C., followed by stirring at −20° C. for 2 hours. The reaction mixture was added with 1 N HCl and filtered under reduced pressure. Ethyl acetate and water were added thereto, followed by extraction. The extracted organic layer was separated, dried (Na$_2$SO$_4$), filtered, and concentrated under reduced pressure. The residue was separated by column chromatography (SiO$_2$, eluent: dichloromethane/methanol, 20/1) to give 0.8 g of the target compound 4,6-dichloro-N-methylpyrimidine-5-carboxamide as a pale yellow solid (3.88 mmol, yield: 69%).

$^1$H NMR (300 MHz, CDCl$_3$) δ 8.81 (s, 1H), 5.87 (brs, 1H), 3.08 (d, J=2.6 Hz, 3H).

Step 3: Preparation of 4-chloro-6-((4-methoxybenzyl)amino)-N-methylpyrimidine-5-carboxamide 3.0 g (14.5 mmol) of 4,6-dichloro-N-methylpyrimidine-5-carboxamide prepared in step 1 and step 2 was dissolved in 80 mL of anhydrous tetrahydrofuran, to which 1.8 mL (15.2 mmol, 1.05 eq) of p-methoxybenzylamine and 2.8 mL (16.0 mmol, 1.1 eq) of diisopropylethylamine (DIPEA) were added, followed by stirring for 6 hours. The reaction mixture was distilled under reduced pressure. Water was added thereto, followed by extraction with ethyl acetate. The extracted organic layer was separated, dried (Na$_2$SO$_4$), filtered, and concentrated under reduced pressure. The residue was separated by column chromatography (SiO$_2$, eluent: hexane/ethylacetate, 4/1) to give 3.73 g of the target compound 4-chloro-6-((4-methoxybenzyl)amino)-N-methylpyrimidine-5-carboxamide as a transparent oil (12.1 mmol, yield: 84%).

$^1$H NMR (300 MHz, CDCl$_3$) δ 8.31 (s, 1H), 8.24 (s, 1H), 7.25 (d, J=8.9 Hz, 2H), 6.86 (d, J=8.5 Hz, 2H), 6.70 (s, 1H), 4.62 (d, J=5.4 Hz, 2H), 3.79 (s, 3H), 2.97 (d, J=4.7 Hz, 2H).

Step 4: Preparation of 5-chloro-1-(4-methoxybenzyl)-3-methyl-2,3-dihydropyrimido[4,5-d]pyrimidine-4(1H)-one 3.7 g (12 mmol) of 4-chloro-6-((4-methoxybenzyl)amino)-N-methyl-pyrimidine-5-carboxamide prepared in step 3, 3.6 g (120 mmol, >10 eq) of paraformaldehyde, and 228 mg (1.2 mmol, 0.1 eq) of p-toluenesulfonic acid were dissolved in 100 mL of toluene, which was stirred at 130° C. for 12 hours in dean-stark trap. The reaction mixture was cooled down to room temperature and distilled under reduced pressure. The resultant product was separated by column chromatography (SiO$_2$, eluent: hexane/ethylacetate, 3/1) to give 3.0 g of the target compound as a white solid (9.4 mmol, yield: 78%).

$^1$H NMR (300 MHz, CDCl$_3$) δ 8.43 (s, 1H), 7.22 (d, J=8.9 Hz, 2H), 6.88 (d, J=8.4 Hz, 2H), 4.86 (s, 2H), 4.55 (s, 2H), 3.81 (s, 3H), 2.98 (s, 3H).

Step 5: Preparation of (S)-5-((1-(5-chloro-4-oxo-3-phenyl-3,4-dihydroquinazoline-2-yl)ethyl)amino)-1-(4-methoxybenzyl)-3-methyl-2,3-dihydropyrimido[4,5-d]pyrimidine-4(1H)-one 50 mg (0.16 mmol) of 5-chloro-1-(4-methoxybenzyl)-3-methyl-2,3-dihydropyrimido[4,5-d]pyrimidine-4(1H)-one prepared in step 4 was dissolved in 2 mL of anhydrous dimethylsulfoxide (DMSO), to which 57 mg (0.19 mmol, 1.2 equivalent) of (S)-2-(1-aminoethyl)-5-chloro-3-phenylquinazoline-4(3H)-one and 0.06 mL (0.35 mmol, 2.2 equivalent) of diisopropylethylamine (DIPEA) were added, followed by stirring at 70° C. for 12 hours. The reaction mixture was cooled down to room temperature. Water was added thereto, followed by extraction with ethyl acetate. The extracted organic layer was separated, dried (Na$_2$SO$_4$), filtered, and concentrated under reduced pressure. The residue was separated by column chromatography (SiO$_2$, eluent: hexane/ethylacetate, 2/1) to give 88 mg of the target compound (S)-5-((1-(5-chloro-4-oxo-3-phenyl-3,4-dihydroquinazoline-2-yl)ethyl)amino)-1-(4-methoxybenzyl)-3-methyl-2,3-dihydropyrimido[4,5-d]pyrimidine-4(1H)-one as a white solid (0.15 mmol, yield: 94%).

$^1$H NMR (300 MHz, CDCl$_3$) δ 9.49 (d, J=7.0 Hz, —NH), 8.03 (s, 1H), 7.70-7.68 (m, 1H), 7.61-7.44 (m, 7H), 7.31-7.28 (m, 1H), 7.21 (d, J=8.6 Hz, 2H), 6.86 (d, J=8.6 Hz, 2H), 5.06-5.02 (m, 1H), 4.74 (s, 2H), 4.45 (s, 2H), 3.79 (s, 3H), 2.89 (s, 3H), 1.44 (d, J=6.6 Hz, 3H).

Step 6: Preparation of (S)-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one 57 mg of (S)-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one was prepared as a white solid by using 70 mg (0.13 mmol) of (S)-5-((1-(5-chloro-4-oxo-3-phenyl-3,4-dihydro-quinazoline-2-yl)ethyl)amino)-1-(4-methoxybenzyl)-3-methyl-2,3-dihydropyrimido[4,5-d]pyrimidine-4(1H)-one prepared in step 5 according to the same manner as described in step 8 of Example 1 (0.12 mmol, yield: 99%).
$^1$H NMR (300 MHz, CDCl$_3$) δ 9.43 (d, J=7.9 Hz, −1H), 7.88 (s, 1H), 7.69-7.67 (m, 1H), 7.61-7.43 (m, 6H), 7.32-7.29 (m, 1H), 6.97 (s, —NH), 5.02-4.97 (m, 1H), 4.69 (s, 2H), 2.97 (s, 3H), 1.43 (d, J=5.9 Hz, 3H).

Example 35: Preparation of (S)-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one

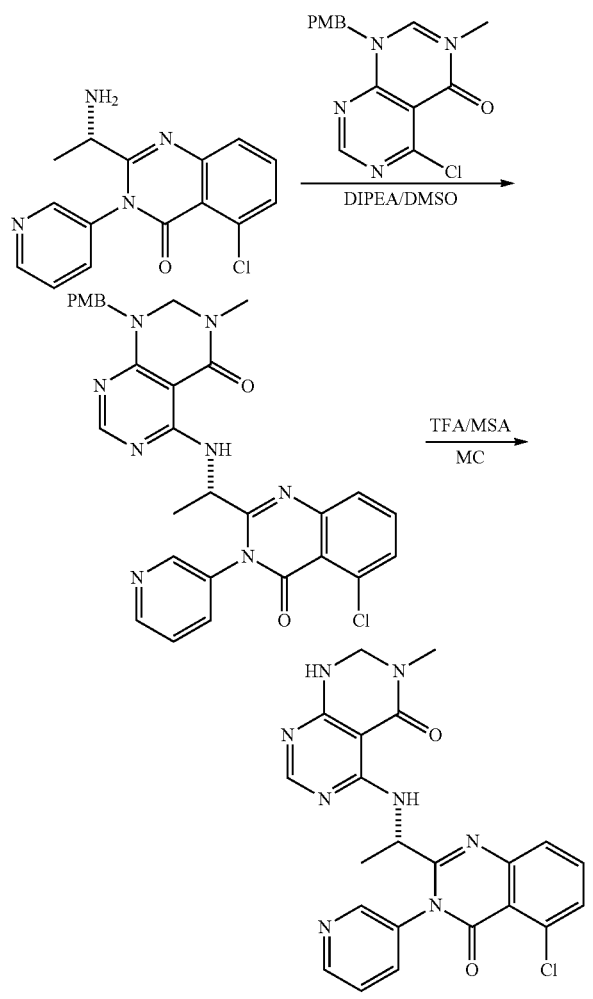

Step 1: Preparation of (S)-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one 83 mg of (S)-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-2-(1-aminoethyl)-5-chloro-3-(pyridine-3-yl)quinazoline-4(3H)-one was used (0.14 mmol, yield: 94%).
$^1$H NMR (300 MHz, CDCl$_3$) δ 9.39-9.35 (m, 1H), 8.76-8.71 (m, 1H), 8.03 (d, J=8.1 Hz, 2H), 7.70-7.46 (m, 3H), 7.20 (d, J=8.6 Hz, 2H), 6.86 (d, J=8.6 Hz, 2H), 5.02-4.89 (m, 1H), 4.8-4.65 (m, 2H), 4.46 (s, 2H), 3.79 (s, 3H), 2.90 (s, 3H), 1.50-1.44 (m, 3H).

Step 2: Preparation of (S)-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one 56 mg of (S)-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one was prepared as a white solid according to the same manner as described in step 6 of Example 34 except that (S)-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one was used (0.12 mmol, yield: 99%).
$^1$H NMR (300 MHz, CDCl$_3$) δ 9.30-9.25 (m, 1H), 8.74-8.71 (m, 1H), 8.57 (s, 1H), 7.91 (d, J=8.9 Hz, 2H), 7.91 (d, J=7.2 Hz, 1H), 7.70-7.59 (m, 2H), 7.53-7.44 (m, 2H), 5.88 (s, 1H), 5.73 (s, 1H), 5.00-4.86 (m, 1H), 4.72 (s, 2H), 2.99 (s, 3H), 1.50-1.43 (m, 3H).

Example 36: Preparation of (S)-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one

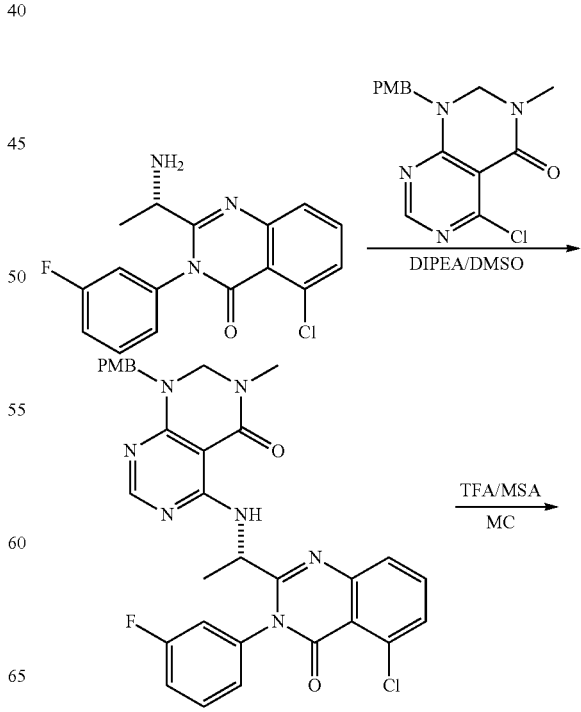

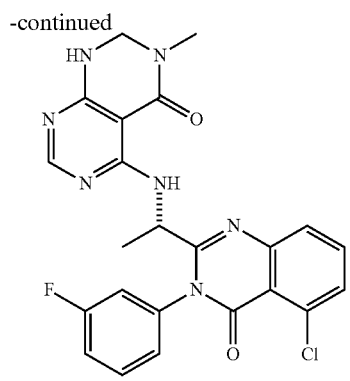

Step 1: Preparation of (S)-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one 87 mg of (S)-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-2-(1-aminoethyl)-5-chloro-3-(3-fluorophenyl)quinazoline-4(3H)-one was used (0.14 mmol, yield: 91%).

$^1$H NMR (300 MHz, CDCl$_3$) δ 9.45-9.36 (m, 1H), 7.62-7.50 (m, 4H), 7.42-7.39 (m, 1H), 7.27-7.14 (m, 4H), 7.07-6.99 (m, 1H), 6.84 (d, J=8.0 Hz, 2H), 4.84-4.69 (m, 3H), 4.73 (s, 2H), 3.89-3.80 (m, 1H), 3.79 (s, 3H), 3.57-3.48 (m, 1H), 2.90 (s, 3H), 2.33-2.24 (m, 1H), 2.13-2.06 (m, 2H), 1.50-1.44 (m, 3H).

Step 2: Preparation of (S)-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one 61 mg of (S)-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one was prepared as a white solid according to the same manner as described in step 6 of Example 34 except that (S)-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 9.40-9.31 (m, 1H), 7.89 (d, J=4.65 Hz, 1H), 7.69-7.44 (m, 4H), 7.25-7.04 (m, 2H), 6.89-6.80 (m, 1H), 5.04-4.95 (m, 1H), 4.71 (s, 2H), 2.98 (m, 2H), 1.46 (m, J=5.98, 3H).

Example 37: Preparation of (S)-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one

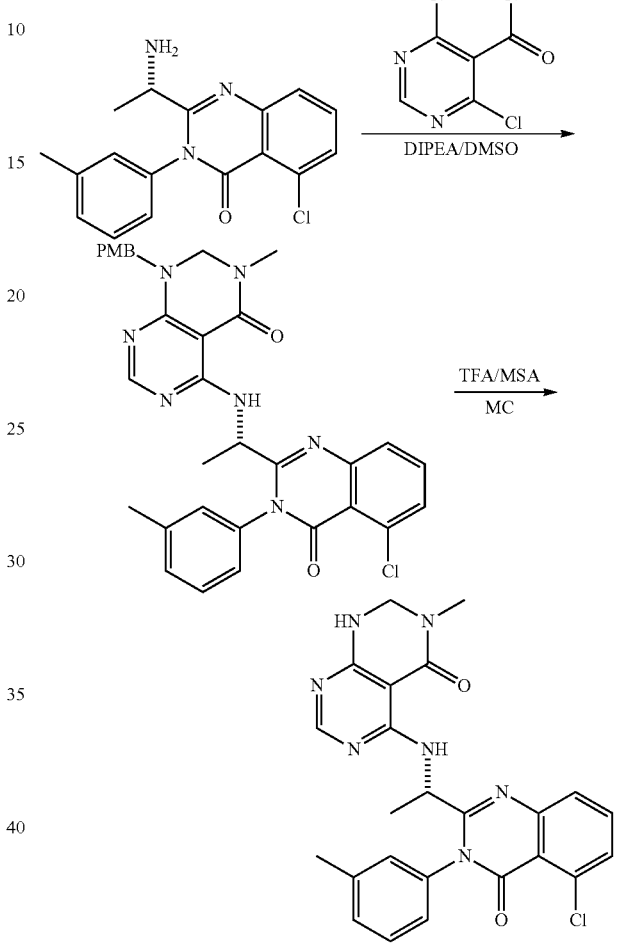

Step 1: Preparation of (S)-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one 85 mg of (S)-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-2-(1-aminoethyl)-5-chloro-3-m-tolylquinazoline-4(3H)-one was used (0.14 mmol, yield: 89%).

$^1$H NMR (300 MHz, CDCl$_3$) δ 9.52-9.43 (m, 1H), 8.03 (s, 1H), 7.70-7.67 (m, 2H), 7.60-54 (m, 1H), 7.44-7.40 (m, 2H), 7.29-7.18 (m, 3H), 7.10 (s, 1H), 6.84 (d, J=8.8 Hz, 2H), 5.10-04 (m, 1H), 4.73 (s, 2H), 4.44 (s, 2H), 3.78 (s, 3H), 2.89 (s, 3H), 2.35 (s, 3H), 1.47-1.43 (m, 3H).

151

Step 2: Preparation of (S)-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one 57 mg of (S)-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one was prepared as a white solid according to the same manner as described in step 6 of Example 34 except that (S)-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 9.44-9.36 (m, 1H), 7.90 (d, J=4.9 Hz, 1H), 7.69 (d, J=6.8 Hz, 1H), 7.61-7.56 (m, 1H), 7.46-7.37 (m, 2H), 7.31-7.28 (m, 1H), 7.23 (s, 1H), 7.07 (s, 1H), 6.11 (m, 1H), 5.08-5.02 (m, 1H), 4.70 (s, 2H), 2.99 (s, 3H), 2.35 (s, 3H), 1.45-1.43 (m, 3H).

Example 38: Preparation of (S)-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one

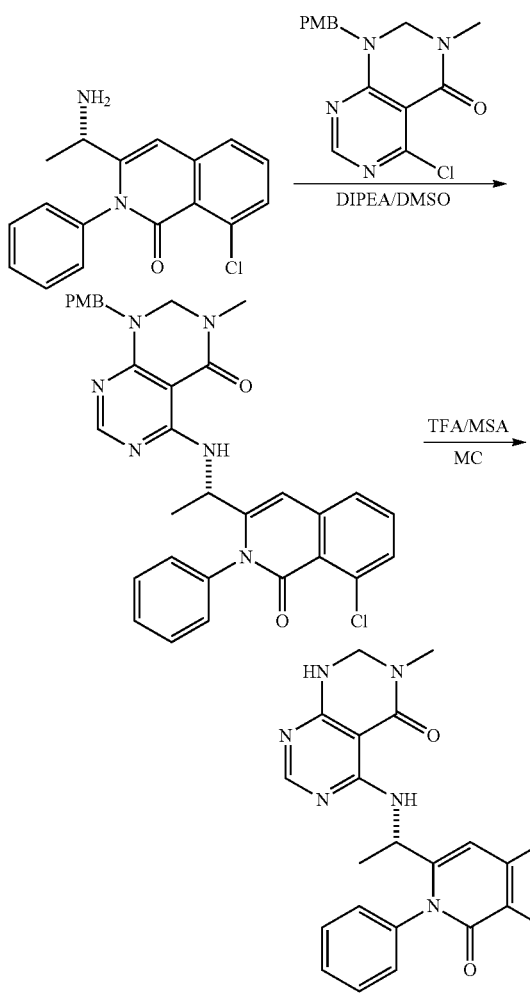

152

Step 1: Preparation of (S)-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one 30 mg of (S)-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one was prepared as a pale yellow solid by using 20 mg (0.063 mmol) of 5-chloro-1-(4-methoxybenzyl)-3-methyl-2,3-dihydropyrimido[4,5-d]pyrimidine-4(1H)-one prepared in step 4 of Example 34 and 19 mg (0.063 mmol) of (S)-3-(1-aminoethyl)-8-chloro-2-phenylisoquinoline-1(2H)-one according to the same manner as described in step 5 of Example 34 (0.052 mmol, yield: 82%).

$^1$H NMR (300 MHz, CDCl$_3$) δ 9.16 (d, J=7.8 Hz, 1H), 8.06 (s, 1H), 7.43-7.54 (m, 8H), 7.32 (d, J=8.6 Hz, 2H), 7.22 (d, J=8.4 Hz, 2H) 6.56 (s, 1H), 4.87 (t, J=7.1 Hz, 1H), 4.75 (s, 2H), 4.47 (s, 2H), 3.80 (s, 3H), 2.91 (s, 3H), 1.38 (d, J=6.8 Hz, 3H).

Step 2: Preparation of (S)-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one 22 mg of (S)-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one was prepared as a yellow solid by using 30 mg (0.052 mmol) of (S)-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one prepared in step 1 according to the same manner as described in step 8 of Example 1 (0.048 mmol, yield: 92%).

$^1$H NMR (300 MHz, CDCl$_3$) δ 9.07 (d, J=6.4 Hz, 1H), 7.92 (s, 1H), 7.36-7.51 (m, 7H), 7.29-7.32 (m, 1H), 6.55 (s, 1H), 6.11 (brs, 1H), 4.85 (t, J=7.9 Hz, 1H), 4.73 (s, 2H), 2.99 (s, 3H), 1.38 (d, J=7.2 Hz, 3H).

Example 39: Preparation of 3-methyl-5-((1-(2-phenylquinoline-3-yl)ethyl)amino)-2,3-dihydropyrimido[4,5-d]pyrimidine-4(1H)-one

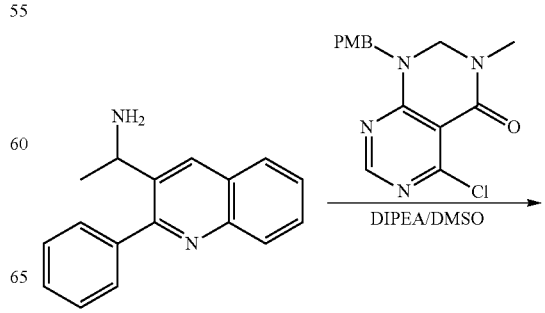

-continued

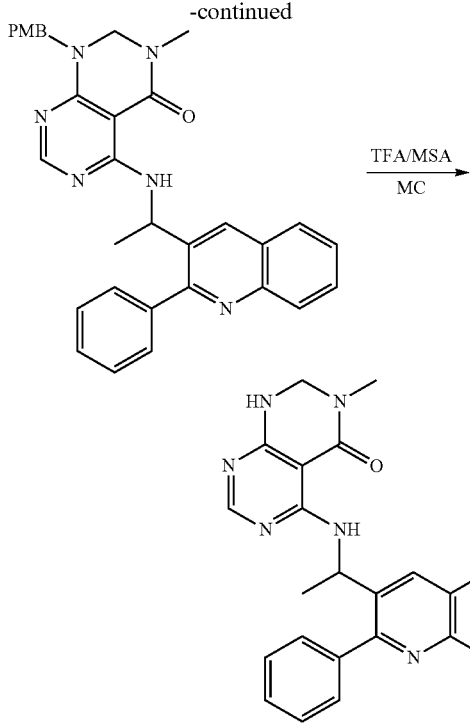

Step 1: Preparation of 1-(4-methoxybenzyl)-3-methyl-5-((1-(2-phenylquinoline-3-yl)ethyl)amino)-2,3-dihydropyrimido[4,5-d]pyrimidine-4(1H)-one 10 mg of 1-(4-methoxybenzyl)-3-methyl-5-((1-(2-phenylquinoline-3-yl)ethyl)amino)-2,3-dihydropyrimido[4,5-d]pyrimidine-4(1H)-one was prepared as a yellow solid by using 8 mg (0.025 mmol) of 5-chloro-1-(4-methoxybenzyl)-3-methyl-2,3-dihydropyrimido[4,5-d]pyrimidine-4(1H)-one prepared in step 4 of Example 34 and 7.5 mg (0.030 mmol) of 1-(2-phenylquinoline-3-yl)ethane-1-amine according to the same manner as described in step 5 of Example 34 (0.019 mmol, yield: 75%).

$^1$H NMR (300 MHz, CDCl$_3$) δ 9.39 (d, J=7.2 Hz, 1H), 8.25 (s, 1H), 8.15 (d, J=9.3 Hz, 1H), 8.01 (s, 1H), 7.83 (d, J=8.6 Hz, 1H), 7.76 (d, J=7.2 Hz, 2H), 7.68-7.70 (m, 1H), 7.47-7.54 (m, 5H), 7.22 (d, J=8.6 Hz, 1H), 6.85 (d, J=8.6 Hz, 2H) 6.64 (t, J=7.2 Hz, 1H), 4.75 (d, J=6.5 Hz, 2H), 4.47 (s, 2H), 3.79 (s, 3H), 2.93 (s, 3H), 1.47 (m, 3H).

Step 2: Preparation of 3-methyl-5-((1-(2-phenylquinoline-3-yl)ethyl)amino)-2,3-dihydropyrimido[4,5-d]pyrimidine-4(1H)-one 6 mg of 3-methyl-5-((1-(2-phenylquinoline-3-yl)ethyl)amino)-2,3-dihydropyrimido[4,5-d]pyrimidine-4(1H)-one was prepared as a yellow solid by using 10 mg (0.019 mmol) of 1-(4-methoxybenzyl)-3-methyl-5-((1-(2-phenylquinoline-3-yl)ethyl)amino)-2,3-dihydropyrimido[4,5-d]pyrimidine-4(1H)-one prepared in step 1 according to the same manner as described in step 8 of Example 1 (0.015 mmol, yield: 78%).

$^1$H NMR (300 MHz, CDCl$_3$) δ 9.52 (d, J=6.1 Hz, 1H), 8.21 (s, 1H), 8.14 (d, J=8.8 Hz, 1H), 7.92 (brs, 1H), 7.83 (d, J=7.5 Hz, 1H), 7.69 (d, J=8.1 Hz, 3H), 7.48-7.59 (m, 5H), 5.65 (t, J=6.8 Hz, 1H), 4.78 (brs, 2H) 2.99 (s, 3H), 1.44 (d, J=6.8 Hz, 3H).

Example 39-1

Preparation of (S)-3-methyl-5-((1-(2-phenylquinoline-3-yl)ethyl)amino)-2,3-dihydropyrimido[4,5-d]pyrimidine-4(1H)-one

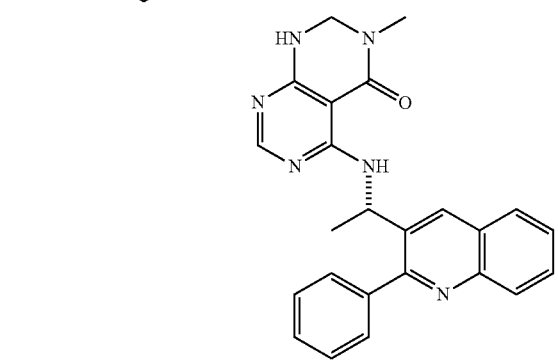

Step 1: Preparation of (S)-5-((1-(2-phenylquinoline-3-yl)ethyl)amino)-1-(4-methoxybenzyl)-3-methyl-2,3-dihydropyrimido[4,5-d]pyrimidine-4(1H)-one 84 mg of (S)-5-((1-(2-phenylquinoline-3-yl)ethyl)amino)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-1-(2-phenylquinoline-3-yl)ethaneamine was used (0.15 mmol, yield: 99%).

$^1$H NMR (300 MHz, CDCl$_3$) δ 9.39 (d, J=7.8 Hz, 1H), 8.23 (s, 1H), 8.44 (d, J=8.1 Hz, 1H), 8.08 (s, 1H), 7.82 (d, J=7.8 Hz, 1H), 7.75 (d, J=7.8 Hz, 2H), 7.69-7.64 (m, 1H), 7.53-7.43 (m, 4H), 7.21 (d, J=8.4 Hz, 1H), 6.85 (d, J=9.0 Hz, 2H), 5.67-5.62 (m, 1H), 4.74 (d, J=8.4 Hz, 2H), 4.47 (s, 2H), 3.79 (s, 3H), 2.92 (s, 3H), 1.40 (d, J=6.5 Hz, 3H).

Step 2: Preparation of (S)-3-methyl-5-((1-(2-phenylquinoline-3-yl)ethyl)amino)-2,3-dihydropyrimido[4,5-d]pyrimidine-4(1H)-one 52 mg of (S)-3-methyl-5-((1-(2-phenylquinoline-3-yl)ethyl)amino)-2,3-dihydropyrimido[4,5-d]pyrimidine-4(1H)-one was prepared as a white solid according to the same manner as described in step 6 of Example 34 except that (S)-5-((1-(2-phenylquinoline-3-yl)ethyl)amino)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 9.31 (d, J=6.9 Hz, 1H), 8.22 (s, 1H), 8.13 (d, J=7.7 Hz, –1H), 7.93 (s, 1H), 7.82 (d, J=7.7 Hz, –1H), 7.75-7.64 (m, 3H), 7.53-7.43 (m, 4H), 6.71 (s, —NH), 5.66-5.56 (m, 1H), 4.69 (s, 2H), 2.98 (s, 3H), 1.41 (d, J=7.4 Hz, 3H).

Example 40: Preparation of (S)-5-((1-(4,8-dichloro-1-oxo-2-phenyl-1,2-dihydroisoquinoline-3-yl)ethyl)amino)-3-methyl-2,3-dihydropyrimido[4,5-d]pyrimidine-4(1H)-one

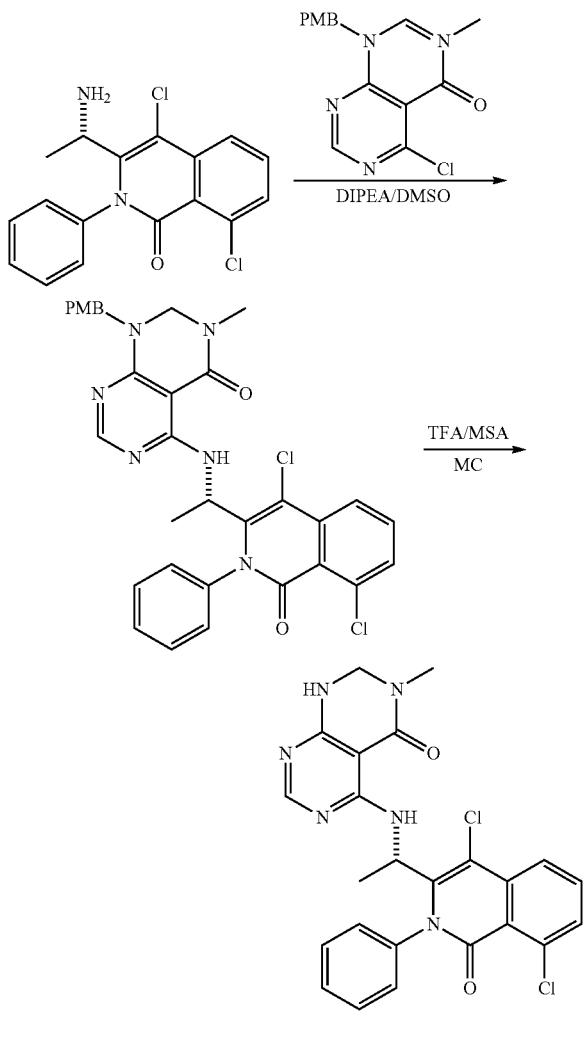

Step 1: Preparation of (S)-5-((1-(4,8-dichloro-1-oxo-2-phenylquinoline-3-yl)ethyl)amino)-1-(4-methoxybenzyl)-3-methyl-2,3-dihydropyrimido[4,5-d]pyrimidine-4(1H)-one (S)-5-((1-(4,8-dichloro-1-oxo-2-phenylquinoline-3-yl)ethyl)amino)-1-(4-methoxybenzyl)-3-methyl-2,3-dihydropyrimido[4,5-d]pyrimidine-4(1H)-one was prepared according to the same manner as described in step 5 of Example 34 except that (S)-3-(1-aminoethyl)-4,8-dihydro-2-phenylisoquinoline-1(2H)-one was used.

$^1$H NMR (300 MHz, CDCl$_3$) δ 9.54 (br d, J=6.6 Hz, 1H), 8.09 (s, 1H), 7.97 (dd, J=7.7, 1.5 Hz, 1H), 7.75 (br d, J=7.7 Hz, 1H), 7.46-7.61 (m, 6H), 7.15-7.21 (m, 3H), 6.80-6.87 (m, 2H), 4.97-5.05 (m, 1H), 4.72 (s, 2H), 4.39-4.47 (m, 2H), 3.78 (s, 3H), 2.88 (s, 3H), 1.60 (d, J=7.2 Hz, 3H).

Step 2: Preparation of (S)-5-((1-(4,8-dichloro-1-oxo-2-phenyl-1,2-dihydroisoquinoline-3-yl)ethyl)amino)-3-methyl-2,3-dihydropyrimido[4,5-d]pyrimidine-4(1H)-one (S)-5-((1-(4,8-dichloro-1-oxo-2-phenyl-1,2-dihydroisoquinoline-3-yl)ethyl)amino)-3-methyl-2,3-dihydropyrimido[4,5-d]pyrimidine-4(1H)-one was prepared according to the same manner as described in step 6 of Example 34 except that (S)-5-((1-(4,8-dichloro-1-oxo-2-phenylquinoline-3-yl)ethyl)amino)-1-(4-methoxybenzyl)-3-methyl-2,3-dihydropyrimido[4,5-d]pyrimidine-4(1H)-one was used.

$^1$H NMR (500 MHz, CDCl$_3$) δ 9.48 (br s, 1H), 7.98 (dd, J=8.1, 0.9 Hz, 1H), 7.96 (s, 1H), 7.74 (d, J=7.8 Hz, 1H), 7.49-7.61 (m, 5H), 7.18-7.21 (m, 1H), 6.70 (br s, 1H), 4.96-4.50 (m, 1H), 4.67-4.72 (m, 2H), 2.98 (s, 3H), 1.62 (d, J=7.2 Hz, 3H).

Example 41: Preparation of (S)-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one

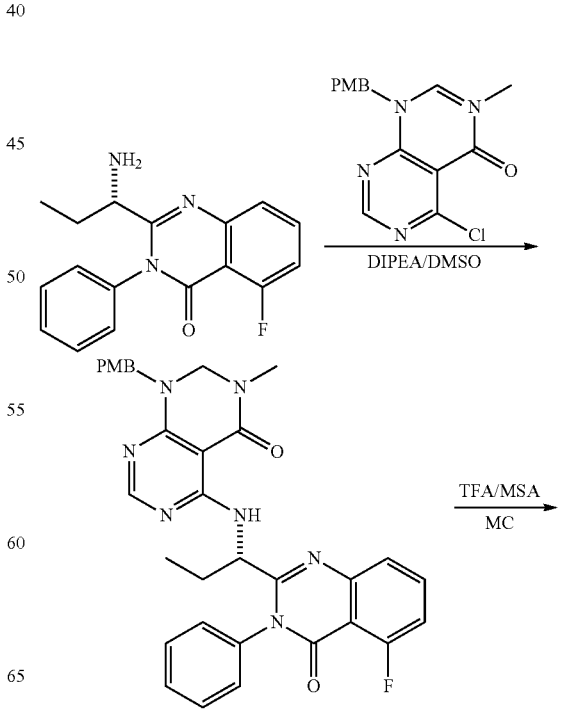

-continued

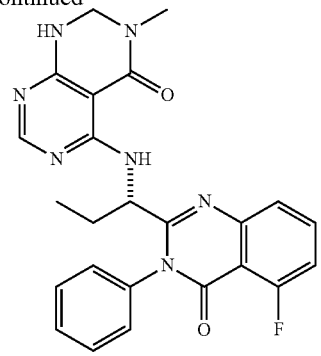

Step 1: Preparation of (S)-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one 91 mg of (S)-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-2-(1-aminopropyl)-5-fluoro-3-phenylquinazoline-4(3H)-one was used (0.15 mmol, yield: 98%).

$^1$H NMR (300 MHz, CDCl$_3$) δ 9.43 (d, J=9.4 Hz, 1H), 8.02 (s, 1H), 7.66-7.45 (m, 6H), 7.31-7.28 (m, 1H), 7.21 (d, J=7.4 Hz, 2H), 7.11-7.05 (m, 1H), 5.01-4.96 (m, 1H), 4.74 (s, 2H), 4.45 (s, 2H), 3.79 (s, 3H), 2.91 (s, 3H), 1.93-1.75 (m, 2H), 0.86-0.82 (m, 3H).

Step 2: Preparation of (S)-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one 55 mg of (S)-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one was prepared as a white solid according to the same manner as described in step 6 of Example 34 except that (S)-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 9.35 (d, J=8.2 Hz, 1H), 7.88 (s, 1H), 7.69-7.62 (m, 1H), 7.57-7.50 (m, 4H), 7.44-7.41 (m, 1H), 7.30-7.28 (m, 1H), 7.11-7.05 (m, 1H), 6.28 (s, 1H), 4.83-4.91 (m, 1H), 4.70 (s, 2H), 2.98 (s, 3H), 1.92-1.75 (m, 2H), 0.87-0.82 (m, 3H).

Example 42: Preparation of (S)-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one

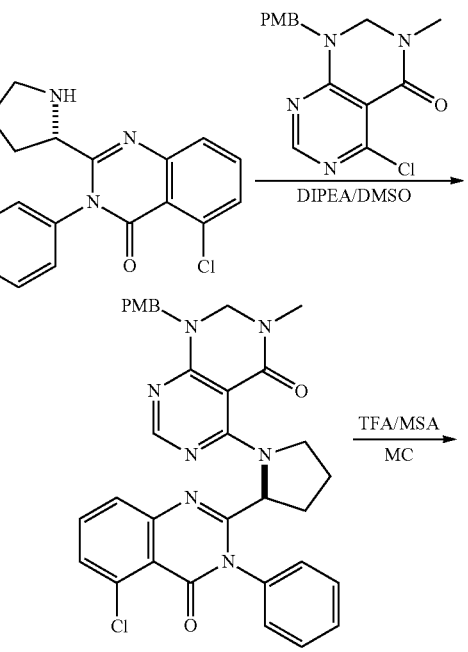

Step 1: Preparation of (S)-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one 102 mg of (S)-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-5-chloro-3-phenyl-2-(pyrrolidine-2-yl)quinazoline-4(3H)-one was used (0.16 mmol, yield: 99%).

$^1$H NMR (300 MHz, CDCl$_3$) δ 8.03 (s, 1H), 7.75-7.73 (m, 1H), 7.60-7.50 (m, 5H), 7.41-7.38 (m, 1H), 7.16 (d, J=7.6 Hz, 2H), 6.84 (d, J=8.6 Hz, 2H), 4.90-4.64 (m, 1H), 3.79 (s, 3H), 3.72-3.65 (m, 1H), 2.89 (s, 3H), 2.38-2.28 (m, 1H), 1.86-1.76 (m, 4H).

Step 2: Preparation of (S)-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one 58 mg of (S)-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 6 of Example 34 except that (S)-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 7.91 (s, 1H), 7.71-7.69 (m, 1H), 7.58-7.48 (m, 5H), 7.40 (d, J=7.5 Hz, 2H), 7.25-7.23 (m, 1H), 4.72-4.68 (m, 1H), 4.56 (s, 2H), 3.90-3.81 (m, 1H), 3.62-3.53 (m, 1H), 3.32-3.25 (m, 2H), 3.05 (s, 3H), 2.31-2.24 (m, 1H), 2.10-2.09 (m, 2H), 1.84-1.75 (m, 1H).

Example 43: Preparation of (S)-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one

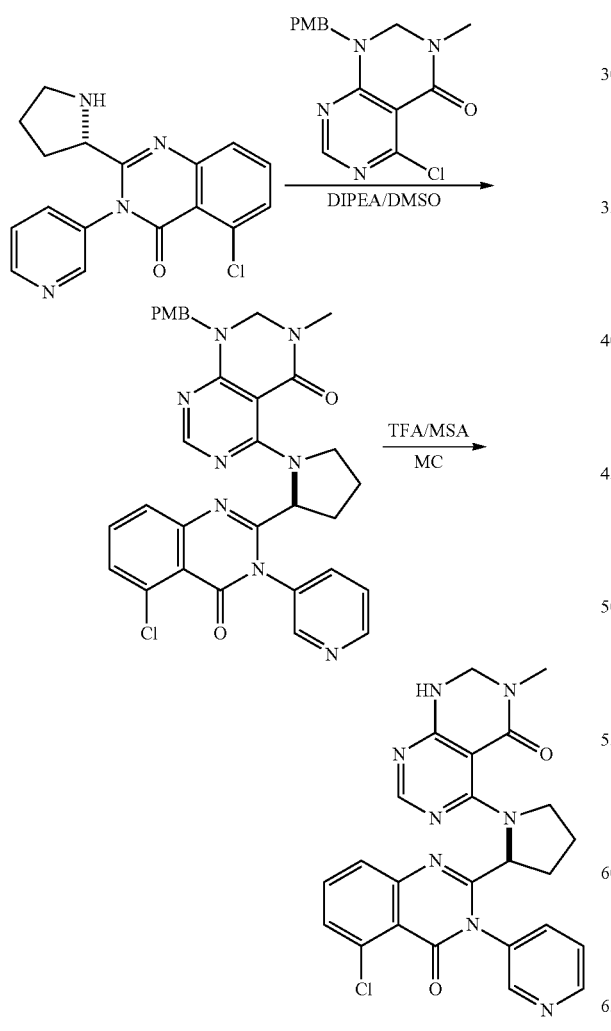

Step 1: Preparation of (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one 106 mg of (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-5-chloro-3-(pyridine-3-yl)-2-(pyrrolidine-2-yl)quinazoline-4(3H)-one was used (0.17 mmol, yield: 99%).

$^1$H NMR (300 MHz, CDCl$_3$) δ 9.04 (s, 1H), 8.76 (d, J=3.5 Hz, 1H), 8.54 (s, 1H), 8.12-8.00 (m, 3H), 7.61-7.40 (m, 7H), 7.17-7.14 (m, 2H), 6.84 (d, J=8.5 Hz, 2H), 4.90-4.64 (m, 1H), 3.87-3.83 (m, 1H), 3.78 (s, 5H), 3.60-3.53 (m, 1H), 2.89 (s, 3H), 2.37-2.30 (m, 2H), 1.87-1.79 (m, 2H).

Step 2: Preparation of (S)-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one 59 mg of (S)-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 6 of Example 34 except that (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 9.04 (s, 1H), 8.77-8.74 (m, 2H), 8.53 (s, 1H), 8.12-8.06 (m, 2H), 8.00 (s, 1H), 7.63-7.50 (m, 7H), 7.46-7.40 (m, 2H), 7.19-7.12 (m, 2H), 6.84 (d, J=8.5 Hz, 2H), 4.87-4.67 (m, 2H), 4.36 (s, 2H), 3.60-3.53 (m, 1H), 2.89 (s, 3H), 2.39-2.27 (m, 2H), 1.87-1.79 (m, 2H).

Example 44: Preparation of (S)-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one

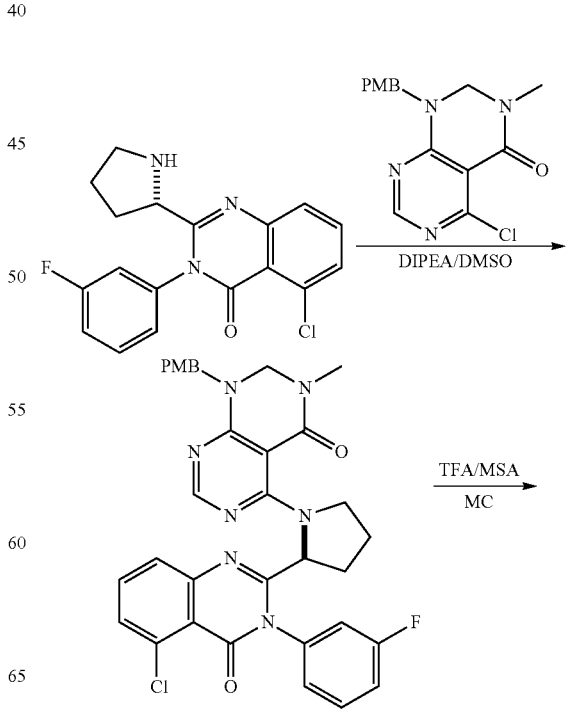

-continued

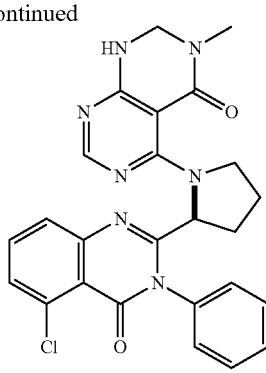

Step 1: Preparation of (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one 102 mg of (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-5-chloro-3-(3-fluorophenyl)-2-(pyrrolidine-2-yl)quinazoline-4(3H)-one was used (0.16 mmol, yield: 99%).

$^1$H NMR (300 MHz, CDCl$_3$) δ 8.06-8.03 (m, 1H), 7.61-7.40 (m, 4H), 7.42-7.39 (m, 1H), 7.27-7.14 (m, 3H), 7.07-6.98 (m, 1H), 6.84 (d, J=8.4 Hz, 2H), 4.85-4.69 (m, 2H), 4.37 (s, 2H), 3.87-3.83 (m, 1H), 3.78 (s, 3H), 3.56-3.48 (m, 1H), 2.90 (s, 3H), 2.32-2.24 (m, 1H), 2.12-2.07 (m, 1H), 1.87-1.76 (m, 2H).

Step 2: Preparation of (S)-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one 60 mg of (S)-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 6 of Example 34 except that (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 7.95-7.91 (m, 1H), 7.57-7.38 (m, 5H), 7.24-7.19 (m, 1H), 7.07-6.98 (m, 1H), 6.13-6.10 (m, 1H), 6.02-6.00 (m, 1H), 4.79-4.37 (m, 1H), 4.66-4.53 (m, 2H), 3.79-3.70 (m, 1H), 3.07 (s, 3H), 2.38-2.32 (m, 1H), 2.13-2.01 (m, 2H), 1.95-1.82 (m, 2H).

Example 45: Preparation of (S)-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one

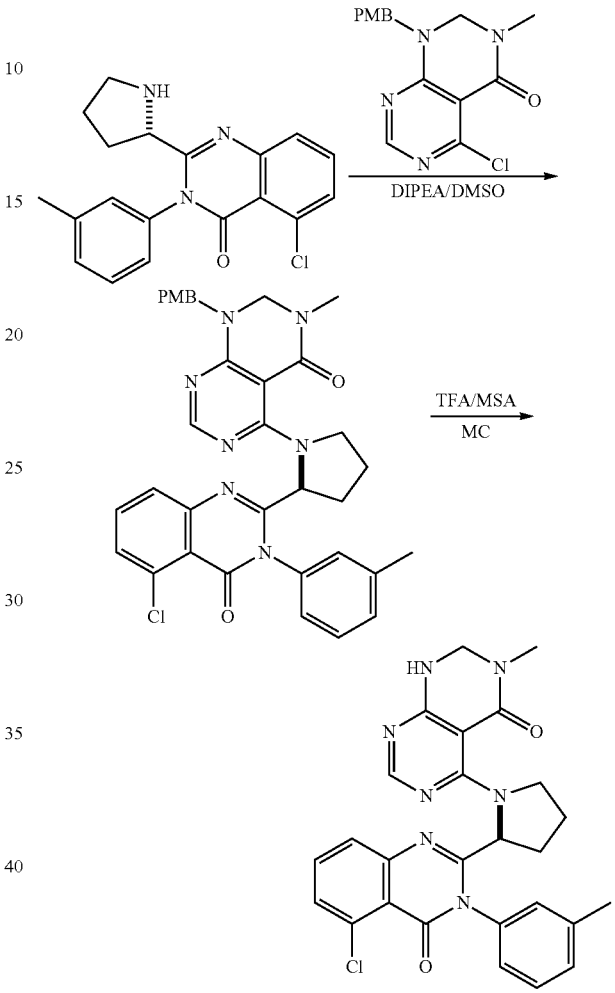

Step 1: Preparation of (S)-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one 95 mg of (S)-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-5-chloro-2-(pyrrolidine-2-yl)-3-m-tolylquinazoline-4(3H)-one was used (0.15 mmol, yield: 95%).

$^1$H NMR (300 MHz, CDCl$_3$) δ 8.04 (d, J=6.3 Hz, 1H), 7.56-7.44 (m, 4H), 7.41-7.38 (m, 2H), 7.30 (d, J=7.6 Hz, 1H), 7.16 (d, J=8.5 Hz, 2H), 7.04-7.02 (m, 1H), 6.84 (d, J=8.5 Hz, 2H), 4.81-4.71 (m, 3H), 4.37 (s, 2H), 3.86-3.81 (m, 1H), 3.78 (s, 3H), 3.56-3.51 (m, 1H), 2.89 (s, 3H), 2.76-2.72 (m, 1H), 2.42 (s, 3H), 2.33-2.26 (m, 1H), 2.13-2.07 (m, 2H), 1.84-1.76 (m, 1H).

Step 2: Preparation of (S)-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one 60 mg of (S)-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 6 of Example 34 except that (S)-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 7.88 (s, 1H), 7.49-7.44 (m, 4H), 7.41-7.37 (m, 2H), 7.30-7.27 (m, 1H), 7.03-7.01 (m, 1H), 4.78-4.75 (m, 1H), 4.61-4.53 (m, 2H), 3.73 (s, 2H), 3.05 (s, 3H), 2.41 (s, 3H), 2.35-2.31 (m, 1H), 1.88-1.81 (m, 2H).

Example 46: Preparation of (S)-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one

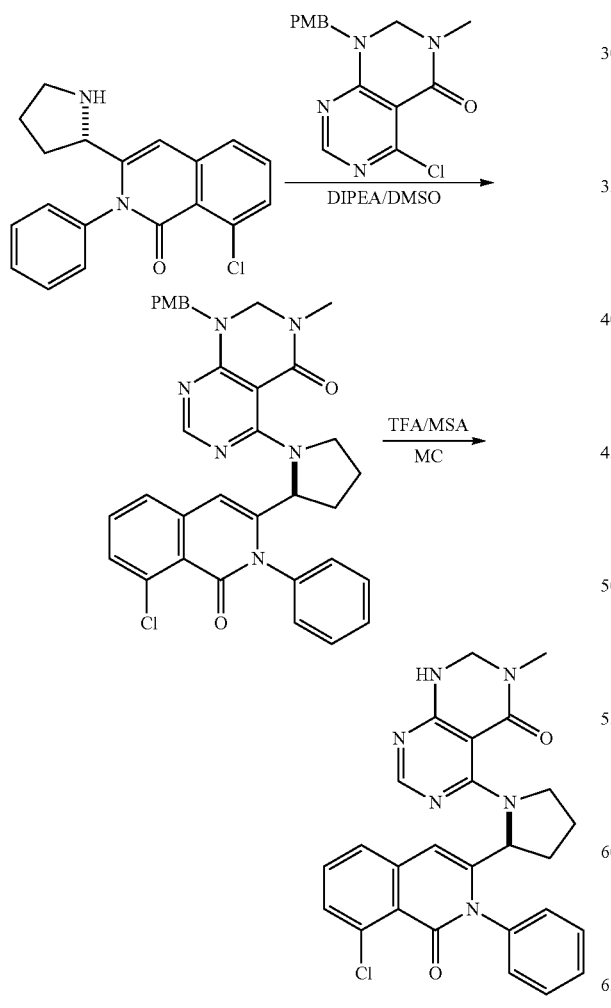

Step 1: Preparation of (S)-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one 97 mg of (S)-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 5 of Example 34 except that (S)-8-chloro-2-phenyl-3-(pyrrolidine-2-yl)isoquinoline-1(2H)-one was used (0.16 mmol, yield: 99%).

$^1$H NMR (300 MHz, CDCl$_3$) δ 8.16 (s, 1H), 7.70-7.47 (m, 6H), 7.38 (s, 2H), 7.33-7.30 (m, 2H), 7.19 (d, J=8.6 Hz, 2H), 6.86 (d, J=8.6 Hz, 2H), 6.72 (s, 2H), 5.03-4.91 (m, 2H), 4.72-4.53 (m, 2H), 4.25-4.12 (m, 2H), 3.79 (s, 3H), 3.12-3.04 (m, 1H), 2.96 (s, 3H), 2.05-1.95 (m, 2H), 1.87-1.79 (m, 1H).

Step 2: Preparation of (S)-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one 58 mg of (S)-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one was prepared as a white solid according to the same manner as described in step 6 of Example 34 except that (S)-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one was used (0.12 mmol, yield: 99%).

$^1$H NMR (300 MHz, CDCl$_3$) δ 8.05 (s, 1H), 7.65-7.46 (m, 4H), 7.37-7.29 (m, 4H), 6.65 (s, 1H), 6.03 (s, 1H), 5.01-4.98 (m, 1H), 4.77-4.73 (m, 1H), 4.48-4.44 (m, 1H), 4.20-4.10 (m, 1H), 3.10 (s, 3H), 2.05-1.96 (m, 2H), 83-1.60 (m, 2H).

Example 47: Preparation of (S)-5-(2-(5-chloro-4-oxo-3-phenyl-3,4-dihydropyrrolo[2,1-f][1,2,4]triazine-2-yl)pyrrolidine-1-yl)-3-methyl-2,3-dihydropyrimido[4,5-d]pyrimidine-4(1H)-one

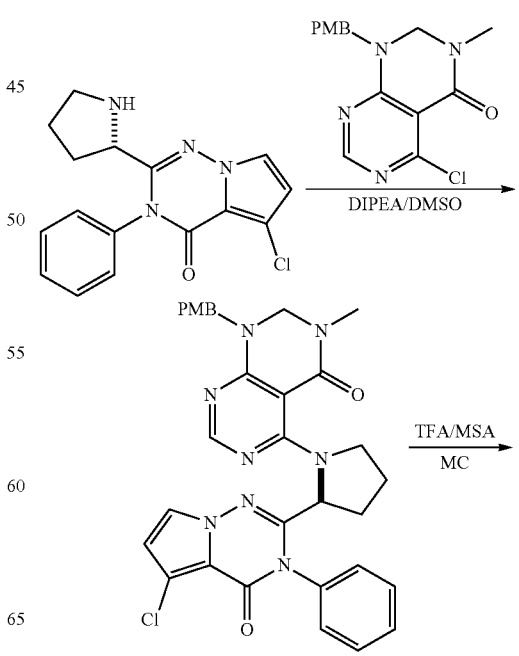

-continued

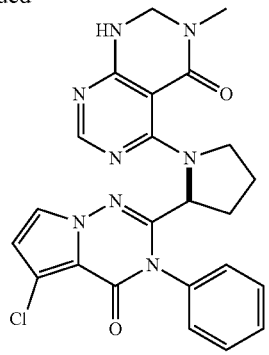

Step 1: Preparation of (S)-5-(2-(5-chloro-4-oxo-3-phenyl-3,4-dihydropyrrolo[2,1-f][1,2,4]triazine-2-yl)pyrrolidine-1-yl)-1-(4-methoxybenzyl)-3-methyl-2,3-dihydropyrimido[4,5-d]pyrimidine-4(1H)-one 35 mg of (S)-5-(2-(5-chloro-4-oxo-3-phenyl-3,4-dihydropyrrolo[2,1-f][1,2,4]triazine-2-yl)pyrrolidine-1-yl)-1-(4-methoxybenzyl)-3-methyl-2,3-dihydropyrimido[4,5-d]pyrimidine-4(1H)-one was prepared as a white solid by using 20 mg (0.064 mmol) of 5-chloro-1-(4-methoxybenzyl)-3-methyl-2,3-dihydropyrimido[4,5-d]pyrimidine-4(1H)-one prepared in step 4 of Example 34 and 20 mg (0.064 mmol) of (S)-5-chloro-3-phenyl-2-(pyrrolidine-2-yl)pyrrolo[2,1-f][1,2,4]triazine-4(3H)-one according to the same manner as described in step 5 of Example 34 (0.059 mmol, yield: 93%).

¹H NMR (500 MHz, CDCl₃) δ 8.14 (s, 1H), 7.74 (d, J=7.7 Hz, 1H), 7.49-7.61 (m, 3H), 7.17-7.28 (m, 4H), 6.87 (d, J=8.5 Hz, 2H), 6.44 (d, J=2.8 Hz, 1H), 4.73-4.91 (m, 3H), 4.35-4.44 (m, 2H), 3.82 (s, 3H), 3.72 (brs, 1H). 3.58 (brs, 1H), 2.90 (s, 3H), 2.26 (brs, 1H), 2.09 (s, 1H), 2.02-2.08 (m, 1H), 1.79-1.87 (m, 1H).

Step 2: Preparation of (S)-5-(2-(5-chloro-4-oxo-3-phenyl-3,4-dihydropyrrolo[2,1-f][1,2,4]triazine-2-yl)pyrrolidine-1-yl)-3-methyl-2,3-dihydropyrimido[4,5-d]pyrimidine-4(1H)-one 11 mg of (S)-5-(2-(5-chloro-4-oxo-3-phenyl-3,4-dihydropyrrolo[2,1-f][1,2,4]triazine-2-yl)pyrrolidine-1-yl)-3-methyl-2,3-dihydropyrimido[4,5-d]pyrimidine-4(1H)-one was prepared as a yellow solid by using 35 mg (0.059 mmol) of (S)-5-(2-(5-chloro-4-oxo-3-phenyl-3,4-dihydropyrrolo[2,1-f][1,2,4]triazine-2-yl)pyrrolidine-1-yl)-1-(4-methoxybenzyl)-3-methyl-2,3-dihydropyrimido[4,5-d]pyrimidine-4(1H)-one according to the same manner as described in step 6 of Example 34 (0.023 mmol, yield: 39%).

¹H NMR (500 MHz, CDCl₃) δ 8.03 (s, 1H), 7.70 (d, J=7.2 Hz, 1H), 7.48-7.60 (m, 3H), 7.25-7.27 (m, 1H), 7.20 (d, J=2.6 Hz, 1H), 6.43 (d, J=3.0 Hz, 1H), 6.16 (brs, 1H), 4.76-4.81 (m, 1H), 4.58-4.67 (m, 2H), 3.64-3.76 (m, 2H), 3.09 (s, 3H), 2.27 (brs, 1H), 2.01-2.11 (m, 2H), 1.83-1.90 (m, 2H).

Example 48: Preparation of (S)-7-amino-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one

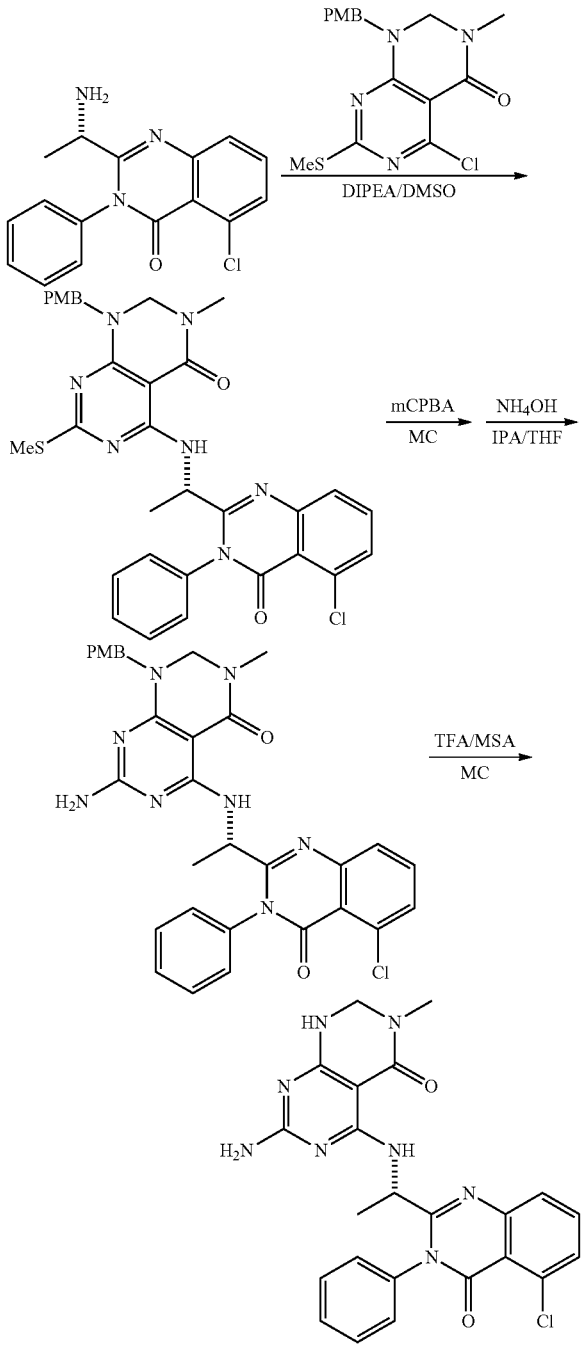

Step 1: Preparation of (S)-5-((1-(5-chloro-4-oxo-3-phenyl-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one 65 mg of (S)-5-((1-(5-chloro-4-oxo-3-phenyl-3,4-dihydroquinazoline-2-yl)ethyl)amino)-1-(4-methoxybenzyl)-3- methyl-7-(methylthio)-2,3-dihydropyrimido[4,5-d]pyrimidine-4(1H)-one was prepared as a white solid by using 40 mg (0.11 mmol, 1.0 equivalent) of 5-chloro-1-(4-methoxybenzyl)-3-methyl-7-(methylthio)-2,3-dihydropyrimido[4,5-d]pyrimidine-4(1H)-one and 40 mg (0.13 mmol, 1.2 equivalent) of (S)-2-(1-aminoethyl)-5-chloro-3-phenylquinazoline-4(3H)-one according to the same manner as described in step 5 of Example 34 (0.10 mmol, yield: 94%).

$^1$H NMR (300 MHz, CDCl$_3$) δ 9.44-9.47 (d, J=4.5 Hz, 1H), 7.69-7.72 (d, J=8.0 Hz, 1H), 7.55-7.61 (m, 5H), 7.46 (s, 1H), 7.27-7.31 (m, 1H), 7.19-7.22 (d, J=4.5 Hz, 2H), 6.84-6.87 (d, J=8.6 Hz, 2H), 5.07-5.12 (m, 1H), 4.74 (s, 2H), 4.41 (s, 2H), 3.79 (s, 3H), 2.89 (s, 3H), 2.29 (s, 3H), 1.39-1.42 (d, J=6.7 Hz, 3H).

Step 2: Preparation of (S)-7-amino-5-((1-(5-chloro-4-oxo-3-phenyl-3,4-dihydroquinazoline-2-yl)ethyl)amino)-1-(4-methoxybenzyl)-3-methyl-2,3-dihydropyrimido[4,5-d]pyrimidine-4(1H)-one 52 mg of (S)-7-amino-5-((1-(5-chloro-4-oxo-3-phenyl-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid by using 65 mg (0.10 mmol) of (S)-5-((1-(5-chloro-4-oxo-3-phenyl-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one prepared in step 1 according to the same manner as described in step 4 of Example 15 (0.09 mmol, yield: 73%).

$^1$H NMR (300 MHz, CDCl$_3$) δ 9.46-9.48 (d, J=7.4 Hz, 1H), 7.70-7.72 (d, J=8.2 Hz, 1H), 7.42-7.61 (m, 5H), 7.29-7.31 (d, J=7.8 Hz, 1H), 7.18-7.21 (d, J=8.1 Hz, 2H), 6.83-6.86 (d, J=7.8 Hz, 2H), 5.05-5.10 (m, 1H), 4.66 (s, 2H), 4.61 (s, 2H), 4.33 (s, 3H), 3.79 (s, 3H), 2.86 (s, 3H), 1.40-1.42 (d, J=6.3 Hz, 3H).

Step 3: Preparation of (S)-7-amino-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one 25 mg of (S)-7-amino-5-((1-(5-chloro-4-oxo-3-phenyl-3,4-dihydroquinazoline-2-yl)ethyl)amino)-3-methyl-2,3-dihydropyrimido[4,5-d]pyrimidine-4(1H)-one was prepared as a white solid by using 52 mg (0.09 mmol) of (S)-7-amino-5-((1-(5-chloro-4-oxo-3-phenyl-3,4-dihydroquinazoline-2-yl)ethyl)amino)-1-(4-methoxybenzyl)-3-methyl-2,3-dihydropyrimido[4,5-d]pyrimidine-4(1H)-one prepared in step 2 according to the same manner as described in step 8 of Example 1 (0.05 mmol, yield: 60%).

$^1$H NMR (300 MHz, CDCl$_3$) δ 9.41-9.43 (d, J=7.9 Hz, 1H), 7.70-7.73 (d, J=7.9 Hz, 1H), 7.44-7.62 (m, 5H), 7.29-7.36 (m, 2H), 5.01-5.06 (m, 1H), 4.74 (s, 2H), 4.60 (s, 2H), 2.94 (s, 3H), 1.40-1.42 (d, J=6.6 Hz, 3H).

Example 49: Preparation of (S)-7-amino-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one

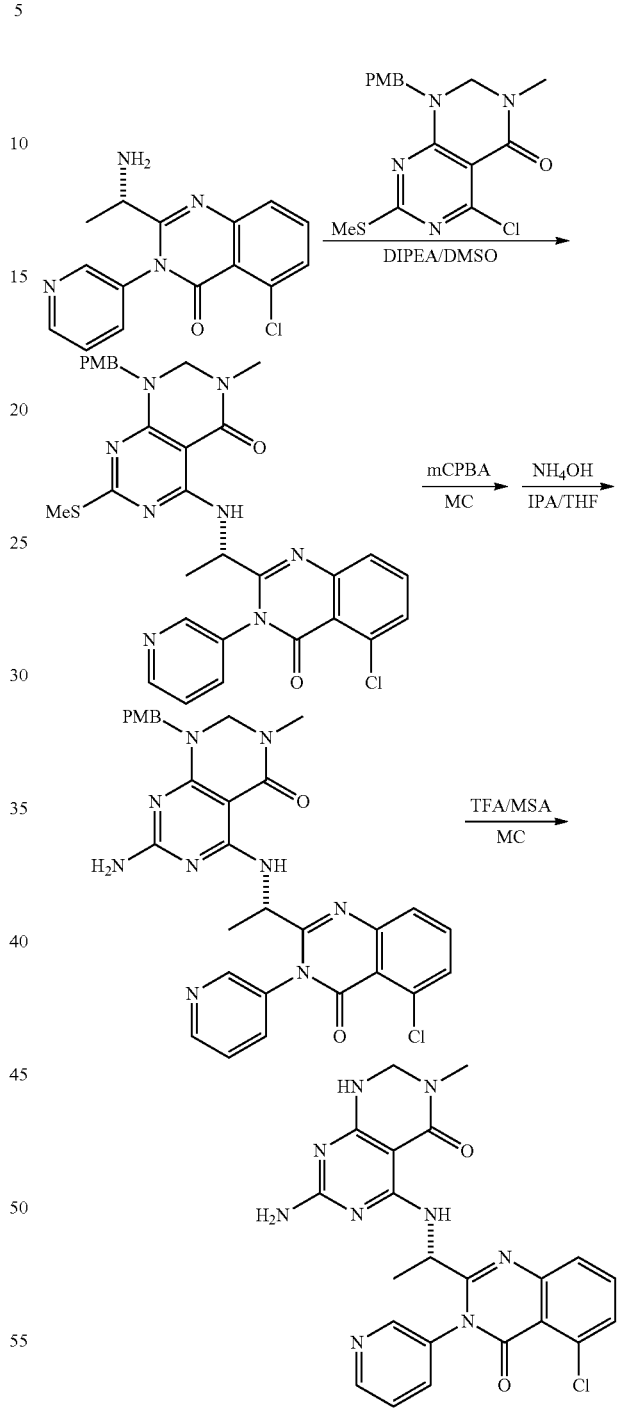

Step 1: Preparation of (S)-5-((1-(5-chloro-4-oxo-3-(pyridine-3-yl)-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one 77 mg of (S)-5-((1-(5-chloro-4-oxo-3-(pyridine-3-yl)-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-2-(1-aminoethyl)-5-chloro-3-(pyridine-3-yl)quinazoline-4(3H)-one was used (0.12 mmol, yield: 90%).

¹H NMR (300 MHz, CDCl₃) δ 9.32-9.34 (m, 1H), 8.72-8.74 (m, 1H), 7.98-8.01 (d, J=4.5 Hz, 1H), 7.59-7.68 (m, 3H), 7.46-7.52 (m, 2H), 7.19-7.22 (d, J=7.4 Hz, 2H), 6.84-6.87 (d, J=7.9 Hz, 2H), 4.92-4.98 (m, 1H), 4.74 (s, 2H), 4.42 (s, 2H), 3.79 (s, 3H), 2.88 (s, 3H), 2.35 (s, 3H), 1.45-1.48 (d, J=6.4 Hz, 3H).

Step 2: Preparation of (S)-7-amino-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one 47 mg of (S)-7-amino-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-((1-(5-chloro-4-oxo-3-(pyridine-3-yl)-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one was used (0.08 mmol, yield: 64%).

¹H NMR (300 MHz, CDCl₃) δ 9.40-9.43 (d, J=8.8 Hz, 1H), 8.75-8.77 (m, 1H), 7.58-7.72 (m, 3H), 6.45-7.55 (m, 2H), 7.18-7.21 (d, J=2.6 Hz, 2H), 6.83-6.87 (t, J=6.8 Hz, 3H), 4.93-5.15 (m, 2H), 4.61-4.73 (m, 2H), 4.33 (s, 2H), 3.79 (s, 3H), 2.86 (s, 3H), 1.41-1.49 (dd, J=17.4, 6.5 Hz, 3H).

Step 3: Preparation of (S)-7-amino-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one 19 mg of (S)-7-amino-5-((1-(5-chloro-4-oxo-3-(pyridine-3-yl)-3,4-dihydroquinazoline-2-yl)ethyl)amino)-3-methyl-2,3-dihydropyrimido[4,5-d]pyrimidine-4(1H)-one was prepared as a white solid according to the same manner as described in step 8 of Example 1 except that (S)-7-amino-5-((1-(5-chloro-4-oxo-3-(pyridine-3-yl)-3,4-dihydroquinazoline-2-yl)ethyl)amino)-1-(4-methoxybenzyl)-3-methyl-2,3-dihydropyrimido[4,5-d]pyrimidine-4(1H)-one was used (0.04 mmol, yield: 51%).

¹H NMR (300 MHz, DMSO-d₆O) δ 9.19-9.27 (m, 1H), 8.70-8.77 (m, 1H), 8.05-8.10 (m, 1H), 7.75-7.80 (m, 1H), 7.57-7.67 (m, 3H), 7.20-7.21 (d, J=5.0 Hz, 1H), 6.14 (s, 2H), 4.61-4.65 (m, 1H), 4.44 (s, 2H), 2.78 (s, 3H), 1.28-1.31 (d, J=6.4 Hz, 3H).

Example 50: Preparation of (S)-7-amino-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one

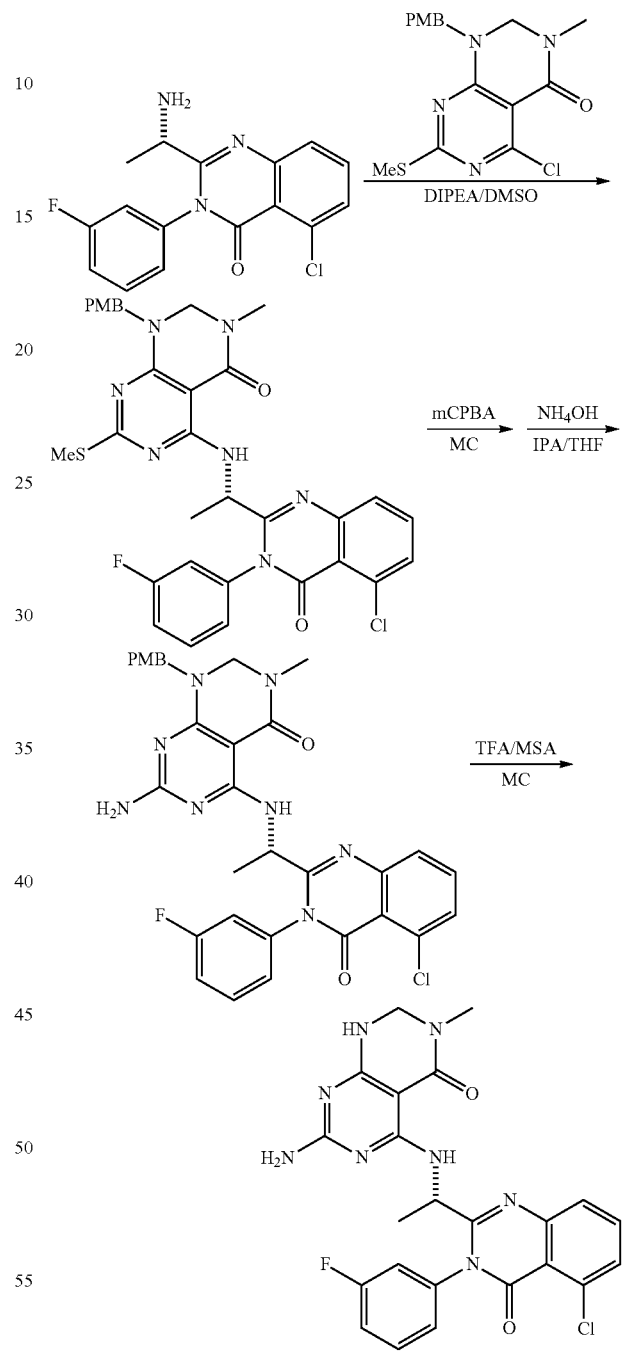

Step 1: Preparation of (S)-5-((1-(5-chloro-3-(3-fluorophenyl)-4-oxo-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one 75 mg of (S)-5-((1-(5-chloro-3-(3-fluorophenyl)-4-oxo-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-2-(1-aminoethyl)-5-chloro-3-(3-fluorophenyl)quinazoline-4(3H)-one was used (0.12 mmol, yield: 94%).

$^1$H NMR (300 MHz, CDCl$_3$) δ 9.43-9.30 (m, 1H), 7.68-7.70 (d, J=7.2 Hz, 1H), 7.44-7.62 (m, 4H), 7.30-7.38 (m, 1H), 7.19-7.21 (d, J=8.0 Hz, 2H), 7.03-7.10 (m, 1H), 6.84-6.87 (d, J=7.8 Hz, 2H), 5.06-5.13 (m, 1H), 4.74 (s, 2H), 4.41 (s, 3H), 3.79 (s, 3H), 2.88 (s, 3H), 2.32 (s, 3H), 1.43-1.45 (d, J=6.1 Hz, 3H).

Step 2: Preparation of (S)-7-amino-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one 56 mg of (S)-7-amino-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-((1-(5-chloro-3-(3-fluorophenyl)-4-oxo-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one was used (0.09 mmol, yield: 78%).

$^1$H NMR (300 MHz, CDCl$_3$) δ 9.39-9.46 (m, 1H), 7.70-7.72 (d, J=7.3 Hz, 1H), 7.58-7.62 (m, 2H), 7.44-7.47 (m, 2H), 7.07-7.21 (m, 4H), 6.84-6.86 (d, J=8.5 Hz, 2H), 5.07-5.14 (m, 1H), 4.63-4.76 (m, 4H), 4.34 (s, 2H), 3.79 (s, 3H), 2.86 (s, 3H), 1.42-1.44 (d, J=3.0 Hz, 3H).

Step 3: Preparation of (S)-7-amino-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one 26 mg of (S)-7-amino-5-((1-(5-chloro-3-(3-fluorophenyl)-4-oxo-3,4-dihydroquinazoline-2-yl)ethyl)amino)-3-methyl-2,3-dihydropyrimido[4,5-d]pyrimidine-4(1H)-one was prepared as a white solid according to the same manner as described in step 8 of Example 1 except that (S)-7-amino-5-((1-(5-chloro-3-(3-fluorophenyl)-4-oxo-3,4-dihydroquinazoline-2-yl)ethyl)amino)-1-(4-methoxybenzyl)-3-methyl-2,3-dihydropyrimido[4,5-d]pyrimidine-4(1H)-one was used (0.05 mmol, yield: 58%).

$^1$H NMR (300 MHz, CDCl$_3$) δ 9.30-9.37 (t, J=9.1 Hz, 1H), 7.69-7.72 (m, 1H), 7.40-7.62 (m, 3H), 7.04-7.23 (m, 3H), 5.50 (s, 1H), 5.00-5.11 (m, 1H), 4.62-4.75 (d, J=22.7 Hz, 2H), 4.60 (s, 2H), 2.94 (s, 3H), 1.40-1.45 (t, J=7.0 Hz, 3H).

Example 51: Preparation of (S)-7-amino-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one

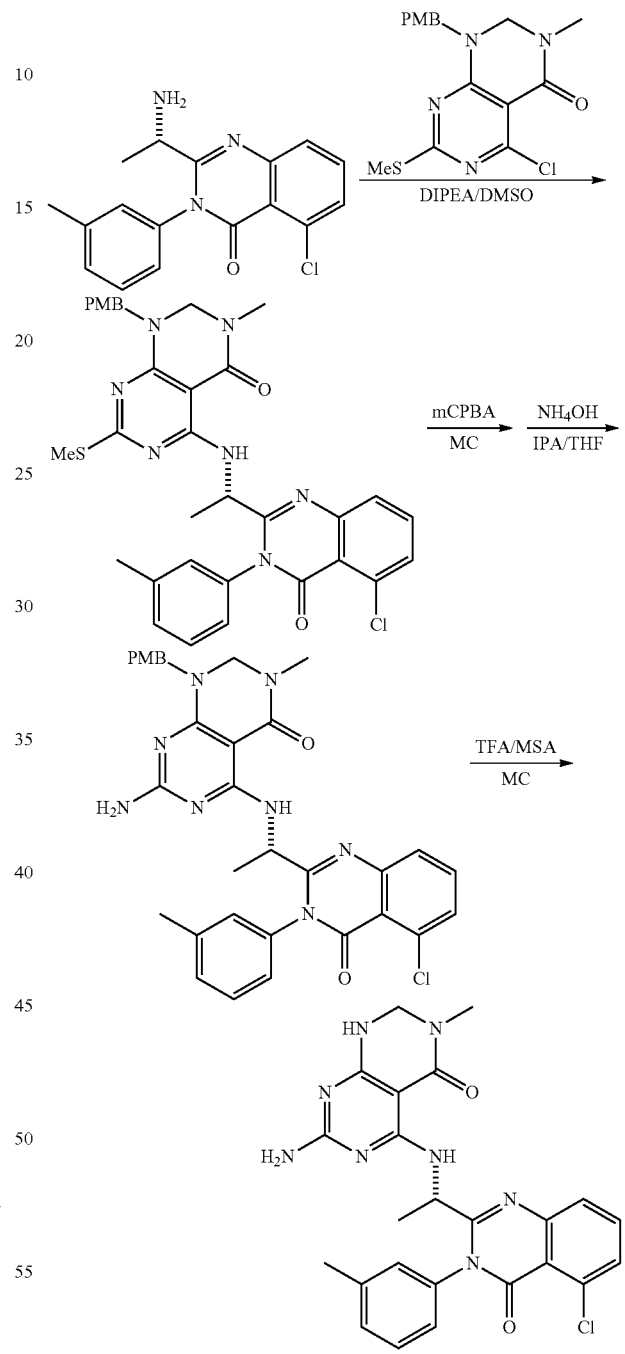

Step 1: Preparation of (S)-5-((1-(5-chloro-4-oxo-3-(m-tolyl)-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one 80 mg of (S)-5-((1-(5-chloro-4-oxo-3-(m-tolyl)-3,4-dihydroquinazoline-2-yl)ethyl)amino)-1-(4-methoxybenzyl)-3- methyl-7-(methylthio)-2,3-dihydropyrimido[4,5-d]pyrimidine-4(1H)-one was prepared as a white solid according to the same manner as described in step 1 of Example 48 except that (S)-2-(1-aminoethyl)-5-chloro-3-m-tolylquinazoline-4(3H)-one was used (0.12 mmol, yield: 88%).

¹H NMR (300 MHz, CDCl₃) δ 9.38-9.46 (m, 1H), 7.69-7.71 (m, 1H), 7.55-7.60 (t, J=7.5 Hz, 1H), 7.42-7.46 (m, 2H), 7.27-7.31 (m, 2H), 7.19-7.22 (d, J=7.9 Hz, 2H), 7.06-7.09 (m, 1H), 6.84-6.86 (d, J=7.8 Hz, 2H), 5.10-5.16 (m, 1H), 4.74 (s, 2H), 4.40 (s, 2H), 3.79 (s, 3H), 2.89 (s, 3H), 2.39-2.43 (d, J=11.3 Hz, 3H), 2.29 (s, 3H), 1.65 (s, 4H), 1.41-1.44 (d, J=7.9 Hz, 3H).

Step 2: Preparation of (S)-7-amino-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one 49 mg of (S)-7-amino-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-((1-(5-chloro-4-oxo-3-(m-tolyl)-3,4-dihydroquinazoline-2-yl)ethyl)amino)-1-(4-methoxybenzyl)-3-methyl-7-(methylthio)-2,3-dihydropyrimido[4,5-d]pyrimidine-4(1H)-one was used (0.12 mmol, yield: 64%).

¹H NMR (300 MHz, CDCl₃) δ 9.42-9.48 (m, 1H), 7.69-7.72 (m, 1H), 7.58-7.60 (m, 1H), 7.42-7.46 (m, 2H), 7.27-7.32 (m, 2H), 7.18-7.20 (m, 2H), 7.09-7.11 (m, 1H), 6.84-6.87 (m, 2H), 5.08-5.12 (m, 1H), 4.62-4.67 (m, 3H), 4.34 (s, 3H), 3.79 (s, 3H), 2.86 (s, 3H), 2.34-2.44 (d, J=30.0 Hz, 3H), 1.42-1.44 (s, J=3.0 Hz, 3H).

Step 3: Preparation of (S)-7-amino-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one 22 mg of (S)-7-amino-5-((1-(5-chloro-4-oxo-3-(m-tolyl)-3,4-dihydroquinazoline-2-yl)ethyl)amino)-3-methyl-2,3-dihydropyrimido[4,5-d]pyrimidine-4(1H)-one was prepared as a white solid according to the same manner as described in step 8 of Example 1 except that (S)-7-amino-5-((1-(5-chloro-4-oxo-3-(m-tolyl)-3,4-dihydroquinazoline-2-yl)ethyl)amino)-1-(4-methoxybenzyl)-3-methyl-2,3-dihydropyrimido[4,5-d]pyrimidine-4(1H)-one was used (0.04 mmol, yield: 56%).

¹H NMR (300 MHz, CDCl₃) δ 9.34-9.44 (dd, J=20.1, 8.4 Hz, 1H), 7.70-7.72 (d, J=7.2 Hz, 1H), 7.56-7.62 (t, J=7.9 Hz, 1H), 7.37-7.43 (m, 2H), 7.29-7.31 (m, 1H), 7.08-7.16 (m, 2H), 5.77 (s, 3H), 5.04-5.16 (m, 1H), 4.72-4.75 (d, J=10.0 Hz, 1H), 4.60 (s, 2H), 2.94 (s, 3H), 2.35-2.44 (d, J=28.7 Hz, 3H), 1.40-1.43 (dd, J=6.3, 3.3 Hz, 3H).

Example 52: Preparation of (S)-7-amino-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one

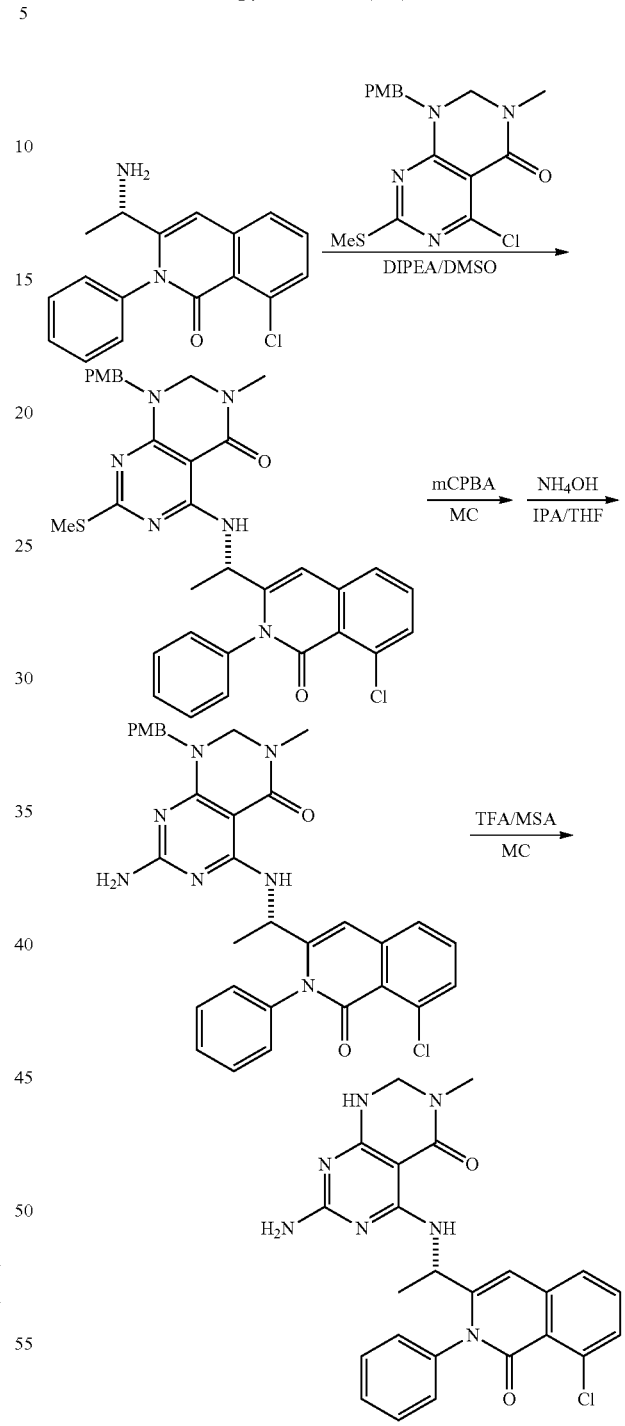

Step 1: Preparation of (S)-5-((1-(8-chloro-1-oxo-2-phenyl-1,2-dihydroisoquinoline-3-yl)ethyl)amino)-1-(4-methoxybenzyl)-3-methyl-7-(methylthio)-2,3-dihydropyrimido[4,5-d]pyrimidine-4(1H)-one 66 mg of (S)-5-((1-(8-chloro-1-oxo-2-phenyl-1,2-dihydroisoquinoline-3-yl)ethyl)amino)-1-(4-methoxybenzyl)-3- methyl-7-(methylthio)-2,3-dihydropyrimido[4,5-d]pyrimidine-4(1H)-one was prepared as a white solid according to the same manner as described in step 1 of Example 48 except that (S)-2-(1-aminoethyl)-5-chloro-3-(S)-3-(1-aminoethyl)-8-chloro-2-phenylisoquinoline-1(2H)-one was used (0.10 mmol, yield: 100%).

$^1$H NMR (300 MHz, CDCl$_3$) δ 9.17-9.19 (d, J=4.6 Hz, 1H), 7.59-7.62 (m, 1H), 7.40-7.50 (m, 6H), 7.30-7.32 (m, 1H), 7.21-7.23 (d, J=5.7 Hz, 2H), 6.85-6.87 (d, J=5.1 Hz, 2H), 6.56 (s, 1H), 4.85-4.91 (m, 1H), 4.70-4.81 (m, 2H), 4.44 (s, 2H), 3.80 (s, 3H), 2.89 (s, 3H), 2.37 (s, 3H), 1.35-1.36 (d, J=3.8 Hz, 3H).

Step 2: Preparation of (S)-7-amino-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one 51 mg of (S)-7-amino-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-((1-(8-chloro-1-oxo-2-phenyl-1,2-dihydroisoquinoline-3-yl)ethyl)amino)-1-(4-methoxybenzyl)-3-methyl-7-(methylthio)-2,3-dihydropyrimido[4,5-d]pyrimidine-4(1H)-one was used (0.09 mmol, yield: 83%).

$^1$H NMR (300 MHz, CDCl$_3$) δ 9.22-9.24 (d, J=7.8 Hz, 1H), 7.31-7.53 (m, 8H), 7.19-7.22 (d, J=7.8 Hz, 2H), 6.84-6.87 (d, J=8.3 Hz, 2H), 6.58 (s, 1H), 4.79-4.83 (m, 1H), 4.67 (s, 2H), 4.36 (s, 2H), 3.79 (s, 3H), 2.87 (s, 3H), 1.32-1.34 (d, J=6.5 Hz, 3H).

Step 3: Preparation of (S)-7-amino-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one 26 mg of (S)-7-amino-5-((1-(8-chloro-1-oxo-2-phenyl-1,2-dihydroisoquinoline-3-yl)ethyl)amino)-3-methyl-2,3-dihydropyrimido[4,5-d]pyrimidine-4(1H)-one was prepared as a white solid according to the same manner as described in step 8 of Example 1 except that (S)-7-amino-5-((1-(8-chloro-1-oxo-2-phenyl-1,2-dihydroisoquinoline-3-yl)ethyl)amino)-1-(4-methoxybenzyl)-3-methyl-2,3-dihydropyrimido[4,5-d]pyrimidine-4(1H)-one was used (0.05 mmol, yield: 64%).

$^1$H NMR (300 MHz, DMSO-d$_6$) δ 9.07-9.10 (d, J=6.7 Hz, 1H), 7.39-7.61 (m, 8H), 7.22 (s, 1H), 6.58 (s, 1H), 6.18 (s, 2H), 4.47-4.53 (m, 3H), 2.80 (s, 3H), 1.20-1.22 (d, J=3.0 Hz, 3H).

Example 53: Preparation of (S)-7-amino-3-methyl-5-((1-(2-phenylquinoline-3-yl)ethyl)amino)-2,3-dihydropyrimido[4,5-d]pyrimidine-4(1H)-one

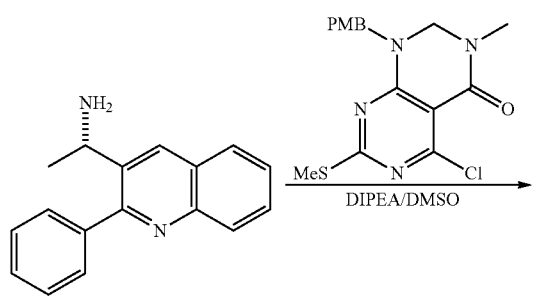

Step 1: Preparation of (S)-1-(4-methoxybenzyl)-3-methyl-7-(methylthio)-5-((1-(2-phenylquinoline-3-yl)ethyl)amino)-2,3-dihydropyrimido[4,5-d]pyrimidine-4(1H)-one 60 mg of (S)-1-(4-methoxybenzyl)-3-methyl-7-(methylthio)-5-((1-(2-phenylquinoline-3-yl)ethyl)amino)-2,3-dihydropyrimido[4,5-d]pyrimidine-4(1H)-one was prepared as a white solid according to the same manner as described in step 1 of Example 48 except that (S)-1-(2-phenylquinoline-3-yl)ethaneamine was used (0.10 mmol, yield: 100%).

$^1$H NMR (300 MHz, CDCl$_3$) δ 9.44-9.46 (d, J=6.7 Hz, 1H), 8.24 (s, 1H), 8.81-8.84 (d, J=8.1 Hz, 1H), 7.75-8.77 (d, J=7.9 Hz, 2H), 7.64-8.69 (t, J=6.8 Hz, 1H), 7.44-7.53 (m, 4H), 7.20-7.22 (d, J=8.0 Hz, 2H), 6.83-6.86 (d, J=8.6 Hz, 2H), 5.67-5.71 (m, 1H), 4.67-4.80 (q, J=15.3, 10.8 Hz, 2H), 4.42 (s, 2H), 3.79 (s, 3H), 2.91 (s, 3H), 2.29 (s, 3H), 1.38-1.40 (d, J=6.7 Hz, 3H).

Step 2: Preparation of (S)-7-amino-1-(4-methoxybenzyl)-3-methyl-5-((1-(2-phenylquinoline-3-yl)ethyl)amino)-2,3-dihydropyrimido[4,5-d]pyrimidine-4(1H)-one 47 mg of (S)-7-amino-1-(4-methoxybenzyl)-3-methyl-5-((1-(2-phenylquinoline-3-yl)ethyl)amino)-2,3-dihydropyrimido[4,5-d]pyrimidine-4(1H)-one was prepared as a white solid according to the same manner as described in step 2 of Example 48 except that (S)-1-(4-methoxybenzyl)-3-methyl-7-(methylthio)-5-((1-(2-phenylquinoline-3-yl)ethyl)amino)-2,3-dihydropyrimido[4,5-d]pyrimidine-4(1H)-one was used (0.09 mmol, yield: 83%).

¹H NMR (300 MHz, CDCl₃) δ 9.44-9.46 (d, J=8.4 Hz, 1H), 8.27 (s, 1H), 8.11-8.14 (d, J=7.9 Hz, 1H), 7.82-7.84 (d, J=7.8 Hz, 1H), 7.75-7.78 (d, J=7.2 Hz, 2H), 7.63-7.68 (t, J=5.7 Hz, 1H), 7.47-7.54 (m, 4H), 7.18-7.20 (d, J=7.4 Hz, 2H), 6.82-6.85 (d, J=8.1 Hz, 2H), 5.56-5.62 (m, 1H), 4.57-4.72 (m, 4H), 4.34 (s, 2H), 3.78 (s, 3H), 2.88 (s, 3H), 1.42-1.44 (d, J=6.2 Hz, 3H).

Step 3: Preparation of (S)-7-amino-3-methyl-5-((1-(2-phenylquinoline-3-yl)ethyl)amino)-2,3-dihydropyrimido[4,5-d]pyrimidine-4(1H)-one 18 mg of (S)-7-amino-3-methyl-5-((1-(2-phenylquinoline-3-yl)ethyl)amino)-2,3-dihydropyrimido[4,5-d]pyrimidine-4(1H)-one was prepared as a white solid according to the same manner as described in step 8 of Example 1 except that (S)-7-amino-1-(4-methoxybenzyl)-3-methyl-5-((1-(2-phenylquinoline-3-yl)ethyl)amino)-2,3-dihydropyrimido[4,5-d]pyrimidine-4(1H)-one was used (0.04 mmol, yield: 49%).

¹H NMR (300 MHz, DMSO-d₆) δ 9.27-9.29 (d, J=6.3 Hz, 1H), 8.30 (s, 1H), 7.97-7.80 (d, J=7.8 Hz, 2H), 7.69-7.75 (m, 2H), 7.50-7.60 (m, 4H), 7.20 (s, 1H), 6.06 (s, 2H), 5.40-5.44 (m, 1H), 4.47 (s, 2H), 2.80 (s, 3H), 1.25-1.27 (d, J=6.7 Hz, 1H).

Example 54: Preparation of (S)-7-amino-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one

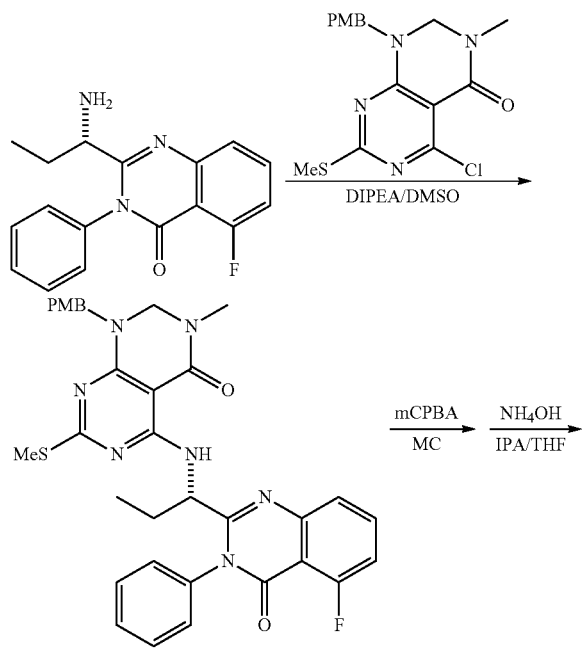

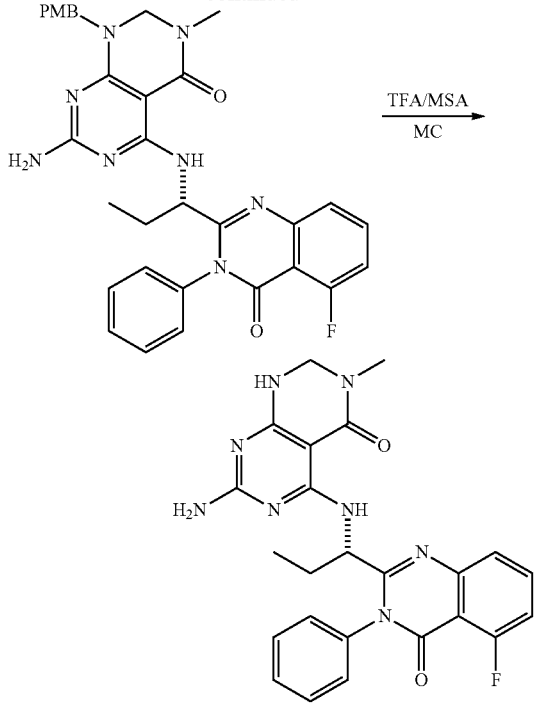

Step 1: Preparation of (S)-5-((1-(5-fluoro-4-oxo-3-phenyl-3,4-dihydroquinazoline-2-yl)propyl)amino)-1-(4-methoxybenzyl)-3-methyl-7-(methylthio)-2,3-dihydropyrimido[4,5-d]pyrimidine-4(1H)-one 64 mg of (S)-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 1 of Example 48 except that (S)-2-(1-aminopropyl)-5-fluoro-3-phenylquinazoline-4(3H)-one was used (0.10 mmol, yield: 100%).

¹H NMR (300 MHz, CDCl₃) δ 9.43-9.46 (d, J=8.5 Hz, 1H), 7.47-7.69 (m, 6H), 7.27-7.31 (m, 1H), 7.19-7.22 (d, J=8.3 Hz, 2H), 7.05-7.11 (m, 1H), 6.84-6.87 (d, J=8.2 Hz, 2H), 5.01-5.08 (m, 1H), 4.73 (s, 2H), 4.41 (s, 2H), 3.79 (s, 3H), 2.89 (s, 3H), 2.26 (s, 3H), 1.73-1.81 (m, 2H), 0.80-0.85 (t, J=7.2 Hz, 3H).

Step 2: Preparation of (S)-7-amino-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one 43 mg of (S)-7-amino-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.07 mmol, yield: 71%).

¹H NMR (300 MHz, CDCl₃) δ 9.39-9.41 (d, J=8.5 Hz, 1H), 7.52-7.64 (m, 5H), 7.37-7.39 (m, 1H), 7.28-7.31 (m, 1H), 7.19-7.21 (d, J=7.5 Hz, 2H), 7.05-7.11 (t, J=8.5 Hz, 1H), 6.84-6.86 (d, J=7.0 Hz, 2), 4.99-5.01 (m, 1H), 4.66 (s,

2H), 4.57 (s, 2H), 4.33 (s, 2H), 3.79 (s, 3H), 2.86 (s, 3H), 1.77-1.79 (m, 2H), 0.82-0.87 (t, J=7.5 Hz, 3H).

Step 3: Preparation of (S)-7-amino-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one 16 mg of (S)-7-amino-5-((1-(5-fluoro-4-oxo-3-phenyl-3,4-dihydroquinazoline-2-yl)propyl)amino)-3-methyl-2,3-dihydropyrimido[4,5-d]pyrimidine-4(1H)-one was prepared as a white solid according to the same manner as described in step 8 of Example 1 except that (S)-7-amino-5-((1-(5-fluoro-4-oxo-3-phenyl-3,4-dihydroquinazoline-2-yl)propyl)amino)-1-(4-methoxybenzyl)-3-methyl-2,3-dihydropyrimido[4,5-d]pyrimidine-4(1H)-one was used (0.03 mmol, yield: 47%).

$^1$H NMR (300 MHz, DMSO-d$_6$) δ 9.22-9.25 (d, J=5.4 Hz, 1H), 7.79-7.81 (m, 1H), 7.45-7.61 (m, 5H), 7.24-7.30 (t, J=4.5 Hz, 1H), 7.18 (s, 1H), 6.06 (s, 2H), 4.54-4.61 (m, 1H), 4.45 (s, 2H), 2.79 (s, 3H), 1.49-1.53 (m, 2H), 0.65-0.70 (t, J=7.9 Hz, 3H).

Example 55: Preparation of (S)-7-amino-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one

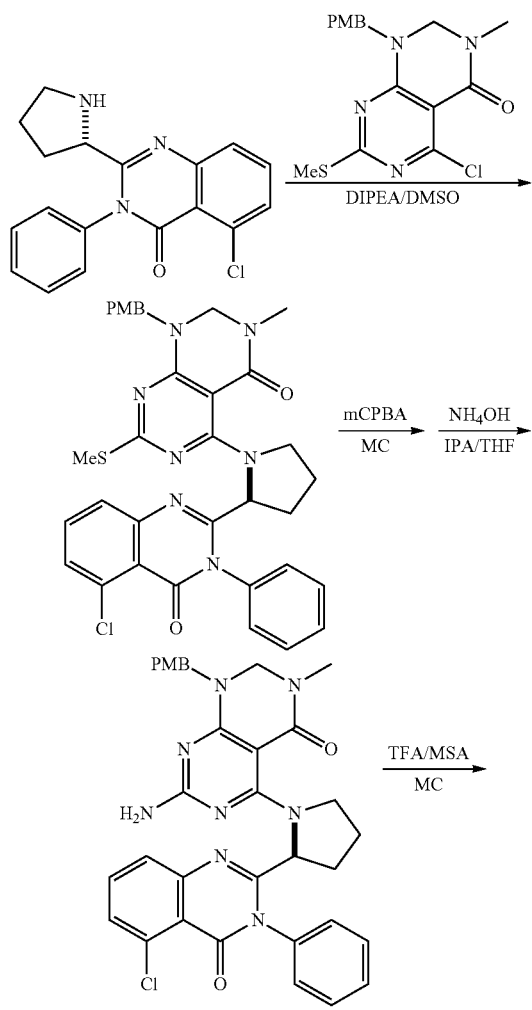

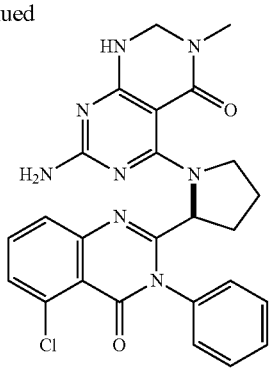

Step 1: Preparation of (S)-5-(2-(5-chloro-4-oxo-3-phenyl-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one 82 mg of (S)-5-(2-(5-chloro-4-oxo-3-phenyl-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-5-chloro-3-phenyl-2-(pyrrolidine-2-yl)quinazoline-4(3H)-one was used (0.13 mmol, yield: 88%).

$^1$H NMR (300 MHz, CDCl$_3$) δ 8.04-8.07 (d, J=4.5 Hz, 1H), 7.62-7.65 (m, 2H), 7.49-7.54 (m, 3H), 7.39-7.41 (m, 1H), 7.15-7.22 (m, 3H), 6.83-6.86 (d, J=8.5 Hz, 2H), 4.77-4.80 (d, J=7.7 Hz, 2H), 4.66-4.72 (m, 1H), 4.30-4.40 (q, J=6.0, 9.2 Hz, 2H), 3.91-3.97 (m, 1H), 3.79 (s, 3H), 3.42-3.47 (m, 1H), 2.90 (s, 3H), 2.38 (s, H), 2.15-2.23 (m, 2H), 1.63-1.75 (m, 2H).

Step 2: Preparation of (S)-7-amino-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one 55 mg of (S)-7-amino-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(5-chloro-4-oxo-3-phenyl-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was used (0.09 mmol, yield: 71%).

$^1$H NMR (300 MHz, CDCl$_3$) δ 7.48-7.64 (m, 6H), 7.37-7.39 (d, J=7.6 Hz, 1H), 7.20-7.23 (d, J=6.9 Hz, 1H), 7.11.7.14 (d, J=7.7 Hz, 2H), 6.81-6.84 (d, J=7.9 Hz, 2H), 4.66-4.70 (m, 2H), 4.23-4.29 (m, 2H), 3.84-3.90 (m, 1H), 3.78 (s, 3H), 3.50-3.53 (m, 1H), 2.85 (s, 3H), 2.06-2.13 (m, 1H), 1.98-2.01 (m, 2H), 1.68-1.71 (m, 1H).

Step 3: Preparation of (S)-7-amino-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one 33 mg of (S)-7-amino-5-(2-(5-chloro-4-oxo-3-phenyl-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 8 of Example 1 except that (S)-7-amino-5-(2-(5-chloro-4-oxo-3-phenyl-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.07 mmol, yield: 74%).

¹H NMR (300 MHz, DMSO-d₆) δ 7.87 (s, 1H), 7.65-7.70 (m, 1H), 7.40-7.54 (m, 7H), 5.94 (s, 2H), 4.79 (s, 1H), 4.35 (s, 2H), 3.57 (s, 1H), 2.86 (s, 3H), 1.98-2.04 (m, 2H), 1.78-1.83 (m, 1H), 1.63-1.69 (m, 1H).

Example 56: Preparation of (S)-7-amino-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one

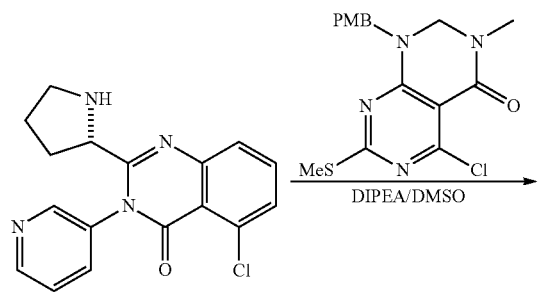

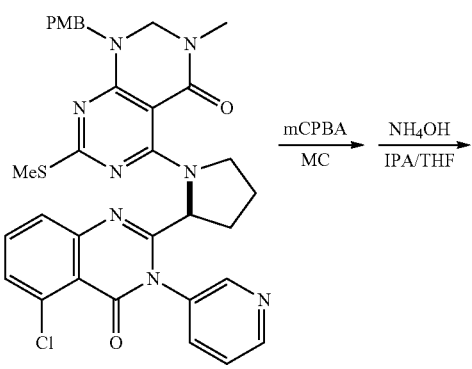

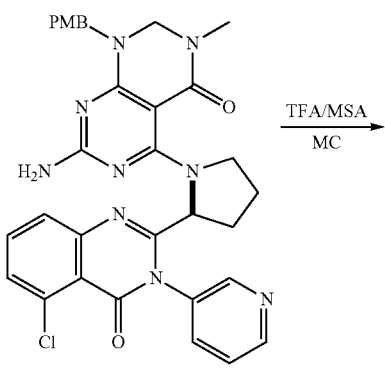

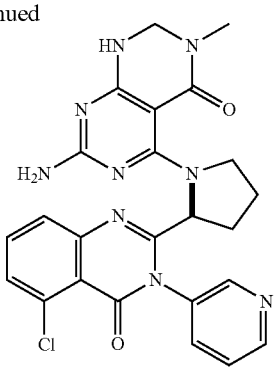

Step 1: Preparation of (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one 79 mg of (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-5-chloro-3-(pyridine-3-yl)-2-(pyrrolidine-2-yl)quinazoline-4(3H)-one was used (0.12 mmol, yield: 91%).

¹H NMR (300 MHz, CDCl₃) δ 8.74-8.76 (d, J=5.9 Hz, 1H), 8.47-8.50 (m, 1H), 7.58-7.66 (m, 3H), 7.42-7.44 (d, J=7.6 Hz, 2H), 7.15-7.18 (d, J=8.4 Hz, 2H), 6.83-6.86 (d, J=8.0 Hz, 2H), 4.78-4.79 (d, J=4.4 Hz, 2H), 4.31-4.37 (m, 2H), 3.85-4.04 (m, 1H), 3.79 (s, 3H), 3.55-3.35 (m, 1H), 2.90 (s, 3H), 2.39 (s, 3H), 2.08-2.13 (m, 2H), 1.60-1.83 (m, 2H).

Step 2: Preparation of (S)-7-amino-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one 49 mg of (S)-7-amino-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(5-chloro-4-oxo-3-(pyridine-3-yl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was used (0.08 mmol, yield: 65%).

¹H NMR (300 MHz, CDCl₃) δ 8.75 (s, 7H), 7.61-7.65 (m, 2H), 7.52-7.57 (m, 3H), 7.40-7.43 (d, J=6.8 Hz, 1H), 7.13-7.17 (m, 2H), 6.81-6.84 (d, J=8.4 Hz, 2H), 4.81 (s, 2H), 4.61-4.76 (m, 2H), 4.19-4.33 (m, 2H), 3.94-4.05 (m, 1H), 3.78 (s, 3H), 3.47-3.57 (m, 1H), 2.86 (s, 3H), 2.15-2.24 (m, 1H), 1.96-2.09 (m, 2H), 1.72-1.79 (m, 1H).

Step 3: Preparation of (S)-7-amino-5-(2-(5-chloro-4-oxo-3-(pyridine-3-yl)-3,4-dihydroquinazoline-2-yl)pyrrolidine-1-yl)-3-methyl-2,3-dihydropyrimido[4,5-d]pyrimidine-4(1H)-one 29 mg of (S)-7-amino-5-(2-(5-chloro-4-oxo-3-(pyridine-3-yl)-3,4-dihydroquinazoline-2-yl)pyrrolidine-1-yl)-3- methyl-2,3-dihydropyrimido[4,5-d]pyrimidine-4(1H)-one was prepared as a white solid according to the same manner as described in step 8 of Example 1 except that (S)-7-amino-5-(2-(5-chloro-4-oxo-3-(pyridine-3-yl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.06 mmol, yield: 73%).

$^1$H NMR (300 MHz, DMSO-$d_6$O) δ 8.72 (s, 2H), 8.00-8.03 (d, J=9.0 Hz, 1H), 7.61-7.73 (m, 2H), 7.43-7.52 (m, 2H), 6.04 (s, 1H), 5.31-5.43 (m, 1H) 4.56-4.65 (m, 1H), 4.36 (s, 2H), 3.97-4.05 (m, 1H), 2.86 (s, 3H), 1.95-2.04 (m, 2H), 1.63-1.82 (m, 2H).

Example 57: Preparation of (S)-7-amino-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one

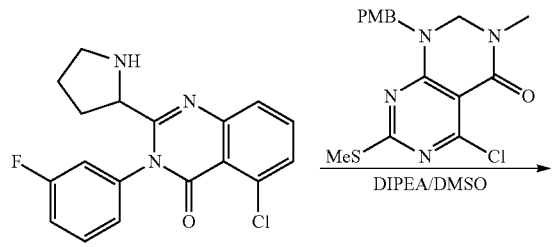

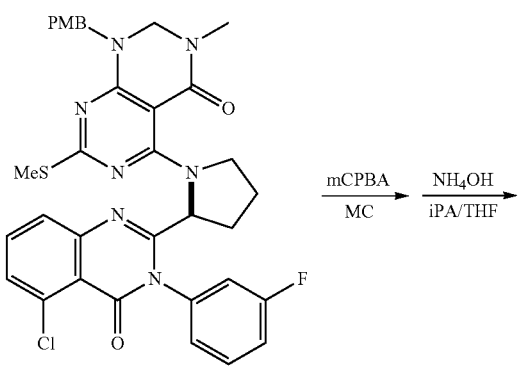

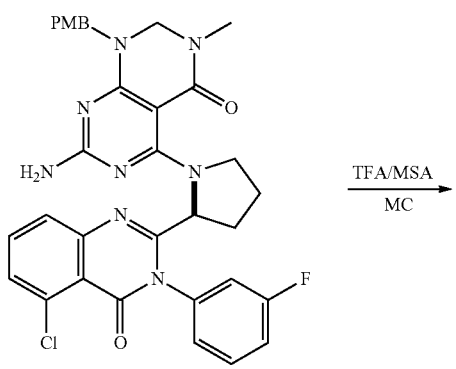

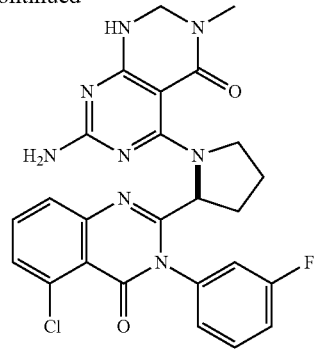

Step 1: Preparation of (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one 84 mg of (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-5-chloro-3-(3-fluorophenyl)-2-(pyrrolidine-2-yl)quinazoline-4(3H)-one was used (0.13 mmol, yield: 88%).

$^1$H NMR (300 MHz, CDCl$_3$) δ 7.89-7.91 (d, J=6.1 Hz, 1H), 7.50-7.66 (m, J=38.5, 9.8 Hz, 3H), 7.40-7.43 (m, 1H), 7.11-7.24 (m, 3H), 6.91-7.06 (m, 1H), 6.83-6.86 (d, J=7.4 Hz, 2H), 4.73-4.78 (d, J=4.9 Hz, 1H), 4.62-4.72 (m, 1H), 4.30-3.41 (m, 2H), 3.86-4.03 (m, 1H), 3.79 (s, 3H), 3.35-3.42 (m, 1H), 2.90 (s, 3H), 2.38 (s, 3H), 2.05-2.22 (m, 3H), 1.72-1.82 (m, 1H).

Step 2: Preparation of (S)-7-amino-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one 54 mg of (S)-7-amino-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(5-chloro-3-(3-fluorophenyl)-4-oxo-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was used (0.08 mmol, yield: 67%).

$^1$H NMR (300 MHz, CDCl$_3$) δ 7.64-7.66 (m, 1H), 7.38-7.58 (m, 4H), 6.98-7.15 (m, 4H), 6.81-6.84 (d, J=8.0 Hz, 2H), 4.62-4.74 (m, 3H), 4.25-4.30 (m, 2H), 3.84-3.96 (m, 1H), 3.78 (s, 3H), 3.48-3.56 (m, 1H), 2.86 (s, 3H), 2.14-2.18 (m, 1H), 2.02-2.05 (m, 2H), 1.72-1.79 (m, 1H).

Step 3: Preparation of (S)-7-amino-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one 30 mg of (S)-7-amino-5-(2-(5-chloro-3-(3-fluorophenyl)-4-oxo-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 8 of Example 1 except that (S)-7-amino-5-(2-(5-chloro-3-(3-fluorophenyl)-4-oxo-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.06 mmol, yield: 68%).

$^1$H NMR (300 MHz, DMSO-d$_6$) δ 7.85 (s, 1H), 7.63-7.71 (m, 2H), 7.36-7.51 (m, 5H), 5.97-6.05 (ss, 2H), 4.49-4.61 (m, 1H), 4.35 (s, 2H), 3.52-3.59 (m, 1H), 2.86 (s, 3H), 1.98-2.06 (m, 2H), 1.81-1.85 (m, 1H), 1.66-1.70 (m, 1H).

Example 58: Preparation of (S)-7-amino-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one

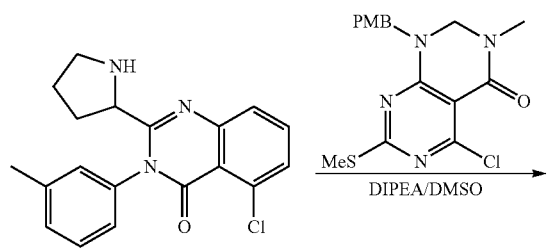

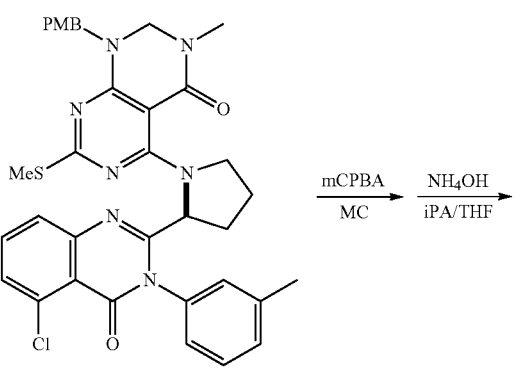

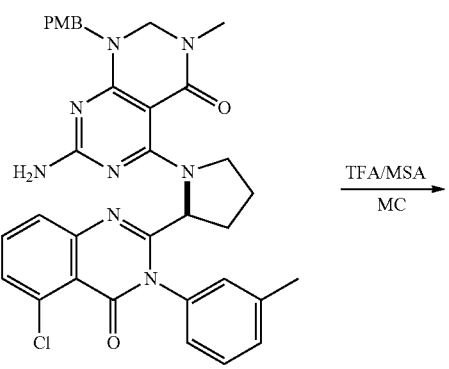

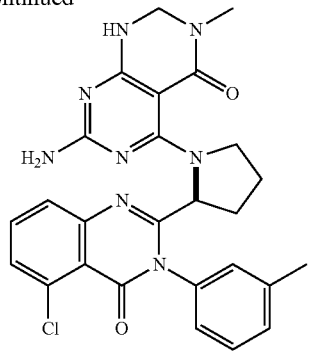

Step 1: Preparation of (S)-5-(2-(5-chloro-4-oxo-3-(m-tolyl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one 76 mg of (S)-5-(2-(5-chloro-4-oxo-3-(m-tolyl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-5-chloro-2-(pyrrolidine-2-yl)-3-m-tolylquinazoline-4(3H)-one was used (0.11 mmol, yield: 96%).

$^1$H NMR (300 MHz, CDCl$_3$) δ 7.83-7.88 (m, 1H), 7.60-7.63 (m, 1H), 7.38-7.58 (m, 3H), 7.29-7.31 (m, 1H), 7.16-7.19 (d, J=7.4 Hz, 2H), 6.99-7.02 (m, 1H), 6.84-6.86 (d, J=5.7 Hz, 2H), 4.73-4.81 (m, 3H), 4.35 (s, 2H), 3.85-3.98 (m, 1H), 3.79 (s, 3H), 3.47-3.58 (m, 1H), 2.89 (s, 3H), 2.41-2.47 (d, J=9.0 Hz, 3H), 2.30-2.41 (m, 3H), 2.15 (s, 3H), 1.70-1.77 (m, 1H).

Step 2: Preparation of (S)-7-amino-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one 57 mg of (S)-7-amino-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(5-chloro-4-oxo-3-(m-tolyl)-3,4-dihydroquinazoline-2-yl)pyrrolidine-1-yl)-1-(4-methoxybenzyl)-3-methyl-7-(methylthio)-2,3-dihydropyrimido[4,5-d]pyrimidine-4(1H)-one was used (0.09 mmol, yield: 79%).

$^1$H NMR (300 MHz, CDCl$_3$) δ 7.62-7.65 (m, 1H), 7.41-7.55 (m, 4H), 7.29-7.32 (m, 1H), 7.13-7.16 (d, J=6.0 Hz, 2H), 7.03 (s, 1H), 6.82-6.85 (d, J=8.9 Hz, 2H), 4.68-4.76 (m, 3H), 4.59 (s, 2H), 4.27 (s, 2H), 3.85-3.91 (m, 1H), 3.78 (s, 3H), 3.52-3.59 (m, 1H), 2.85 (s, 3H), 2.43 (s, 3H), 2.14-2.22 (m, 1H), 2.00-2.04 (m, 2H), 1.72-1.77 (m, 1H).

Step 3: Preparation of (S)-7-amino-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one 31 mg of (S)-7-amino-5-(2-(5-chloro-4-oxo-3-(m-tolyl)-3,4-dihydroquinazoline-2-yl)pyrrolidine-1-yl)-3-methyl-2,3-dihydropyrimido[4,5-d]pyrimidine-4(1H)-one was prepared as a white solid according to the same manner as described in step 8 of Example 1 except that (S)-7-amino-5-(2-(5-chloro-4-oxo-3-(m-tolyl)-3,4-dihydroquinazoline-2-yl)pyrrolidine-1-yl)-1-(4-methoxybenzyl)-3-methyl-2,3-dihydropyrimido[4,5-d]pyrimidine-4(1H)-one was used (0.06 mmol, yield: 67%).

¹H NMR (300 MHz, CDCl₃) δ 7.63-7.65 (m, 1H), 7.51-7.56 (t, J=7.7 Hz, 1H), 7.39-7.45 (m, 3H), 7.30-7.32 (d, J=7.4 Hz, 1H), 7.01-7.03 (m, 1H), 6.56 (s, 9H), 4.71-4.76 (m, 2H), 4.42-4.58 (m, 1H), 4.94-4.00 (m, 1H), 3.79-3.85 (m, 2H), 3.52-3.60 (m, 1H), 3.02 (s, 3H), 2.42 (s, 3H), 2.12-2.25 (m, 1H), 1.98-2.06 (m, 2H), 1.69-1.76 (m, 1H).

Example 59: Preparation of (S)-7-amino-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one

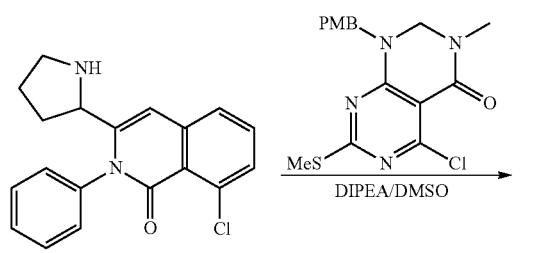

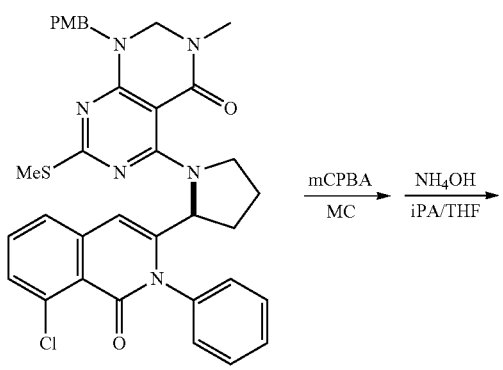

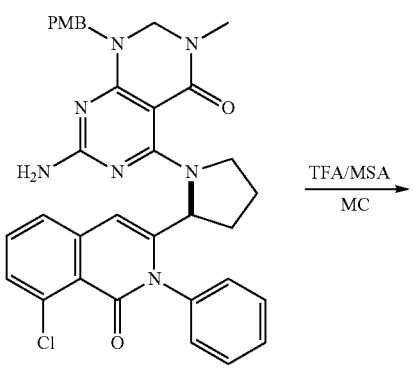

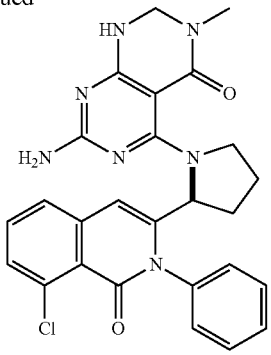

Step 1: Preparation of (S)-5-(2-(8-chloro-1-oxo-2-phenyl-1,2-dihydroisoquinoline-3-yl)pyrrolidine-1-yl)-1-(4-methoxybenzyl)-3-methyl-7-(methylthio)-2,3-dihydropyrimido[4,5-d]pyrimidine-4(1H)-one 81 mg of (S)-5-(2-(8-chloro-1-oxo-2-phenyl-1,2-dihydroisoquinoline-3-yl)pyrrolidine-1-yl)-1-(4-methoxybenzyl)-3-methyl-7-(methylthio)-2,3-dihydropyrimido[4,5-d]pyrimidine-4(1H)-one was prepared as a white solid according to the same manner as described in step 1 of Example 48 except that (S)-8-chloro-2-phenyl-3-(pyrrolidine-2-yl)isoquinoline-1(2H)-one was used (0.12 mmol, yield: 88%).

¹H NMR (300 MHz, CDCl₃) δ 7.76-7.78 (d, J=5.8 Hz, 1H), 7.59-7.64 (t, J=6.4 Hz, 1H), 7.42-7.52 (m, 2H), 7.36-7.41 (m, 3H), 7.30-7.32 (d, J=6.4 Hz, 1H), 7.18-7.20 (m, 1H), 6.84-6.86 (d, J=8.1 Hz, 2H), 6.77 (s, 1H), 5.05-5.09 (t, J=6.1 Hz, 1H), 4.89-4.94 (d, J=15.3 Hz, 1H), 4.69-4.74 (d, J=15.0 Hz, 1H), 4.52-4.56 (d, J=10.5 Hz, 1H), 4.18-4.22 (d, J=10.9 Hz, 1H), 4.11-4.16 (m, 1H), 3.79 (s, 3H), 3.07-3.13 (m, 1H), 2.94 (s, 3H), 2.44 (s, 3H), 1.93-1.99 (m, 2H), 1.61-1.81 (m, 2H).

Step 2: Preparation of (S)-7-amino-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one 38 mg of (S)-7-amino-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one was prepared as a white solid according to the same manner as described in step 2 of Example 48 except that (S)-5-(2-(8-chloro-1-oxo-2-phenyl-1,2-dihydroisoquinoline-3-yl)pyrrolidine-1-yl)-1-(4-methoxybenzyl)-3-methyl-7-(methylthio)-2,3-dihydropyrimido[4,5-d]pyrimidine-4(1H)-one was used (0.06 mmol, yield: 49%).

¹H NMR (300 MHz, CDCl₃) δ 7.48-7.55 (m, 4H), 7.31-7.38 (m, 4H), 7.16-7.18 (d, J=7.9 Hz, 2H), 6.83-6.86 (m, 3H), 5.01-5.07 (m, 1H), 4.84-4.89 (d, J=15.4 Hz, 1H), 4.69 (s, 2H), 4.48-4.59 (m, 2H), 4.10-4.13 (d, J=10.3 Hz, 2H), 3.78 (s, 3H), 3.11-3.19 (m, 1H), 2.91 (s, 3H), 1.89-1.93 (m, 2H), 1.73-1.79 (m, 1H), 1.55-1.62 (m, 1H).

Step 3: Preparation of (S)-7-amino-5-(2-(8-chloro-1-oxo-2-phenyl-1,2-dihydroisoquinoline-3-yl)pyrrolidine-1-yl)-3-methyl-2,3-dihydropyrimido[4,5-d]pyrimidine-4(1H)-one 13 mg of (S)-7-amino-5-(2-(5-chloro-3-(3-fluorophenyl)-4-oxo-3,4-dihydroquinazoline-2-yl)pyrrolidine-1-yl)-3- methyl-2,3-dihydropyrimido[4,5-d]pyrimidine-4(1H)-one was prepared as a white solid according to the same manner as described in step 8 of Example 1 except that (S)-7-amino-5-(2-(8-chloro-1-oxo-2-phenyl-1,2-dihydroisoquinoline-3-yl)pyrrolidine-1-yl)-1-(4-methoxybenzyl)-3-methyl-2,3-dihydropyrimido[4,5-d]pyrimidine-4(1H)-one was used (0.03 mmol, yield: 42%).

$^1$H NMR (300 MHz, DMSO-$d_6$) δ 7.49-7.63 (m, 7H), 7.23-7.33 (m, 1H), 6.82 (s, 1H), 6.19 (s, 2H), 6.12 (s, 1H), 5.47-5.58 (m, 1H), 4.42 (s, 2H), 3.98-4.04 (m, 1H), 3.06-3.09 (m, 1H), 2.76 (s, 3H), 1.90-1.98 (m, 2H), 1.46-1.57 (m, 2H).

Example 60: Preparation of (S)-5-(1-(8-chloro-1-oxo-2-phenyl-1,2-dihydroisoquinoline-3-yl)ethylamino)-3-ethyl-2,3-dihydropyrimido[4,5-d]pyrimidine-4(1H)-one

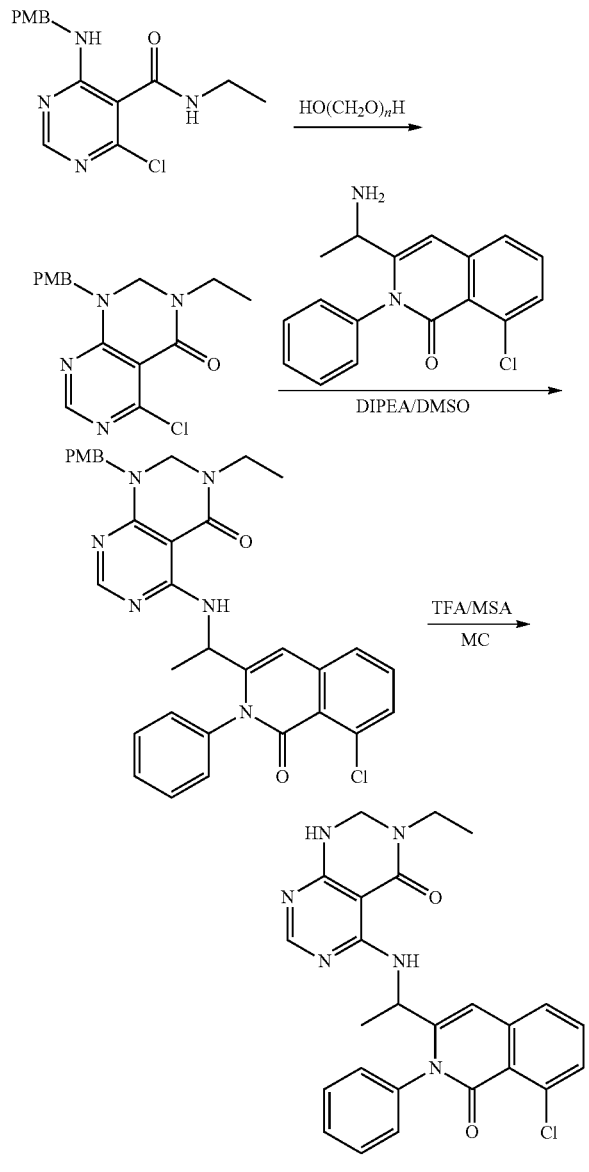

Step 1: Preparation of 5-chloro-3-ethyl-1-(4-methoxybenzyl)-2,3-dihydropyrimido[4,5-d]pyrimidine-4(1H)-one 400 mg of 5-chloro-3-ethyl-1-(4-methoxybenzyl)-2,3-dihydropyrimido[4,5-d]pyrimidine-4(1H)-one was prepared as a white solid by using 600 mg 1.87 mmol) of 4-chloro-N-ethyl-6-(4-methoxybenzylamino)pyrimidine-5-carboxamide according to the same manner as described in step 4 of Example (1.2 mmol, yield: 64%).

$^1$H NMR (300 MHz, CDCl$_3$) δ 8.44 (s, 1H), 7.22 (d, J=8.4 Hz, 2H), 6.89 (d, J=8.6 Hz, 2H), 4.85 (s, 2H), 4.54 (s, 2H), 3.82 (s, 3H), 3.46 (q, J=7.2 Hz, 2H), 1.08 (t, J=7.2 Hz, 3H).

Step 2: Preparation of (S)-5-(1-(8-chloro-1-oxo-2-phenyl-1,2-dihydroisoquinoline-3-yl)ethylamino)-3-ethyl-1-(4-methoxybenzyl)-2,3-dihydropyrimido[4,5-d]pyrimidine-4(1H)-one 60 mg of (S)-5-(1-(8-chloro-1-oxo-2-phenyl-1,2-dihydroisoquinoline-3-yl)ethylamino)-3-ethyl-1-(4-methoxybenzyl)-2,3-dihydropyrimido[4,5-d]pyrimidine-4(1H)-one was prepared as a yellow solid by using 40 mg (0.12 mmol) of 5-chloro-3-ethyl-1-(4-methoxybenzyl)-2,3-dihydropyrimido[4,5-d]pyrimidine-4(1H)-one prepared in step 1 according to the same manner as described in step 5 of Example 34 (0.1 mmol, yield: 84%).

$^1$H NMR (300 MHz, CDCl$_3$) δ 9.15 (s, —NH), 7.99 (s, 1H), 7.51-7.30 (m, 8H), 7.23 (d, J=8.7 Hz, 2H), 6.87 (d, J=8.1 Hz, 2H), 6.58 (s, 1H), 4.86 (s, 1H), 4.75 (s, 2H), 4.47 (s, 2H), 3.80 (s, 3H), 3.44-3.39 (m, 2H), 1.39 (d, J=6.8 Hz, 3H), 1.11 (t, J=7.2 Hz, 3H).

Step 3: Preparation of (S)-5-(1-(8-chloro-1-oxo-2-phenyl-1,2-dihydroisoquinoline-3-yl)ethylamino)-3-ethyl-2,3-dihydropyrimido[4,5-d]pyrimidine-4(1H)-one 47 mg of (S)-5-(1-(8-chloro-1-oxo-2-phenyl-1,2-dihydroisoquinoline-3-yl)ethylamino)-3-ethyl-2,3-dihydropyrimido[4,5-d]pyrimidine-4(1H)-one was prepared as a white solid by using 60 mg (0.1 mmol) of (S)-5-((1-(8-chloro-1-oxo-2-phenyl-1,2-dihydro-isoquinoline-3-yl)ethyl)amino)-3-ethyl-1-(4-methoxybenzyl)-2,3-dihydropyrimido[4,5-d]pyrimidine-4(1H)-one prepared in step 2 according to the same manner as described in step 8 of Example 1 (0.1 mmol, yield: 99%).

$^1$H NMR (300 MHz, CDCl$_3$) δ 9.06 (d, J=6.9 Hz, —NH), 7.94 (s, 1H), 7.49-7.39 (m, 8H), 6.56 (s, 1H), 5.80 (s, 1H), 4.87-4.82 (m, 1H), 4.74 (s, 2H), 3.52-3.45 (m, 2H), 1.39 (d, J=6.7 Hz, 3H), 1.23 (t, J=7.2 Hz, 3H).

Example 61: Preparation of (S)-5-(1-(8-chloro-1-oxo-2-phenyl-1,2-dihydroisoquinoline-3-yl)ethylamino)-3-propyl-2,3-dihydropyrimido[4,5-d]pyrimidine-4(1H)-one

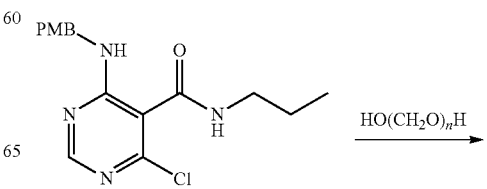

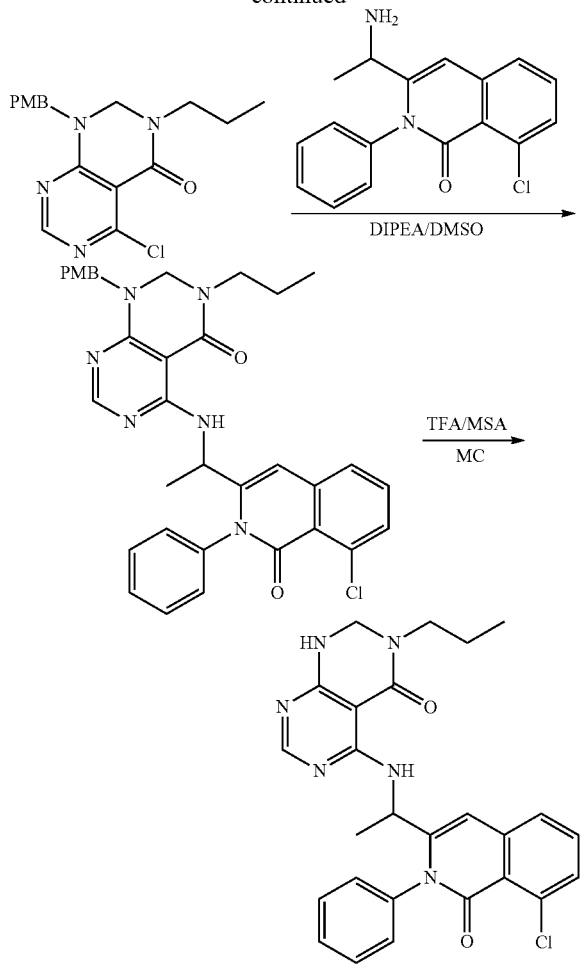

Step 1: Preparation of 5-chloro-1-(4-methoxybenzyl)-3-propyl-2,3-dihydropyrimido[4,5-d]pyrimidine-4(1H)-one 289 mg of 5-chloro-1-(4-methoxybenzyl)-3-propyl-2,3-dihydropyrimido[4,5-d]pyrimidine-4(1H)-one was prepared as a white solid by using 653 mg (1.95 mmol) of 4-chloro-6-(4-methoxybenzylamino)-N-propylpyrimidine-5-carboxamide according to the same manner as described in step 4 of Example 34 (1.12 mmol, yield: 57%).

$^{1}$H NMR (300 MHz, CDCl$_3$) δ 8.44 (s, 1H), 7.22 (d, J=8.5 Hz, 2H), 6.89 (d, J=8.5 Hz, 2H), 4.85 (s, 2H), 4.52 (s, 2H), 3.82 (s, 3H), 3.37 (t, J=7.4 Hz, 2H), 1.52-1.45 (m, 2H), 0.86 (t, J=7.4 Hz, 3H).

Step 2: Preparation of (S)-5-(1-(8-chloro-1-oxo-2-phenyl-1,2-dihydroisoquinoline-3-yl)ethylamino)-1-(4-methoxybenzyl)-3-propyl-2,3-dihydropyrimido[4,5-d]pyrimidine-4(1H)-one 56 mg of (S)-5-(1-(8-chloro-1-oxo-2-phenyl-1,2-dihydroisoquinoline-3-yl)ethylamino)-1-(4-methoxybenzyl)-3-propyl-2,3-dihydropyrimido[4,5-d]pyrimidine-4(1H)-one was prepared as a yellow solid by using 41 mg (0.12 mmol) of 5-chloro-1-(4-methoxybenzyl)-3-propyl-2,3-dihydropyrimido[4,5-d]pyrimidine-4(1H)-one prepared in step 1 according to the same manner as described in step 5 of Example 34 (0.09 mmol, yield: 73%).

$^{1}$H NMR (300 MHz, CDCl$_3$) δ 9.17-9.15 (m, —NH), 7.99 (s, 1H), 7.51-7.29 (m, 8H), 7.21-7.07 (m, 1H), 6.87 (d, J=8.0 Hz, 2H), 6.52 (s, 1H), 4.96-4.87 (s, 1H), 4.75 (s, 2H), 4.47 (s, 2H), 3.80 (s, 3H), 3.44-3.39 (m, 2H), 1.68-1.63 (m, 2H), 1.39 (d, J=6.9 Hz, 3H), 1.01-0.96 (m, 3H).

Step 3: Preparation of (S)-5-(1-(8-chloro-1-oxo-2-phenyl-1,2-dihydroisoquinoline-3-yl)ethylamino)-3-propyl-2,3-dihydropyrimido[4,5-d]pyrimidine-4(1H)-one 45 mg of (S)-5-(1-(8-chloro-1-oxo-2-phenyl-1,2-dihydroisoquinoline-3-yl)ethylamino)-3-propyl-2,3-dihydropyrimido[4,5-d]pyrimidine-4(1H)-one was prepared as a white solid by using 56 mg (0.09 mmol) of (S)-5-(1-(8-chloro-1-oxo-2-phenyl-1,2-dihydroisoquinoline-3-yl)ethylamino)-1-(4-methoxybenzyl)-3-propyl-2,3-dihydropyrimido[4,5-d]pyrimidine-4(1H)-one prepared in step 2 according to the same manner as described in step 8 of Example 1 (0.09 mmol, yield: 99%).

$^{1}$H NMR (300 MHz, CDCl$_3$) δ 9.04 (s, —NH), 7.95 (s, 1H), 7.50-7.31 (m, 8H), 6.57 (s, 1H), 5.28 (s, 1H), 4.91-4.84 (m, 1H), 4.73 (s, 2H), 3.41-3.36 (m, 2H), 1.68-1.63 (m, 2H), 1.39 (d, J=6.9 Hz, 3H), 1.01-0.96 (m, 3H).

Example 62: Preparation of (S)-5-(1-(8-chloro-1-oxo-2-phenyl-1,2-dihydroisoquinoline-3-yl)ethylamino)-3-cyclopropyl-2,3-dihydropyrimido[4,5-d]pyrimidine-4(1H)-one

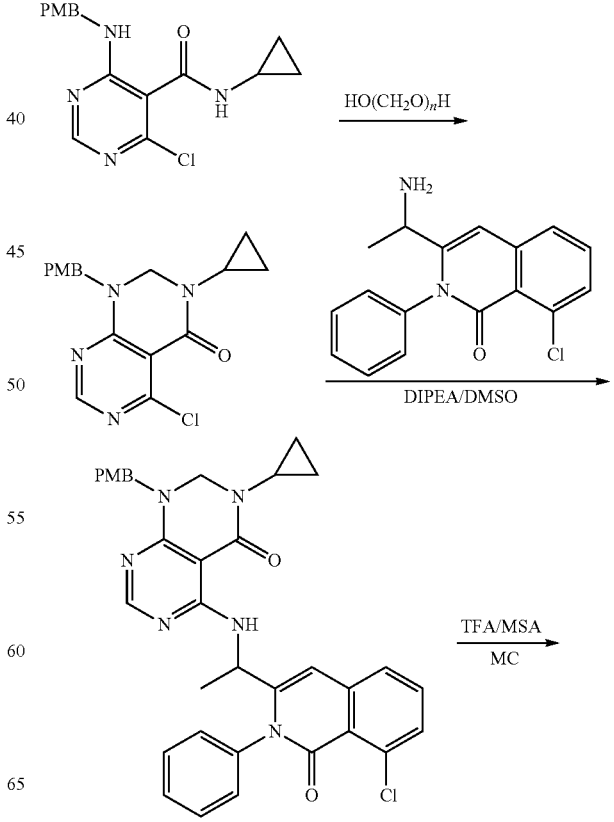

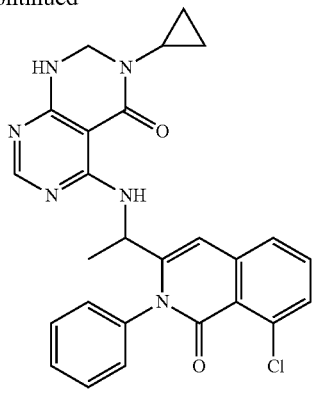

Step 1: Preparation of 5-chloro-3-cyclopropyl-1-(4-methoxybenzyl)-2,3-dihydropyrimido[4,5-d]pyrimidine-4(1H)-one 224 mg of 5-chloro-3-cyclopropyl-1-(4-methoxybenzyl)-2,3-dihydropyrimido[4,5-d]pyrimidine-4(1H)-one was prepared as a white solid by using 360 mg (1.08 mmol) of 4-chloro-N-cyclopropyl-6-(4-methoxybenzylamino)pyrimidine-5-carboxamide according to the same manner as described in step 4 of Example (0.65 mmol, yield: 60%).

$^1$H NMR (300 MHz, CDCl$_3$) δ 8.43 (s, 1H), 7.21 (d, J=7.8 Hz, 2H), 6.90 (d, J=8.5 Hz, 2H), 4.84 (s, 2H), 4.52 (s, 2H), 3.82 (s, 3H), 2.60-2.56 (m, 1H), 0.84-0.82 (m, 2H), 0.52-0.50 (m, 2H).

Step 2: Preparation of (S)-5-(1-(8-chloro-1-oxo-2-phenyl-1,2-dihydroisoquinoline-3-yl)ethylamino)-3-cyclopropyl-1-(4-methoxybenzyl)-2,3-dihydropyrimido[4,5-d]pyrimidine-4(1H)-one 43 mg of (S)-5-(1-(8-chloro-1-oxo-2-phenyl-1,2-dihydroisoquinoline-3-yl)ethylamino)-3-cyclopropyl-1-(4-methoxybenzyl)-2,3-dihydropyrimido[4,5-d]pyrimidine-4(1H)-one was prepared as a white solid by using 40 mg (0.12 mmol) of 5-chloro-3-cyclopropyl-1-(4-methoxybenzyl)-2,3-dihydropyrimido[4,5-d]pyrimidine-4(1H)-one prepared in step 1 according to the same manner as described in step 5 of Example 34 (0.07 mmol, yield: 59%).

$^1$H NMR (300 MHz, CDCl$_3$) δ 9.19-9.15 (m, —NH), 8.05 (s, 1H), 7.53-7.32 (m, 4H), 7.23-7.18 (m, 1H), 6.87 (d, J=9.4 Hz, 2H), 6.56 (s, 1H), 4.84 (s, 1H), 4.43 (s, 1H), 3.79 (s, 2H), 2.03 (s, 1H), 1.38 (d, J=6.2 Hz, 3H), 0.86-0.80 (m, 2H), 0.56-0.52 (m, 2H).

Step 3: Preparation of (S)-5-(1-(8-chloro-1-oxo-2-phenyl-1,2-dihydroisoquinoline-3-yl)ethylamino)-3-cyclopropyl-2,3-dihydropyrimido[4,5-d]pyrimidine-4(1H)-one 34 mg of (S)-5-(1-(8-chloro-1-oxo-2-phenyl-1,2-dihydroisoquinoline-3-yl)ethylamino)-3-cyclopropyl-2,3-dihydropyrimido[4,5-d]pyrimidine-4(1H)-one was prepared as a white solid by using 43 mg (0.07 mmol) of (S)-5-(1-(8-chloro-1-oxo-2-phenyl-1,2-dihydroisoquinoline-3-yl)ethylamino)-3-cyclopropyl-1-(4-methoxybenzyl)-2,3-dihydropyrimido[4,5-d]pyrimidine-4(1H)-one prepared in step 2 according to the same manner as described in step 8 of Example 1 (0.07 mmol, yield: 99%).

$^1$H NMR (300 MHz, CDCl$_3$) δ 9.09 (d, J=6.8 Hz, 1H), 7.94 (s, 1H), 7.51-7.32 (m, 8H), 6.56 (s, 1H), 5.66 (s, 1H), 4.88-4.84 (m, 1H), 4.71 (s, 2H), 2.59-2.53 (m, 1H), 1.39 (d, J=6.7 Hz, 3H), 0.95-0.92 (m, 2H), 0.75-0.73 (m, 2H).

Example 63: Preparation of (S)-5-(1-(8-chloro-1-oxo-2-phenyl-1,2-dihydroisoquinoline-3-yl)ethylamino)-3-cyclopentyl-2,3-dihydropyrimido[4,5-d]pyrimidine-4(1H)-one

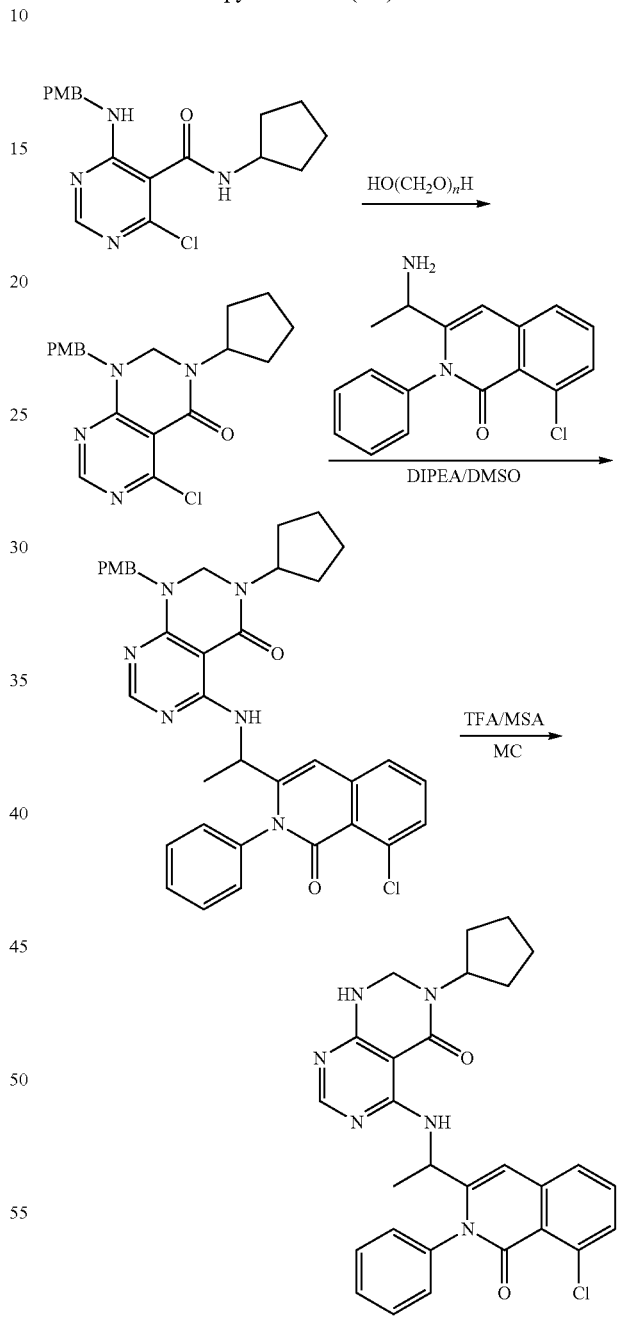

Step 1: Preparation of 5-chloro-3-cyclopentyl-1-(4-methoxybenzyl)-2,3-dihydropyrimido[4,5-d]pyrimidine-4(1H)-one 405 mg of 5-chloro-3-cyclopentyl-1-(4-methoxybenzyl)-2,3-dihydropyrimido[4,5-d]pyrimidine-4(1H)-one was prepared as a white solid by using 620 mg (1.72 mmol) of 4-chloro-N-cyclopentyl-6-(4-methoxybenzylamino)pyrimidine-5-carboxamide according to the same manner as described in step 4 of Example 34 (1.08 mmol, yield: 63%).

$^1$H NMR (300 MHz, CDCl$_3$) δ 8.44 (s, 1H), 7.22 (d, J=8.6 Hz, 2H), 6.90 (d, J=8.7 Hz, 2H), 5.31 (s, 2H), 4.97-4.88 (m, 1H), 4.83 (s, 2H), 4.41 (s, 2H), 3.82 (s, 3H), 1.86-1.77 (m, 2H), 1.57-1.53 (m, 2H), 1.26-1.16 (m, 2H).

Step 2: Preparation of (S)-5-(1-(8-chloro-1-oxo-2-phenyl-1,2-dihydroisoquinoline-3-yl)ethylamino)-3-cyclopentyl-1-(4-methoxybenzyl)-2,3-dihydropyrimido[4,5-d]pyrimidine-4(1H)-one 45 mg of (S)-5-(1-(8-chloro-1-oxo-2-phenyl-1,2-dihydroisoquinoline-3-yl)ethylamino)-3-cyclopentyl-1-(4-methoxybenzyl)-2,3-dihydropyrimido[4,5-d]pyrimidine-4(1H)-one was prepared as a yellow solid by using 40 mg (0.1 mmol) of 5-chloro-3-cyclopentyl-1-(4-methoxybenzyl)-2,3-dihydropyrimido[4,5-d]pyrimidine-4(1H)-one prepared in step 1 according to the same manner as described in step 5 of Example 34 (0.07 mmol, yield: 70%).

$^1$H NMR (300 MHz, CDCl$_3$) δ 9.20 (d, J=6.8 Hz, 1H), 8.06 (s, 1H), 7.56-7.30 (m, 8H), 7.23 (d, J=8.4 Hz, 2H), 6.87 (d, J=8.4 Hz, 2H), 6.59 (s, 1H), 4.91-4.82 (m, 2H), 4.74 (s, 2H), 4.36 (d, J=2.3 Hz, 1H), 1.86-1.74 (m, 2H), 1.38 (d, J=6.8 Hz, 3H).

Step 3: Preparation of (S)-5-(1-(8-chloro-1-oxo-2-phenyl-1,2-dihydroisoquinoline-3-yl)ethylamino)-3-cyclopentyl-2,3-dihydropyrimido[4,5-d]pyrimidine-4(1H)-one 37 mg of (S)-5-(1-(8-chloro-1-oxo-2-phenyl-1,2-dihydroisoquinoline-3-yl)ethylamino)-3-cyclopentyl-2,3-dihydropyrimido[4,5-d]pyrimidine-4(1H)-one was prepared as a white solid by using 45 mg (0.07 mmol) of (S)-5-(1-(8-chloro-1-oxo-2-phenyl-1,2-dihydroisoquinoline-3-yl)ethylamino)-3-cyclopentyl-1-(4-methoxybenzyl)-2,3-dihydropyrimido[4,5-d]pyrimidine-4(1H)-one prepared in step 2 according to the same manner as described in step 8 of Example 1 (0.07 mmol, yield: 99%).

$^1$H NMR (300 MHz, CDCl$_3$) δ 9.11 (d, J=6.7 Hz, 1H), 7.96 (s, 1H), 7.51-7.32 (m, 8H), 6.57 (s, 1H), 5.56 (s, 1H), 4.95-4.65 (m, 2H), 4.65 (s, 2H), 1.99-1.94 (m, 2H), 1.75-1.65 (m, 4H), 1.57-1.49 (m, 2H), 1.38 (d, J=6.6 Hz, 3H).

Example 64: Preparation of (S)-5-(1-(8-chloro-1-oxo-2-phenyl-1,2-dihydroisoquinoline-3-yl)ethylamino)-3-isopropyl-2,3-dihydropyrimido[4,5-d]pyrimidine-4(1H)-one

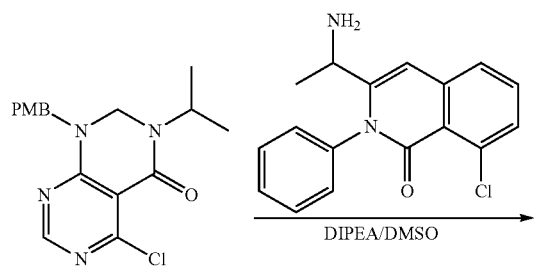

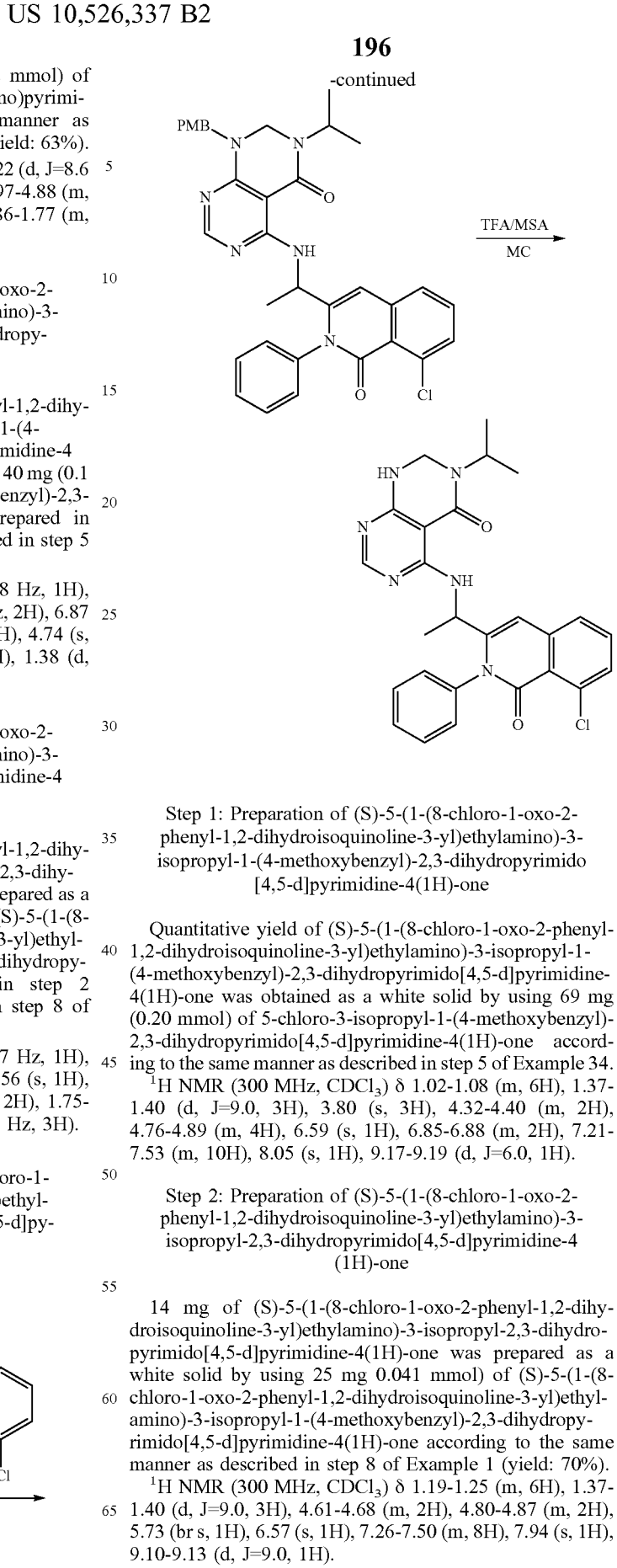

Step 1: Preparation of (S)-5-(1-(8-chloro-1-oxo-2-phenyl-1,2-dihydroisoquinoline-3-yl)ethylamino)-3-isopropyl-1-(4-methoxybenzyl)-2,3-dihydropyrimido[4,5-d]pyrimidine-4(1H)-one Quantitative yield of (S)-5-(1-(8-chloro-1-oxo-2-phenyl-1,2-dihydroisoquinoline-3-yl)ethylamino)-3-isopropyl-1-(4-methoxybenzyl)-2,3-dihydropyrimido[4,5-d]pyrimidine-4(1H)-one was obtained as a white solid by using 69 mg (0.20 mmol) of 5-chloro-3-isopropyl-1-(4-methoxybenzyl)-2,3-dihydropyrimido[4,5-d]pyrimidine-4(1H)-one according to the same manner as described in step 5 of Example 34.

$^1$H NMR (300 MHz, CDCl$_3$) δ 1.02-1.08 (m, 6H), 1.37-1.40 (d, J=9.0, 3H), 3.80 (s, 3H), 4.32-4.40 (m, 2H), 4.76-4.89 (m, 4H), 6.59 (s, 1H), 6.85-6.88 (m, 2H), 7.21-7.53 (m, 10H), 8.05 (s, 1H), 9.17-9.19 (d, J=6.0, 1H).

Step 2: Preparation of (S)-5-(1-(8-chloro-1-oxo-2-phenyl-1,2-dihydroisoquinoline-3-yl)ethylamino)-3-isopropyl-2,3-dihydropyrimido[4,5-d]pyrimidine-4(1H)-one 14 mg of (S)-5-(1-(8-chloro-1-oxo-2-phenyl-1,2-dihydroisoquinoline-3-yl)ethylamino)-3-isopropyl-2,3-dihydropyrimido[4,5-d]pyrimidine-4(1H)-one was prepared as a white solid by using 25 mg 0.041 mmol) of (S)-5-(1-(8-chloro-1-oxo-2-phenyl-1,2-dihydroisoquinoline-3-yl)ethylamino)-3-isopropyl-1-(4-methoxybenzyl)-2,3-dihydropyrimido[4,5-d]pyrimidine-4(1H)-one according to the same manner as described in step 8 of Example 1 (yield: 70%).

$^1$H NMR (300 MHz, CDCl$_3$) δ 1.19-1.25 (m, 6H), 1.37-1.40 (d, J=9.0, 3H), 4.61-4.68 (m, 2H), 4.80-4.87 (m, 2H), 5.73 (br s, 1H), 6.57 (s, 1H), 7.26-7.50 (m, 8H), 7.94 (s, 1H), 9.10-9.13 (d, J=9.0, 1H).

Example 65: Preparation of (S)-5-(1-(5-fluoro-4-oxo-3-phenyl-3,4-dihydroquinazoline-2-yl)propylamino)-3-isopropyl-2,3-dihydropyrimido[4,5-d]pyrimidine-4(1H)-one

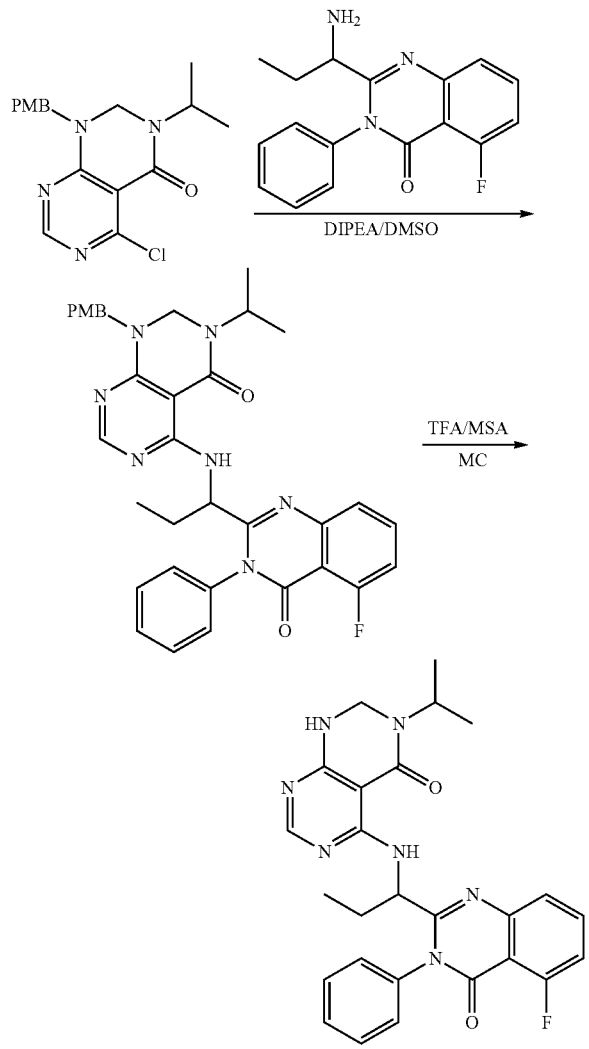

Step 1: Preparation of (S)-5-(1-(5-fluoro-4-oxo-3-phenyl-3,4-dihydroquinazoline-2-yl)propylamino)-3-isopropyl-1-(4-methoxybenzyl)-2,3-dihydropyrimido[4,5-d]pyrimidine-4(1H)-one 97 mg of (S)-5-(1-(5-fluoro-4-oxo-3-phenyl-3,4-dihydroquinazoline-2-yl)propylamino)-3-isopropyl-1-(4-methoxybenzyl)-2,3-dihydropyrimido[4,5-d]pyrimidine-4(1H)-one was prepared as a white solid according to the same manner as described in step 5 of Example 34 except that 69 mg (0.20 mmol) of 5-chloro-3-isopropyl-1-(4-methoxybenzyl)-2,3-dihydropyrimido[4,5-d]pyrimidine-4(1H)-one and (S)-2-(1-aminopropyl)-5-fluoro-3-phenylquinazoline-4(3H)-one (1.1 equivalent) were used (0.20 mmol, yield: 100%).

$^1$H NMR (300 MHz, CDCl$_3$) δ 0.84-0.88 (t, J=6.0, 3H), 1.02-1.04 (d, J=6.0, 6H), 1.74-1.94 (m, 2H), 3.79 (s, 3H), 4.34 (s, 2H), 4.73 (s, 2H), 4.79-4.86 (m, 1H), 4.96-5.03 (m, 1H), 6.84-6.87 (m, 2H), 7.05-7.30 (m, 4H), 7.45-7.69 (m, 6H), 8.02 (s, 1H), 9.44-9.46 (d, J=6.0, 1H).

Step 2: Preparation of (S)-5-(1-(5-fluoro-4-oxo-3-phenyl-3,4-dihydroquinazoline-2-yl)propylamino)-3-isopropyl-2,3-dihydropyrimido[4,5-d]pyrimidine-4(1H)-one 14 mg of (S)-5-(1-(5-fluoro-4-oxo-3-phenyl-3,4-dihydroquinazoline-2-yl)propylamino)-3-isopropyl-2,3-dihydropyrimido[4,5-d]pyrimidine-4(1H)-one was prepared as a white solid by using 30 mg (0.049 mmol, 1.0 eq) of (S)-5-(1-(5-fluoro-4-oxo-3-phenyl-3,4-dihydroquinazoline-2-yl)propylamino)-3-isopropyl-1-(4-methoxybenzyl)-2,3-dihydropyrimido[4,5-d]pyrimidine-4(1H)-one prepared in step 1 according to the same manner as described in step 8 of Example 1 (yield: 75%).

$^1$H NMR (300 MHz, CDCl$_3$) δ 0.83-0.87 (t, J=6.0, 3H), 1.19-1.21 (d, J=6.0, 6H), 1.73-1.95 (m, 2H), 4.61 (s, 2H), 4.84-4.99 (m, 2H), 6.33 (br s, 1H), 7.05-7.12 (m, 1H), 7.26-7.30 (m, 1H), 7.44-7.69 (m, 6H), 7.90 (s, 1H), 9.39-9.41 (d, J=6.0, 1H).

The following examples 66~98 were performed by the method represented by the reaction formula 3A.

[Reaction Formula 3A]

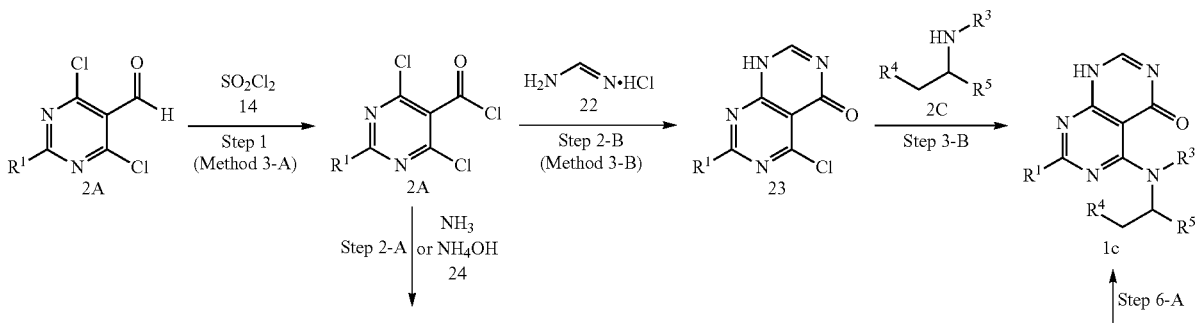

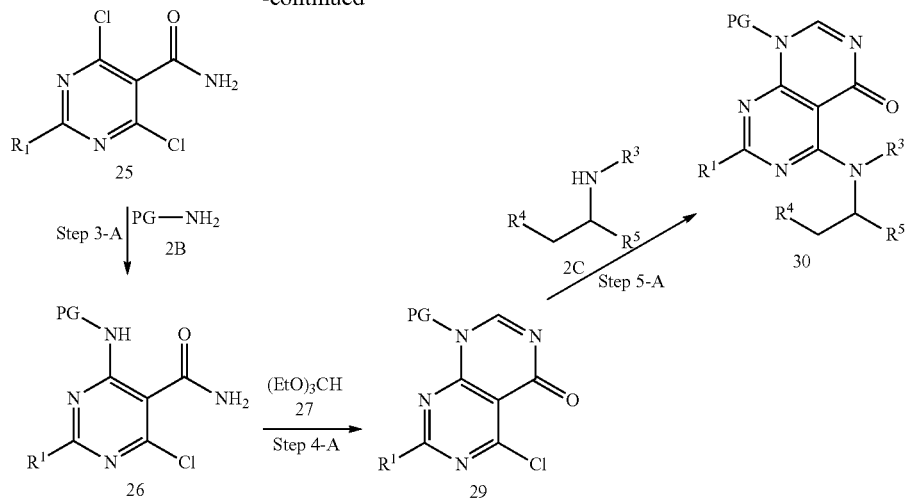

Example 66: Preparation of (S)-5-((1-(5-chloro-4-oxo-3-phenyl-3,4-dihydroquinazoline-2-yl)ethyl)amino)pyrimido[4,5-d]pyrimidine-4(1H)-one

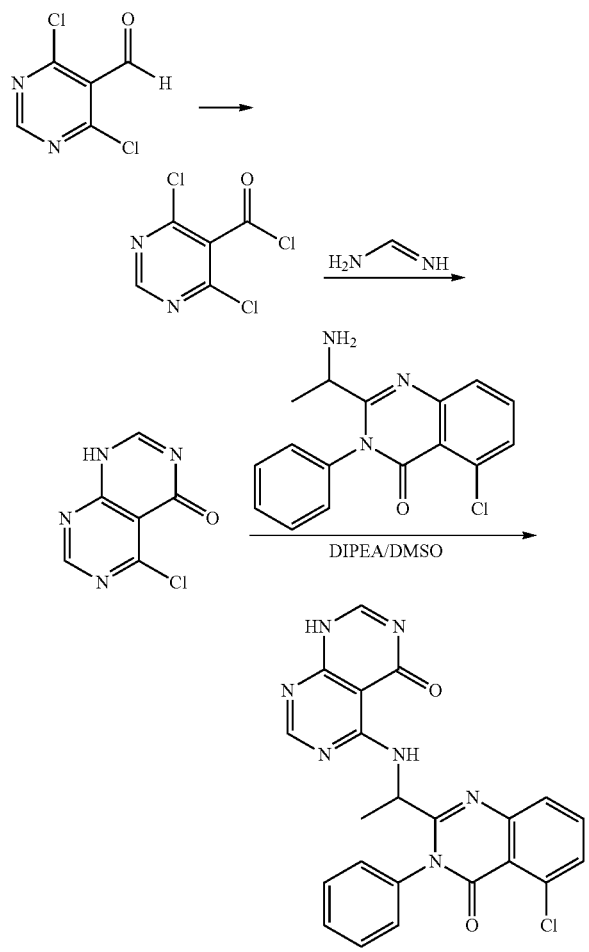

Step 1: Preparation of 4,6-dichloropyrimidine-5-carbonyl Chloride 1 g (5.65 mmol) of 4,6-dichloropyrimidine-5-carboxaldehyde was dissolved in 15 mL of $CCl_4$, to which 0.78 mL (9.61 mmol) of sulfuryl chloride and 46 mg (0.28 mmol) of 2-2-azobis(2-methyl propionitrile) were added, followed by stirring at 80° C. for 3 hours. The reaction mixture was filtered under reduced pressure. 5 mL of anhydrous toluene was added thereto, followed by filtration under reduced pressure. As a result, 4,6-dichloropyrimidine-5-carbonyl chloride was obtained.

Step 2: Preparation of 5-chloropyrimido[4,5-d]pyrimidine-4(1H)-one 4,6-dichloropyrimidine-5-carbonyl chloride (1.0 eq) prepared in step 1 was dissolved in toluene, to which excessive thionyl chloride ($SOCl_2$) was added, followed by stirring at 115° C. for 12 hours. The reaction mixture was cooled down to room temperature. The reaction solvent was concentrated under reduced pressure and dried to give acid chloride. Formamidine hydrochloride (1.1 equivalent) was dissolved in tetrahydrofuran at 0° C., to which triethylamine (4.0 equivalent) was added. The prepared acid chloride was dissolved in 5.0 mL of anhydrous tetrahydrofuran, which was slowly added to the mixture above. The reaction mixture was heated at room temperature, followed by stirring for 4 hours. Water was added thereto, followed by extraction with diethyl ether. The water layer was extracted by using ethylacetate:tetrahydrofuran (1:1). Then, the organic layer was separated, dried ($Na_2SO_4$), filtered, and concentrated under reduced pressure. The residue was separated by column chromatography ($SiO_2$, eluent: dichloromethane/methanol, 15/1→dichloromethane/methanol, 10/1) to give the target compound 5-chloropyrimido[4,5-d]pyrimidine-4(1H)-one.

Step 3: Preparation of (S)-5-((1-(5-chloro-4-oxo-3-phenyl-3,4-dihydroquinazoline-2-yl)ethyl)amino)pyrimido[4,5-d]pyrimidine-4(1H)-one 25 mg of (S)-5-((1-(5-chloro-4-oxo-3-phenyl-3,4-dihydroquinazoline-2-yl)ethyl)amino)pyrimido[4,5-d]pyrimidine-4(1H)-one was prepared as a white solid by using 15 mg (0.08 mmol, 1.0 eq) of 5-chloropyrimido[4,5-d]pyrimidine-4(1H)-one prepared in step 2 and 30 mg (0.10 mmol, 1.2 equivalent) of (S)-2-(1-aminoethyl)-5-chloro-3-phenylquinazoline-4(3H)-one according to the same manner as described in step 5 of Example 34 (0.06 mmol, yield: 68%).

$^1$H NMR (300 MHz, CDCl$_3$) δ 9.77 (s, 1H), 8.82 (s, 1H), 8.67 (s, 1H), 7.49-7.58 (m, 7H), 7.37 (s, 1H), 5.11-5.16 (m, 1H), 1.51-1.53 (d, J=3.0 Hz, 3H).

Example 67: Preparation of (S)-5-((1-(5-chloro-4-oxo-3-(pyridine-3-yl)-3,4-dihydroquinazoline-2-yl)ethyl)amino)pyrimido[4,5-d]pyrimidine-4(1H)-one

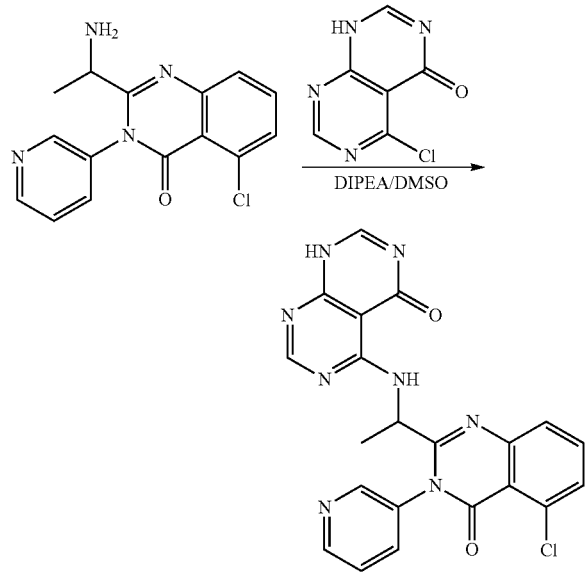

18.8 mg of (S)-5-((1-(5-chloro-4-oxo-3-(pyridine-3-yl)-3,4-dihydroquinazoline-2-yl)ethyl)amino)pyrimido[4,5-d]pyrimidine-4(1H)-one was prepared as a white solid according to the same manner as described in step 3 of Example 66 except that (S)-2-(1-aminoethyl)-5-chloro-3-(pyridine-3-yl)quinazoline-4(3H)-one was used (0.04 mmol, yield: 77%).

$^1$H NMR (300 MHz, DMSO-d$_6$) δ 9.69 (s, 1H), 8.66-8.69 (m, 2H), 8.40 (s, 1H), 8.31 (s, 1H), 8.00-8.11 (m, 1H), 7.74-7.78 (m, 1H), 7.56-7.65 (m, 3H), 4.82-4.86 (m, 1H), 1.34-1.39 (m, 3H).

Example 68: Preparation of (S)-5-((1-(5-chloro-3-(3-fluorophenyl)-4-oxo-3,4-dihydroquinazoline-2-yl)ethyl)amino)pyrimido[4,5-d]pyrimidine-4(1H)-one

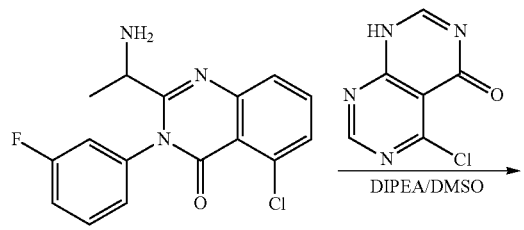

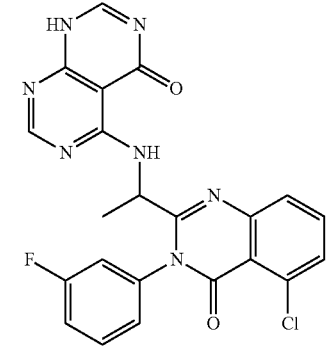 [SMILES: C[C@H](Nc1ncnc2[nH]ccc(=O)c12)c1cc2cccc(Cl)c2c(=O)n1-c1ccccc1]

13.8 mg of (S)-5-((1-(5-chloro-3-(3-fluorophenyl)-4-oxo-3,4-dihydroquinazoline-2-yl)ethyl)amino)pyrimido[4,5-d]pyrimidine-4(1H)-one was prepared as a white solid according to the same manner as described in step 3 of Example 66 except that (S)-2-(1-aminoethyl)-5-chloro-3-(3-fluorophenyl)quinazoline-4(3H)-one was used (0.03 mmol, yield: 55%).

$^1$H NMR (300 MHz, CDCl$_3$) δ 9.53-9.62 (m, 1H), 8.63-8.65 (d, J=3.0 Hz 1H), 8.43-8.44 (m, 1H), 7.63-7.69 (m, 3H), 7.58-7.62 (m, 2H), 7.50-7.55 (m, 1H), 7.28-7.29 (m, 1H), 7.12-7.19 (m, 1H), 5.12-5.18 (m, 1H), 1.47-1.56 (m, 3H).

Example 69: Preparation of (S)-5-((1-(5-chloro-4-oxo-3-(m-tolyl)-3,4-dihydroquinazoline-2-yl)ethyl)amino)pyrimido[4,5-d]pyrimidine-4(1H)-one

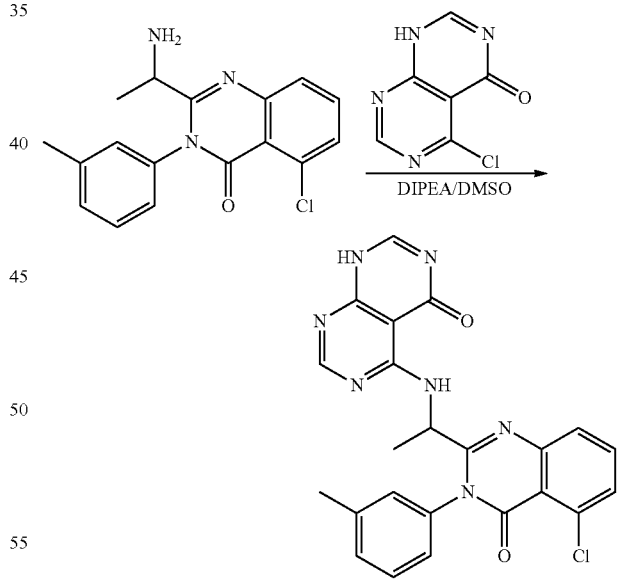

10.5 mg of (S)-5-((1-(5-chloro-4-oxo-3-(m-tolyl)-3,4-dihydroquinazoline-2-yl)ethyl)amino)pyrimido[4,5-d]pyrimidine-4(1H)-one was prepared as a white solid according to the same manner as described in step 3 of Example 66 except that (S)-2-(1-aminoethyl)-5-chloro-3-(m-tolyl)quinazoline-4(3H)-one was used (0.02 mmol, yield: 42%).

$^1$H NMR (300 MHz, CDCl$_3$) δ 9.79-9.81 (d, J=4.5 Hz, 1H), 8.77-8.79 (d, J=3.0 Hz, 1H), 8.66-8.68 (d, J=3.0 Hz, 1H), 7.61-7.68 (m, 2H), 7.46-7.51 (m, 3H), 7.35-7.38 (m,

1H), 7.17-7.18 (m, 1H), 5.18-5.22 (m, 1H), 2.41-2.49 (d, J=12.0 Hz, 3H), 1.53-1.55 (m, 3H).

Example 70: Preparation of (S)-5-((1-(8-chloro-1-oxo-2-phenyl-1,2-dihydroisoquinoline-3-yl)ethyl)amino)pyrimido[4,5-d]pyrimidine-4(1H)-one

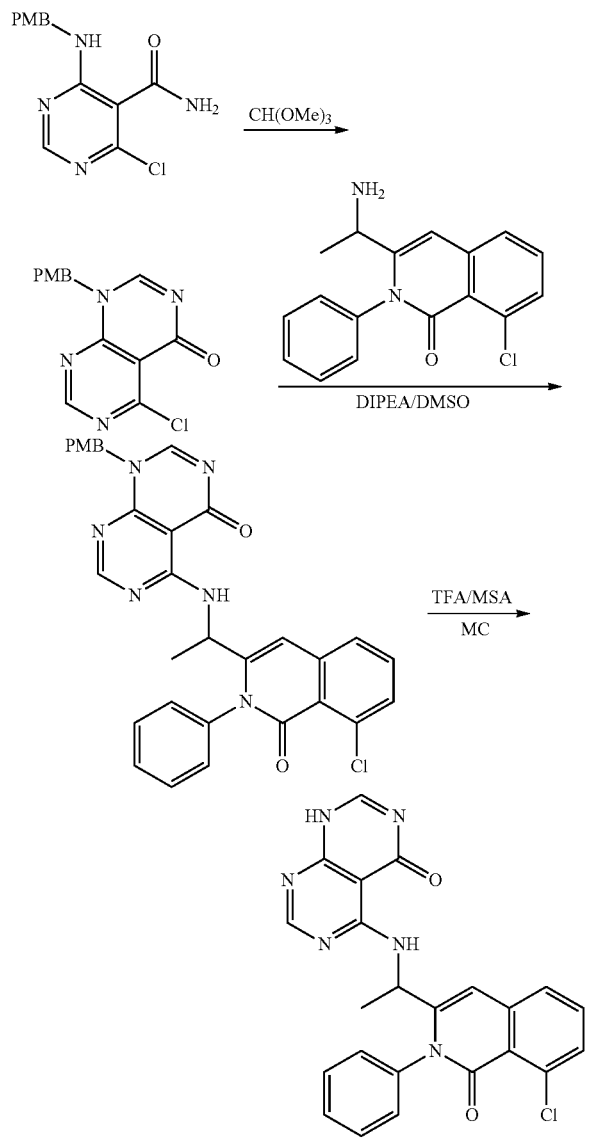

Step 1: Preparation of 5-chloro-1-(4-methoxybenzyl)pyrimido[4,5-d]pyrimidine-4(1H)-one 50 mg (0.171 mmol) of 4-chloro-6-((4-methoxybenzyl)amino)pyrimidine-5-carboxamide, 1 mL of triethyl orthoformate, and 10 μL of methanesulfonic acid were mixed together, which was stirred at 50° C. for 2 hours. The reaction mixture was cooled down to room temperature. Ethyl acetate and water were added thereto, followed by extraction. The extracted organic layer was separated, dried ($Na_2SO_4$), filtered, and concentrated under reduced pressure. The residue was separated by column chromatography ($SiO_2$, eluent: hexane/ethyl acetate, 4/1→hexane/ethyl acetate, 1/1) to give 10 mg of the target compound 5-chloro-1-(4-methoxybenzyl)pyrimido[4,5-d]pyrimidine-4(1H)-one as a pale yellow liquid (0.033 mmol, yield: 19%).

$^1$H NMR (300 MHz, $CDCl_3$) δ 8.96 (s, 1H), 8.44 (s, 1H), 7.29 (d, J=8.9 Hz, 2H), 6.89 (d, J=8.9 Hz, 2H), 5.37 (s, 2H), 3.80 (s, 3H).

Step 2: Preparation of (S)-5-((1-(8-chloro-1-oxo-2-phenyl-1,2-dihydroisoquinoline-3-yl)ethyl)amino)-1-(4-methoxybenzyl)pyrimido[4,5-d]pyrimidine-4(1H)-one 18 mg of (S)-5-((1-(8-chloro-1-oxo-2-phenyl-1,2-dihydroisoquinoline-3-yl)ethyl)amino)-1-(4-methoxybenzyl)pyrimido[4,5-d]pyrimidine-4(1H)-one was prepared as a pale yellow solid by using 10 mg (0.033 mmol) of 5-chloro-1-(4-methoxybenzyl)pyrimido[4,5-d]pyrimidine-4(1H)-one prepared in step 1 and 9 mg (0.036 mmol) of (S)-3-(1-aminoethyl)-8-chloro-2-phenylisoquinoline-1(2H)-one according to the same manner as described in step 5 of Example 34 (0.032 mmol, yield: 96%).

$^1$H NMR (300 MHz, $CDCl_3$) δ 9.89 (d, J=7.1 Hz, 1H), 8.36 (d, J=9.4 Hz, 2H), 7.38-7.54 (m, 5H), 7.29-7.37 (m, 5H), 6.87 (d, J=8.6 Hz, 2H), 6.56 (s, 1H), 5.29 (s, 2H), 4.95 (t, J=6.3 Hz, 1H), 3.77 (s, 3H), 1.44 (d, J=6.3 Hz, 3H).

Step 3: Preparation of (S)-5-((1-(8-chloro-1-oxo-2-phenyl-1,2-dihydroisoquinoline-3-yl)ethyl)amino)pyrimido[4,5-d]pyrimidine-4(1H)-one 13 mg of (S)-5-((1-(8-chloro-1-oxo-2-phenyl-1,2-dihydroisoquinoline-3-yl)ethyl)amino)pyrimido[4,5-d]pyrimidine-4(1H)-one was prepared as a pale yellow solid in 25 ml round-bottom flask by using 18 mg (0.032 mmol) of (S)-5-((1-(8-chloro-1-oxo-2-phenyl-1,2-dihydroisoquinoline-3-yl)ethyl)amino)-1-(4-methoxybenzyl)pyrimido[4,5-d]pyrimidine-4(1H)-one prepared in step 1 according to the same manner as described in step 8 of Example 1 (0.029 mmol, yield: 92%).

$^1$H NMR (300 MHz, $CDCl_3$) δ 9.24 (d, J=5.5 Hz, 1H), 8.57 (s, 1H), 7.47-7.52 (m, 5H), 7.32-7.38 (m, 4H), 6.60 (s, 1H), 5.03 (t, J=7.0 Hz, 1H), 1.50 (d, J=6.5 Hz, 3H).

Example 71: Preparation of (S)-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one

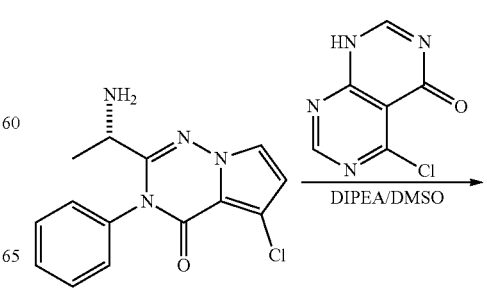

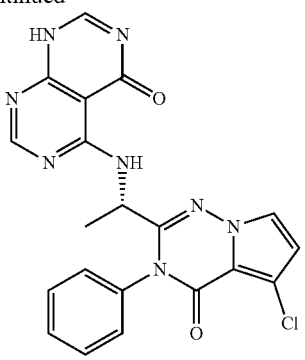

20 mg of (S)-5-((1-(5-chloro-4-oxo-3-phenyl-3,4-dihydropyrrolo[2,1-f][1,2,4]triazin-2-yl)ethyl)amino)pyrimido[4,5-d]pyrimidine-4(1H)-one was prepared as a white solid by using 15 mg (0.08 mmol, 1.0 equivalent) of 5-chloropyrimido[4,5-d]pyrimidine-4(1H)-one and 28 mg (0.10 mmol, 1.2 equivalent) of (S)-2-(1-aminoethyl)-5-chloro-3-phenylpyrrolo[2,1-f][1,2,4]triazine-4(3H)-one according to the same manner as described in step 5 of Example 34 (0.05 mmol, yield: 58%).

$^1$H NMR (300 MHz, CDCl$_3$) δ 9.44 (s, 1H), 8.81 (s, 1H), 8.64 (s, 1H), 7.49-7.56 (m, 5H), 7.27-7.36 (m, 2H), 7.50 (s, 1H), 5.10-5.14 (m, 1H), 1.51-1.53 (d, J=3.2 Hz, 3H).

Example 72: Preparation of (S)-5-((1-(2-phenylquinoline-3-yl)ethyl)amino)pyrimido[4,5-d]pyrimidine-4(1H)-one

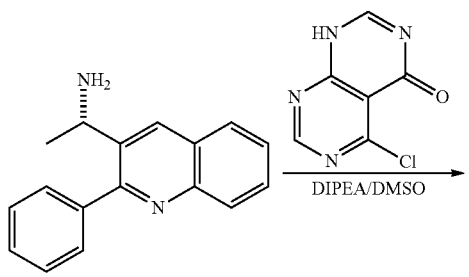

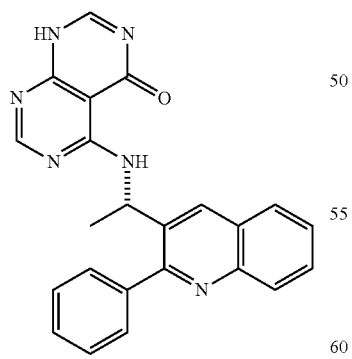

6 mg of (S)-5-((1-(2-phenylquinoline-3-yl)ethyl)amino)pyrimido[4,5-d]pyrimidine-4(1H)-one was prepared as a white solid according to the same manner as described in step 5 of Example 34 except that (S)-1-(2-phenylquinoline-3-yl)ethaneamine was used (0.015 mmol, yield: 28%).

$^1$H NMR (300 MHz, DMSO-d$_6$) δ 12.86 (s, 1H), 9.42-9.44 (m, 1H), 8.46 (s, 1H), 8.39 (s, 1H), 8.31 (s, 1H), 9.58-7.74 (m, 5H), 7.42-7.45 (m, 3H), 5.48-5.52 (m, 1H), 1.46-1.48 (d, J=3.0 Hz, 3H).

Example 73: Preparation of (S)-5-((1-(5-fluoro-4-oxo-3-phenyl-3,4-dihydroquinazoline-2-yl)propyl)amino)pyrimido[4,5-d]pyrimidine-4(1H)-one

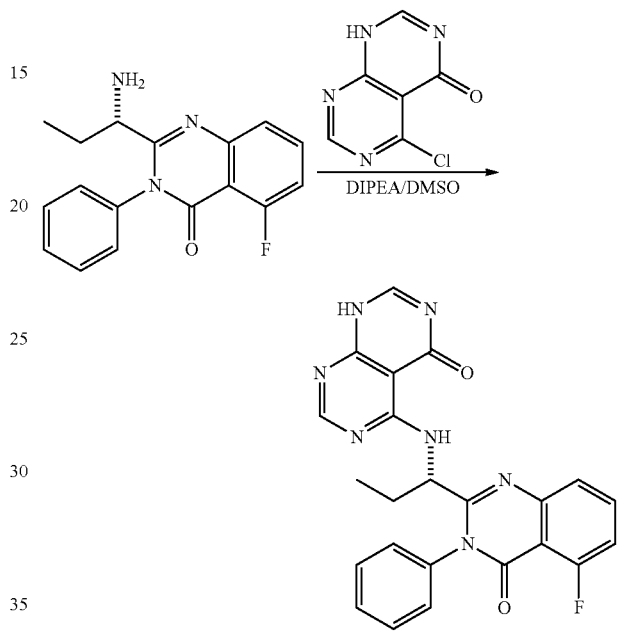

10.7 mg of (S)-5-((1-(5-fluoro-4-oxo-3-phenyl-3,4-dihydroquinazoline-2-yl)propyl)amino)pyrimido[4,5-d]pyrimidine-4(1H)-one was prepared as a white solid according to the same manner as described in step 5 of Example 34 except that (S)-2-(1-aminopropyl)-5-fluoro-3-(phenylquinazoline-4(3H)-one was used (0.02 mmol, yield: 44%).

$^1$H NMR (300 MHz, CDCl$_3$) δ 9.69-9.72 (d, J=4.5 Hz, 1H), 8.84 (s, 1H), 8.68 (s, 1H), 7.51-7.69 (m, 7H), 7.34-7.36 (m, 1H), 7.09-7.15 (t, J=9.1 Hz, 1H), 5.07-5.11 (m, 1H), 1.86-1.96 (m, 2H), 0.87-0.92 (t, J=7.1 Hz, 6H).

Example 74: Preparation of (S)-5-(2-(5-chloro-4-oxo-3-phenyl-3,4-dihydroquinazoline-2-yl)pyrrolidine-1-yl)pyrimido[4,5-d]pyrimidine-4(1H)-one

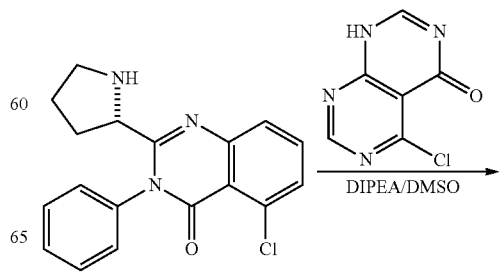

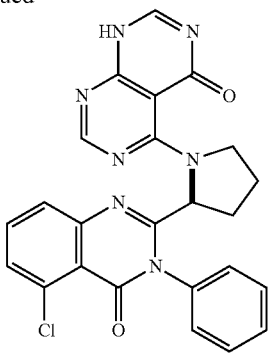

24.7 mg of (S)-5-(2-(5-chloro-4-oxo-3-phenyl-3,4-dihydroquinazoline-2-yl)pyrrolidine-1-yl)pyrimido[4,5-d]pyrimidine-4(1H)-one was prepared as a white solid according to the same manner as described in step 5 of Example 34 except that (S)-5-chloro-3-phenyl-2-(pyrrolidine-2-yl)quinazoline-4(3H)-one was used (0.05 mmol, yield: 95%).

¹H NMR (300 MHz, CDCl₃) δ 9.56 (s, 1H), 8.53 (s, 1H), 7.74-7.61 (m, 1H), 7.42-7.63 (m, 6H), 7.29 (s, 1H), 4.84-4.88 (m, 1H), 4.00-4.02 (m, 1H), 3.70-3.74 (m, 1H), 2.04-2.29 (m, 2H), 1.83-1.87 (m, 2H).

Example 75: Preparation of (S)-5-(2-(8-chloro-1-oxo-2-(pyridine-3-yl)-1,2-dihydroisoquinoline-3-yl)pyrrolidine-1-yl)pyrimido[4,5-d]pyrimidine-4(1H)-one

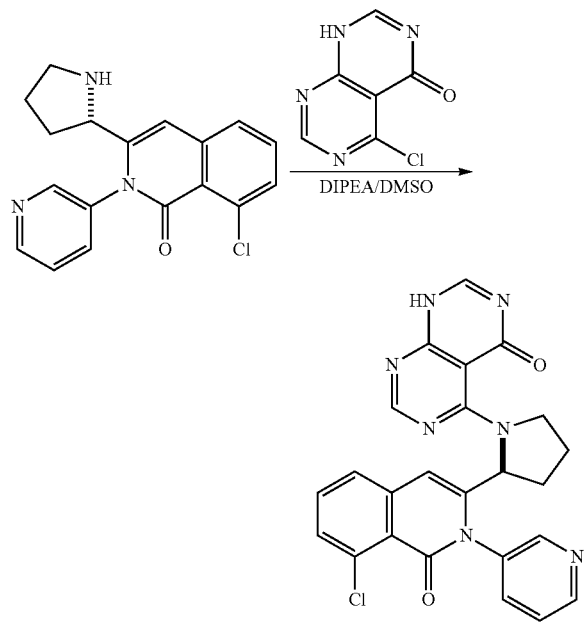

10.6 mg of (S)-5-(2-(8-chloro-1-oxo-2-(pyridine-3-yl)-1,2-dihydroisoquinoline-3-yl)pyrrolidine-1-yl)pyrimido[4,5-d]pyrimidine-4(1H)-one was prepared as a white solid according to the same manner as described in step 5 of Example 34 except that (S)-8-chloro-2-(pyridine-3-yl)-3-(pyrrolidine-2-yl)isoquinoline-1(2H)-one was used (0.02 mmol, yield: 41%).

¹H NMR (300 MHz, DMSO-d₆) δ 8.49 (s, 1H), 8.25 (s, 1H), 7.48-7.61 (m, 6H), 7.35-7.41 (m, 3H), 6.46 (s, 1H), 4.67-4.71 (m, 1H), 4.09-4.15 (m, 1H), 3.09-3.16 (m, 1H), 1.88-1.97 (m, 3H), 1.49-1.53 (m, 1H).

Example 76: Preparation of (S)-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one

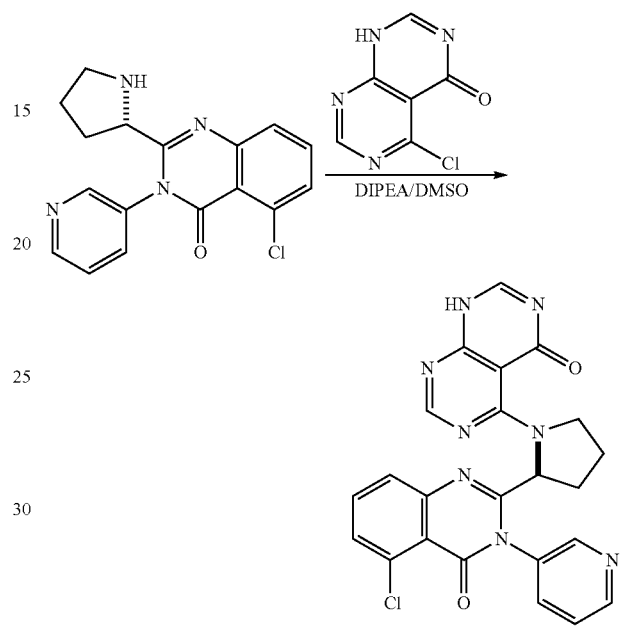

15.8 mg of (S)-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one was prepared as a white solid according to the same manner as described in step 5 of Example 34 except that (S)-5-chloro-3-(pyridine-3-yl)-2-(pyrrolidine-2-yl)quinazoline-4(3H)-one was used (0.03 mmol, yield: 61%).

¹H NMR (300 MHz, DMSO-d₆) δ 12.41 (s, 1H), 8.44 (s, 1H), 8.01-8.22 (m, 3H), 7.39-7.63 (m, 4H), 4.41-4.47 (m, 1H), 3.77-3.83 (m, 1H), 3.45-3.52 (m, 1H), 1.99-2.15 (m, 3H), 1.69-1.75 (m, 1H).

Example 77: Preparation of (S)-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one

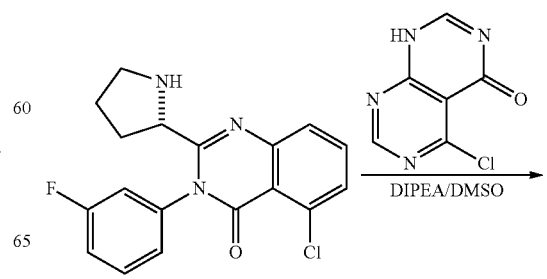

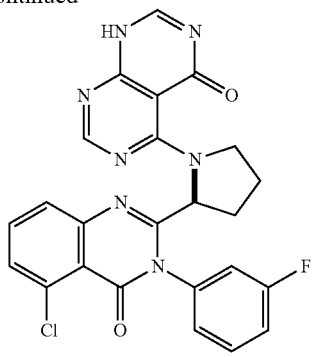

4.1 mg of (S)-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one was prepared as a white solid according to the same manner as described in step 5 of Example 34 except that (S)-5-chloro-3-(3-fluorophenyl)-2-(pyrrolidine-2-yl)isoquinoline-4(3H)-one was used (0.01 mmol, yield: 15%).

$^1$H NMR (300 MHz, CDCl$_3$) δ 9.56 (s, 1H), 8.54 (s, 1H), 7.52-7.64 (m, 4H), 7.44-7.47 (m, 2H), 7.07-7.14 (m, 1H), 4.86-4.90 (q, J=3.0, 1.5 Hz, 1H), 4.03-4.08 (m, 1H), 3.74-3.76 (m, 1H), 2.32-2.37 (m, 1H), 2.11-2.23 (m, 2H), 1.87-1.91 (m, 1H).

Example 78: Preparation of (S)-5-(2-(5-chloro-4-oxo-3-(m-tolyl)-3,4-dihydroquinazoline-2-yl)pyrrolidine-1-yl)pyrimidine[4,5-d]pyrimidine-4(1H)-one

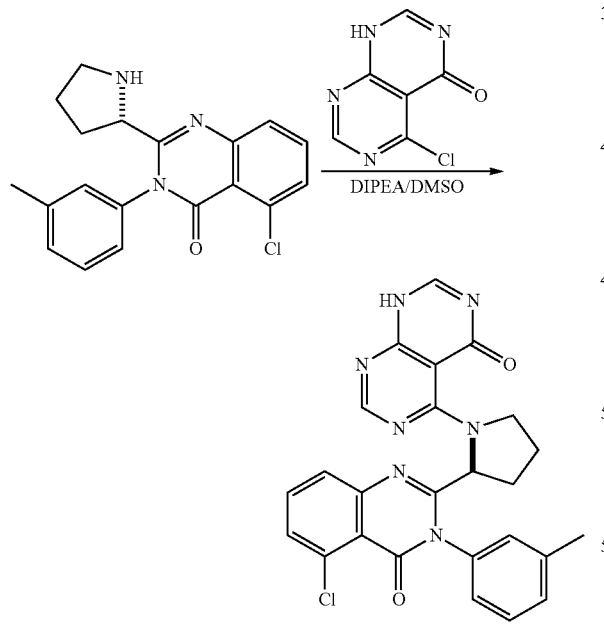

10.7 mg of (S)-5-(2-(5-chloro-4-oxo-3-(m-tolyl)-3,4-dihydroquinazoline-2-yl)pyrrolidine-1-yl)pyrimido[4,5-d]pyrimidine-4(1H)-one was prepared as a white solid according to the same manner as described in step 5 of Example 34 except that (S)-5-chloro-2-(pyrrolidine-2-yl)-3-m-tolylquinazoline-4(3H)-one was used (0.02 mmol, yield: 40%).

$^1$H NMR (300 MHz, CDCl$_3$) δ 8.53 (s, 1H), 8.47-8.48 (d, J=1.5 Hz, 1H), 7.42-7.57 (m, 6H), 7.35-7.36 (m, 1H), 7.09-7.11 (m, 1H), 4.86-4.92 (m, 1H), 4.04-4.07 (m, 1H), 3.68-3.72 (m, 1H), 2.46-2.49 (d, J=4.5 Hz, 3H), 2.31-2.34 (m, 1H), 2.15-2.19 (m, 3H).

Example 79: Preparation of (S)-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one

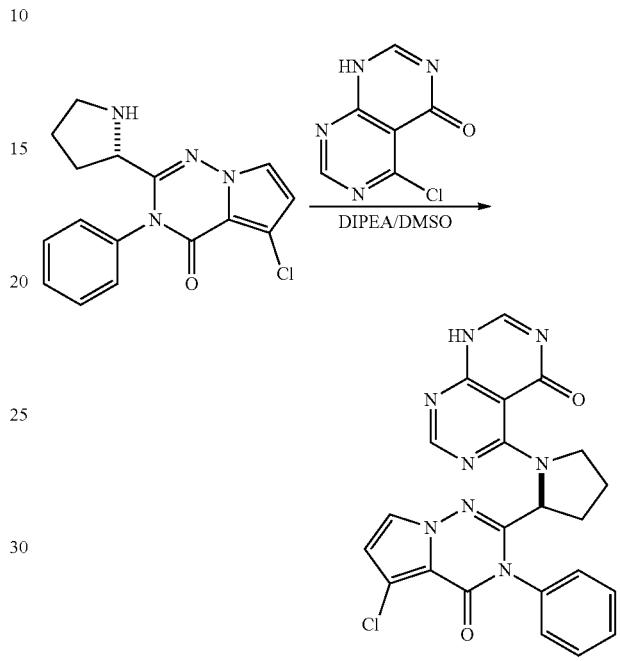

10 mg of (S)-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one was prepared as a white solid by using 13 mg (0.07 mmol, 1.0 equivalent) of 5-chloropyrimido[4,5-d]pyrimidine-4(1H)-one and 30 mg (0.09 mmol, 1.3 eq) of (S)-5-chloro-3-phenyl-2-(pyrrolidine-2-yl)pyrrolo[2,1-f][1,2,4]triazine-4(3H)-one according to the same manner as described in step 5 of Example 34 (0.02 mmol, yield: 31%).

$^1$H NMR (300 MHz, DMSO-d$_6$) δ 8.55 (s, 1H), 8.27 (s, 1H), 7.72-7.77 (m, 1H), 7.50-7.62 (m, 5H), 6.61 (s, 1H), 4.52 (s, 1H), 3.78-3.83 (m, 1H), 3.40-3.46 (m, 1H), 1.96-2.15 (m, 3H), 1.70-1.76 (m, 1H).

Example 80: Preparation of (S)-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one

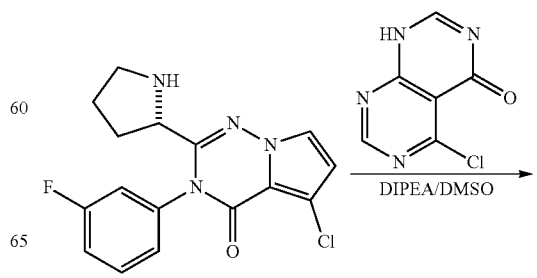

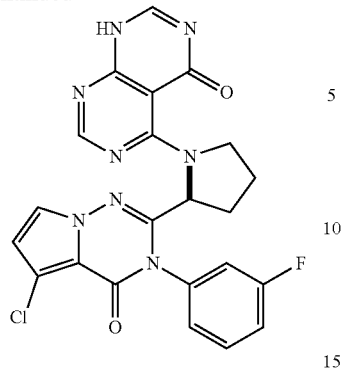

20 mg of (S)-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one was prepared as a white solid by using 16 mg (0.09 mmol, 1.0 equivalent) of 5-chloropyrimido[4,5-d]pyrimidine-4(1H)-one and 30 mg (0.09 mmol, 1.2 equivalent) of (S)-5-chloro-3-(3-fluorophenyl)-2-(pyrrolidine-2-yl)pyrrolo[2,1-f][1,2,4]triazine-4(3H)-one according to the same manner as described in step 5 of Example 34 (0.04 mmol, yield: 47%).

$^1$H NMR (300 MHz, CDCl$_3$) δ 8.56-8.63 (m, 2H), 7.51-7.60 (m, 2H), 7.28-7.31 (m, 1H), 7.03-7.14 (m, 2H), 6.42 (s, 1H), 4.87 (s, 1H), 3.94-4.02 (m, 1H), 3.65-3.75 (m, 1H), 3.26-3.33 (m, 1H), 1.86-2.28 (m, 4H).

Example 81: Preparation of (S)-7-amino-5-((1-(5-chloro-4-oxo-3-phenyl-3,4-dihydroquinazoline-2-yl)ethyl)amino)pyrimido[4,5-d]pyrimidine-4(1H)-one

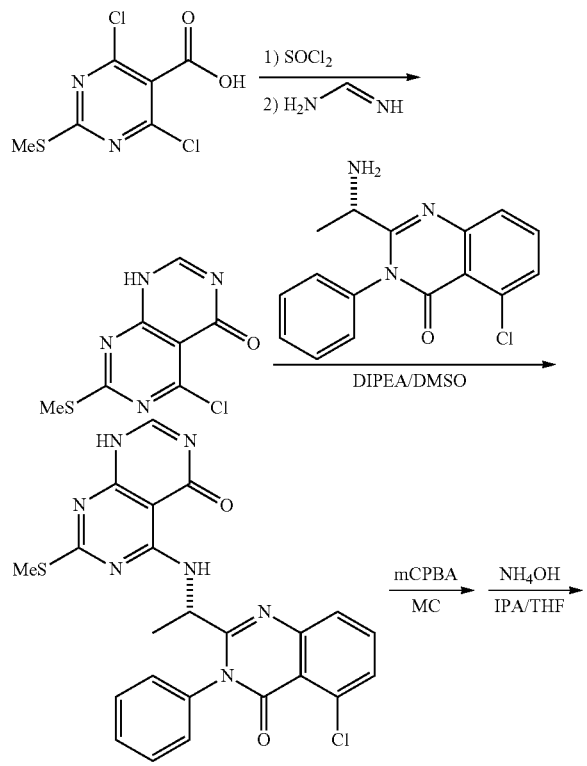

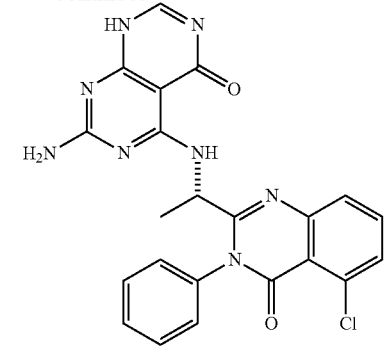

Step 1: Preparation of 5-chloro-7-(methylthio)pyrimido[4,5-d]pyrimidine-4(1H)-one 3.0 g (12.55 mmol, 1.0 eq) of 4,6-dichloro-2-(methylthio)pyrimidine-5-carboxylic acid was dissolved in 40 mL of anhydrous toluene, to which 15 mL of thionyl chloride (SOCl$_2$) was added, followed by stirring at 115° C. for 12 hours. The reaction solvent was concentrated under reduced pressure and dried to give acid chloride. Then, 1.6 g of 5-chloro-7-(methylthio)pyrimido[4,5-d]pyrimidine-4(1H)-one was prepared as a white solid according to the same manner as described in step 2 of Example 66 (2 step yield: 56%).

$^1$H NMR (300 MHz, DMSO-d$_6$) δ 2.56-2.58 (d, J=6.0, 3H), 8.42-8.44 (d, J=6.0, 1H), 12.88 (br s, 1H).

Step 2: Preparation of (S)-5-(1-(5-chloro-4-oxo-3-phenyl-3,4-dihydroquinazoline-2-yl)ethylamino)-7-(methylthio)pyrimido[4,5-d]pyrimidine-4(1H)-one 22 mg of (S)-5-(1-(5-chloro-4-oxo-3-phenyl-3,4-dihydroquinazoline-2-yl)ethylamino)-7-(methylthio)pyrimido[4,5-d]pyrimidine-4(1H)-one was prepared as a white solid by using 10 mg (0.055 mmol) of 5-chloro-7-(methylthio)pyrimido[4,5-d]pyrimidine-4(1H)-one prepared in step 1 and 20 mg (0.066 mmol, 1.2 equivalent) of (S)-2-(1-aminoethyl)-5-chloro-2-phenylquinazoline-4(3H)-one according to the same manner as described in step 5 of Example 34 (0.044 mmol, yield: 80%).

$^1$H NMR (300 MHz, CDCl$_3$) δ 9.42 (s, 1H), 8.21 (s, 1H), 7.64-7.33 (m, 7H), 7.36-7.33 (m, 1H), 5.19-5.13 (m, 1H), 2.43 (s, 3H), 1.47 (d, J=6.5 Hz, 3H).

Step 3: Preparation of (S)-7-amino-5-((1-(5-chloro-4-oxo-3-phenyl-3,4-dihydroquinazoline-2-yl)ethyl)amino)pyrimido[4,5-d]pyrimidine-4(1H)-one 16 mg of (S)-7-amino-5-((1-(8-chloro-1-oxo-2-phenyl-1,2-dihydroisoquinoline-3-yl)ethyl)amino)pyrimido[4,5-d]pyrimidine-4(1H)-one was prepared as a white solid by using 19.6 mg (0.04 mmol) of (S)-5-((1-(5-chloro-4-oxo-3-phenyl-3,4-dihydroquinazoline-2-yl)ethyl)amino)-7-(methylthio)pyrimido[4,5-d]pyrimidine-4(1H)-one prepared in step 2 according to the same manner as described in step 4 of Example 15 (0.034 mmol, yield: 85%).

$^1$H NMR (300 MHz, DMSO-d$_6$) δ 9.61-9.58 (m, —NH), 8.06 (s, 1H), 7.77-7.72 (m, 1H), 7.61-7.54 (m, 6H), 4.77-4.72 (m, 1H), 1.31 (d, J=6.5 Hz, 3H).

Example 82: Preparation of (S)-7-amino-5-((1-(5-chloro-4-oxo-3-(pyridine-3-yl)-3,4-dihydroquinazoline-2-yl)ethyl)amino)pyrimido[4,5-d]pyrimidine-4(1H)-one

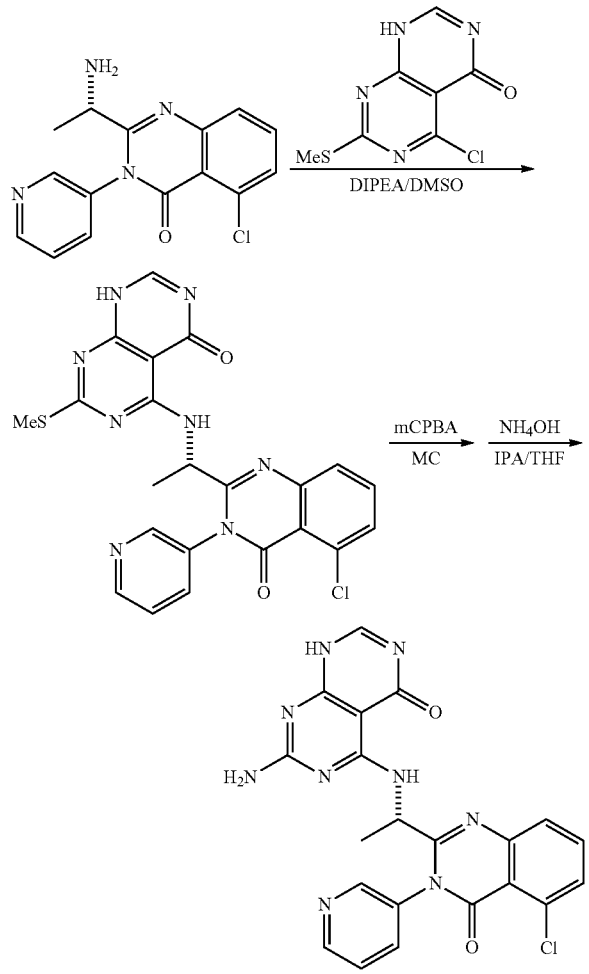

Step 1: Preparation of (S)-5-((1-(5-chloro-4-oxo-3-(pyridine-3-yl)-3,4-dihydroquinazoline-2-yl)ethyl)amino)-7-(methylthio)pyrimido[4,5-d]pyrimidine-4(1H)-one 30 mg of (S)-5-((1-(5-chloro-4-oxo-3-(pyridine-3-yl)-3,4-dihydroquinazoline-2-yl)ethyl)amino)-7-(methylthio)pyrimido[4,5-d]pyrimidine-4(1H)-one was prepared as a white solid according to the same manner as described in step 5 of Example 34 except that (S)-2-(1-aminoethyl)-5-chloro-3-(pyridine-3-yl)quinazoline-4(3H)-one was used (0.06 mmol, yield: 60%).

$^1$H NMR (300 MHz, CDCl$_3$) δ 11.77 (s, 1H), 11.32 (s, 1H), 9.28-9.20 (m, 1H), 8.89 (s, 1H), 8.81-8.79 (m, 1H), 8.72-8.70 (m, 1H), 8.63-8.62 (m, 1H), 8.24 (s, 1H), 8.10-8.05 (m, 1H), 7.77-7.75 (m, 1H), 7.66-7.48 (m, 5H), 5.18-5.13 (m, 1H), 4.95-4.90 (m, 1H), 2.49 (d, J=11.7 Hz, 3H), 1.56-1.52 (m, 3H).

Step 2: Preparation of (S)-7-amino-5-((1-(5-chloro-4-oxo-3-(pyridine-3-yl)-3,4-dihydroquinazoline-2-yl)ethyl)amino)pyrimido[4,5-d]pyrimidine-4(1H)-one 11 mg of (S)-7-amino-5-((1-(5-chloro-4-oxo-3-(pyridine-3-yl)-3,4-dihydroquinazoline-2-yl)ethyl)amino)pyrimido[4,5-d]pyrimidine-4(1H)-one was prepared as a pale yellow solid by using 24 mg (0.049 mmol) of (S)-5-(1-(5-chloro-4-oxo-3-phenyl-3,4-dihydroisoquinoline-2-yl)ethylamino)-7-(methylthio)pyrimido[4,5-d]pyrimidine-4(1H)-one prepared in step 1 according to the same manner as described in step 4 of Example 15 (0.024 mmol, yield: 49%).

$^1$H NMR (300 MHz, DMSO-d$_6$) δ 12.14 (brs, 1H), 9.40 (brs, 1H), 8.74-8.81 (m, 1H), 8.64-8.73 (m, 1H), 8.03-8.14 (m, 2H), 7.72-7.84 (m, 1H), 7.52-7.67 (m, 3H), 6.80 (brs, 2H), 4.62-4.75 (m, 1H), 1.33 (d, J=6.6 Hz, 3H).

Example 83: Preparation of (S)-7-amino-5-((1-(5-chloro-3-(3-fluorophenyl)-4-oxo-3,4-dihydroquinazoline-2-yl)ethyl)amino)pyrimido[4,5-d]pyrimidine-4(1H)-one

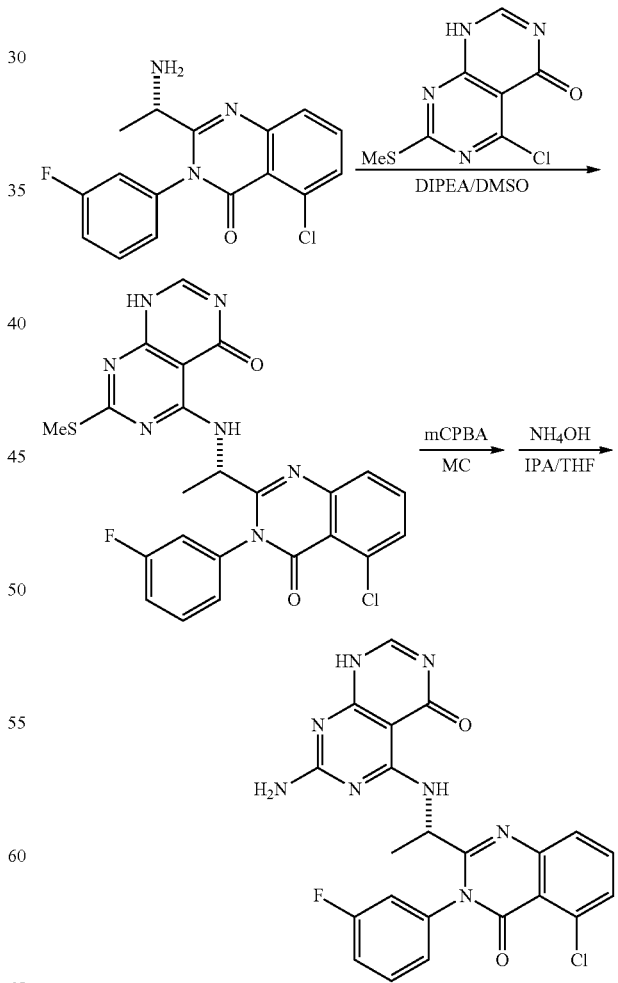

Step 1: Preparation of (S)-5-((1-(5-chloro-3-(3-fluorophenyl)-4-oxo-3,4-dihydroquinazoline-2-yl)ethyl)amino)-7-(methylthio)pyrimido[4,5-d]pyrimidine-4(1H)-one 38 mg of (S)-5-((1-(5-chloro-3-(3-fluorophenyl)-4-oxo-3,4-dihydroquinazoline-2-yl)ethyl)amino)-7-(methylthio)pyrimido[4,5-d]pyrimidine-4(1H)-one was prepared as a white solid according to the same manner as described in step 5 of Example 34 except that (S)-2-(1-aminoethyl)-5-chloro-3-(3-fluorophenyl)quinazoline-4(3H)-one was used (0.075 mmol, yield: 75%).

$^1$H NMR (300 MHz, CDCl$_3$) δ 9.40 (s, —NH), 8.26 (s, 1H), 7.65-7.47 (m, 5H), 7.37-7.29 (m, 1H), 7.16-7.09 (m, 1H), 5.19-5.12 (m, 1H), 4.09-4.02 (m, 1H), 2.46 (s, 3H), 1.50 (d, J=6.5 Hz, 1H).

Step 2: Preparation of (S)-7-amino-5-((1-(5-chloro-3-(3-fluorophenyl)-4-oxo-3,4-dihydroquinazoline-2-yl)ethyl)amino)pyrimido[4,5-d]pyrimidine-4(1H)-one 27 mg of (S)-7-amino-5-((1-(5-chloro-3-(3-fluorophenyl)-4-oxo-3,4-dihydroquinazoline-2-yl)ethyl)amino)pyrimido[4,5-d]pyrimidine-4(1H)-one was prepared as a white solid according to the same manner as described in step 4 of Example 15 except that (S)-5-((1-(5-chloro-3-(3-fluorophenyl)-4-oxo-3,4-dihydroquinazoline-2-yl)ethyl)amino)-7-(methylthio)pyrimido[4,5-d]pyrimidine-4(1H)-one was used (0.056 mmol, yield: 81%).

$^1$H NMR (300 MHz, DMSO-d$_6$) δ 12.13 (s, —NH), 9.46 (s, —NH), 8.06 (s, 1H), 7.78-7.73 (m, 1H), 7.62-7.31 (m, 6H), 6.87 (s, —NH), 6.64 (s, —NH), 4.80-4.72 (m, 1H), 1.35-1.33 (m, 3H).

Example 84: Preparation of (S)-7-amino-5-((1-(5-chloro-4-oxo-3-(m-tolyl)-3,4-dihydroquinazoline-2-yl)ethyl)amino)pyrimido[4,5-d]pyrimidine-4(1H)-one

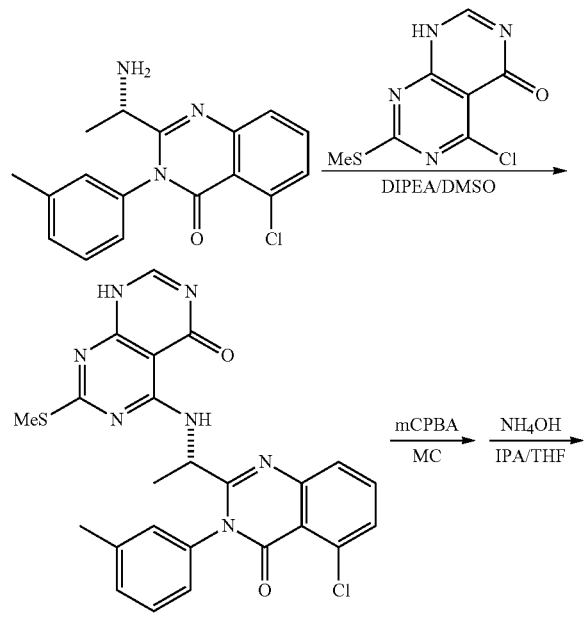

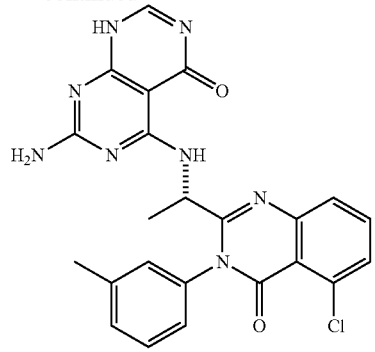

Step 1: Preparation of (S)-5-((1-(5-chloro-4-oxo-3-(m-tolyl)-3,4-dihydroquinazoline-2-yl)ethyl)amino)-7-(methylthio)pyrimido[4,5-d]pyrimidine-4(1H)-one 45 mg of (S)-5-((1-(5-chloro-4-oxo-3-(m-tolyl)-3,4-dihydroquinazoline-2-yl)ethyl)amino)-7-(methylthio)pyrimido[4,5-d]pyrimidine-4(1H)-one was prepared as a white solid according to the same manner as described in step 5 of Example 34 except that (S)-2-(1-aminoethyl)-5-chloro-3-m-tolylquinazoline-4(3H)-one was used (0.089 mmol, yield: 89%).

$^1$H NMR (300 MHz, CDCl$_3$) δ 9.46 (s, 1H), 8.23 (s, 1H), 7.65-7.56 (m, 2H), 7.47-7.41 (m, 2H), 7.30-7.27 (m, 1H), 7.14 (s, 1H), 5.22-5.15 (m, 1H), 2.46-2.39 (m, 6H), 2.48-47 (m, 3H).

Step 2: Preparation of (S)-7-amino-5-((1-(5-chloro-4-oxo-3-(m-tolyl)-3,4-dihydroquinazoline-2-yl)ethyl)amino)pyrimido[4,5-d]pyrimidine-4(1H)-one 35 mg of (S)-7-amino-5-((1-(5-chloro-4-oxo-3-(m-tolyl)-3,4-dihydroquinazoline-2-yl)ethyl)amino)pyrimido[4,5-d]pyrimidine-4(1H)-one was prepared as a white solid according to the same manner as described in step 4 of Example 15 except that (S)-5-((1-(5-chloro-4-oxo-3-(m-tolyl)-3,4-dihydroquinazoline-2-yl)ethyl)amino)-7-(methylthio)pyrimido[4,5-d]pyrimidine-4(1H)-one was used (0.073 mmol, yield: 82%).

$^1$H NMR (300 MHz, DMSO-d$_6$) δ 12.13 (s, —NH), 9.60-9.48 (s, —NH), 8.06 (s, 1H), 7.78-7.72 (m, 1H), 7.63-7.53 (m, 2H), 7.45-7.27 (m, 4H), 6.80-6.71 (m, —NH2), 4.84-4.77 (m, 1H), 2.47 (s, 3H), 1.35-1.30 (m, 3H).

Example 85: Preparation of (S)-7-amino-5-(1-(8-chloro-1-oxo-2-phenyl-1,2-dihydroisoquinoline-3-yl)ethylamino)pyrimido[4,5-d]pyrimidine-4(1H)-one

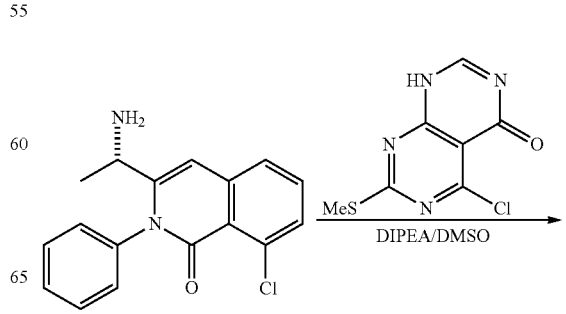

217
-continued

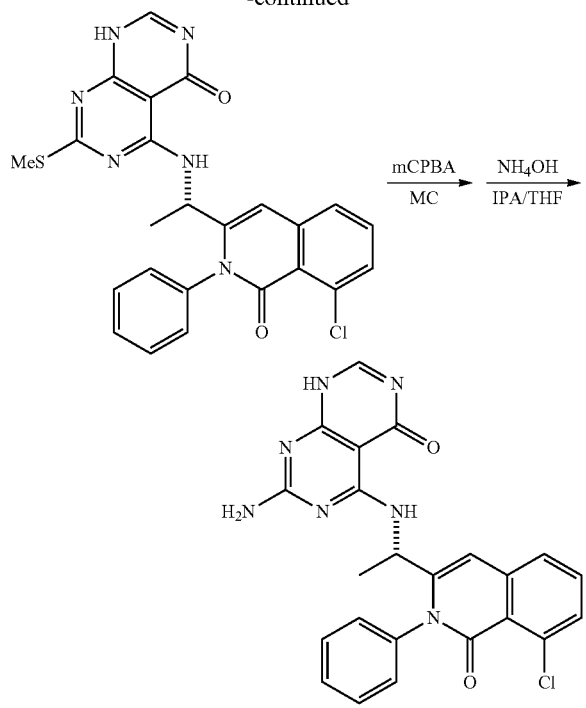

Step 1: Preparation of (S)-5-(1-(8-chloro-1-oxo-2-phenyl-1,2-dihydroisoquinoline-3-yl)ethylamino)-7-(methylthio)pyrimido[4,5-d]pyrimidine-4(1H)-one 35 mg of (S)-5-(1-(8-chloro-1-oxo-2-phenyl-1,2-dihydroisoquinoline-3-yl)ethylamino)-7-(methylthio)pyrimido[4,5-d]pyrimidine-4(1H)-one was prepared as a white solid by using 17 mg (0.0743 mmol, 1.0 equivalent) of 5-chloro-7-(methylthio)pyrimido[4,5-d]pyrimidine-4(1H)-one prepared in step 1 of Example 81 and 27 mg (0.0892 mmol, 1.2 equivalent) of (S)-3-(1-aminoethyl)-8-chloro-2-phenylisoquinoline-1(2H)-one according to the same manner as described in step 5 of Example 34 (yield: 96%).

$^1$H NMR (300 MHz, DMSO-$d_6$) δ 1.40-1.42 (d, J=6.0, 3H), 2.34 (s, 3H), 4.75-4.80 (m, 1H), 6.82 (s, 1H), 7.27-7.36 (m, 3H), 7.42-7.44 (m, 1H), 7.49-7.54 (m, 2H), 7.60-7.67 (m, 2H), 8.28 (s, 1H), 9.13-9.15 (d, J=6.0, 1H), 12.78 (br s, 1H).

Step 2: Preparation of (S)-7-amino-5-(1-(8-chloro-1-oxo-2-phenyl-1,2-dihydroisoquinoline-3-yl)ethylamino)pyrimido[4,5-d]pyrimidine-4(1H)-one 60 mg of (S)-7-amino-5-(1-(8-chloro-1-oxo-2-phenyl-1,2-dihydroisoquinoline-3-yl)ethylamino)pyrimido[4,5-d]pyrimidine-4(1H)-one was prepared as a white solid by using 170 mg (0.346 mmol) of (S)-5-(1-(8-chloro-1-oxo-2-phenyl-1,2-dihydroisoquinoline-3-yl)ethylamino)-7-(methylthio)pyrimido[4,5-d]pyrimidine-4(1H)-one prepared in step 2 according to the same manner as described in step 4 of Example 15 (yield: 38%).

$^1$H NMR (300 MHz, DMSO-$d_6$) δ 1.29-1.31 (d, J=6.0, 3H), 4.58-4.62 (m, 1H), 6.57-6.94 (m, 3H), 7.42-7.64 (m, 8H), 8.08 (s, 1H), 9.05-9.06 (d, J=3.0, 1H), 12.24 (s, 1H).

218
Example 86: Preparation of (S)-7-amino-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one

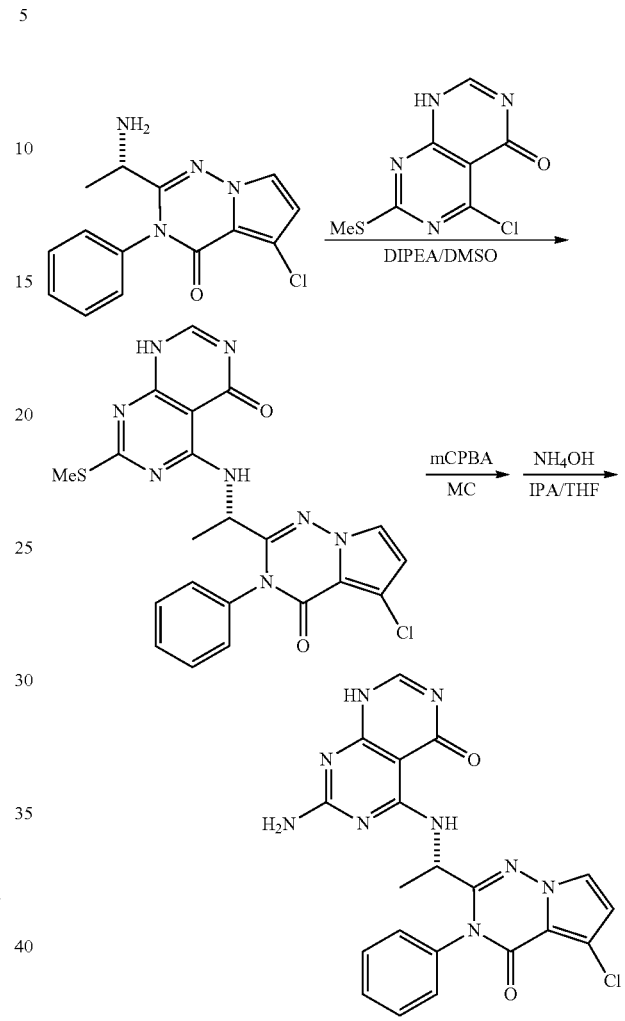

Step 1: Preparation of (S)-5-((1-(5-chloro-4-oxo-3-phenyl-3,4-dihydropyrrolo[2,1-f][1,2,4]triazine-2-yl)ethyl)amino)-7-(methylthio)pyrimido[4,5-d]pyrimidine-4(1H)-one 102 mg of (S)-5-((1-(5-chloro-4-oxo-3-phenyl-3,4-dihydropyrrolo[2,1-f][1,2,4]triazine-2-yl)ethyl)amino)-7-(methylthio)pyrimido[4,5-d]pyrimidine-4(1H)-one was prepared as a white solid by using 58 mg (0.20 mmol) of (S)-5-((1-(5-chloro-4-oxo-3-phenyl-3,4-dihydropyrrolo[2,1-f][1,2,4]triazine-2-yl)ethyl)amino)-7-(methylthio)pyrimido[4,5-d]pyrimidine-4(1H)-one according to the same manner as described in step 5 of Example 34 (yield: 94%).

$^1$H NMR (300 MHz, CDCl$_3$) δ 9.15 (br s, 1H), 8.32 (s, 1H), 7.30-7.65 (m, 7H), 6.52 (s, 1H), 5.10-5.25 (m, 1H), 2.47 (s, 3H), 1.50 (d, J=6.4 Hz, 3H).

Step 2: Preparation of (S)-7-amino-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one 14 mg of (S)-7-amino-5-((1-(5-chloro-4-oxo-3-phenyl-3,4-dihydropyrrolo[2,1-f][1,2,4]triazine-2-yl)ethyl)amino)pyrimido[4,5-d]pyrimidine-4(1H)-one was prepared as a white solid by using 43 mg (0.089 mmol) of (S)-5-((1-(5-chloro-4-oxo-3-phenyl-3,4-dihydropyrrolo[2,1-f][1,2,4]triazine-2-yl)ethyl)amino)-7-(methylthio)pyrimido[4,5-d]pyrimidine-4(1H)-one according to the same manner as described in step 4 of Example 15 (0.031 mmol, yield: 35%).

$^1$H NMR (500 MHz, DMSO-$d_6$) δ 12.18 (brs, 1H), 9.11 (brs, 1H), 8.10 (s, 1H), 7.70-7.73 (m, 1H), 7.54-7.62 (m, 1H), 7.42-7.52 (m, 2H), 7.24-7.35 (m, 1H), 6.93 (brs, 1H), 6.70 (dd, J=1.0 Hz, J=3.1 Hz, 1H), 6.62 (brs, 1H), 4.75-4.83 (m, 1H), 1.35-1.41 (m, 3H).

Example 87: Preparation of (S)-7-amino-5-((1-(5-chloro-3-(3-fluorophenyl)-4-oxo-3,4-dihydropyrrolo[2,1-f][1,2,4]triazine-2-yl)ethyl)amino)pyrimido[4,5-d]pyrimidine-4(1H)-one

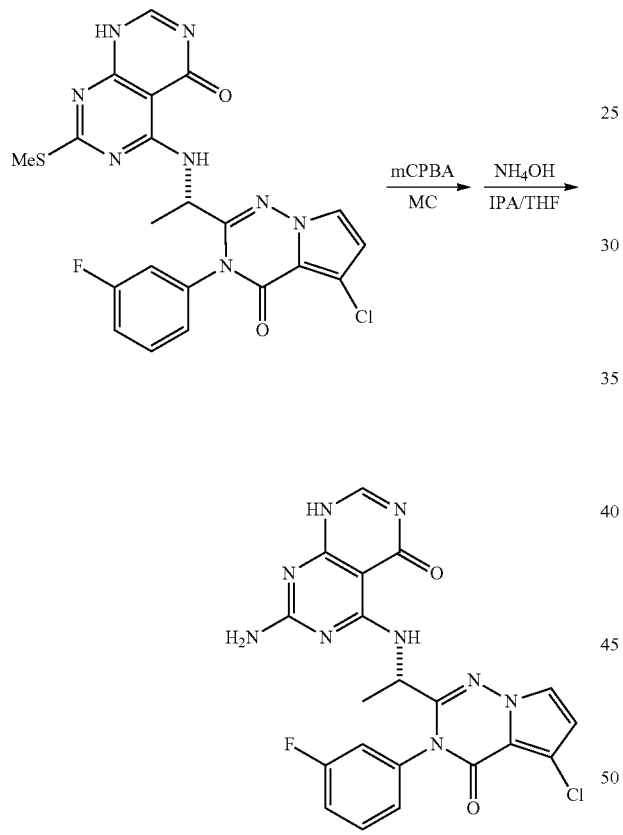

20 mg of (S)-7-amino-5-((1-(5-chloro-3-(3-fluorophenyl)-4-oxo-3,4-dihydropyrrolo[2,1-f][1,2,4]triazine-2-yl)ethyl)amino)pyrimido[4,5-d]pyrimidine-4(1H)-one was prepared as a white solid by using 86 mg (0.172 mmol) of (S)-5-((1-(5-chloro-3-(3-fluorophenyl)-4-oxo-3,4-dihydropyrrolo[2,1-f][1,2,4]triazine-2-yl)ethyl)amino)-7-(methylthio)pyrimido[4,5-d]pyrimidine-4(1H)-one according to the same manner as described in step 4 of Example 15 (0.043 mmol, yield: 25%).

$^1$H NMR (500 MHz, DMSO-$d_6$) δ 9.19 (brs, 1H), 8.09 (s, 1H), 7.68 (s, 1H), 7.53-7.63 (m, 3H), 7.48 (s, 2H), 6.95 (brs, 1H), 6.68 (s, 1H), 6.60 (brs, 1H), 7.71-7.78 (m, 1H), 1.32-1.38 (m, 3H).

Example 88: Preparation of (S)-7-amino-5-((1-(2-phenylquinoline-3-yl)ethyl)amino)pyrimido[4,5-d]pyrimidine-4(1H)-one

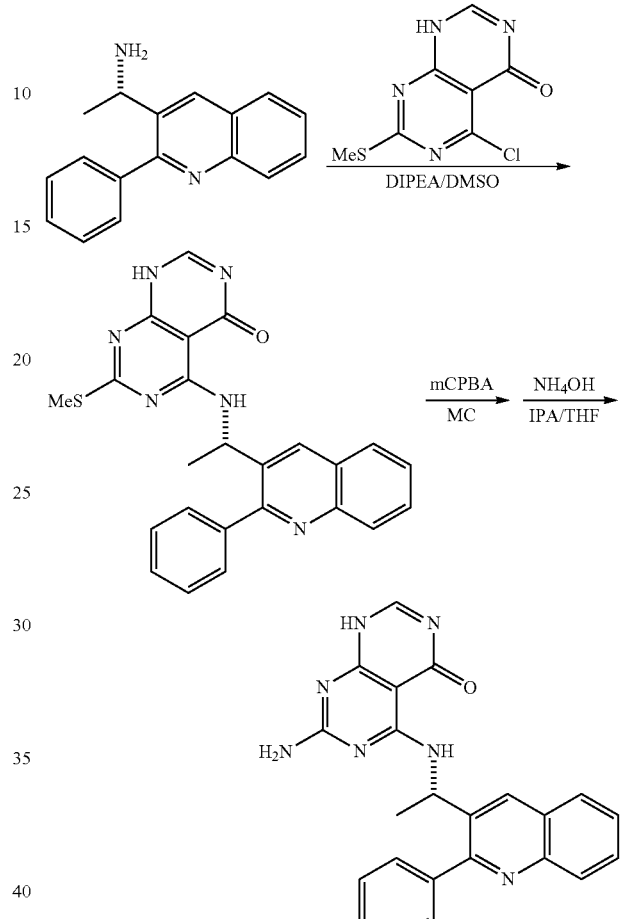

Step 1: Preparation of (S)-7-(methylthio)-5-((1-(2-phenylquinoline-3-yl)ethyl)amino)pyrimido[4,5-d]pyrimidine-4(1H)-one 23 mg of (S)-7-(methylthio)-5-((1-(2-phenylquinoline-3-yl)ethyl)amino)pyrimido[4,5-d]pyrimidine-4(1H)-one was prepared as a white solid according to the same manner as described in step 5 of Example 34 except that (S)-1-(2-phenylquinoline-3-yl)ethaneamine was used (0.052 mmol, yield: 52%).

$^1$H NMR (300 MHz, CDCl$_3$) δ 12.32 (s, —NH), 9.31-9.29 (m, 1H), 8.26 (s, 1H), 8.20 (d, J=8.5 Hz, 1H), 8.04 (s, 1H), 7.83 (d, J=8.2 Hz, 1H), 7.74-7.68 (m, 3H), 7.57-7.43 (m, 4H), 5.78-5.68 (m, 1H), 1.51 (d, J=6.6 Hz, 3H).

Step 2: Preparation of (S)-7-amino-5-((1-(2-phenylquinoline-3-yl)ethyl)amino)pyrimido[4,5-d]pyrimidine-4(1H)-one 16 mg of (S)-7-amino-5-((1-(2-phenylquinoline-3-yl)ethyl)amino)pyrimido[4,5-d]pyrimidine-4(1H)-one was prepared as a white solid according to the same manner as described in step 4 of Example 15 except that (S)-7-(methylthio)-5-((1-(2-phenylquinoline-3-yl)ethyl)amino)py-rimido[4,5-d]pyrimidine-4(1H)-one was used (0.039 mmol, yield: 81%).

¹H NMR (300 MHz, DMSO-d₆) δ 12.16 (s, —NH), 9.36 (s, —NH), 8.36 (s, 1H), 8.07 (s, 1H), 8.01-7.96 (m, 2H), 7.75-7.44 (m, 7H), 7.63-7.53 (m, 2H), 7.45-7.27 (m, 4H), 6.86 (m, —NH), 6.75 (m, —NH), 5.48-5.44 (m, 1H), 1.33 (d, J=6.1 Hz, 3H).

Example 89: Preparation of (S)-7-amino-5-((1-(5-fluoro-4-oxo-3-phenyl-3,4-dihydroquinazoline-2-yl)propyl)amino)pyrimido[4,5-d]pyrimidine-4(1H)-one

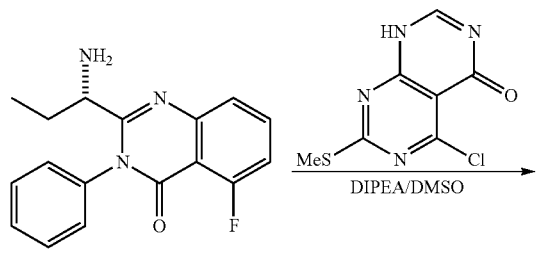

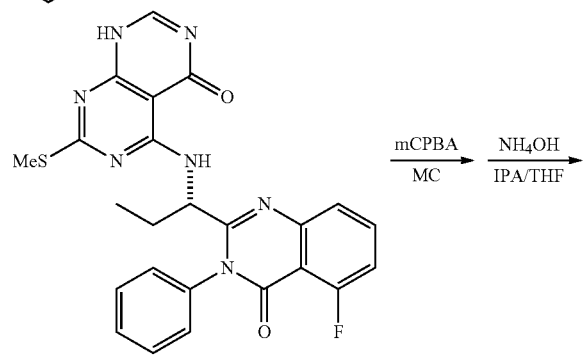

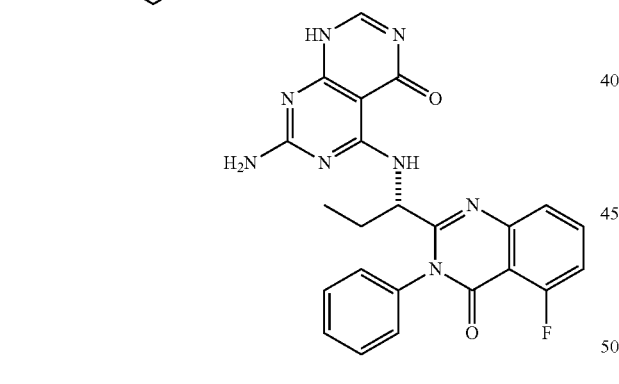

Step 1: Preparation of (S)-5-((1-(5-fluoro-4-oxo-3-phenyl-3,4-dihydroquinazoline-2-yl)propyl)amino)-7-(methylthio)pyrimido[4,5-d]pyrimidine-4(1H)-one 45 mg of (S)-5-((1-(5-fluoro-4-oxo-3-phenyl-3,4-dihydroquinazoline-2-yl)propyl)amino)-7-(methylthio)pyrimido[4,5-d]pyrimidine-4(1H)-one was prepared as a white solid according to the same manner as described in step 5 of Example 34 except that (S)-2-(1-aminopropyl)-5-fluoro-3-(pyridine-3-yl)quinazoline-4(3H)-one was used (0.089 mmol, yield: 89%).

¹H NMR (300 MHz, CDCl₃) δ 9.49-9.45 (m, 1H), 8.21 (s, 1H), 7.72-7.47 (m, 5H), 7.35-7.31 (m, 1H), 7.15-7.08 (m, 1H), 5.13-5.06 (m, 1H), 2.38 (s, 3H), 1.98-1.76 (m, 2H), 0.87-0.78 (m, 3H).

Step 2: Preparation of (S)-7-amino-5-((1-(5-fluoro-4-oxo-3-phenyl-3,4-dihydroquinazoline-2-yl)propyl)amino)pyrimido[4,5-d]pyrimidine-4(1H)-one 34 mg of (S)-7-amino-5-((1-(5-fluoro-4-oxo-3-phenyl-3,4-dihydroquinazoline-2-yl)propyl)amino)pyrimido[4,5-d]pyrimidine-4(1H)-one was prepared as a white solid according to the same manner as described in step 4 of Example 15 except that (S)-5-((1-(5-fluoro-4-oxo-3-phenyl-3,4-dihydroquinazoline-2-yl)propyl)amino)-7-(methylthio)pyrimido[4,5-d]pyrimidine-4(1H)-one was used (0.075 mmol, yield: 88%).

¹H NMR (300 MHz, DMSO-d₆) δ 12.14 (s, —NH), 9.45 (s, —NH), 8.06 (s, 1H), 7.82-7.74 (m, 1H), 7.61-7.51 (m, 5H), 7.46-7.43 (m, 1H), 7.30-7.23 (m, 1H), 6.85 (s, —NH), 6.50 (s, —NH), 4.67 (s, 1H), 1.90-1.82 (m, 1H), 1.60-1.50 (m, 1H), 0.71-0.66 (m, 3H).

Example 90: Preparation of (S)-7-amino-5-(2-(5-chloro-4-oxo-3-phenyl-3,4-dihydroquinazoline-2-yl)pyrrolidine-1-yl)pyrimido[4,5-d]pyrimidine-4(1H)-one

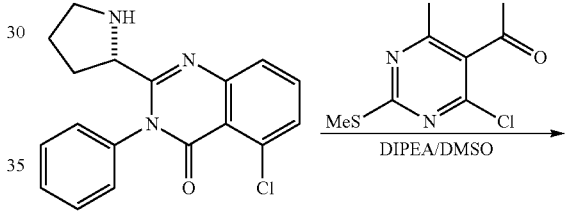

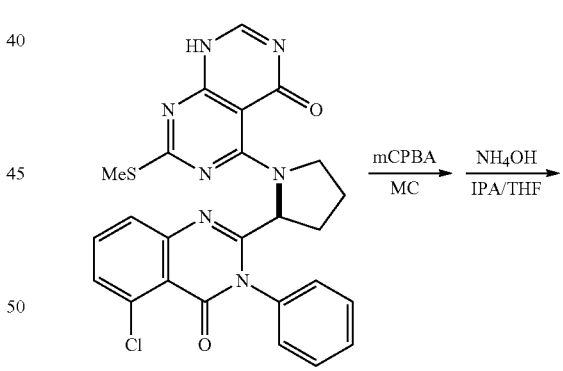

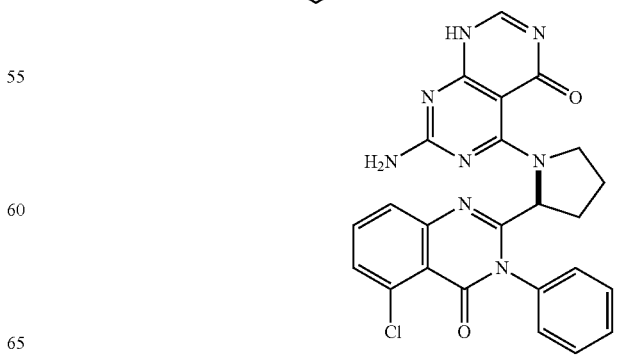

Step 1: Preparation of (S)-5-(2-(5-chloro-4-oxo-3-phenyl-3,4-dihydroquinazoline-2-yl)pyrrolidine-1-yl)-7-(methylthio)pyrimido[4,5-d]pyrimidine-4(1H)-one 23 mg of (S)-5-(2-(5-chloro-4-oxo-3-phenyl-3,4-dihydroquinazoline-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-3-phenyl-2-(pyrrolidine-2-yl)quinazoline-4(3H)-one was used (0.044 mmol, yield: 80%).

$^1$H NMR (300 MHz, CDCl$_3$) δ 8.17 (s, 1H), 8.03-8.00 (m, 1H), 7.69-7.40 (m, 8H), 4.85-4.80 (m, 1H), 4.06-4.00 (m, 1H), 3.68-3.60 (m, 1H), 2.53 (s, 3H), 2.29-2.10 (2H), 1.83-1.76 (m, 2H).

Step 2: Preparation of (S)-7-amino-5-(2-(5-chloro-4-oxo-3-phenyl-3,4-dihydroquinazoline-2-yl)pyrrolidine-1-yl)pyrimido[4,5-d]pyrimidine-4(1H)-one 20 mg of (S)-7-amino-5-(2-(5-chloro-4-oxo-3-phenyl-3,4-dihydroquinazoline-2-yl)pyrrolidine-1-yl)pyrimido[4,5-d]pyrimidine-4(1H)-one was prepared as a white solid according to the same manner as described in step 4 of Example 15 except that (S)-5-(2-(5-chloro-4-oxo-3-phenyl-3,4-dihydroquinazoline-2-yl)pyrrolidine-1-yl)-7-(methylthio)pyrimido[4,5-d]pyrimidine-4(1H)-one was used (0.043 mmol, yield: 86%).

$^1$H NMR (300 MHz, CDCl$_3$) δ 11.77 (s, 1H), 9.10 (s, 1H), 8.72-8.70 (m, 2H), 8.37 (s, 1H), 8.00 (s, 1H), 7.69-7.47 (m, 4H), 4.83-4.80 (m, 1H), 4.49-4.41 (m, 1H), 3.87-3.73 (m, 2H), 1.28-1.24 (m, 4H).

Example 91: Preparation of (S)-7-amino-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one

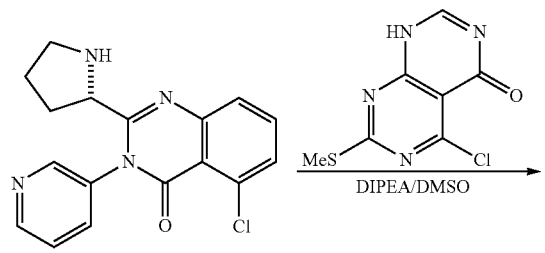

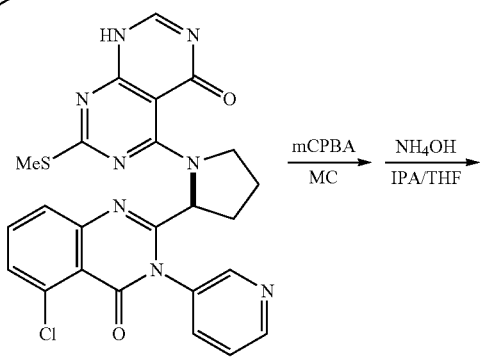

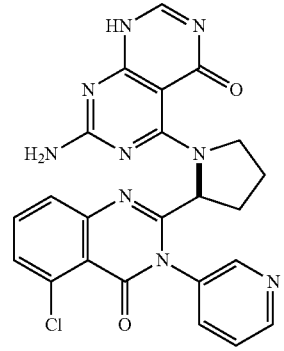

Step 1: Preparation of (S)-5-(2-(5-chloro-4-oxo-3-(pyridine-3-yl)-3,4-dihydroquinazoline-2-yl)pyrrolidine-1-yl)-7-(methylthio)pyrimido[4,5-d]pyrimidine-4(1H)-one 30 mg of (S)-5-(2-(5-chloro-4-oxo-3-(pyridine-3-yl)-3,4-dihydroquinazoline-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-3-(pyridine-3-yl)-2-(pyrrolidine-2-yl)quinazoline-4(3H)-one was used (0.057 mmol, yield: 57%).

$^1$H NMR (300 MHz, CDCl$_3$) δ 10.96 (s, 1H), 9.31 (s, 1H), 8.82-8.78 (m, 1H), 8.56 (s, 1H), 8.45-8.42 (m, 1H), 8.24 (s, 1H), 7.56-7.43 (m, 4H), 4.83-4.80 (m, 1H), 4.69-4.64 (m, 1H), 3.71-3.60 (m, 1H), 2.53 (s, 3H), 1.28-1.24 (m, 1H).

Step 2: Preparation of (S)-7-amino-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one 20 mg of (S)-7-amino-5-(2-(5-chloro-4-oxo-3-(pyridine-3-yl)-3,4-dihydroquinazoline-2-yl)pyrrolidine-1-yl)pyrimido[4,5-d]pyrimidine-4(1H)-one was prepared as a white solid according to the same manner as described in step 4 of Example 15 except that (S)-5-(2-(5-chloro-4-oxo-3-(pyridine-3-yl)-3,4-dihydroquinazoline-2-yl)pyrrolidine-1-yl)-7-(methylthio)pyrimido[4,5-d]pyrimidine-4(1H)-one was used (0.043 mmol, yield: 86%).

$^1$H NMR (300 MHz, CDCl$_3$) δ 11.77 (s, 1H), 9.10 (s, 1H), 8.72-8.70 (m, 2H), 8.37 (s, 1H), 8.00 (s, 1H), 7.69-7.47 (m, 4H), 4.83-4.80 (m, 1H), 4.49-4.41 (m, 1H), 3.87-3.73 (m, 2H), 1.28-1.24 (m, 4H).

Example 92: Preparation of (S)-7-amino-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one

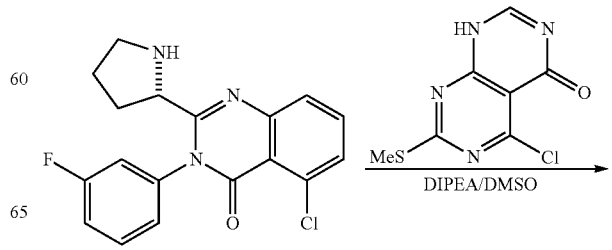

225

-continued

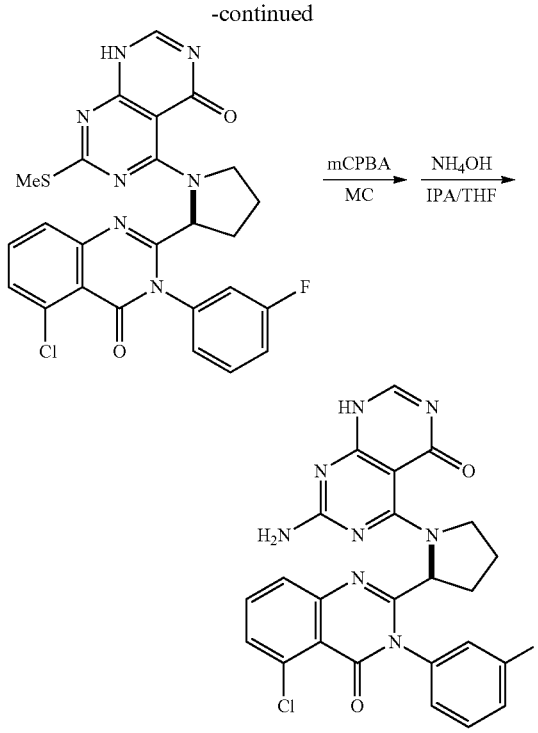

Step 1: Preparation of (S)-5-(2-(5-chloro-3-(3-fluorophenyl)-4-oxo-3,4-dihydroquinazoline-2-yl)pyrrolidine-1-yl)-7-(methylthio)pyrimido[4,5-d]pyrimidine-4(1H)-one 38 mg of (S)-5-(2-(5-chloro-3-(3-fluorophenyl)-4-oxo-3,4-dihydroquinazoline-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-3-(3-fluorophenyl)-2-(pyrrolidine-2-yl)quinazoline-4(3H)-one was used (0.071 mmol, yield: 71%).

$^1$H NMR (300 MHz, CDCl$_3$) δ δ 11.62 (s, —NH), 8.29 (s, 1H), 7.86-8.72 (m, 1H), 7.68-7.41 (m, 5H), 7.29-7.24 (m, 1H), 7.09-7.02 (m, 1H), 4.84-4.78 (m, 1H), 4.09-4.02 (m, 1H), 3.65-3.60 (m, 1H), 2.52 (s, 3H), 2.25-2.08 (m, 4H), 1.84-1.77 (m, 1H).

Step 2: Preparation of (S)-7-amino-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one (S)-7-amino-5-(2-(5-chloro-3-(3-fluorophenyl)-4-oxo-3,4-dihydroquinazoline-2-yl)pyrrolidine-1-yl)pyrimido[4,5-d]pyrimidine-4(1H)-one was prepared according to the same manner as described in step 4 of Example 15 except that (S)-5-(2-(5-chloro-3-(3-fluorophenyl)-4-oxo-3,4-dihydroquinazoline-2-yl)pyrrolidine-1-yl)-7-(methylthio)pyrimido[4,5-d]pyrimidine-4(1H)-one was used.

$^1$H NMR (300 MHz, DMSO-d6) δ δ 11.76 (br s, 1H), 8.00 (s, 1H), 7.95-7.30 (m, 8H), 6.62 (br s, 2H), 4.60-4.40 (m, 1H), 3.90-3.70 (m, 1H), 3.65-1.77 (m, 6H).

226

Example 93: Preparation of (S)-7-amino-5-(2-(5-chloro-4-oxo-3-(m-tolyl)-3,4-dihydroquinazoline-2-yl)pyrrolidine-1-yl)pyrimido[4,5-d]pyrimidine-4(1H)-one

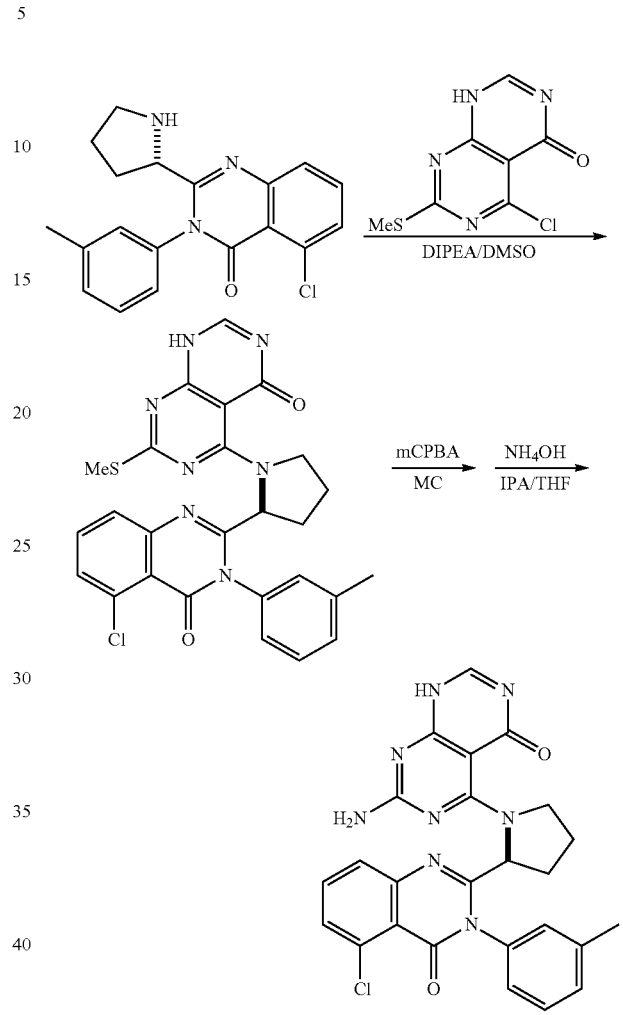

Step 1: Preparation of (S)-5-(2-(5-chloro-4-oxo-3-(m-tolyl)-3,4-dihydroquinazoline-2-yl)pyrrolidine-1-yl)-7-(methylthio)pyrimido[4,5-d]pyrimidine-4(1H)-one 45 mg of (S)-5-(2-(5-chloro-4-oxo-3-(m-tolyl)-3,4-dihydroquinazoline-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-2-(pyrrolidine-2-yl)-3-m-tolylquinazoline-4(3H)-one was used (0.085 mmol, yield: 85%).

$^1$H NMR (300 MHz, CDCl$_3$) δ 11.72 (s —NH), 8.26 (s, 1H), 7.84 (s, 1H), 7.55-7.41 (m, 5H), 7.07 (s, 1H), 4.87-4.81 (m, 1H), 4.13-4.07 (m, 1H), 3.58-3.51 (m, 1H), 2.50 (s, 3H), 2.20-2.04 (m, 4H), 1.79-1.73 (m, 2H).

Step 2: Preparation of (S)-7-amino-5-(2-(5-chloro-4-oxo-3-(m-tolyl)-3,4-dihydroquinazoline-2-yl)pyrrolidine-1-yl)pyrimido[4,5-d]pyrimidine-4(1H)-one 31 mg of (S)-7-amino-5-(2-(5-chloro-4-oxo-3-(m-tolyl)-3,4-dihydroquinazoline-2-yl)pyrrolidine-1-yl)pyrimido[4,5- d]pyrimidine-4(1H)-one was prepared as a white solid according to the same manner as described in step 4 of Example 15 except that (S)-5-(2-(5-chloro-4-oxo-3-(m-tolyl)-3,4-dihydroquinazoline-2-yl)pyrrolidine-1-yl)-7-(methylthio)pyrimido[4,5-d]pyrimidine-4(1H)-one was used (0.061 mmol, yield: 77%).

$^1$H NMR (300 MHz, DMSO-d6) δ 11.75 (br s, 1H), 8.00 (s, 1H), 7.80-7.20 (m, 7H), 6.53 (br s, 2H), 4.63-4.53 (m, 1H), 3.84-3.74 (m, 1H), 3.60-3.40 (m, 1H), 2.37 (s, 3H), 2.10-1.27 (m, 4H).

Example 94: Preparation of (S)-7-amino-5-(2-(8-chloro-1-oxo-2-phenyl-1,2-dihydroisoquinoline-3-yl)pyrrolidine-1-yl)pyrimido[4,5-d]pyrimidine-4(1H)-one

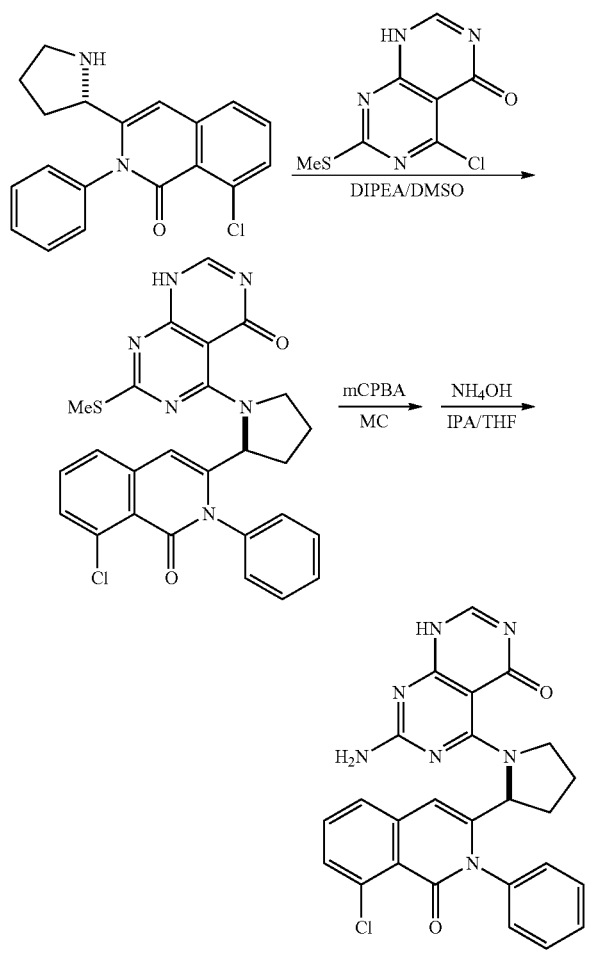

Step 1: Preparation of (S)-5-(2-(8-chloro-1-oxo-2-phenyl-1,2-dihydroisoquinoline-3-yl)pyrrolidine-1-yl)-7-(methylthio)pyrimido[4,5-d]pyrimidine-4(1H)-one 42 mg of (S)-5-(2-(8-chloro-1-oxo-2-phenyl-1,2-dihydroisoquinoline3-yl)pyrrolidine-1-yl)-7-(methylthio)pyrimido[4,5-d]pyrimidine-4(1H)-one was prepared as a white solid according to the same manner as described in step 5 of Example 34 except that (S)-8-chloro-2-phenyl-3-(pyrrolidine-2-yl)isoquinoline-4(3H)-one was used (0.081 mmol, yield: 81%).

$^1$H NMR (300 MHz, CDCl$_3$) δ 11.55 (s, —NH), 8.08 (s, 1H), 7.85-7.83 (m, 1H), 7.69-7.64 (m, 1H), 7.69-7.33 (m, 7H), 6.63 (s, 1H), 5.02-4.96 (m, 1H), 4.40-4.31 (m, 1H), 3.18-3.12 (m, 1H), 2.57 (s, 3H), 2.12-1.98 (m, 2H), 1.87-1.81 (m, 1H), 1.64-1.55 (m, 1H).

Step 2: Preparation of (S)-7-amino-5-(2-(8-chloro-1-oxo-2-phenyl-1,2-dihydroisoquinoline-3-yl)pyrrolidine-1-yl)pyrimido[4,5-d]pyrimidine-4(1H)-one (S)-7-amino-5-(2-(8-chloro-1-oxo-2-phenyl-1,2-dihydroisoquinoline-3-yl)pyrrolidine-1-yl)pyrimido[4,5-d]pyrimidine-4(1H)-one was prepared according to the same manner as described in step 4 of Example 15 except that (S)-5-(2-(8-chloro-1-oxo-2-phenyl-1,2-dihydroisoquinoline-3-yl)pyrrolidine-1-yl)-7-(methylthio)pyrimido[4,5-d]pyrimidine-4(1H)-one was used.

$^1$H NMR (300 MHz, DMSO-d6) δ 11.86 (br s, 1H), 8.04 (s, 1H), 7.85-7.83 (m, 1H), 7.69-7.33 (m, 8H), 6.65 (br s, 2H), 6.48 (s, 1H), 4.96-4.80 (m, 1H), 4.20-4.00 (m, 1H), 3.18-3.00 (m, 1H), 1.90-1.30 (m, 4H).

Example 95: Preparation of (S)-7-amino-5-(2-(5-chloro-4-oxo-3-phenyl-3,4-dihydropyrrolo[2,1-f][1,2,4]triazine-2-yl)pyrrolidine-1-yl)pyrimido[4,5-d]pyrimidine-4(1H)-one

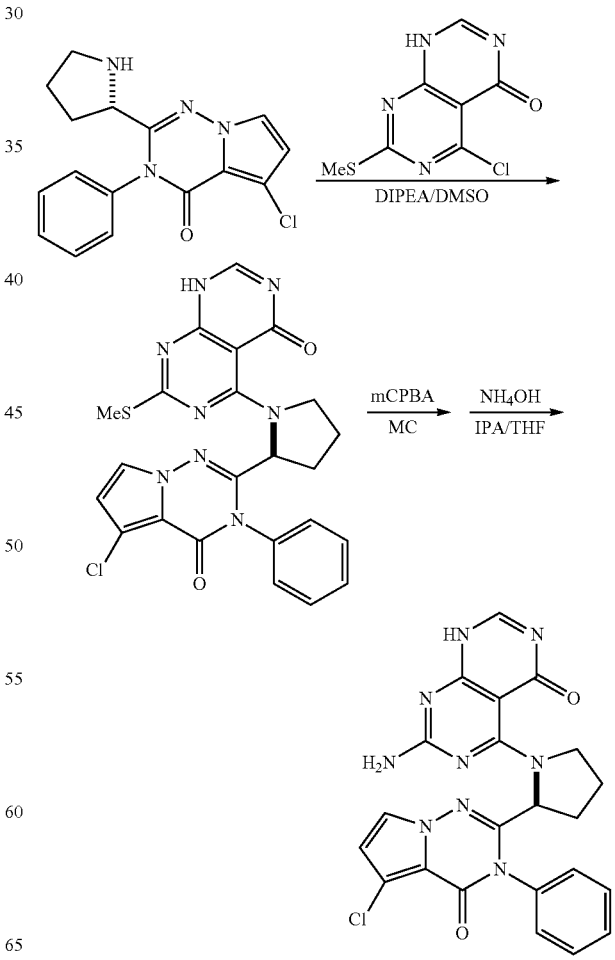

Step 1: Preparation of (S)-5-(2-(5-chloro-4-oxo-3-phenyl-3,4-dihydropyrrolo[2,1-f][1,2,4]triazine-2-yl)pyrrolidine-1-yl)-7-(methylthio)pyrimido[4,5-d]pyrimidine-4(1H)-one 30 mg of (S)-5-(2-(5-chloro-4-oxo-3-phenyl-3,4-dihydropyrrolo[2,1-f][1,2,4]triazine-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-3-phenyl-2-(pyrrolidine-2-yl)pyrrolo[1,2-f][1,2,4]triazine-4(3H)-one hydrochloride was used (0.06 mmol, yield: 66%).

¹H NMR (300 MHz, CDCl₃) δ 8.10 (s, 1H), 7.96-7.93 (m, 1H), 7.65-7.61 (m, 1H), 7.55-7.53 (m, 2H), 7.35 (s, 1H), 7.35-7.34 (m, 1H), 7.28-7.26 (m, 1H), 6.45-6.44 (m, 1H), 4.85-4.81 (m, 1H), 4.16-4.09 (m, 1H), 4.03-3.93 (m, 1H), 2.56 (s, 3H), 2.21-2.12 (m, 1H), 2.08-2.05 (m, 2H), 1.82-1.72 (s, 1H).

Step 2: Preparation of (S)-7-amino-5-(2-(5-chloro-4-oxo-3-phenyl-3,4-dihydropyrrolo[1,2-f][1,2,4]triazine-2-yl)pyrrolidine-1-yl)pyrimido[4,5-d]pyrimidine-4(1H)-one (S)-7-amino-5-(2-(5-chloro-4-oxo-3-phenyl-3,4-dihydropyrrolo[1,2-f][1,2,4]triazine-2-yl)pyrrolidine-1-yl)pyrimido[4,5-d]pyrimidine-4(1H)-one was prepared according to the same manner as described in step 4 of Example 15 except that (S)-5-(2-(5-chloro-4-oxo-3-phenyl-3,4-dihydropyrrolo[2,1-f][1,2,4]triazine-2-yl)pyrrolidine-1-yl)-7-(methylthio)pyrimido[4,5-d]pyrimidine-4(1H)-one was used.

¹H NMR (300 MHz, CDCl₃) δ 8.45 (s, 1H), 7.60-7.05 (m, 7H), 6.43 (s, 1H), 4.85-4.81 (m, 1H), 4.16-4.09 (m, 1H), 3.80-3.60 (m, 1H), 2.45-1.65 (m, 4H).

Example 96: Preparation of (S)-7-amino-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one

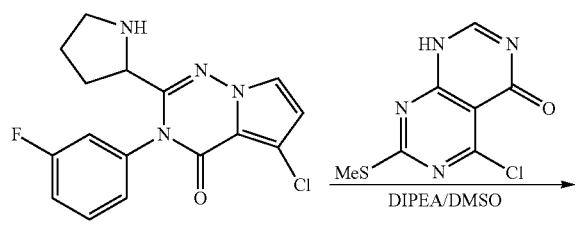

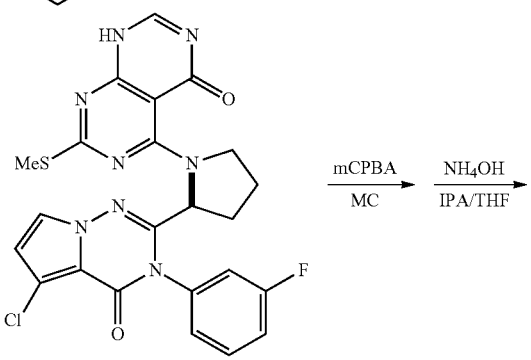

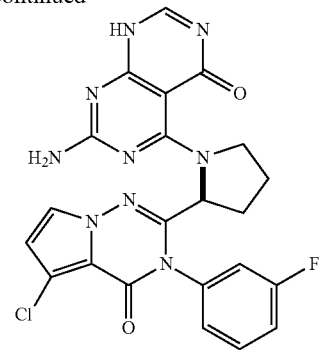

Step 1: Preparation of (S)-5-(2-(5-chloro-3-(3-fluorophenyl)4-oxo-3,4-dihydropyrrolo[2,1-f][1,2,4]triazine-2-yl)pyrrolidine-1-yl)-7-(methylthio)pyrimido[4,5-d]pyrimidine-4(1H)-one 60 mg of (S)-5-(2-(5-chloro-3-(3-fluorophenyl)4-oxo-3,4-dihydropyrrolo[2,1-f][1,2,4]triazine-2-yl)pyrrolidine-1-yl)-7-(methylthio)pyrimido[4,5-d]pyrimidine-4(1H)-one was prepared as a white solid according to the same manner as described in step 5 of Example 34 except that (S)-5-chloro-3-(3-fluorophenyl)-2-(pyrrolidine-2-yl)pyrrolo[1,2-f][1,2,4]triazine-4(3H)-one hydrochloride was used (0.011 mmol, yield: 79%).

¹H NMR (300 MHz, CDCl₃) δ 9.94 (s, —NH), 8.16 (s 1H), 7.81-7.74 (m, 1H), 7.62-7.48 (m, 2H), 7.14 (s, 1H), 7.09-7.01 (m, 1H), 6.43 (s, 1H), 4.84 (s, 1H), 4.02-3.96 (m, 1H), 3.69-3.58 (m, 1H), 2.58 (s, 3H), 2.21-2.04 (m, 2H), 1.85-1.77 (m, 2H).

Step 2: Preparation of (S)-7-amino-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one (S)-7-amino-5-(2-(5-chloro-3-(3-fluorophenyl)-4-oxo-3,4-dihydropyrrolo[2,1-f][1,2,4]triazine-2-yl)pyrrolidine-1-yl)pyrimido[4,5-d]pyrimidine-4(1H)-one was prepared according to the same manner as described in step 4 of Example 15 except that (S)-5-(2-(5-chloro-3-(3-fluorophenyl)4-oxo-3,4-dihydropyrrolo[2,1-f][1,2,4]triazine-2-yl)pyrrolidine-1-yl)-7-(methylthio)pyrimido[4,5-d]pyrimidine-4(1H)-one was used.

¹H NMR (300 MHz, CDCl₃) δ 8.58 (br s, 1H), 7.65-6.80 (m, 6H), 6.44 (s, 1H), 6.10 (s, 1H), 4.90 (s, 1H), 4.25-4.10 (m, 1H), 3.75-3.50 (m, 1H), 2.25-1.10 (m, 4H).

Example 97: Preparation of (S)-4-((1-(8-chloro-1-oxo-2-phenyl-1,2-dihydroisoquinoline-3-yl)ethyl)amino)-7,8-dihydropyrido[2,3-d]pyrimidine-5(6H)-one

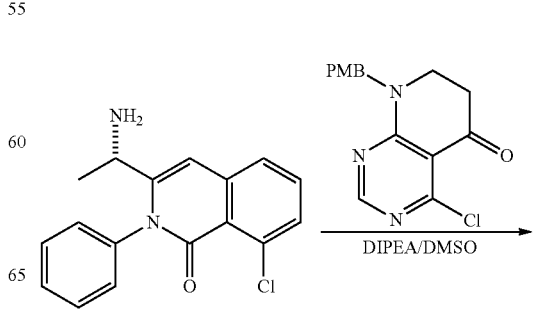

231

-continued

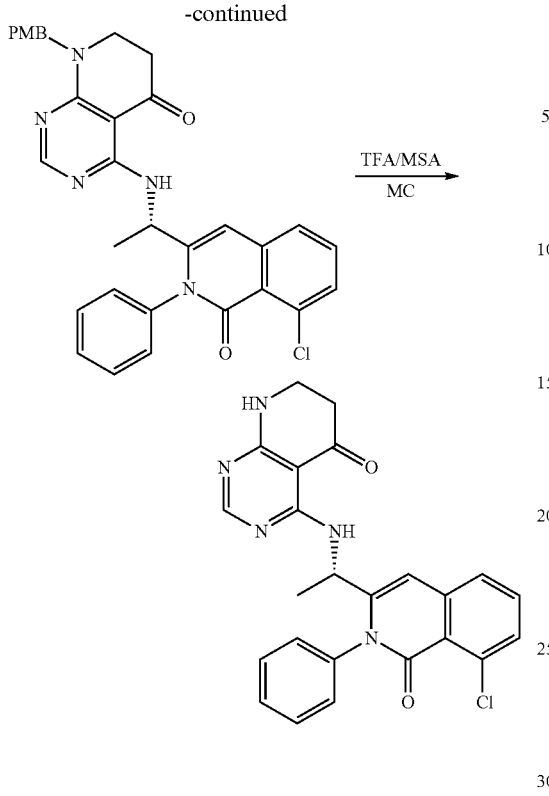

Step 1: Preparation of (S)-4-((1-(8-chloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one 326 mg of (S)-4-((1-(8-chloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one was prepared as a white solid by using 200 mg (0.658 mmol) of 4-chloro-8-(4-methoxybenzyl)-7,8-dihydropyrido[2,3-d]pyrimidine-5(6H)-one and 136 mg (0.790 mmol) of (S)-3-(1-aminoethyl)-8-chloro-2-phenylisoquinoline-1(2H)-one according to the same manner as described in step 5 of Example 34 (0.576 mmol, yield: 87%).

$^1$H NMR (300 MHz, CDCl$_3$) δ 9.52 (d, J=6.4 Hz, 1H), 8.04 (s, 1H), 7.35-7.56 (m, 7H), 7.31 (d, J=6.4 Hz, 1H), 7.21 (d, J=8.3 Hz, 2H), 6.86 (d, J=8.3 Hz, 2H), 6.52 (s, 1H), 4.93 (t, J=7.4 Hz, 1H), 4.83 (s, 2H), 3.79 (s, 3H), 3.45 (t, J=6.4 Hz, 2H), 2.58-2.67 (m, 2H), 1.40 (d, J=6.4 Hz, 3H).

Step 2: Preparation of (S)-4-((1-(8-chloro-1-oxo-2-phenyl-1,2-dihydroisoquinoline-3-yl)ethyl)amino)-7,8-dihydropyrido[2,3-d]pyrimidine-5(6H)-one 36 mg of (S)-4-((1-(8-chloro-1-oxo-2-phenyl-1,2-dihydroisoquinoline-3-yl)ethyl)amino)-7,8-dihydropyrido[2,3-d]pyrimidine-5(6H)-one was prepared as a white solid by using 50 mg (0.088 mmol) of (S)-4-((1-(8-chloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one according to the same manner as described in step 8 of Example 1 (0.081 mmol, yield: 91%).

$^1$H NMR (300 MHz, CDCl$_3$) δ 9.35 (d, J=7.2 Hz, 1H), 7.93 (s, 1H), 7.34-7.55 (m, 7H), 7.30 (d, J=8.4 Hz, 1H), 6.51 (s, 1H), 6.11 (brs, 1H), 4.91 (t, J=6.1 Hz, 1H), 3.58-3.67 (m, 2H), 2.67-2.75 (m, 2H), 1.40 (d, J=6.9 Hz, 3H).

232

Example 98: Preparation of (S)-4-((1-(4,8-dichloro-1-oxo-2-phenyl-1,2-dihydroisoquinoline-3-yl)ethyl)amino)-7,8-dihydropyrido[2,3-d]pyrimidine-5(6H)-one

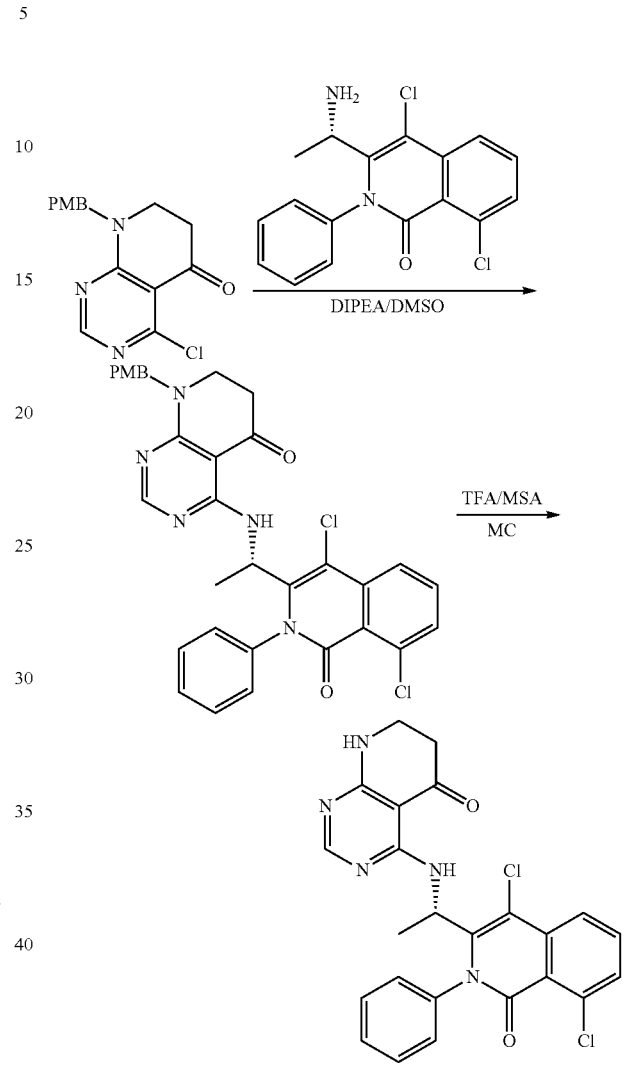

Step 1: Preparation of (S)-4-((4,8-dichloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one 150 mg of (S)-4-((4,8-dichloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one was prepared as a white solid by using 100 mg (0.30 mmol) of (S)-3-(1-aminoethyl)-4,8-dichloro-2-phenylisoquinoline-1(2H)-one prepared in step 8 of Preparative Example 10 according to the same manner as described in step 5 of Example 34 (0.25 mmol, yield: 83%).

$^1$H NMR (300 MHz, CDCl$_3$) δ 9.97 (br s, 1H), 8.11 (s, 1H), 8.00 (d, J=8.2 Hz, 1H), 7.76 (d, J=7.7 Hz, 1H), 7.51-7.64 (m, 5H), 7.19-7.24 (m, 3H), 6.86 (d, J=8.6 Hz, 2H), 5.07-5.11 (m, 1H), 4.80-4.87 (m, 2H), 3.81 (s, 3H), 3.42-3.46 (m, 2H), 2.59-2.63 (m, 2H), 1.64 (d, J=7.2 Hz, 3H).

Step 2: Preparation of (S)-4-((4,8-dichloro-1-oxo-2-phenyl-1,2-dihydroisoquinoline-3-yl)ethyl)amino)-7,8-dihydropyrido[2,3-d]pyrimidine-5(6H)-one 78 mg of (S)-4-((4,8-dichloro-1-oxo-2-phenyl-1,2-dihydroisoquinoline-3-yl)ethyl)amino)-7,8-dihydropyrido[2,3-d]pyrimidine-5(6H)-one was prepared as a white solid by using 100 mg (0.17 mmol) of (S)-4-((4,8-dichloro-1-oxo-2-phenyl-1,2-dihydroisoquinoline-3-yl)ethyl)amino)-8-(4-methoxybenzyl)-7,8-dihydropyrido[2,3-d]pyrimidine-5(6H)-one prepared in step 1 according to the same manner as described in step 8 of Example 1 (0.16 mmol, yield: 98%).

$^1$H NMR (300 MHz, CDCl$_3$) δ 9.82 (br s, 1H), 7.99 (d, J=6.7 Hz, 1H), 7.98 (s, 1H), 7.68-7.73 (m, 1H), 9.48-7.63 (m, 5H), 7.19-7.21 (m, 1H), 5.80 (s, 1H), 5.03-5.11 (m, 2H), 3.58-3.65 (m, 2H), 2.65-2.72 (m, 2H), 1.64 (d, J=7.2 Hz, 3H).

The formulae of the compounds prepared in Examples 1~98 are shown in Table 1 and Table 2.

TABLE 1-continued

| Example | Formula |
|---|---|
| 7-1 | |
| 8 | |
| 9 | |
| 10 | |
| 11 | |
| 12 | |
| 13 | |
| 14 | |

TABLE 1-continued

| Example | Formula |
|---|---|
| 15 | |
| 16 | |
| 17 | |
| 18 | |
| 19 | |
| 20 | |
| 21 | |
| 22 | |

TABLE 1-continued

| Example | Formula |
|---|---|
| 23 | (structure) |
| 24 | (structure) |
| 25 | (structure) |
| 26 | (structure) |
| 27 | (structure) |
| 28 | (structure) |
| 29 | (structure) |
| 30 | (structure) |

TABLE 1-continued

| Example | Formula |
|---------|---------|
| 31 | |
| 32 | |
| 33 | |
| 34 | |
| 35 | |
| 36 | |
| 37 | |
| 38 | |

TABLE 1-continued

| Example | Formula |
|---|---|
| 39 | |
| 39-1 | |
| 40 | |
| 41 | |
| 42 | |
| 43 | |
| 44 | |
| 45 | |

TABLE 1-continued

| Example | Formula |
|---|---|
| 46 | |
| 47 | |
| 48 | |

TABLE 2

| Example | Formula |
|---|---|
| 49 | |

TABLE 2-continued

| Example | Formula |
|---|---|
| 50 | |
| 51 | |
| 52 | |
| 53 | |

TABLE 2-continued

| Example | Formula |
|---|---|
| 54 | |
| 55 | |
| 56 | |
| 57 | |
| 58 | |
| 59 | |
| 60 | |
| 61 | |

TABLE 2-continued

| Example | Formula |
|---------|---------|
| 62 | |
| 63 | |
| 64 | |
| 65 | |
| 66 | |
| 67 | |
| 68 | |
| 69 | |

TABLE 2-continued

| Example | Formula |
|---------|---------|
| 70 | |
| 71 | |
| 72 | |
| 73 | |
| 74 | |
| 75 | |
| 76 | |
| 77 | |

TABLE 2-continued
| Example | Formula |
|---|---|
| 78 | 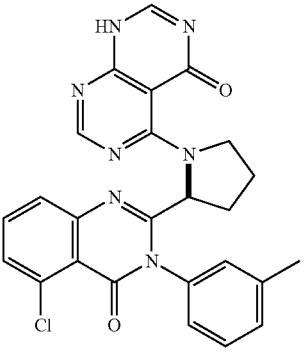 [SMILES: Cc1cccc(-n2c([C@@H]3CCCN3c3ncnc4[nH]cnc(=O)c34)nc3cccc(Cl)c3c2=O)c1] |
| 79 | 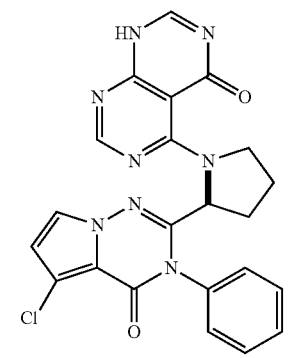 [SMILES: O=c1nc[nH]c2ncnc(N3CCC[C@H]3c3nn4ccc(Cl)c4c(=O)n3-c3ccccc3)c12] |
| 80 | 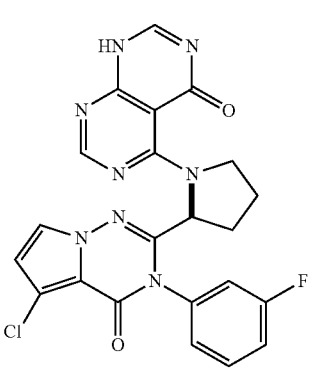 [SMILES: O=c1nc[nH]c2ncnc(N3CCC[C@H]3c3nn4ccc(Cl)c4c(=O)n3-c3cccc(F)c3)c12] |
| 81 | 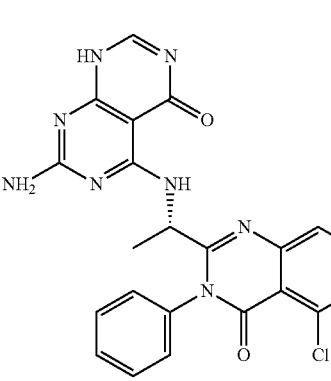 |
| 82 | 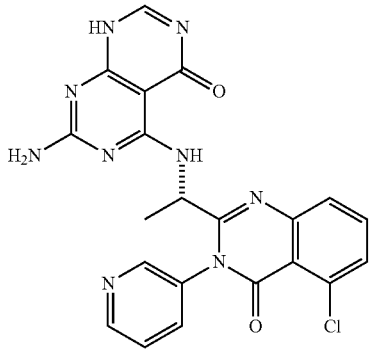 [SMILES: C[C@H](Nc1nc(N)nc2[nH]cnc(=O)c12)c1nc2cccc(Cl)c2c(=O)n1-c1cccnc1] |
| 83 | 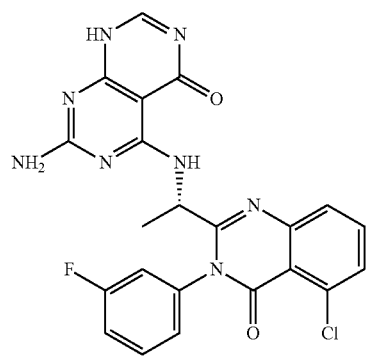 [SMILES: C[C@H](Nc1nc(N)nc2[nH]cnc(=O)c12)c1nc2cccc(Cl)c2c(=O)n1-c1cccc(F)c1] |
| 84 | 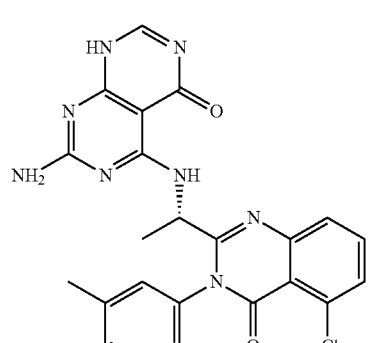 |
| 85 | 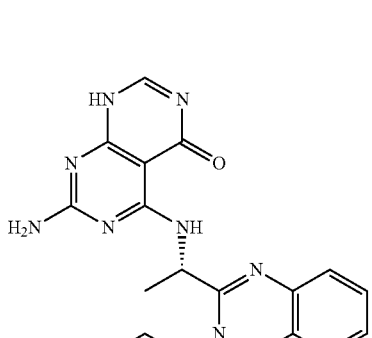 |

TABLE 2-continued

| Example | Formula |
|---|---|
| 86 | (structure) |
| 87 | (structure) |
| 88 | (structure) |
| 89 | (structure) |
| 90 | (structure) |
| 91 | (structure) |
| 92 | (structure) |
| 93 | (structure) |

TABLE 2-continued

| Example | Formula |
|---------|---------|
| 94 | (structure) |
| 95 | (structure) |
| 96 | (structure) |
| 97 | (structure) |
| 98 | (structure) |

Experimental Example 1: Inhibition of phosphatidylinositol 3-kinase Alpha (PI3K α)

The inhibition of phosphatidylinositol 3 kinase alpha (PI3K α) by those compounds prepared in Examples 1~98 was investigated by the following experiment. The inhibition activity of each compound was measured in the following conditions: ATP=10 uM, and sample concentration=100 nM.

Step 1

Human breast cancer cells (MDA-MB-453) cultured in DMEM (Dulbecco's Modified Eagle Medium, Hyclon, SH30243.01) supplemented with 10% fetal bovine serum (Hyclon, USA) were distributed in a 12-well plate at the density of 1,000,000 cells/well. The cells were stabilized in a 37° C. $CO_2$ for 24 hours and then treated with each compound for 1 and half hours. The cells were treated with 10 ng/mL of EGF (Epidermal Growth Factor, 10 μg/mL; R&D, 2150-C5) to increase the intracellular activity of PI3K alpha. 5 minutes later, the medium was discarded and the cells were washed with cold PBS (phosphate buffered saline, Gibco, 14190-250). PBS was then eliminated completely by using a pipette. Western blotting was performed as described in step 2 to evaluate the intracellular PI3K alpha activity.

Step 2: Western Blotting

The stimulated cells were transferred in a 1.5 mL tube, followed by centrifugation at 3000 rpm for 1 minute. 100 μL of RIPA buffer (radioimmunoprecipitation assay buffer, 50 mM Tris-HCl, 5 mM EDTA, 150 mM NaCl, 1% NP-40, 1 mM PMSF, pH 8.0; ELPIS, Korea) was added thereto, which was stored in a 4° C. refrigerator for 12 hours. Centrifugation was performed at 4° C. at 14,000 rpm for 20 minutes. The supernatant was transferred into a new 1.5 mL tube. Protein was quantified by BCA (bicinchoninic acid) method and samples were prepared. The composition of the sample was as follows: sample buffer (ELPIS, EBA-1052) 5×, protein 10 μg, and 1× sample buffer to make the total volume 20 μL. The sample was heated at 100° C. for 5 minutes. The evaporated water vapor was condensed in a refrigerator. The liquid stained on the wall was fallen down by centrifugation for a few seconds. The sample proceeded to 10% SDS (Sodium Dodecyl Sulfate) acrylamide gel for separation. The separated protein was transferred onto PVDF (poly-vinyl difluoride) membrane, followed by reaction with pAkt (phospho protein kinase B) antibody (Ser473 or Thr308; Cell signaling, 9271s or 13038s) for 12 hours at 4° C. The membrane was washed with TBST (Tris-Buffered Saline with Tween 20, 10 mM Tris-HCl, pH 7.5, 150 mM NaCl, 0.1% Tween-20) three times for 5 minutes each, to which the secondary antibody (rabbit antibody, Santacruz, sc-2004) was added, followed by reaction at room temperature for 2 hours. The membrane was washed with TBST three times for 10 minutes each, to which ECL (enhanced chemiluminescence, Thermo, NCI34095KR) was sprayed. Bands were investigated by using LAS-3000.

Experimental Example 2: Inhibition of phosphatidylinositol 3-kinase Beta (PI3K β)

The inhibition of phosphatidylinositol 3 kinase beta (PI3K β) by those compounds prepared in Examples 1~98 was investigated by the following experiment. The inhibition activity of each compound was measured in the following conditions: ATP=10 uM, and sample concentration=100 nM.

Human prostate cancer cells (PC3 cells) cultured in DMEM (Dulbecco's Modified Eagle Medium, Hyclon, SH30243.01) supplemented with 10% fetal bovine serum (Hyclon, USA) were distributed in a 12-well plate at the density of 1,000,000 cells/well. The cells were stabilized in a 37° C. $CO_2$ for 24 hours and then treated with each compound for 1 and half hours. The cells were treated with 10 ng/mL of LPA (lysophosphatidic acid, 10 μg/mL; R&D, 2150-05) to increase the intracellular activity of PI3K beta. 5 minutes later, the medium was discarded and the cells were washed with cold PBS (phosphate buffered saline, Gibco, 14190-250). PBS was then eliminated completely by using a pipette. Western blotting was performed according to the same manner as described in step 2 of Experimental Example 1 to evaluate the intracellular PI3K beta activity.

Experimental Example 3: Inhibition of phosphatidylinositol 3-kinase Gamma (PI3K γ)

The inhibition of phosphatidylinositol 3 kinase gamma (PI3K γ) by those compounds prepared in Examples 1~98 was investigated by the following experiment. The inhibition activity of each compound was measured in the following conditions: ATP=10 uM, and sample concentration=100 nM.

Macrophages (RAW264.7) cultured in DMEM (Dulbecco's Modified Eagle Medium, Hyclon, SH30243.01) supplemented with 10% fetal bovine serum (Hyclon, USA) were distributed in a 12-well plate at the density of 1,000,000 cells/well. The cells were stabilized in a 37° C. $CO_2$ for 24 hours and then treated with each compound for 1 and half hours. The cells were treated with 10 ng/mL of C5a (complement component 5a, 10 μg/mL; R&D, 2150-C5) to increase the intracellular activity of PI3K gamma. 5 minutes later, the medium was discarded and the cells were washed with cold PBS (phosphate buffered saline, Gibco, 14190-250). PBS was then eliminated completely by using a pipette. Western blotting was performed according to the same manner as described in step 2 of Experimental Example 1 to evaluate the intracellular PI3K gamma activity.

Experimental Example 4: Inhibition of phosphatidylinositol 3-kinase Delta (PI3K δ)

The inhibition of phosphatidylinositol 3 kinase delta (PI3K δ) by those compounds prepared in Examples 1~98 was investigated by the following experiment. The inhibition activity of each compound was measured in the following conditions: ATP=10 uM, and sample concentration=100 nM.

Raji cells cultured in RPMI1640 (Hyclone, SH30027.02) supplemented with 10% fetal bovine serum (Hyclon, USA) were distributed in a 12-well plate at the density of 1,000,000 cells/well. The cells were stabilized in a 37° C. $CO_2$ for 24 hours and then treated with each compound for 1 and half hours. The cells were treated with 0.25 μg/mL of IgM (immunoglobulin M, Southern Biotech, USA) to increase the intracellular activity of PI3K delta. 30 minutes later, the medium was discarded and the cells were washed with cold PBS (phosphate buffered saline, Gibco, 14190-250). PBS was then eliminated completely by using a pipette. Western blotting was performed according to the same manner as described in step 2 of Experimental Example 1 to evaluate the intracellular PI3K delta activity.

The inhibition of phosphatidylinositol 3-kinase alpha, beta, gamma, and delta (PI3K α, β, γ, and δ) by those compounds prepared in Examples 1~98 was investigated and the results obtained in Experimental Examples 1~4 are shown in Table 3.

TABLE 3

| Example | PI3 Kinase (p110α/p85α) (h) | PI3 Kinase (p110β/p86α) (h) | PI3 Kinase (p120γ) (h) | PI3 Kinase (p110δ/p85α) (h) |
|---|---|---|---|---|
| 1 | + | ++ | ++ | +++ |
| 2 | + | + | ++ | +++ |
| 3 | + | + | ++ | +++ |
| 4 | + | + | ++ | +++ |
| 5 | + | ++ | ++ | +++ |
| 6 | + | + | ++ | +++ |
| 7 | + | + | + | +++ |
| 7-1 | + | + | + | ++ |
| 8 | + | + | ++ | +++ |
| 9 | + | + | ++ | +++ |
| 10 | + | + | ++ | +++ |
| 11 | + | + | ++ | +++ |
| 12 | + | + | ++ | +++ |
| 13 | + | + | ++ | +++ |
| 14 | + | + | ++ | ++ |
| 15 | ++ | ++ | ++ | +++ |
| 16 | + | + | ++ | ++ |
| 17 | + | + | ++ | ++ |
| 18 | ++ | ++ | ++ | +++ |
| 19 | + | + | + | + |
| 20 | + | + | ++ | +++ |
| 21 | ++ | ++ | ++ | +++ |
| 22 | + | + | ++ | +++ |
| 23 | + | + | ++ | +++ |
| 24 | + | + | ++ | ++ |
| 25 | + | + | +++ | +++ |
| 26 | + | + | + | ++ |
| 27 | + | + | ++ | ++ |
| 28 | + | + | + | ++ |
| 29 | + | + | ++ | +++ |
| 30 | + | + | ++ | +++ |
| 31 | + | + | + | ++ |
| 32 | | | | + |
| 33 | + | + | ++ | +++ |
| 34 | | | ++ | +++ |
| 35 | | | ++ | ++ |
| 36 | | | ++ | +++ |
| 37 | | | ++ | +++ |
| 38 | ++ | + | +++ | +++ |
| 39 | | | ++ | ++ |
| 39-1 | | | +++ | ++ |
| 40 | + | + | ++ | +++ |
| 41 | | | ++ | ++ |
| 42 | | | ++ | ++ |
| 43 | | | + | + |
| 44 | | | ++ | +++ |

TABLE 3-continued

| Example | PI3 Kinase (p110α/p85α) (h) | PI3 Kinase (p110β/p86α) (h) | PI3 Kinase (p120γ) (h) | PI3 Kinase (p110δ/p85α) (h) |
|---|---|---|---|---|
| 45 | | | ++ | ++ |
| 46 | | | ++ | +++ |
| 47 | | | ++ | ++ |
| 48 | | | +++ | +++ |
| 49 | | | ++ | +++ |
| 50 | | | ++ | +++ |
| 51 | | | ++ | +++ |
| 52 | | | +++ | +++ |
| 53 | | | ++ | ++ |
| 54 | | | ++ | ++ |
| 55 | | | ++ | ++ |
| 56 | | | + | + |
| 57 | | | ++ | + |
| 58 | | | + | + |
| 59 | | | + | + |
| 60 | + | + | ++ | ++ |
| 61 | + | + | + | + |
| 62 | + | + | + | + |
| 63 | + | + | + | + |
| 64 | | | + | + |
| 65 | | | + | + |
| 66 | | | + | ++ |
| 67 | | | + | + |
| 68 | | | + | + |
| 69 | | | + | ++ |
| 70 | | | ++ | ++ |
| 71 | | | + | ++ |
| 72 | | | + | + |
| 73 | | | + | + |
| 74 | | | + | + |
| 75 | | | + | ++ |
| 76 | | | + | + |
| 77 | | | + | + |
| 78 | | | + | + |
| 79 | + | + | + | + |
| 80 | | | + | + |
| 81 | | | ++ | ++ |
| 82 | | | ++ | ++ |
| 83 | | | + | + |
| 84 | | | ++ | ++ |
| 85 | + | + | ++ | ++ |
| 86 | | | ++ | ++ |
| 87 | | | ++ | +++ |
| 88 | ++ | ++ | ++ | ++ |
| 89 | | | ++ | ++ |
| 90 | | | + | + |
| 91 | | | + | + |
| 92 | | | + | + |
| 93 | | | + | + |
| 94 | | | ++ | ++ |
| 95 | + | + | ++ | ++ |
| 96 | | | + | + |
| 97 | | | ++ | +++ |
| 98 | + | ++ | ++ | +++ |

(In Table 3,
+ indicates 'over 500 nM';
++ indicates 'over 10 nM~up to 500 nM'; and
+++ indicates 'up to 10 uM'.

As shown in Table 3, as a result of the investigation of the inhibition of PI3K α, β, γ, and δ by the compounds represented by formula 1 of the present invention, the compounds of the invention were excellent in inhibiting the activity of PI3K α, β, γ, and δ. In particular, the compounds inhibited the activity of PI3 kinase γ or δ even at a very low concentration.

Therefore, the compounds of the present invention can act as a PI3 kinase inhibitor, so that they can be effectively used for the prevention or treatment of PI3 kinase related diseases including cancer such as hematological malignance, ovarian cancer, cervical cancer, breast cancer, colorectal cancer, liver cancer, stomach cancer, pancreatic cancer, colon cancer, peritoneal metastasis, skin cancer, bladder cancer, prostate cancer, thyroid cancer, lung cancer, osteosarcoma, fibrous tumor, and brain tumor; autoimmune disease such as rheumatoid arthritis, systemic lupus erythematosus, multiple sclerosis, type diabetes, hyperthyroidism, myasthenia, Crohn's disease, ankylosing spondylitis, psoriasis, autoimmune pernicious anemia, and Sjogren's syndrome; and respiratory disease such as chronic obstructive pulmonary disease (COPD), rhinitis, asthma, chronic bronchitis, chronic inflammatory lung disease, silicosis, pulmonary sarcoidosis, pleurisy, alveolitis, vasculitis, emphysema, pneumonia, and bronchiectasis.

The preparation methods of the invention represented by reaction formulae 1~3 are novel methods not only facilitating the preparation of those compounds represented by formulae 11, 20, and 23, which are the intermediates of the compound represented by formula 1, but also providing various steps to prepare the compound represented by formula 1 by reacting the intermediate compounds represented by formulae 11, 20, and 23 with the compound that can react to the substituents of the said compounds.

Manufacturing Example 1: Preparation of Powders

| | |
|---|---|
| The compound represented by formula 1 | 2 g |
| Lactose | 1 g |

Powders were prepared by mixing all the above components, which were filled in airtight packs according to the conventional method for preparing powders.

Manufacturing Example 2: Preparation of Tablets

| | |
|---|---|
| The compound represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

Manufacturing Example 3: Preparation of Capsules

| | |
|---|---|
| The compound represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4: Preparation of Injectable Solution

| | |
|---|---|
| The compound represented by formula 1 | 100 mg |
| Mannitol | 180 mg |
| Na$_2$HPO$_4$•2H$_2$O | 26 mg |
| Distilled water | 2974 mg |

Injectable solutions were prepared by mixing all the above components by the conventional method for preparing injectable solutions.

Manufacturing Example 5: Preparation of Health Food

| | |
|---|---|
| The compound represented by formula 1 | 500 ng |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound represented by formula 1, an optical isomer thereof, or a pharmaceutically acceptable salt thereof:

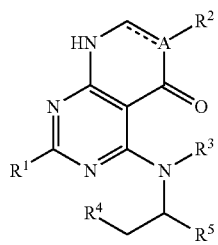

[Formula 1]

wherein:

---- is single bond or double bond;

A is carbon (C);

$R^1$ is hydrogen (H), $-NH_2$, or $C_{1-5}$ straight or branched alkylthio;

$R^2$ is H, $-CN$, $C_{1-5}$ straight or branched alkyl, unsubstituted $C_{3-7}$ cycloalkyl or halogen;

$R^3$ and $R^4$ are independently H or $C_{1-5}$ straight or branched alkyl; and $R^5$ is

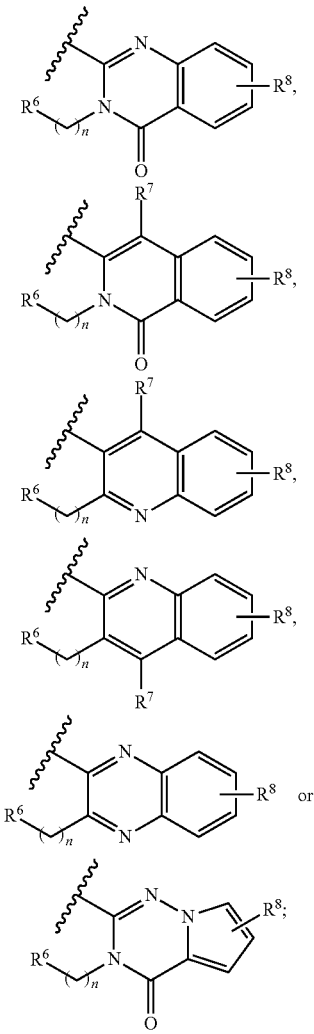

wherein, n is an integer of 0~3, $R^6$ is unsubstituted or substituted $C_{6-10}$ aryl or unsubstituted or substituted 5~10 membered heteroaryl containing one or more hetero atoms selected from the group consisting of N, O, and S, in which said substituted aryl and said substituted heteroaryl have one or more substituents selected from the group consisting of halogen, $C_{1-5}$ straight or branched alkyl, and $C_{1-5}$ straight or branched alkylsulfonyl, wherein $R^7$ and $R^8$ are independently H, halogen, $-CN$, $-OH$, unsubstituted or substituted $C_{6-10}$ aryl, unsubstituted or substituted 5~10 membered heteroaryl containing one or more hetero atoms selected from the group consisting of N, O, and S, $C_{1-5}$ straight or branched alkyl, $C_{1-5}$ straight or branched alkoxy, $C_{1-5}$ straight or branched alkyloxyalkyl, $C_{1-5}$ straight or branched alkylsulfonyl, $C_{1-5}$ straight or branched alkylthio, or $-NR^9R^{10}$, wherein $R^9$ and $R^{10}$ are independently H, $C_{1-5}$ straight or branched alkyl, $C_{1-5}$ straight or branched alkylamino, unsubstituted or substituted $C_{6-10}$ aryl, unsubstituted or substituted 5~10 membered heteroaryl containing one or more hetero atoms selected from the group consisting of N, O, and S, or unsubstituted or substituted 3~8 membered heterocycloalkyl containing one or more hetero atoms selected from the group consisting of N, O, and S, in which said substituted $C_{6-10}$aryl, said substituted 5~10 membered heteroaryl, and said substituted 3~8 membered heterocycloalkyl are substituted with have one or more substituents selected from the group consisting of halogen and $C_{1-5}$ straight or branched alkyl.

2. The compound represented by formula 1, the optical isomer thereof, or the pharmaceutically acceptable salt thereof according to claim 1, wherein:

---- is single bond or double bond;

A is carbon (C);

$R^1$ is H, —$NH_2$, or methylthio;

$R^2$ is H, —CN, $C_{1-3}$ straight or branched alkyl, unsubstituted $C_{3-5}$ cycloalkyl or halogen;

$R^3$ and $R^4$ are independently H or $C_{1-5}$ straight or branched alkyl; and $R^5$ is

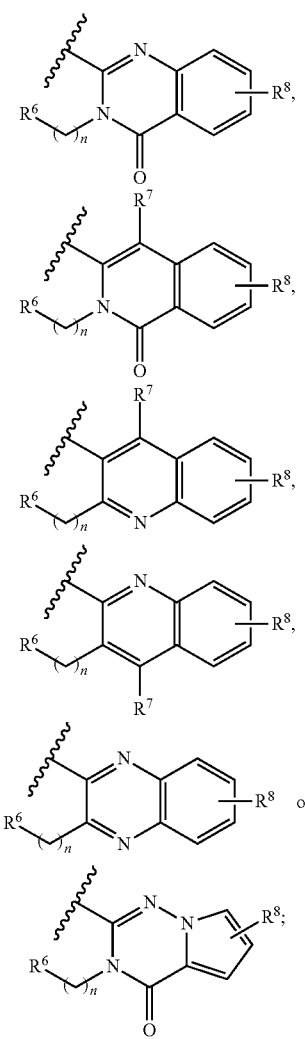

wherein, n is an integer of 0 or 1, $R^6$ is unsubstituted or substituted $C_{6-10}$ aryl or unsubstituted or substituted 5~10 membered heteroaryl containing one or more hetero atoms selected from the group consisting of N, O, and S, in which said substituted aryl and said substituted heteroaryl have one or more substituents selected from the group consisting of halogen and $C_{1-5}$ straight or branched alkyl, $R^7$ is H, halogen, unsubstituted or substituted $C_{6-10}$ aryl, or unsubstituted or substituted 5~7 membered heteroaryl containing one or more hetero atoms selected from the group consisting of N, O, and S, in which said substituted aryl and said substituted heteroaryl have one or more substituents selected from the group consisting of halogen and $C_{1-5}$ straight or branched alkyl, and $R^8$ is H, halogen, $C_{1-3}$ straight or branched alkyl, or $C_{1-3}$ straight or branched alkoxy.

3. The compound represented by formula 1, the optical isomer thereof, or the pharmaceutically acceptable salt thereof according to claim 1, wherein:

---- is single bond or double bond;

A is carbon (C);

$R^1$ is H or —$NH_2$;

$R^2$ is H, —CN, $C_{1-3}$ straight or branched alkyl, unsubstituted $C_{3-5}$ cycloalkyl or halogen;

$R^3$ is H;

$R^4$ is H or $C_{1-3}$ straight or branched alkyl; and $R^5$ is

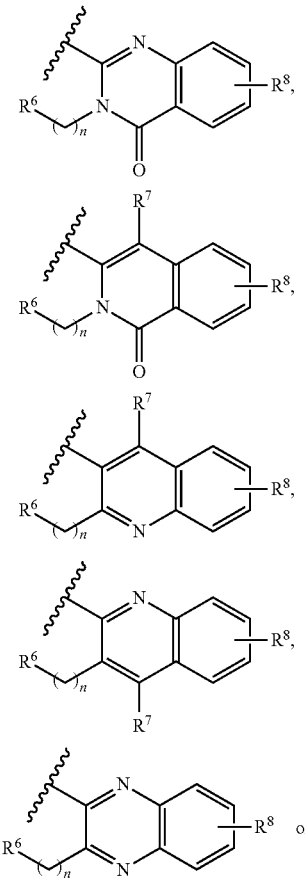

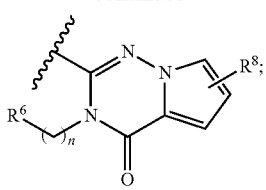

wherein, n is an integer of 0 or 1, $R^6$ is unsubstituted or substituted phenyl or pyridinyl, in which said substituted phenyl and pyridinyl have one or more substituents selected from the group consisting of halogen and $C_{1-3}$ straight or branched alkyl;

$R^7$ is H, halogen, or unsubstituted or substituted 5~7 membered heteroaryl containing one or more hetero atoms of N, in which said substituted heteroaryl has one or more substituents selected from the group consisting of halogen and $C_{1-3}$ straight or branched alkyl, and $R^8$ is H, halogen, or $C_{1-3}$ straight or branched alkyl.

4. The compound represented by formula 1, the optical isomer thereof, or the pharmaceutically acceptable salt thereof according to claim 1, wherein:

----- is single bond or double bond;

A is carbon (C);

$R^1$ is H or —$NH_2$;

$R^2$ is H, —F, —Cl, —CN, methyl, ethyl, propyl, isopropyl, cyclopropyl, or cyclopentyl;

$R^3$ is H;

$R^4$ is H or methyl; and $R^5$ is

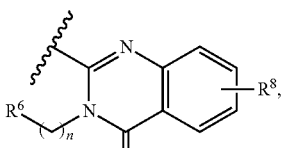

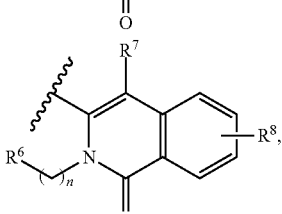

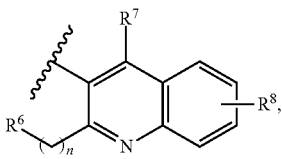

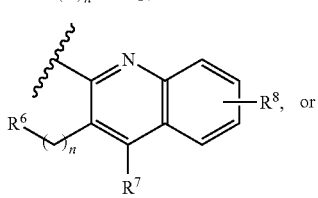

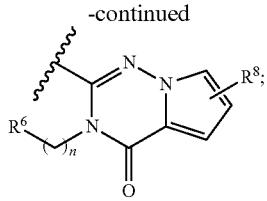

wherein, n is an integer of 0 or 1, $R^6$ is unsubstituted or substituted phenyl or pyridinyl, in which said substituted phenyl and pyridinyl have one or more substituents selected from the group consisting of —F, —Cl, and methyl;

$R^7$ is H, —F, —Cl, or pyridinyl; and $R^8$ is H, —F, or —Cl.

5. The compound represented by formula 1, the optical isomer thereof, or the pharmaceutically acceptable salt thereof according to claim 1, wherein the ring containing A and $R^2$ is exemplified by

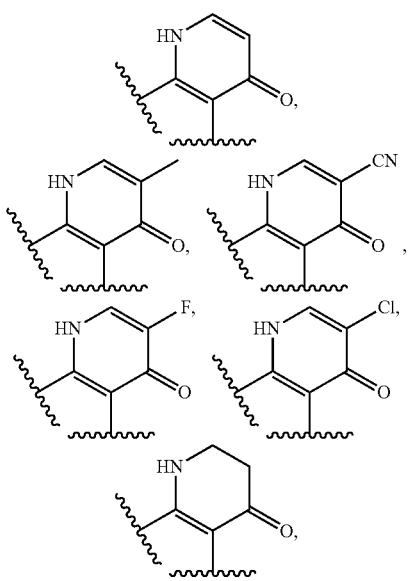

or and $R^5$ is exemplified by

269
-continued
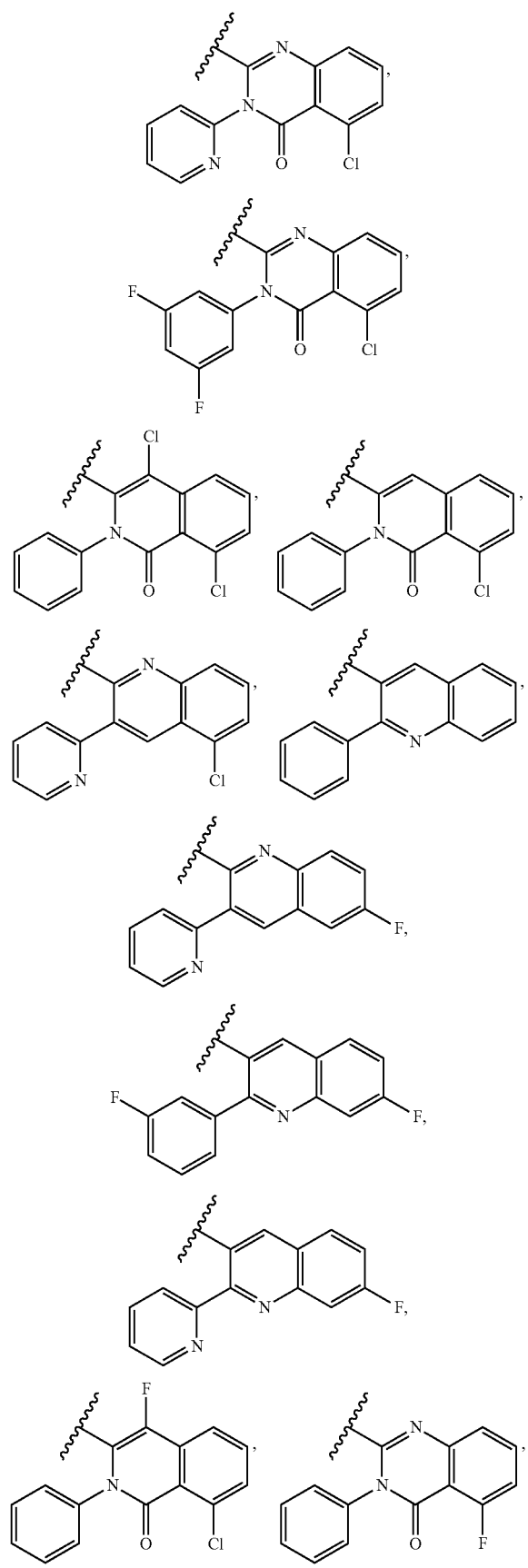
270
-continued
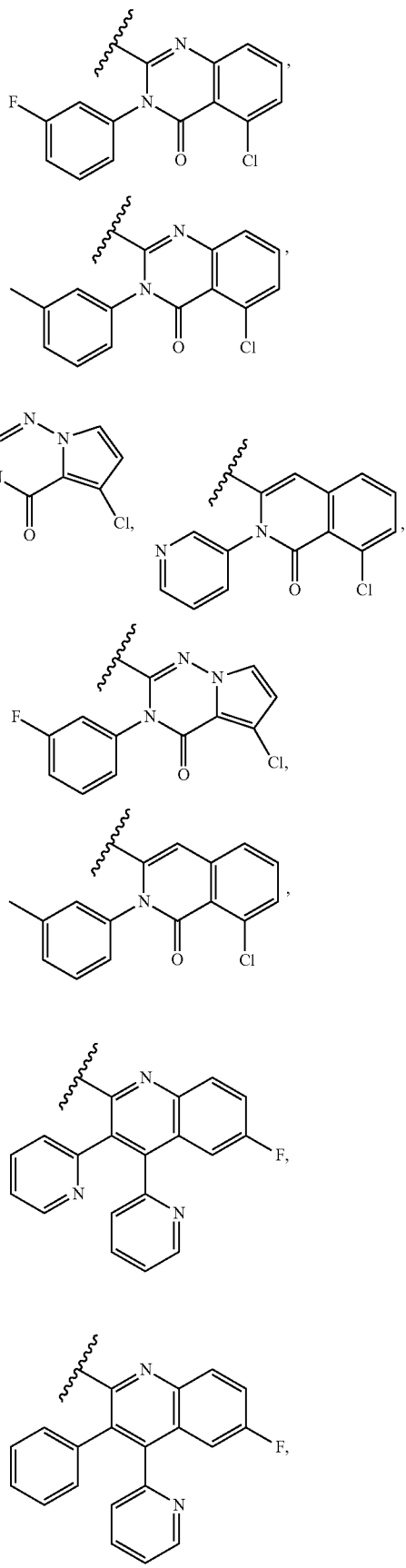

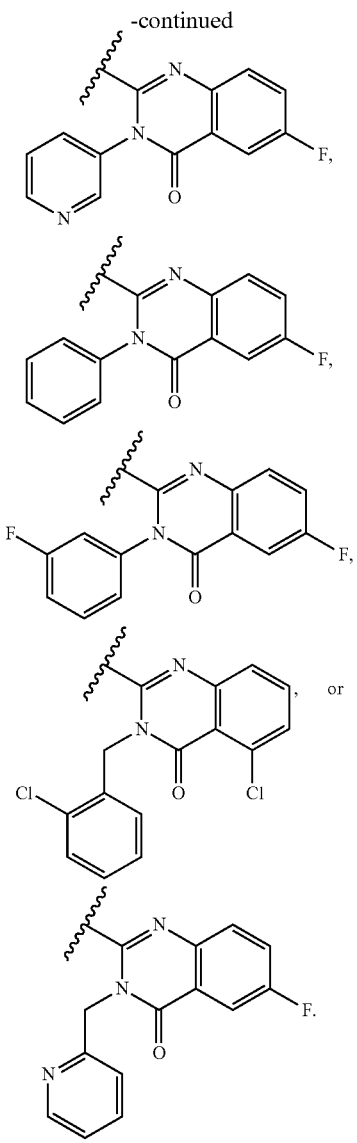

6. The compound represented by formula 1, the optical isomer thereof, or the pharmaceutically acceptable salt thereof according to claim 1, wherein the compound represented by formula 1 is characteristically the compound represented by formula 1A:

[Formula 1A]

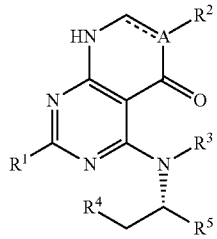

wherein
----, A, $R^1$, $R^2$, $R^3$, $R^4$, and $R^5$ are as defined in formula 1.

7. The compound represented by formula 1, the optical isomer thereof, or the pharmaceutically acceptable salt thereof according to claim 1, wherein the compound represented by formula 1 is selected from the group consisting of the following compounds:
<1> 4-((1-(5-chloro-4-oxo-3-phenyl-3,4-dihydroquinazoline-2-yl)ethyl)amino)pyrido[2,3-d]pyrimidine-5(8H)-one;
<2> 4-((1-(5-chloro-4-oxo-3-(pyridine-3-yl)-3,4-dihydroquinazoline-2-yl)ethyl)amino)pyrido[2,3-d]pyrimidine-5(8H)-one;
<3> 4-((1-(5-chloro-4-oxo-3-(pyridine-2-yl)-3,4-dihydroquinazoline-2-yl)ethyl)amino)pyrido[2,3-d]pyrimidine-5(8H)-one;
<4> 4-((1-(5-chloro-3-(3,5-difluorophenyl)-4-oxo-3,4-dihydroquinazoline-2-yl)ethyl)amino)pyrido[2,3-d]pyrimidine-5(8H)-one;
<5> 4-((1-(8-chloro-1-oxo-2-phenyl-1,2-dihydroisoquinoline-3-yl)ethyl)amino)pyrido[2,3-d]pyrimidine-5(8H)-one;
<6> 44(1-(2-phenylquinoline-3-yl)ethyl)amino)pyrido[2,3-d]pyrimidine-5(8H)-one;
<7> 44(1-(6-fluoro-3-(pyridine-2-yl)quinoline-2-yl)ethyl)amino)pyrido[2,3-d]pyrimidine-5(8H)-one;
<8> 44(1-(7-fluoro-2-(3-fluorophenyl)quinoline-3-yl)ethyl)amino)pyrido[2,3-d]pyrimidine-5(8H)-one;
<9> 4-(1-(7-fluoro-2-(pyridine-2-yl)quinoline-3-yl)ethylamino)pyrido[2,3-d]pyrimidine-5(8H)-one;
<10> 4-((1-(4,8-dichloro-1-oxo-2-phenyl-1,2-dihydroisoquinoline-3-yl)ethyl)amino)pyrido[2,3-d]pyrimidine-5(8H)-one;
<11> 4-((1-(8-chloro-4-fluoro-1-oxo-2-phenyl-1,2-dihydroisoquinoline-3-yl)ethyl)amino)pyrido[2,3-d]pyrimidine-5(8H)-one;
<12> 4-((1-(5-fluoro-4-oxo-3-phenyl-3,4-dihydroquinazoline-2-yl)propyl)amino)pyrido[2,3-d]pyrimidine-5(8H)-one;
<15> 2-amino-4-((1-(8-chloro-1-oxo-2-phenyl-1,2-dihydroisoquinoline-3-yl)ethyl)amino)pyrido[2,3-d]pyrimidine-5(8H)-one;
<17> 4-((1-(8-chloro-1-oxo-2-phenyl-1,2-dihydroisoquinoline-3-yl)ethyl)amino)-6-methylpyrido[2,3-d]pyrimidine-5(8H)-one;
<18> 2-amino-4-((1-(8-chloro-1-oxo-2-phenyl-1,2-dihydroisoquinoline-3-yl)ethyl)amino)-6-methylpyrido[2,3-d]pyrimidine-5(8H)-one;
<19> 4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile;
<20> 4-((1-(8-chloro-1-oxo-2-phenyl-1,2-dihydroisoquinoline-3-yl)ethyl)amino)-6-fluoropyrido[2,3-d]pyrimidine-5(8H)-one;
<21> 4-((1-(5-chloro-4-oxo-3-phenyl-3,4-dihydroquinazoline-2-yl)ethyl)amino)-6-fluoropyrido[2,3-d]pyrimidine-5(8H)-one;
<22> 6-chloro-4-((1-(5-chloro-4-oxo-3-phenyl-3,4-dihydroquinazoline-2-yl)ethyl)amino)pyrido[2,3-d]pyrimidine-5(8H)-one;
<23> 6-chloro-4-((1-(8-chloro-1-oxo-2-phenyl-1,2-dihydroisoquinoline-3-yl)ethyl)amino)pyrido[2,3-d]pyrimidine-5(8H)-one;
<24> 6-chloro-4-((1-(4,8-dichloro-1-oxo-2-phenyl-1,2-dihydroisoquinoline-3-yl)ethyl)amino)pyrido[2,3-d]pyrimidine-5(8H)-one;
<25> 2-amino-4-((1-(6-fluoro-3-(pyridine-2-yl)quinoline-2-yl)ethyl)amino)pyrido[2,3-d]pyrimidine-5(8H)-one;
<26> 4-((1-(6-fluoro-3,4-di(pyridine-2-yl)quinoline-2-yl)ethyl)amino)pyrido[2,3-d]pyrimidine-5(8H)-one;

<27> 4-((1-(6-fluoro-3-phenyl-4-(pyridine-2-yl)quinoline-2-yl)ethyl)amino)pyrido[2,3-d]pyrimidine-5(8H)-one;

<28> 4-((1-(6-fluoro-4-oxo-3-(pyridine-3-yl)-3,4-dihydroquinazoline-2-yl)ethyl)amino)pyrido[2,3-d]pyrimidine-5(8H)-one;

<29> 4-((1-(6-fluoro-4-oxo-3-phenyl-3,4-dihydroquinazoline-2-yl)ethyl)amino)pyrido[2,3-d]pyrimidine-5(8H)-one;

<30> 4-((1-(6-fluoro-3-(3-fluorophenyl)-4-oxo-3,4-dihydroquinazoline-2-yl)ethyl)amino)pyrido[2,3-d]pyrimidine-5(8H)-one;

<31> 4-((1-(5-chloro-3-(2-chlorobenzyl)-4-oxo-3,4-dihydroquinazoline-2-yl)ethyl)amino)pyrido[2,3-d]pyrimidine-5(8H)-one;

<32> 4-((1-(6-fluoro-4-oxo-3-(pyridine-2-ylmethyl)-3,4-dihydroquinazoline-2-yl)ethyl)amino)pyrido[2,3-d]pyrimidine-5(8H)-one;

<33> 4-((1-(5-chloro-3-(pyridine-2-yl)quinoline-2-yl)ethyl)amino)pyrido[2,3-d]pyrimidine-5(8H)-one;

<97> 4-((1-(8-chloro-1-oxo-2-phenyl-1,2-dihydroisoquinoline-3-yl)ethyl)amino)-7,8-dihydropyrido[2,3-d]pyrimidine-5(6H)-one; and <98> 4-((1-(4,8-dichloro-1-oxo-2-phenyl-1,2-dihydroisoquinoline-3-yl)ethyl)amino)-7,8-dihydropyrido[2,3-d]pyrimidine-5(6H)-one.

8. The compound represented by formula 1, the optical isomer thereof, or the pharmaceutically acceptable salt thereof according to claim 1, wherein the compound represented by formula 1 is selected from the group consisting of the following compounds:

<1> (S)-4-((1-(5-chloro-4-oxo-3-phenyl-3,4-dihydroquinazoline-2-yl)ethyl)amino)pyrido[2,3-d]pyrimidine-5(8H)-one;

<2> (S)-4-((1-(5-chloro-4-oxo-3-(pyridine-3-yl)-3,4-dihydroquinazoline-2-yl)ethyl)amino)pyrido[2,3-d]pyrimidine-5(8H)-one;

<3> (S)-4-((1-(5-chloro-4-oxo-3-(pyridine-2-yl)-3,4-dihydroquinazoline-2-yl)ethyl)amino)pyrido[2,3-d]pyrimidine-5(8H)-one;

<4> (S)-4-((1-(5-chloro-3-(3,5-difluorophenyl)-4-oxo-3,4-dihydroquinazoline-2-yl)ethyl)amino)pyrido[2,3-d]pyrimidine-5(8H)-one;

<5> (S)-4-((1-(8-chloro-1-oxo-2-phenyl-1,2-dihydroisoquinoline-3-yl)ethyl)amino)pyrido[2,3-d]pyrimidine-5(8H)-one;

<6> (S)-4-((1-(2-phenylquinoline-3-yl)ethyl)amino)pyrido[2,3-d]pyrimidine-5(8H)-one;

<7> (S)-4-((1-(6-fluoro-3-(pyridine-2-yl)quinoline-2-yl)ethyl)amino)pyrido[2,3-d]pyrimidine-5(8H)-one;

<8> (S)-4-((1-(7-fluoro-2-(3-fluorophenyl)quinoline-3-yl)ethyl)amino)pyrido[2,3-d]pyrimidine-5(8H)-one;

<9> (S)-4-(1-(7-fluoro-2-(pyridine-2-yl)quinoline-3-yl)ethylamino)pyrido[2,3-d]pyrimidine-5(8H)-one;

<10> (S)-4-((1-(4,8-dichloro-1-oxo-2-phenyl-1,2-dihydroisoquinoline-3-yl)ethyl)amino)pyrido[2,3-d]pyrimidine-5(8H)-one;

<11> (S)-4-((1-(8-chloro-4-fluoro-1-oxo-2-phenyl-1,2-dihydroisoquinoline-3-yl)ethyl)amino)pyrido[2,3-d]pyrimidine-5(8H)-one;

<12> (S)-4-((1-(5-fluoro-4-oxo-3-phenyl-3,4-dihydroquinazoline-2-yl)propyl)amino)pyrido[2,3-d]pyrimidine-5(8H)-one;

<15> (S)-2-amino-4-((1-(8-chloro-1-oxo-2-phenyl-1,2-dihydroisoquinoline-3-yl)ethyl)amino)pyrido[2,3-d]pyrimidine-5(8H)-one;

<17> (S)-4-((1-(8-chloro-1-oxo-2-phenyl-1,2-dihydroisoquinoline-3-yl)ethyl)amino)-6-methylpyrido[2,3-d]pyrimidine-5(8H)-one;

<18> (S)-2-amino-4-((1-(8-chloro-1-oxo-2-phenyl-1,2-dihydroisoquinoline-3-yl)ethyl)amino)-6-methylpyrido[2,3-d]pyrimidine-5(8H)-one;

<19> (S)-4-((1-(8-chloro-1-oxo-2-phenyl-1,2-dihydroisoquinoline-3-yl)ethyl)amino)-5-oxo-5,8-dihydropyrido[2,3-d]pyrimidine-6-carbonitrile;

<20> (S)-4-((1-(8-chloro-1-oxo-2-phenyl-1,2-dihydroisoquinoline-3-yl)ethyl)amino)-6-fluoropyrido[2,3-d]pyrimidine-5(8H)-one;

<21> (S)-4-((1-(5-chloro-4-oxo-3-phenyl-3,4-dihydroquinazoline-2-yl)ethyl)amino)-6-fluoropyrido[2,3-d]pyrimidine-5(8H)-one;

<22> (S)-6-chloro-4-((1-(5-chloro-4-oxo-3-phenyl-3,4-dihydroquinazoline-2-yl)ethyl)amino)pyrido[2,3-d]pyrimidine-5(8H)-one;

<23> (S)-6-chloro-4-((1-(8-chloro-1-oxo-2-phenyl-1,2-dihydroisoquinoline-3-yl)ethyl)amino)pyrido[2,3-d]pyrimidine-5(8H)-one;

<24> (S)-6-chloro-4-((1-(4,8-dichloro-1-oxo-2-phenyl-1,2-dihydroisoquinoline-3-yl)ethyl)amino)pyrido[2,3-d]pyrimidine-5(8H)-one;

<25> (S)-2-amino-4-((1-(6-fluoro-3-(pyridine-2-yl)quinoline-2-yl)ethyl)amino)pyrido[2,3-d]pyrimidine-5(8H)-one;

<26> (S)-4-((1-(6-fluoro-3,4-di(pyridine-2-yl)quinoline-2-yl)ethyl)amino)pyrido[2,3-d]pyrimidine-5(8H)-one;

<27> (S)-4-((1-(6-fluoro-3-phenyl-4-(pyridine-2-yl)quinoline-2-yl)ethyl)amino)pyrido[2,3-d]pyrimidine-5(8H)-one;

<28> (S)-4-((1-(6-fluoro-4-oxo-3-(pyridine-3-yl)-3,4-dihydroquinazoline-2-yl)ethyl)amino)pyrido[2,3-d]pyrimidine-5(8H)-one;

<29> (S)-4-((1-(6-fluoro-4-oxo-3-phenyl-3,4-dihydroquinazoline-2-yl)ethyl)amino)pyrido[2,3-d]pyrimidine-5(8H)-one;

<30> (S)-4-((1-(6-fluoro-3-(3-fluorophenyl)-4-oxo-3,4-dihydroquinazoline-2-yl)ethyl)amino)pyrido[2,3-d]pyrimidine-5(8H)-one;

<31> (S)-4-((1-(5-chloro-3-(2-chlorobenzyl)-4-oxo-3,4-dihydroquinazoline-2-yl)ethyl)amino)pyrido[2,3-d]pyrimidine-5(8H)-one;

<32> (S)-4-((1-(6-fluoro-4-oxo-3-(pyridine-2-ylmethyl)-3,4-dihydroquinazoline-2-yl)ethyl)amino)pyrido[2,3-d]pyrimidine-5(8H)-one;

<33> (S)-4-((1-(5-chloro-3-(pyridine-2-yl)quinoline-2-yl)ethyl)amino)pyrido[2,3-d]pyrimidine-5(8H)-one;

<97> (S)-4-((1-(8-chloro-1-oxo-2-phenyl-1,2-dihydroisoquinoline-3-yl)ethyl)amino)-7,8-dihydropyrido[2,3-d]pyrimidine-5(6H)-one; and <98> (S)-4-((1-(4,8-dichloro-1-oxo-2-phenyl-1,2-dihydroisoquinoline-3-yl)ethyl)amino)-7,8-dihydropyrido[2,3-d]pyrimidine-5(6H)-one.

9. An intermediate compound represented by formula 1B below or an optical isomer of the same:

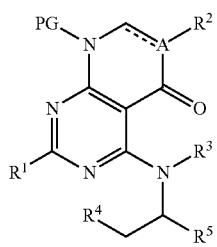

[Formula 1B]

wherein:
---- is single bond or double bond;
A is carbon (C);
$R^1$ is hydrogen (H), —$NH_2$, or $C_{1-5}$ straight or branched alkylthio;
$R^2$ is H, —CN, $C_{1-5}$ straight or branched alkyl, unsubstituted $C_{3-7}$ cycloalkyl or halogen;
$R^3$ and $R^4$ are independently H or $C_{1-5}$ straight or branched alkyl; and

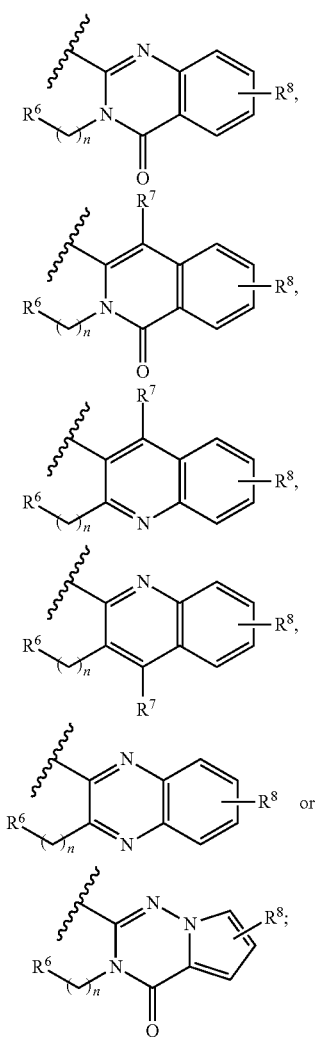

wherein, n is an integer of 0~3,
$R^6$ is unsubstituted or substituted $C_{6-10}$ aryl or unsubstituted or substituted 5~10 membered heteroaryl containing one or more hetero atoms selected from the group consisting of N, O, and S, in which said substituted aryl and said substituted heteroaryl have one or more substituents selected from the group consisting of halogen, $C_{1-5}$ straight or branched alkyl, and $C_{1-5}$ straight or branched alkylsulfonyl,
$R^7$ and $R^8$ are independently H, halogen, —CN, —OH, unsubstituted or substituted $C_{6-10}$ aryl, unsubstituted or substituted 5~10 membered heteroaryl containing one or more hetero atoms selected from the group consisting of N, O, and S, $C_{1-5}$ straight or branched alkyl, $C_{1-5}$ straight or branched alkoxy, $C_{1-5}$ straight or branched alkyloxyalkyl, $C_{1-5}$ straight or branched alkylsulfonyl, $C_{1-5}$ straight or branched alkylthio, or —$NR^9R^{10}$, wherein $R^9$ and $R^{10}$ are independently H, $C_{1-5}$ straight or branched alkyl, $C_{1-5}$ straight or branched alkylamino, unsubstituted or substituted $C_{6-10}$ aryl, unsubstituted or substituted 5~10 membered heteroaryl containing one or more hetero atoms selected from the group consisting of N, O, and S, or unsubstituted or substituted 3~8 membered heterocycloalkyl containing one or more hetero atoms selected from the group consisting of N, O, and S, in which said substituted $C_{6-10}$aryl, said substituted 5~10 membered heteroaryl, and said substituted 3~8 membered heterocycloalkyl have one or more substituents selected from the group consisting of halogen and $C_{1-5}$ straight or branched alkyl; and
PG is an amine protecting group selected from the group consisting of t-butyloxycarbonyl (Boc), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), and aryloxycarbonyl (Alloc).

10. A method for preparing the compound represented by formula 1 comprising the following steps as shown in the below reaction formula 1:
preparing the compound represented by formula 2A by reacting the compound represented by formula 2 and the compound represented by formula 3 (step 1);
preparing the compound represented by formula 5 by reacting the compound represented by formula 2A prepared in step 1 and the compound represented by formula 4 (step 2);
preparing the compound represented by formula 7 by reacting the compound represented by formula 5 prepared in step 2 and the compound represented by formula 6 (step 3);
preparing the compound represented by formula 8 by reacting the compound represented by formula 7 prepared in step 3 and the compound represented by formula 2B under basic condition (step 4);
preparing the compound represented by formula 10 by reacting the compound represented by formula 8 prepared in step 4 and the compound represented by formula 9 (step 5);
preparing the compound represented by formula 11 by reacting the compound represented by formula 10 prepared in step 5 under acidic condition (step 6);
preparing the compound represented by formula 12 by reacting the compound represented by formula 11 prepared in step 6 and the compound represented by formula 2C (step 7); and
preparing the compound represented by formula 1a by eliminating the amine protecting group from the compound represented by formula 12 prepared in step 7 under acidic condition (step 8):

[Reaction Formula 1]

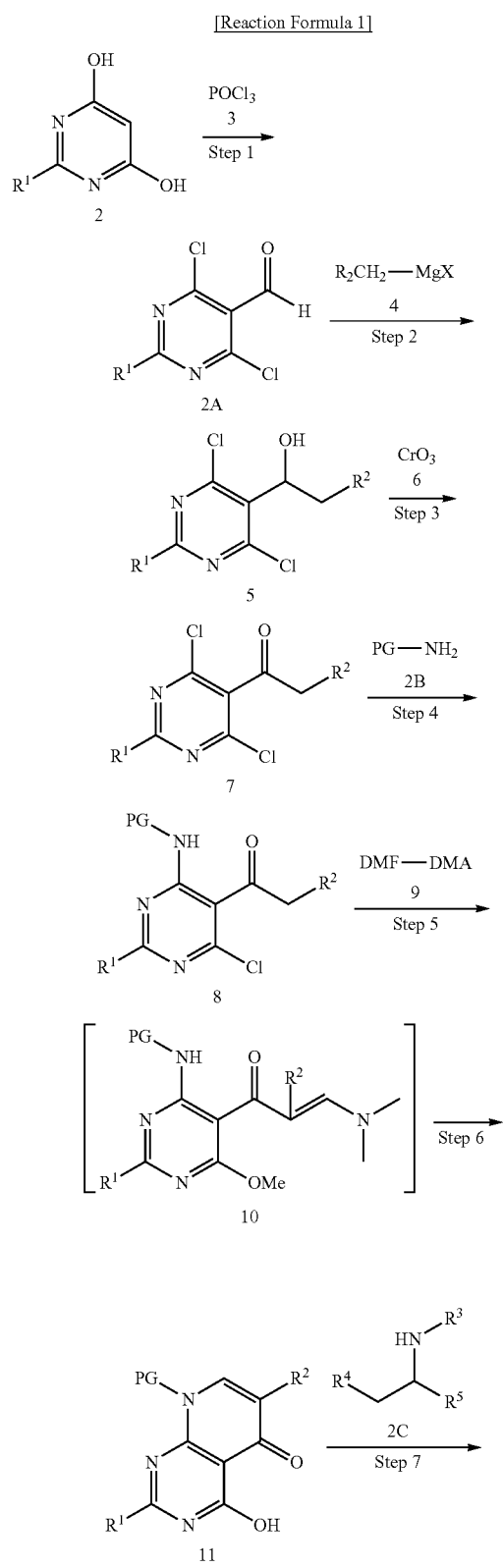

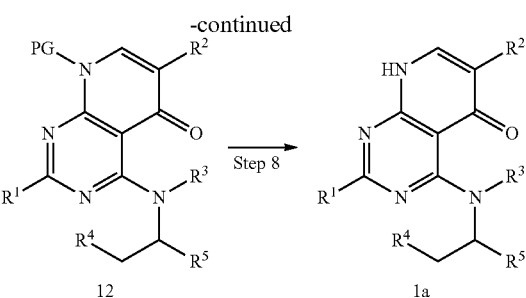

wherein in the reaction formula 1,

PG is amine protecting group;

the compound represented by formula 1a is a derivative of the compound represented by formula 1, in which ---- is double bond and A is carbon, and $R^1$ is hydrogen (H), —$NH_2$, or $C_{1-5}$ straight or branched alkylthio;

$R^2$ is H, —CN, $C_{1-5}$ straight or branched alkyl, unsubstituted $C_{3-7}$ cycloalkyl or halogen;

$R^3$ and $R^4$ are independently H or $C_{1-5}$ straight or branched alkyl; and

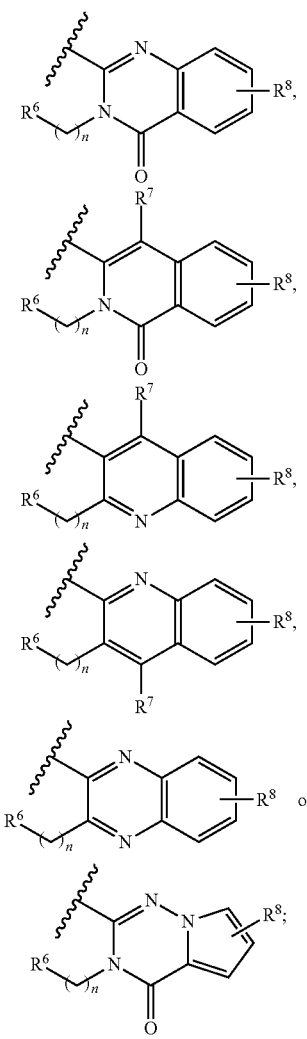

wherein, n is an integer of 0~3, $R^6$ is unsubstituted or substituted $C_{6-10}$ aryl or unsubstituted or substituted 5~10 membered heteroaryl containing one or more hetero atoms selected from the group consisting of N, O, and S, in which said substituted aryl and said substituted heteroaryl have one or more substituents selected from the group consisting of halogen, $C_{1-5}$ straight or branched alkyl, and $C_{1-5}$ straight or branched alkylsulfonyl, $R^7$ and $R^8$ are independently H, halogen, —CN, —OH, unsubstituted or substituted $C_{6-10}$ aryl, unsubstituted or substituted 5~10 membered heteroaryl containing one or more hetero atoms selected from the group consisting of N, O, and S, $C_{1-5}$ straight or branched alkyl, $C_{1-5}$ straight or branched alkoxy, $C_{1-5}$ straight or branched alkyloxyalkyl, $C_{1-5}$ straight or branched alkylsulfonyl, $C_{1-5}$ straight or branched alkylthio, or —NR$^9$R$^{10}$, wherein $R^9$ and $R^{10}$ are independently H, $C_{1-5}$ straight or branched alkyl, $C_{1-5}$ straight or branched alkylamino, unsubstituted or substituted $C_{6-10}$aryl, unsubstituted or substituted 5~10 membered heteroaryl containing one or more hetero atoms selected from the group consisting of N, O, and S, or unsubstituted or substituted 3~8 membered heterocycloalkyl containing one or more hetero atoms selected from the group consisting of N, O, and S, in which said substituted $C_{6-10}$aryl, said substituted 5~10 membered heteroaryl, and said substituted 3~8 membered heterocycloalkyl have one or more substituents selected from the group consisting of halogen and $C_{1-5}$ straight or branched alkyl.

11. A pharmaceutical composition for the prevention or treatment of PI3 kinase related disease, which comprises the compound represented by formula 1, the optical isomer thereof, or the pharmaceutically acceptable salt thereof of claim 1 as an active ingredient.

12. A health functional food composition for the prevention or improvement of PI3 kinase related disease, which comprises the compound represented by formula 1, the optical isomer thereof, or the pharmaceutically acceptable salt thereof of claim 1 as an active ingredient.

* * * * *